(12) United States Patent
Chou et al.

(10) Patent No.: US 11,370,787 B2
(45) Date of Patent: Jun. 28, 2022

(54) PYRAZOLE COMPOUNDS, FORMULATIONS THEREOF, AND A METHOD FOR USING THE COMPOUNDS AND/OR FORMULATIONS

(71) Applicant: Rigel Pharmaceuticals, Inc., South San Francisco, CA (US)

(72) Inventors: Lu Chou, Burlingame, CA (US); Matt Duan, Foster City, CA (US); Ihab Darwish, South San Francisco, CA (US); Simon Shaw, Oakland, CA (US); Somasekhar Bhamidipati, Foster City, CA (US); Vanessa Taylor, San Francisco, CA (US); Yan Chen, Foster City, CA (US); Dazhong Fan, South San Francisco, CA (US); Zhushou Luo, South San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 71 days.

(21) Appl. No.: 17/006,150

(22) Filed: Aug. 28, 2020

(65) Prior Publication Data

US 2021/0061798 A1  Mar. 4, 2021

Related U.S. Application Data

(60) Provisional application No. 62/894,547, filed on Aug. 30, 2019.

(51) Int. Cl.
*C07D 417/14* (2006.01)
(52) U.S. Cl.
CPC .................. *C07D 417/14* (2013.01)
(58) Field of Classification Search
CPC .......................................................... C07D 417/14
USPC ....................................................... 514/365
See application file for complete search history.

(56) References Cited

U.S. PATENT DOCUMENTS

| | | | |
|---|---|---|---|
| 7,977,477 B2 | 7/2011 | Berdini | |
| 8,575,336 B2 | 11/2013 | Coe et al. | |
| 8,895,544 B2 | 11/2014 | Coe et al. | |
| 9,982,000 B2 | 5/2018 | Kelley et al. | |
| 10,208,074 B2 * | 2/2019 | Kelley | A61P 5/14 |
| 10,208,075 B2 | 2/2019 | Kelley et al. | |
| 2014/0088117 A1 | 3/2014 | Burch | |

FOREIGN PATENT DOCUMENTS

| | | |
|---|---|---|
| EP | 2 231 654 | 9/2010 |
| EP | 2 674 423 | 12/2013 |
| WO | WO 2009/054468 | 4/2000 |
| WO | WO 2004/037248 | 5/2004 |
| WO | WO 2006/070198 | 7/2006 |
| WO | WO 2006/070202 | 7/2006 |
| WO | WO 2010/121243 | 10/2010 |
| WO | WO 2010/121834 | 10/2010 |
| WO | WO 2011/043371 | 4/2011 |
| WO | WO 2011/124580 | 10/2011 |
| WO | WO 2012/068546 | 5/2012 |
| WO | WO 2012/072685 | 6/2012 |
| WO | WO 2012/084704 | 6/2012 |
| WO | WO 2012/097013 | 7/2012 |
| WO | WO 2013/045461 | 4/2013 |
| WO | WO 2013/106535 | 7/2013 |
| WO | WO 2014/058691 | 4/2014 |
| WO | WO 2014/121931 | 8/2014 |

(Continued)

OTHER PUBLICATIONS

Buckley et al., "IRAK-4 inhibitors. Part 1: A series of amides," *Bioorganic & Medicinal Chemistry Letters* 18:3211-3214, available online Apr. 26, 2008.
CAS Registry No. 1376284-17-1 dated Jun. 7, 2012.
Chaudhary et al., "Recent Advances in the Discovery of Small Molecule Inhibitors of Interleukin-1 Receptor-Associated Kinase (IRAK4) as a Therapeutic Target for Inflammation and Oncology Disorders," *Journal of Medical Chemistry* 58(1):96-110, Jan. 8, 2015.
Lim et al., "Discovery of 5-Amino-N-(1H-pyrazol-4-yl)pyrazolo[1,5-c]pyrimidine-3-carboxamide Inhibitors of IRAK4," *ACS Medicinal Chemistry Letters* 6(6):683-688, 2015.

(Continued)

*Primary Examiner* — Kahsay Habte
(74) *Attorney, Agent, or Firm* — Klarquist Sparkman, LLP

(57) ABSTRACT

Disclosed herein are embodiments of a pyrazole compound according to formula I.

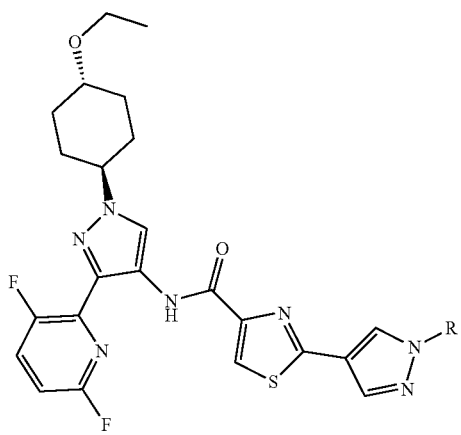

Formula I

Compositions comprising the compound, and a method for making the composition also are disclosed. The composition may comprise a carrier, such as a polymer and/or the composition may be a spray-dried formulation. Also disclosed is a method for using the compound and/or composition. The compound and/or composition may be useful to inhibit an IRAK protein and/or to ameliorate, treat and/or prevent an IRAK-associated disease or condition in a subject.

23 Claims, 15 Drawing Sheets

(56) References Cited

FOREIGN PATENT DOCUMENTS

| WO | WO 2014/121942 | 8/2014 |
|----|----------------|--------|
| WO | WO 2015/106058 | 7/2015 |
| WO | WO 2016/081679 | 5/2016 |

OTHER PUBLICATIONS

Unbekandt et al., "A novel small-molecule MRCK inhibitor cancer cell invasion," *Cell Communication and Signaling* 12(54):1-15, 2014.

* cited by examiner

| Test Article | Dose, mg/kg (Range) | Average AUC₀-₂₄ ± SD (5 mg/kg basis) | | T1/2 (hrs) | | Cmax (ng/ml) | | %F |
|---|---|---|---|---|---|---|---|---|
| | | I-1 | Metabolite | I-1 | Metabolite | I-1 | Metabolite | I-1 |
| SDD | 5.5 – 6.6 | 10200 ± 871 | 275 ± 64 | 4.3 | 4.3 | 1140 | 54 | 88 |
| Organic/juice | 5.5 – 6.6 | 7740 ± 1020 | 236 ± 55 | 3.3 | 3.2 | 1100 | 52 | 67 |

FIG. 19

PYRAZOLE COMPOUNDS, FORMULATIONS THEREOF, AND A METHOD FOR USING THE COMPOUNDS AND/OR FORMULATIONS

CROSS REFERENCE TO RELATED APPLICATION

This application claims the benefit of the earlier filing date of U.S. provisional patent application No. 62/894,547, filed Aug. 30, 2019, which is incorporated herein by reference in its entirety.

FIELD

The present disclosure concerns compounds, formulations thereof, and embodiments of a method using the compounds and/or formulations, such as for inhibiting interleukin receptor-associated kinase (IRAK) and/or delivering an IRAK inhibitor to a subject, and for treating diseases and conditions related to IRAK.

BACKGROUND

Interleukin-1 receptor-associated kinases (IRAKs) are important mediators of signaling processes, such as toll-like receptors (TLR) and interleukin-1 receptor (IL-1R) signaling processes. IRAKs have been implicated in modulating signaling networks that control inflammation, apoptosis, and cellular differentiation. Four IRAK genes have been identified in the human genome (IRAK1, IRAK2, IRAK3 and IRAK4), and studies have revealed distinct, non-redundant biological roles. IRAK1 and IRAK4 have been shown to exhibit kinase activity.

SUMMARY

Disclosed herein are compounds, and compositions comprising such compounds that are useful as, inter alia, kinase inhibitors, such as IRAK inhibitors and/or useful for delivering an IRAK inhibitor to a subject in need thereof. In some embodiments, the compounds are prodrugs and/or salts of IRAK inhibitor compounds. Certain disclosed embodiments concern compounds having a formula I:

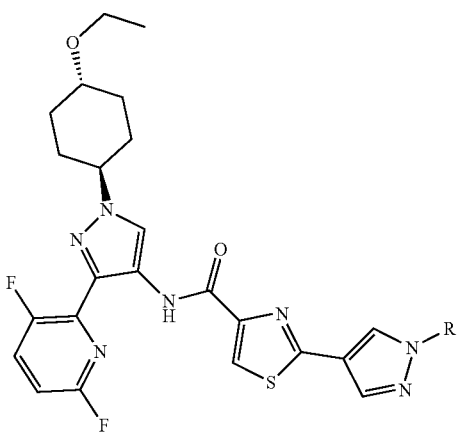

Formula I wherein R is hydrogen, aliphatic, acyl, heterocyclyl, carboxyl ester, amide, alkyl phosphoramidate, or alkyl phosphate, such as alkyl, acyl, carboxyl ester, amide, nonaromatic heterocyclyl, alkyl phosphoramidate, or alkyl phosphate. Alternatively, R is hydrogen and the compound is a salt. In some embodiments, R is $C_{1-4}$alkyl phosphate, $C_{1-4}$alkyl phosphoramidate, $C_{1-6}$alkyl, $C_{1-6}$acyl, —C(O)O—$C_{1-6}$aliphatic, —C(O)N($R^b$)$_2$, or 5- or 6-membered nonaromatic heterocyclyl. And each $R^b$ independently is H, unsubstituted $C_{1-6}$alkyl, $C_{1-6}$alkyl substituted with —N($R^g$)$_2$, carboxyl ester, or 5- or 6-membered nonaromatic heterocyclyl, or two R together with the nitrogen to which they are attached form a $C_{3-6}$nonaromatic heterocyclyl moiety optionally interrupted with one or two —O— or —N($R^g$), where $R^g$ is H or $C_{1-4}$alkyl. R may be $C_{1-6}$alkyl optionally substituted with a 5- or 6-membered nonaromatic heterocyclyl, OH, —OC(O)—$R^a$, —N($R^b$)$_2$, —OC(O)—$R^c$, carboxyl, or a combination thereof, where R is 5-membered nonaromatic heterocyclyl, aryl substituted with —CH$_2$N($R^b$)$_2$, $C_{3-6}$cycloalkyl substituted with carboxyl, $C_{1-6}$alkoxy, unsubstituted $C_{1-6}$alkyl, or $C_{1-6}$alkyl substituted with one or more of N($R^b$)$_2$, carboxyl, carboxyl ester, —O$C_{1-6}$acyl, —NHC(O)(NH$_2$)$C_{1-6}$alkyl, or —(OCH$_2$CH$_2$)$_{1-8}$N($R^b$)$_2$. And, —OC(O)—$R^c$ is derived from an amino acid where the —OC(O)— moiety of —OC(O)—$R^c$ corresponds to an acid moiety on the amino acid and $R^c$ comprises —N($R^b$)$_2$ or a nitrogen-containing nonaromatic heterocyclyl. The amino acid may be a naturally occurring amino acid, and/or may be selected from glycine, valine, alanine, leucine, isoleucine, methionine, phenylalanine, tryptophan, tyrosine, serine, threonine, asparagine, glutamine, arginine, histidine, lysine, aspartic acid, glutamic acid, cysteine, or proline.

Alternatively, R may be $C_{1-6}$acyl moiety optionally substituted with —C(O)O—$C_{1-4}$alkyl, —C(O)O—$C_{1-4}$alkyl-N($R^b$)$_2$, N($R^b$)$_2$, —NHC(O)$C_{1-4}$alkyl, or a combination thereof. In some embodiments, R is 5- or 6-membered nonaromatic heterocyclyl moiety optionally substituted with hydroxyl, hydroxymethyl, or a combination thereof. But in other embodiments, R is —C(O)O—$C_{1-6}$alkyl optionally substituted with —OC(O)$C_{1-4}$alkyl or N($R^b$)$_2$, or R is —C(O)O—$C_{3-6}$cycloalkyl optionally substituted with $C_{1-4}$alkyl.

In certain embodiments, R is hydrogen and the salt is a hydrochloride, citrate, hemicitrate, hemitartrate, tartrate, benzene sulfonate, mesylate, sodium, hemisuccinate, or succinate salt. But in other embodiments, R is not a salt and/or the compound may be a prodrug of

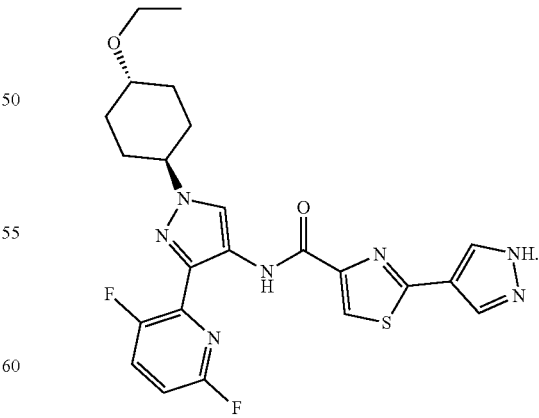

Also disclosed herein are embodiments of a composition comprising the compound and a pharmaceutically acceptable carrier. The composition may be a spray-dried composition comprising a carrier and a compound according to Formula I. However, with respect to the spray-dried composition, R may be H, aliphatic, acyl, heterocyclyl, carboxyl ester, amide, alkyl phosphoramidate, or alkyl phosphate, such as H, alkyl, acyl, carboxyl ester, amide, nonaromatic heterocyclyl, alkyl phosphoramidate, or alkyl phosphate. Typically the compound according to Formula I is not in the form of a salt when spray-dried. For example, suitable compounds for spray-dried formulations disclosed herein include compounds of Formula I wherein R is hydrogen, aliphatic, acyl, heterocyclyl, carboxyl ester or amide.

The carrier may be a polymer, for example, a cellulose derivative, vinyl polymer, lactide polymer, sugar, or a combination thereof. In some embodiments, the cellulose derivative is hydroxypropylmethylcellulose acetate succinate (HPMCAS), hydroxypropyl methylcellulose phthalate (HPMCP), hydroxypropyl methylcellulose (HPMC), or a combination thereof, the vinyl polymer is poly(vinylpyrrolidone) (PVP), poly(vinylpyrrolidone-co-vinyl acetate) (PVPVA), or a combination thereof, the lactide polymer is polylactide (PLA), polylactide-co-glycolide (PLGA), or a combination thereof, or the sugar is sucrose, trehalose, or a combination thereof. In certain embodiments, the carrier is hydroxypropylmethylcellulose acetate succinate, and may be an M grade and/or fine grade hydroxypropylmethylcellulose acetate succinate.

The composition may comprise an effective amount of the compound according to formula I, such as from 1% to 50% w/w with respect to the carrier, or from 10% to 35% w/w with respect to the carrier. Additionally, or alternatively, the spray-dried composition may further comprise a flavoring, a stabilizer, a filler, or a combination thereof. And in any embodiments, the composition is amorphous, and/or may have a glass transition temperature of from 100° C. to 120° C., such as from 105° C. to 110° C. or from 107° C. to 110° C.

In certain embodiments, the composition comprises 20% the disclosed compound(s) and 80% HPMCAS-MF.

Also disclosed herein are embodiments of a method for making a spray-dried composition. The method may comprise forming a mixture of the compound according to formula I, a carrier and a solvent, and spray-drying the mixture to form a spray dried formulation comprising the compound and the carrier.

Embodiments of a method for using the disclosed compounds and/or compositions comprising the compounds also are disclosed. The method may comprise administering the compound of a composition comprising the compound to a subject, such as administering an effective amount of the compound or the composition to a subject in need thereof. The method may be a method for treating a disease or condition for which an IRAK inhibitor is indicated. In some embodiments, the disease is an auto-immune disease, inflammatory disorder, cardiovascular disease, neurodegenerative disorder, allergic disorder, multi-organ failure, kidney disease, platelet aggregation, cancer, transplantation, sperm motility, erythrocyte deficiency, graft rejection, lung injury, respiratory disease, ischemic condition, bacterial infection, viral infection, immune regulatory disorder or a combination thereof.

The method may comprise administering a second therapeutic agent. The second therapeutic agent may be an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. In some embodiments, the second therapeutic agent is administered substantially simultaneously with the compound or composition. In other embodiments, the second therapeutic agent is administered sequentially in any order with the compound or composition, and the compound or composition and the second therapeutic agent may be administered such that an effective time period of the compound or composition overlaps with an effective time period of the second therapeutic agent.

Additionally, disclosed are embodiments of a method for inhibiting an IRAK protein, comprising contacting the IRAK protein with an effective amount of a disclosed compound or a composition comprising the compound. And in some embodiments, the IRAK protein is in a subject.

The foregoing and other objects, features, and advantages of the invention will become more apparent from the following detailed description, which proceeds with reference to the accompanying figures.

BRIEF DESCRIPTION OF THE DRAWINGS

FIG. 19 is a table of pharmacokinetic data for one embodiment of the disclosed spray-dried formulation and an organic solution/organic juice formulation.

DETAILED DESCRIPTION

I. Definitions

Figure 1:
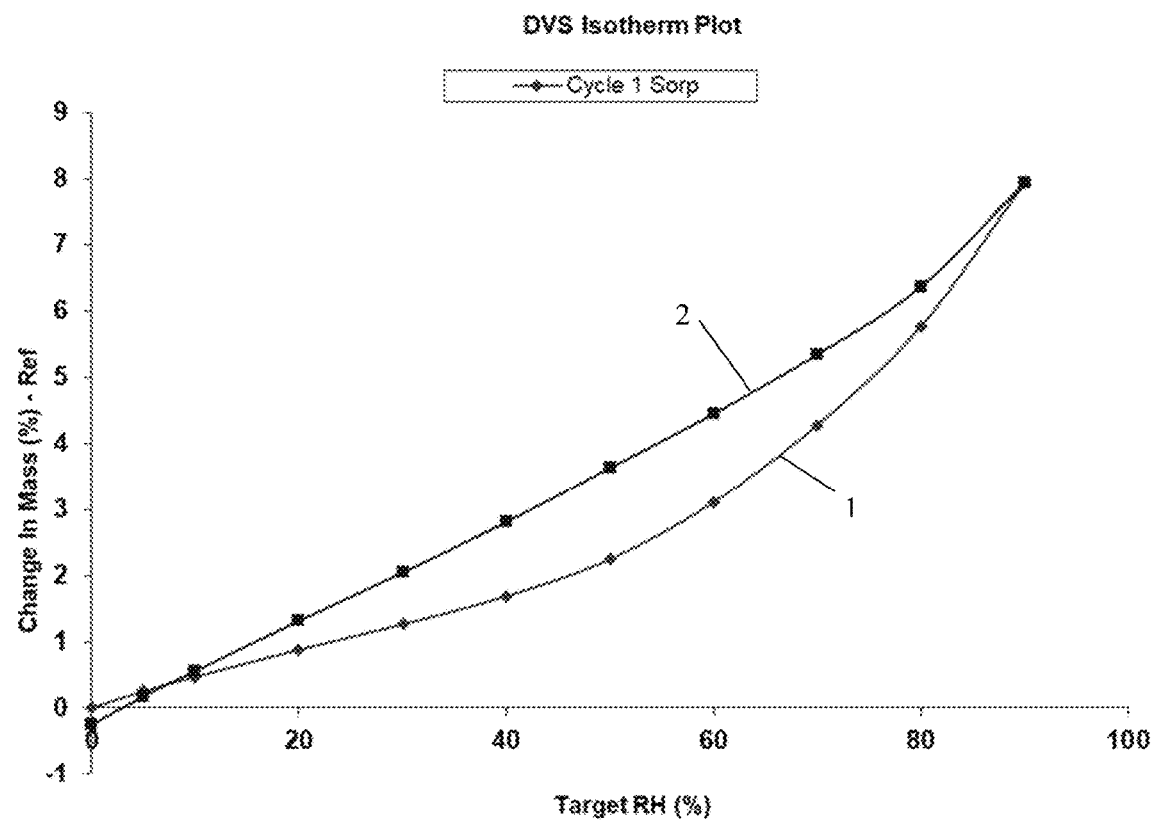
FIG. 1 is a dynamic vapor sorption (DVS) plot of percent change in mass versus target relative humidity (RH), illustrating the change in mass of one embodiment of the disclosed spray-dried formulation at 25° C. under various relative humidity conditions. The plot provides two isotherms: 1 is the sorption plot, illustrating the change in mass with increasing relative humidity steps; and 2 is the desorption plot, illustrating the change in mass with decreasing relative humidity steps.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

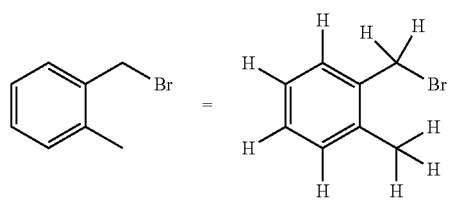

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

A person of ordinary skill in the art will appreciate that the definitions may be combined to further describe a particular compound. For example, hydroxyaliphatic refers to an aliphatic group substituted with an hydroxy (—OH) group, and haloalkylaryl refers to an aryl group substituted with an alkyl group, where the alkyl group too is substituted with a halogen, and where the point of attachment to the parent structure is via the aryl moiety since aryl is the base name of the substituent.

As used herein, the term "substituted" refers to all subsequent modifiers in a term, for example in the term "substituted aryl$C_{1-8}$alkyl," substitution may occur on the "$C_{1-8}$ alkyl" portion, the "aryl" portion or both portions of the aryl$C_{1-8}$alkyl group. Also by way of example, alkyl includes substituted cycloalkyl groups.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" substituent may be unsubstituted or substituted, but an "unsubstituted alkyl" may not be substituted.

"Substituents" or "substituent groups" for substituting for one or more hydrogen atoms on saturated carbon atoms in the specified group or moiety are, unless otherwise specified, —$R^{60}$, halo, =O, —$OR^{70}$, —$SR^{70}$, —$N(R^{80})_2$, haloalkyl, perhaloalkyl, —CN, —$NO_2$, =$N_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$P(O)(O^-)_2(M^+)_2$, —$P(O)(O^-)_2M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)N(R^{80})_2$, —$C(NR^{70})(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$ is $C_{1-6}$alkyl optionally substituted with 1, 2, or 3 OH; each $R^{70}$ is independently for each occurrence hydrogen or $R^{60}$; each $R^{80}$ is independently for each occurrence $R^{70}$ or alternatively, two $R^{80}$ groups, taken together with the nitrogen atom to which they are bonded, form a 3- to 7-membered nonaromatic heterocyclyl which optionally includes from 1 to 4 of the same or different additional heteroatoms selected from O, N and S, of which N optionally has H or $C_1$-$C_3$alkyl substitution; and each $M^+$ is a counter ion with a net single positive charge. Each $M^+$ is independently for each occurrence, for example, an alkali metal ion, such as $K^+$, $Na^+$, $Li^+$; an ammonium ion, such as $^+NH_4$ or $^+N(R^{60})_4$; a protonated amino acid ion, such as a naturally occurring amino acid counter ion, such as a lysine ion (for example, L-lysine ion), or an arginine ion, such as an L-arginine ion; an amino sugar, such as meglumine; or an alkaline metal earth ion, such as $[Ca^{2+}]_{0.5}$, $[Mg^{2+}]_{0.5}$, or $[Ba^{2+}]_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —$N(R^{80})_2$ includes —$NH_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon can be replaced with =O, =$NR^{70}$, =N—$OR^{70}$, =$N_2$ or =S.

Substituent groups for replacing hydrogen atoms on unsaturated carbon atoms in groups containing unsaturated carbons are, unless otherwise specified, —$R^{60}$, halo, —$O^-M^+$, —$OR^{70}$, —$SR^{70}$, —$S^-M^+$, —$N(R^{80})_2$, perhaloalkyl, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$PO_3^{-2}M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})N(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{70})_2$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

Substituent groups for replacing hydrogen atoms on nitrogen atoms in groups containing such nitrogen atoms are, unless otherwise specified, —$R^{60}$, —$O^-M^+$, —$OR^{70}$, —$SR^{70}$, —$S^-M^+$, —$N(R^{80})_2$, perhaloalkyl, —CN, —NO, —$NO_2$, —$S(O)_2R^{70}$, —$SO_3^-M^+$, —$SO_3R^{70}$, —$OS(O)_2R^{70}$, —$OSO_3^-M^+$, —$OSO_3R^{70}$, —$PO_3^{2-}(M^+)_2$, —$PO_3^{2-}M^{2+}$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2R^{70}$, —$OC(S)OR^{70}$, —$NR^{70}C(O)R^{70}$, —$NR^{70}C(S)R^{70}$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined.

In one embodiment, a group that is substituted has 1 substituent, 2 substituents, substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

"Acyl" refers to the group —C(O)R, where R is H, aliphatic, heteroaliphatic, heterocyclic or aryl. Exemplary acyl moieties include, but are not limited to, —C(O)H, —C(O)alkyl, —C(O)$C_1$-$C_6$alkyl, —C(O)$C_1$-$C_6$haloalkyl-C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety, including alkyl, alkenyl, alkynyl groups, cyclic versions thereof, such as cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms, and a cyclic aliphatic contains from three to twenty-five carbon atoms; for example, from three to fifteen, from three to ten, from three to six, or from three to four carbon atoms.

"Alkyl" refers to a saturated aliphatic hydrocarbyl group having from 1 to 25 carbon atoms, typically 1 to 10 carbon atoms such as 1 to 6 carbon atoms ($C_{1-6}$alkyl) or 1 to 4 carbon atoms, ($C_{1-4}$alkyl). An alkyl moiety may be substituted or unsubstituted. This term includes, by way of example, linear and branched hydrocarbyl groups such as methyl ($CH_3$), ethyl (—$CH_2CH_3$), n-propyl (—$CH_2CH_2CH_3$), isopropyl (—$CH(CH_3)_2$), n-butyl (—CH₂CH₂CH₂CH₃), isobutyl (—CH₂CH₂(CH₃)₂), sec-butyl (—CH(CH₃)(CH₂CH₃), t-butyl (—C(CH₃)₃), n-pentyl (—CH₂CH₂CH₂CH₂CH₃), and neopentyl (—CH₂C(CH₃)₃).

"Alkoxy" refers to the group —O-alkyl.

"Amino" refers to the group —NH₂, —NHR, or —NRR, where each R independently is selected from H, aliphatic, aryl or heterocyclic, or two R groups together with the nitrogen attached thereto form a heterocyclic ring. Examples of such heterocyclic rings include those wherein two R groups together with the nitrogen to which they are attached form a —(CH₂)₂₋₅-ring optionally interrupted by one or two heteroatom groups, such as —O— or —N(R^g) such as in the groups

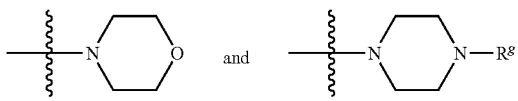

wherein R^g is R⁷⁰, —C(O)R⁷⁰, —C(O)OR⁶⁰ or —C(O)N(R⁸⁰)₂.

"Amide" refers to the group —N(H)acyl, or —C(O)amino.

"Araliphatic" refers to an aryl group attached to the parent via an aliphatic moiety. Araliphatic includes aralkyl or arylalkyl groups such as benzyl and phenylethyl.

"Aryl" refers to an aromatic group of, unless specified otherwise, from 5 to 15 ring atoms having a single ring (e.g., phenyl) or multiple fused rings in which at least one ring is aromatic (e.g., naphthyl). For groups having multiple rings, at least one of which is aromatic and one is not, such groups are nevertheless referred to as "aryl" provided that the point of attachment to the remainder of the compound is through an atom of an aromatic portion of the aryl group. Aryl groups may be monocyclic, bicyclic, tricyclic or tetracyclic. Unless otherwise stated, an aryl group may be substituted or unsubstituted.

"Carboxyl," "carboxy" or "carboxylate" refers to —CO₂H, —C(O)O⁻ or salts thereof.

Combination: A combination includes two or more components that are administered such that the effective time period of at least one component overlaps with the effective time period of at least one other component. A combination, or a component thereof, may be a composition. In some embodiments, effective time periods of all components administered overlap with each other. In an exemplary embodiment of a combination comprising three components, the effective time period of the first component administered may overlap with the effective time periods of the second and third components, but the effective time periods of the second and third components independently may or may not overlap with one another. In another exemplary embodiment of a combination comprising three components, the effective time period of the first component administered overlaps with the effective time period of the second component, but not that of the third component; and the effective time period of the second component overlaps with those of the first and third components. A combination may be a composition comprising the components, a composition comprising one or more components and another separate component (or components) or composition(s) comprising the remaining component(s), or the combination may be two or more individual components. In some embodiments, the two or more components may comprise the same component administered at two or more different times, two or more different components administered substantially simultaneously or sequentially in any order, or a combination thereof.

"Carboxyl ester" or "carboxy ester" refers to the group —C(O)OR, where R is aliphatic, heteroaliphatic, and heterocyclic, including aryl and heteroaryl.

"Cycloaliphatic" refers to a cyclic aliphatic group having a single ring (e.g., cyclohexyl), or multiple rings, such as in a fused, bridged or spirocyclic system, at least one of which is aliphatic, provided that the point of attachment is through an atom of an aliphatic region of the cycloaliphatic group. Cycloaliphatic includes saturated and unsaturated systems, including cycloalkyl, cycloalkenyl and cycloalkynyl. Exemplary cycloaliphatic groups include, but are not limited to, cyclopropyl, cyclobutyl, cyclopentyl, cyclohexyl, cycloheptyl, cyclopentenyl, or cyclohexenyl.

"Heteroaliphatic" refers to an aliphatic compound or group having at least one heteroatom and at least one carbon atom, i.e., one or more carbon atoms from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heterocyclyl," and "heterocycle" refer to aromatic and non-aromatic ring systems, and more specifically refer to a stable three- to fifteen-membered ring moiety comprising carbon atoms and at least one, such as from one to five heteroatoms. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and the nitrogen, phosphorus, carbon, silicon or sulfur atoms in the heterocyclyl moiety can be optionally oxidized to various oxidation states. For convenience, nitrogens, particularly but not exclusively, those defined as annular aromatic nitrogens, are meant to include their corresponding N-oxide form, although not explicitly defined as such in a particular example. In addition, annular nitrogen atoms can be optionally quaternized. Heterocycle includes heteroaryl or aromatic heterocyclyl moieties, and nonaromatic heterocyclyl moieties, which are heterocyclyl rings which are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Pharmaceutically acceptable excipient" refers to a substance, other than the active ingredient or prodrug thereof, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as freund's complete adjuvant or freund's incomplete adjuvant.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, tris(hydroxymethyl)aminomethane (tris) and the like; and when the molecule contains a basic functionality, salts of organic or inorganic acids, such as hydrochloride, hydrobromide, tartrate, mesylate, benzene sulfonate, tosylate, succinate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid, gentisic acid, and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine (for example, L-lysine), arginine (for example, L-arginine), histidine, caffeine, procaine, hydrabamine, choline, betaine, ethylenediamine, glucosamine, meglumine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the compound is in the form of a benzene sulfonate, hydrochloride, sodium, succinate, tris, mesylate, or tartrate salt.

"Phosphate" refers to the group —O—P(O)(OR')$_2$, where each —OR' independently is —OH, —O-aliphatic, such as —O-alkyl, —O-aryl, or —O-aralkyl, or —OR' is —O$^-$M$^+$, where M$^+$ is a counter ion with a single positive charge as disclosed herein. For example, each M$^+$ may be an alkali ion, such as K$^+$, Na$^+$, Li$^+$; an ammonium ion, such as $^+$N(R")$_4$ where each R" independently is H, aliphatic, such as alkyl, hydroxyalkyl, or a combination thereof, heterocyclyl, or aryl; an amino acid, such as arginine or lysine; an amino sugar, such as meglumine; or an alkaline earth ion, such as [Ca$^{2+}$]$_{0.5}$, [Mg$^{2+}$]$_{0.5}$, or [Ba$^{2+}$]$_{0.5}$. Alkyl phosphate refers to the group -alkyl-phosphate, such as, —CH$_2$—P(O)(OR')$_2$ or —CH$_2$(CH$_3$)O—P(O)(OR')$_2$ for example, —CH$_2$OP(O)(O-isopropyl)$_2$, —CH$_2$OP(O)(OH)(O-tert-butyl), —CH$_2$OP(O)(O-tert-butyl)$_2$, —CH$_2$OP(O)(OCH$_2$OCO$_2$isopropyl)$_2$, —CH$_2$P(O)(OH)$_2$, or a salt thereof, such as —CH$_2$OP(O)(O$^-$Na$^+$)$_2$, —CH$_2$OP(O)(O$^-$)$_2$Mg$^{2+}$, or —CH$_2$OP(O)(OH)(O$^-$Na$^+$)

"Phosphoramidate" refers to the group —O—P(O)(OR')(N(R')$_2$), where each R' independently is H, aliphatic, such as alkyl, aryl, or aralkyl, or —OR' is —O$^-$M$^+$, and where M$^+$ is a counter ion with a single positive charge, as disclosed herein. For example, each M$^+$ may be an alkali ion, such as K$^+$, Na$^+$, Li$^+$; an ammonium ion, such as $^+$N(R")$_4$ where each R" independently is H, aliphatic, such as alkyl, hydroxyalkyl, or a combination thereof, heterocyclyl, or aryl; an amino acid, such as arginine or lysine; an amino sugar, such as meglumine; or an alkaline earth ion, such as [Ca$^{2+}$]$_{0.5}$, [Mg$^{2+}$]$_{0.5}$, or [Ba$^{2+}$]$_{0.5}$. Alkyl phosphoramidate refers to the group -alkyl-phosphoramidate, such as, for example, —CH$_2$O—P(O)(OR')(N(R'$_2$)) or —CH$_2$(CH$_3$)O—P(O)(OR')(N(R'$_2$)), such as, —CH$_2$OP(O)(O-phenyl)[NHC(CH$_3$)CO$_2$isopropyl], or —CH$_2$OP(O)(OH)(N(H)alkyl), or a salt thereof, such as —CH$_2$OP(O)(O$^-$Na$^+$)(N(H)alkyl).

"Pharmaceutically acceptable carrier" refers to an excipient that is a carrier or vehicle, such as a suspension aid, solubilizing aid, or aerosolization aid. Pharmaceutically acceptable carriers are conventional. *Remington: The Sci-*

*ence and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Effective amount" with respect to a compound or composition refer to an amount of the compound or composition sufficient to achieve a particular desired result, such as to inhibit a protein or enzyme, particularly an interleukin-1 receptor-associated kinase; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the age of the patient to be treated, and the like.

"Prodrug" refers to compounds that are transformed in vivo to yield a biologically active compound, particularly the parent compound, for example, by hydrolysis in the gut or enzymatic conversion. Typically, a prodrug compound of a compound has less activity against a desired biological target that the parent compound. A prodrug negligible or less activity with respect to a desired target until it is metabolized to the active form. Common examples of prodrug moieties include, but are not limited to, ester, amide, carbamate, and urea forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$(CH_2)_n$—O—P(O)(OR')$_2$, wherein n is 1 or 2 and R' is H or $C_{1-6}$alkyl, such as —$CH_2$—O—P(O)(OR')$_2$ wherein each R' is independently H or $C_{1-6}$alkyl, when at least one R' is H, the phosphate moiety can be in the form of a salt, such as a mono or dianion salt with an organic or inorganic cationic counter ion. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between one and six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Spray-dried dispersion" refers to a single-phase dispersion of a compound or compounds in a polymer matrix. Typically, the compound or compounds are amorphous.

"Subject" refers to humans and non-human subjects.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substituents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diastereomers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as the pyrazole and pyridinyl rings, atropisomers are also possible and are also specifically included in the compounds of the invention.

Particular examples of the presently disclosed compounds include one or more asymmetric centers; thus these compounds can exist in different stereoisomeric forms. Accordingly, compounds and compositions may be provided as individual pure enantiomers or diastereomers, or as stereoisomeric mixtures, including racemic mixtures. In certain embodiments the compounds disclosed herein are synthesized in or are purified to be in substantially enantiopure form, such as in at least 90% enantiomeric excess, 95% enantiomeric excess, 97% enantiomeric excess, 98% enantiomeric excess, 99% enantiomeric excess, 99.5% enantiomeric excess, or greater than 99.5% enantiomeric excess, such as in enantiopure form.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium.

II. Compounds

Disclosed herein are pyrazole compounds, methods of making the compounds, and methods of using the compounds. In one embodiment, the disclosed compounds are tyrosine kinase inhibitors and/or may be useful in blocking one or more cytokine signaling pathways, such as the IL-17 signaling pathway. For certain embodiments, the pyrazole compounds are useful for treating conditions in which inhibition of an interleukin-1 receptor-associated kinase (IRAK) pathway is therapeutically useful. In some embodiments, the compounds inhibit an IRAK protein, such as IRAK1, IRAK2, IRAK3 or IRAK4. In other embodiments, the compounds are useful for delivering an IRAK inhibitor compound, and/or may be a prodrug of an IRAK inhibitor. In certain embodiments, the pyrazole compound is a prodrug of

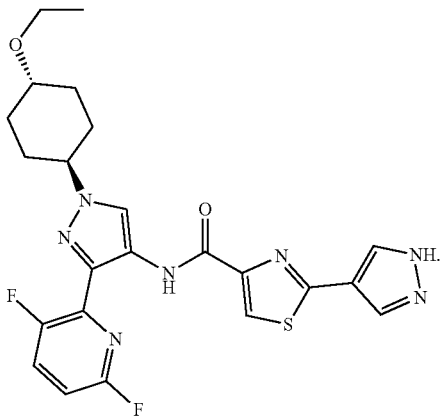 [SMILES: CCO[C@H]1CC[C@H](n2cc(NC(=O)c3csc(-c4cn[nH]c4)n3)c(-c3nc(F)ccc3F)n2)CC1]

In some embodiments, the pyrazole compound has a general formula I

Formula I

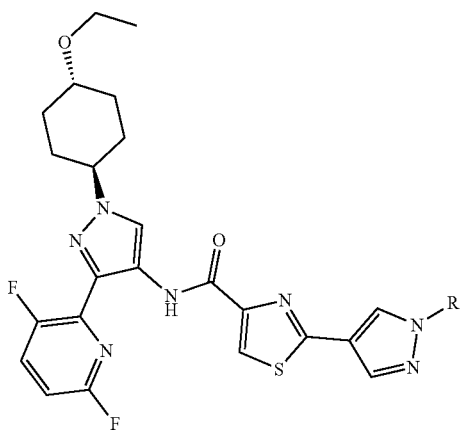

With respect to formula I, R is H, aliphatic, acyl, heterocyclyl, carboxyl ester, amide, alkyl phosphoramidate, or alkyl phosphate. A person of ordinary skill in the art understands that Formula I also includes solvates, co-crystals, salts, and/or N-oxides of the compounds, as well as free base compounds. In some embodiments, R is not H, or alternatively, R is hydrogen. When R is hydrogen the compound may be a free base or in the form of a salt. In other embodiments, R is alkyl, acyl, carboxyl ester, amide, non-aromatic heterocyclyl, alkyl phosphoramidate, or alkyl phosphate. A person of ordinary skill in the art understands that compounds where R is not H may act a prodrug of the compound where R is H, for example, when administered to a subject.

In one aspect, the compound of Formula I is in the form of a co-crystal. Examples of co-crystals include, but are not limited to, a succinate co-crystal, a phosphate co-crystal, a gentisate co-crystal, or a tartrate co-crystal.

In some embodiments, R is H, $C_{1-4}$alkyl phosphate, $C_{1-4}$alkyl phosphoramidate, $C_{1-6}$alkyl, $C_{1-6}$acyl, —C(O)O—$C_{1-6}$aliphatic, —C(O)N(R$^b$)$_2$, or 5- or 6-membered nonaromatic heterocyclyl, but in certain embodiments, R is not H, or R is H and the compound is a salt.

With respect to the R moiety, the $C_{1-6}$alkyl moiety may be unsubstituted, or it may be substituted, such as with a 5- or 6-membered nonaromatic heterocyclyl, OH, —OC(O)—R$^a$, —N(R$^b$)$_2$, —OC(O)—R$^c$, carboxyl, or a combination thereof, the $C_{1-6}$acyl moiety may be unsubstituted or it may be substituted with —C(O)O—$C_{1-4}$alkyl, —C(O)O—$C_{1-4}$alkyl-N(R$^b$)$_2$, N(R$^b$)$_2$, —NHC(O)$C_{1-4}$alkyl, or a combination thereof, the 5- or 6-membered heterocyclyl moiety may be a 5- or 6-membered oxygen-containing heterocyclyl, and/or may be substituted with hydroxyl, hydroxymethyl, or a combination thereof, or the —C(O)O—$C_{1-6}$aliphatic may be —C(O)O—$C_{1-6}$alkyl optionally substituted with —OC(O)$C_{1-4}$alkyl, or N(R$^b$)$_2$, or the —C(O)O—$C_{1-6}$aliphatic may be —C(O)O—$C_{3-6}$cycloalkyl optionally substituted with $C_{1-4}$alkyl.

In any embodiments, each R$^a$ independently is 5-membered nonaromatic heterocyclyl, aryl substituted with —CH$_2$N(R$^b$)$_2$, $C_{3-6}$cycloalkyl substituted with carboxyl, $C_{1-6}$alkoxy, unsubstituted $C_{1-6}$alkyl, or $C_{1-6}$alkyl substituted with one or more, such as 1, 2 or 3, of N(R$^b$)$_2$, carboxyl, carboxyl ester, —OC$_{1-6}$acyl, —NHC(O)(NH$_2$)C$_{1-6}$alkyl, or —(OCH$_2$CH$_2$)$_{1-8}$N(R$^b$)$_2$;

each R$^b$ independently is H, unsubstituted $C_{1-6}$alkyl, $C_{1-6}$alkyl substituted with —N(R$^g$)$_2$, carboxyl ester, or 5- or 6-membered nonaromatic heterocyclyl, or two R$^b$ together with the nitrogen to which they are attached form a $C_{3-6}$nonaromatic heterocyclyl moiety optionally interrupted with one or two —O— or —N(R$^g$), where R$^g$ is H or $C_{1-4}$alkyl; and —OC(O)—R$^c$ is derived from an amino acid where the —OC(O)— moiety of —OC(O)—R$^c$ corresponds to an acid moiety on the amino acid, and R$^c$ comprises —N(R$^b$)$_2$ or a nitrogen-containing nonaromatic heterocyclyl, such as a 5- or 6-membered unsaturated nitrogen-containing heterocyclyl, for example, pyrrolidinyl. The amino acid can be any amino acid, such as a naturally occurring amino acid, and may be an amino acid selected from glycine, valine, alanine, leucine, isoleucine, methionine, phenylalanine, tryptophan, tyrosine, serine, threonine, asparagine, glutamine, arginine, histidine, lysine, aspartic acid, glutamic acid, cysteine, or proline. A person of ordinary skill in the art will understand that where the amino acid comprises one or more chiral center, all enantiomers, diastereomers and/or mixtures thereof are contemplated. For example, the amino acid may be the L-amino acid, the D-amino acid or a mixture thereof.

In some embodiments, the amino acid is the L-amino acid. And in certain embodiments, —OC(O)—R$^c$ is —OC(O)CH(NH$_2$)R$^d$,

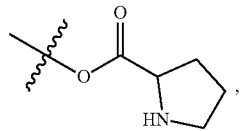 [SMILES: *OC(=O)C1CCCN1]

or —OC(O)—(CH$_2$)$_{1-2}$C(NH$_2$)CO$_2$H, where R$^d$ is an amino acid side chain, and/or may be H, —CH$_3$, isopropyl, —CH$_2$CH(CH$_3$)$_2$, —CH(CH$_3$)Et, —CH$_2$CH$_2$SCH$_3$,

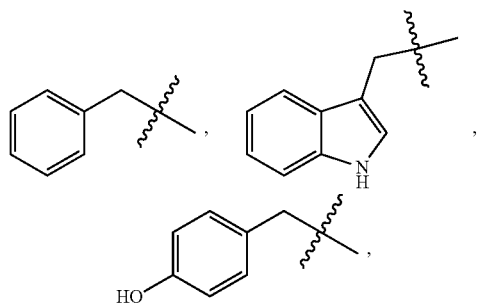

—CH$_2$OH, —CH(OH)CH$_3$, —CH$_2$C(O)NH$_2$, —CH$_2$CH$_2$C(O)NH$_2$, —CH$_2$SH, —CH$_2$CH$_2$CH$_2$NHC(O)(NH)NH$_2$,

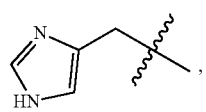 [SMILES: *Cc1c[nH]cn1]

—CH$_2$CH$_2$CH$_2$CH$_2$NH$_2$, —CH$_2$CO$_2$H, or CH$_2$CH$_2$CO$_2$H.

In any embodiments, the compound may be a salt, such as a pharmaceutically acceptable salt as defined herein, and in some embodiments, the salt is a hydrochloride, citrate, hemicitrate, hemitartrate, tartrate, benzene sulfonate, mesylate, sodium, hemisuccinate, or succinate salt.

Some exemplary compounds according to formula I include:

I-1

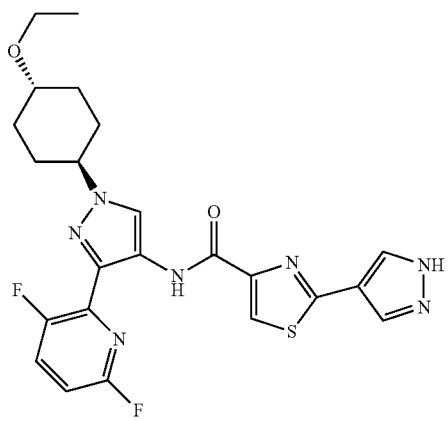

I-2

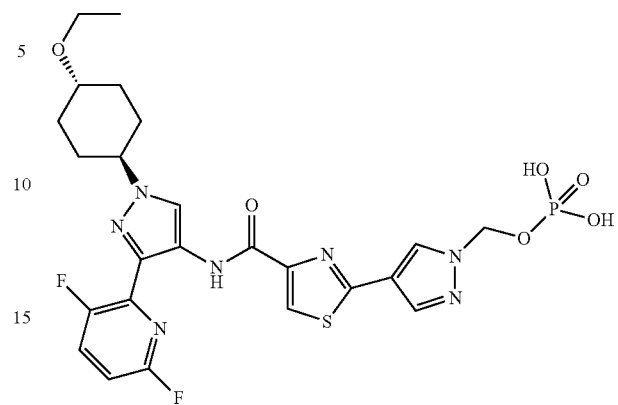

I-3

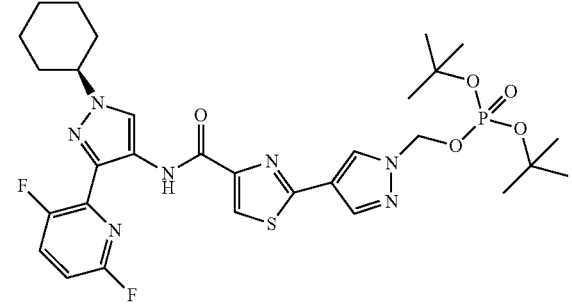

I-4

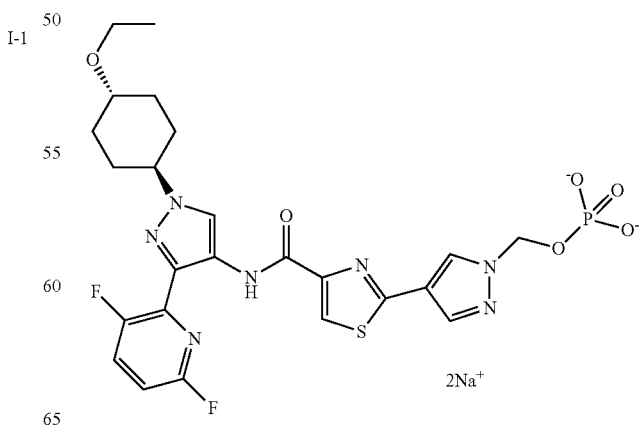

I-5
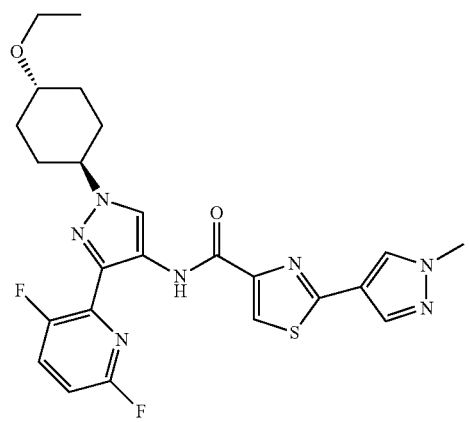
I-6
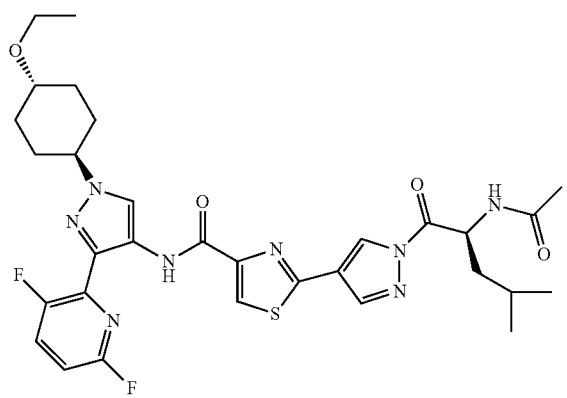
I-7
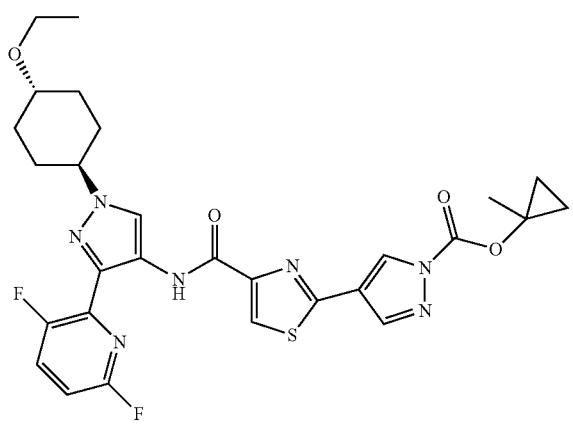
I-8
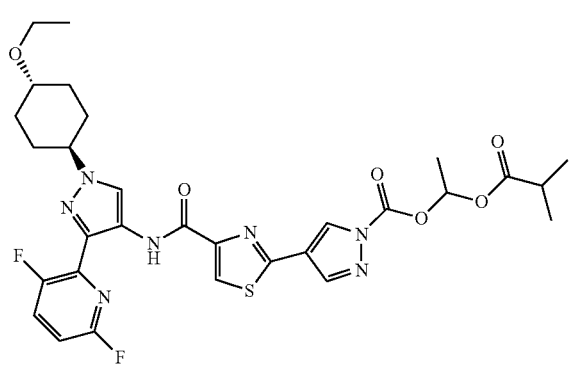
I-9
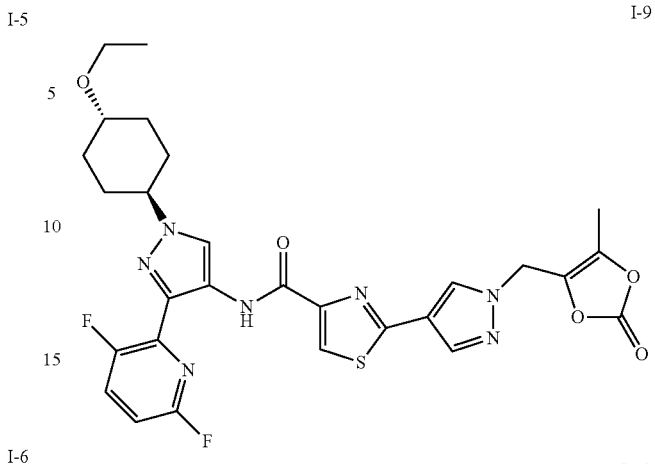
I-10
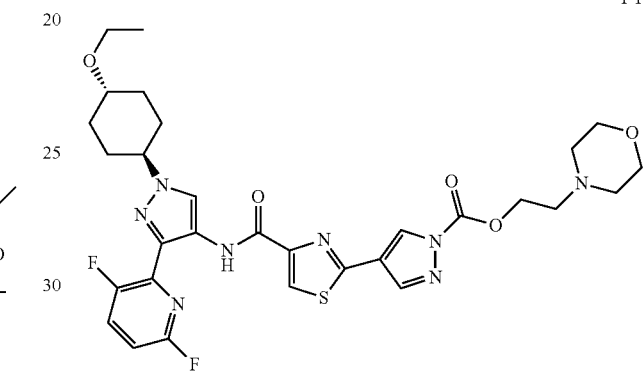
I-11
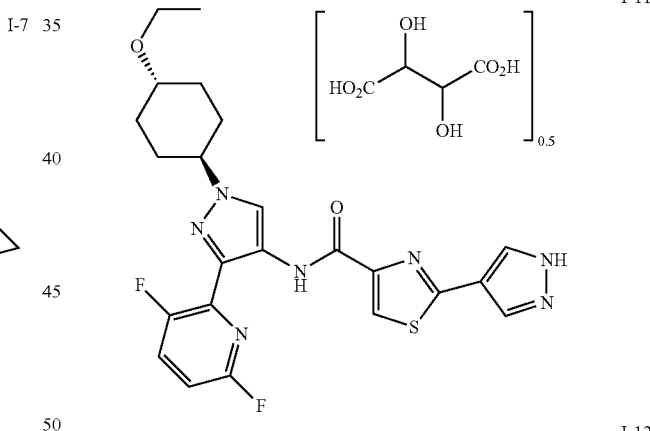
I-12
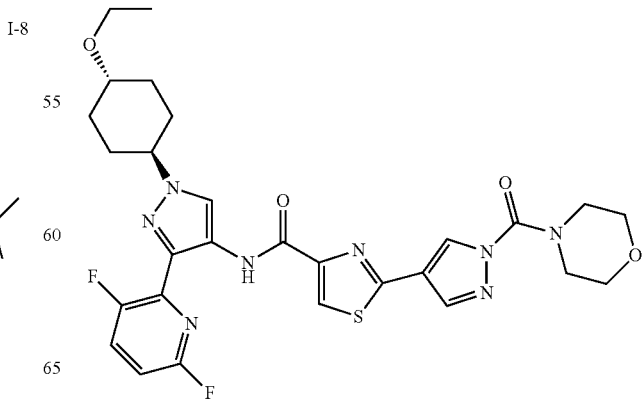

I-13
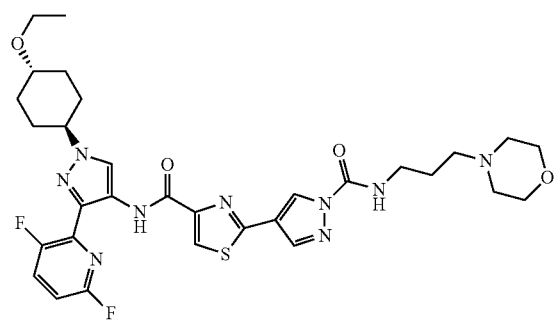
I-17
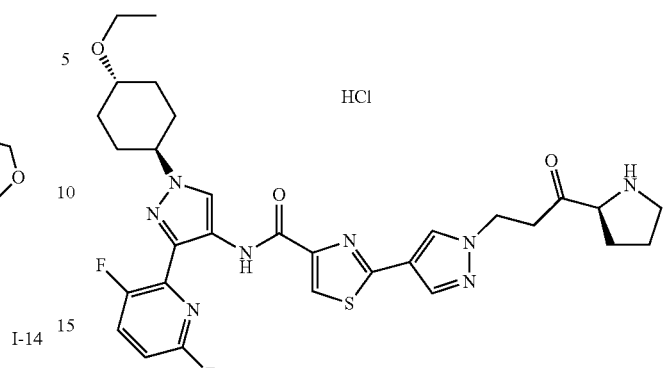
I-14
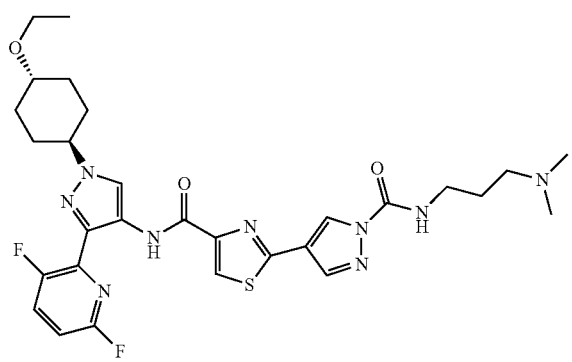
I-18
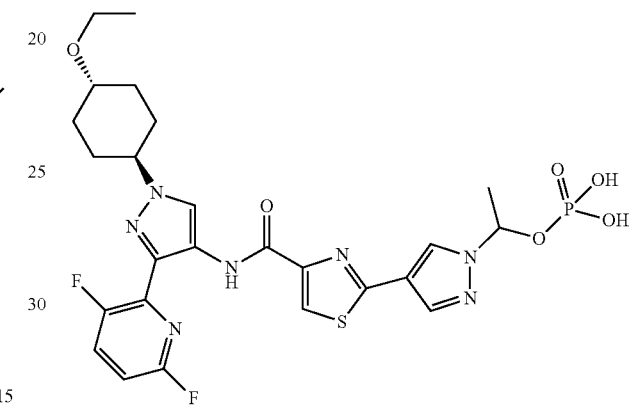
I-15
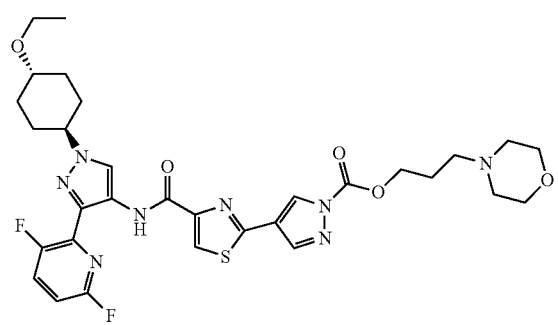
I-19
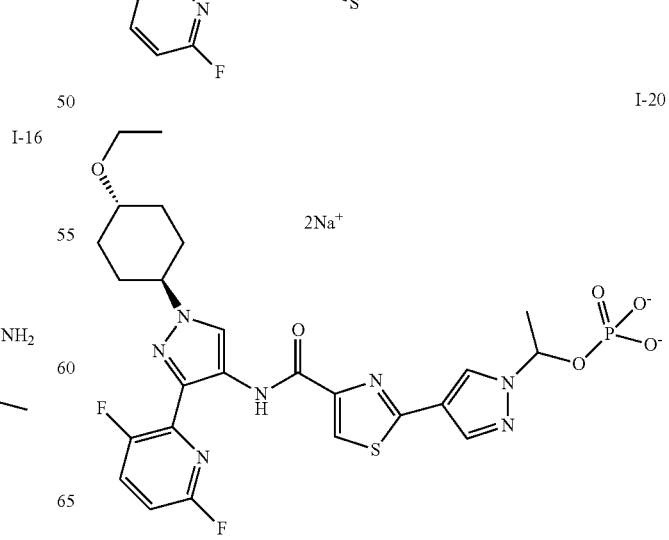
I-16
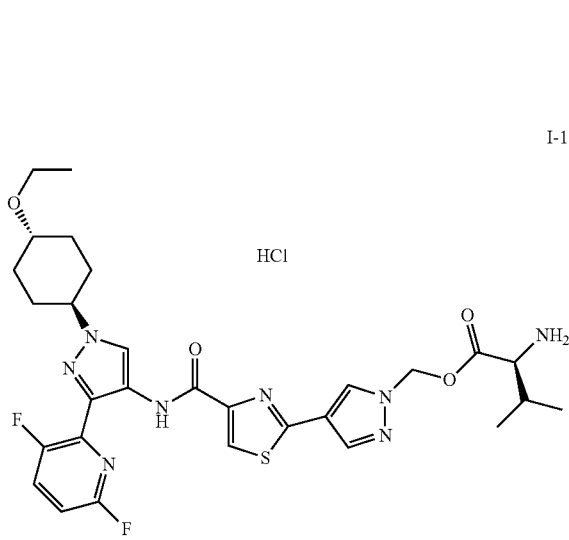
I-20

-continued
I-21
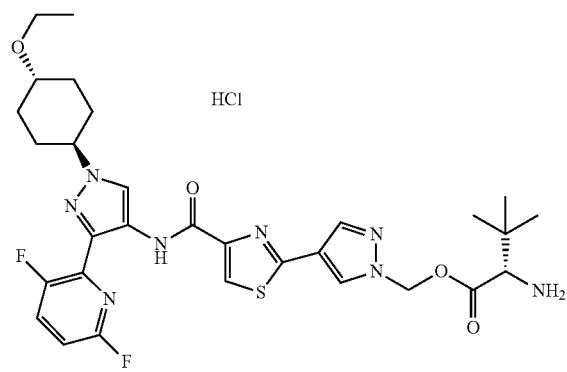
I-25
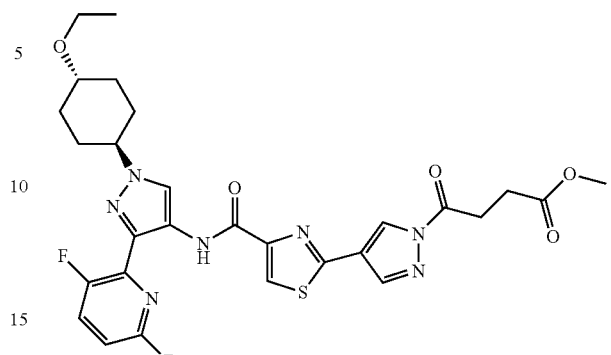
I-22
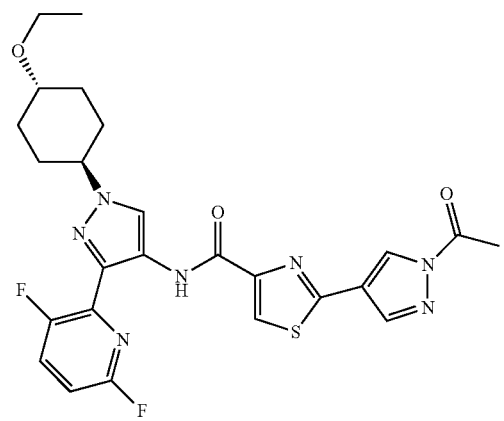
I-26
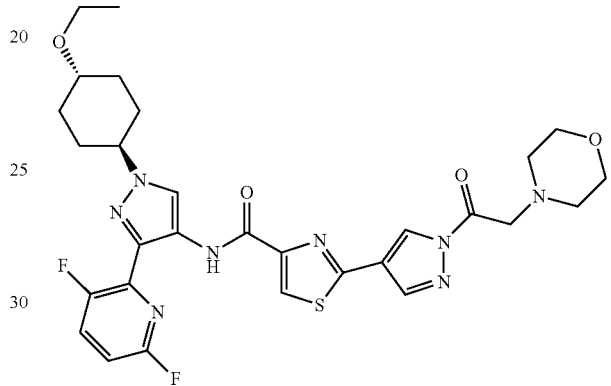
I-23
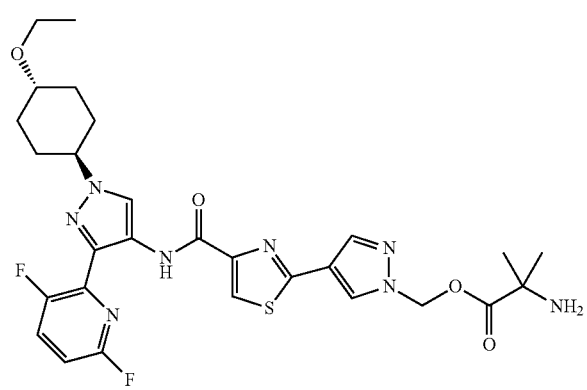
I-27
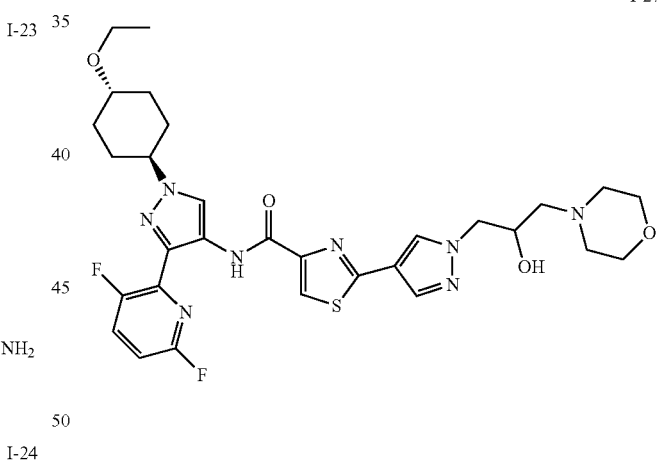
I-24
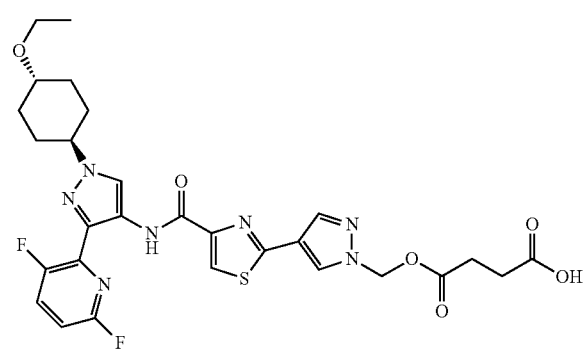
I-28
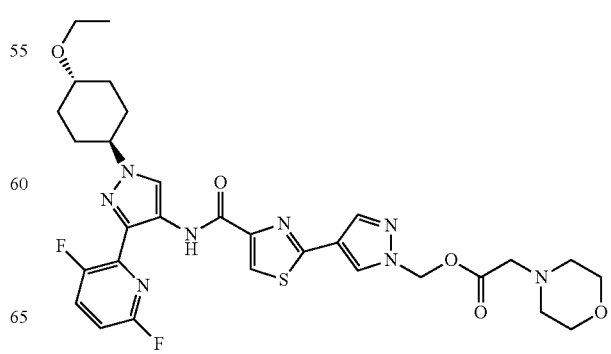

I-29
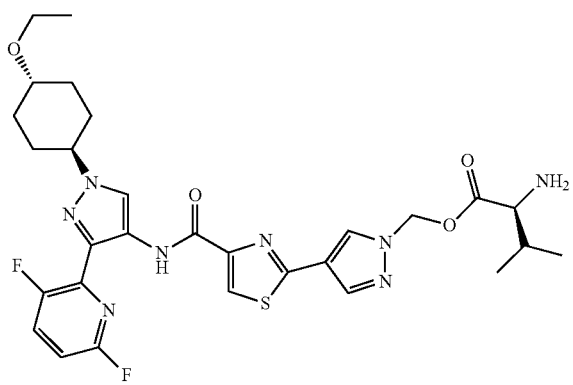
I-32
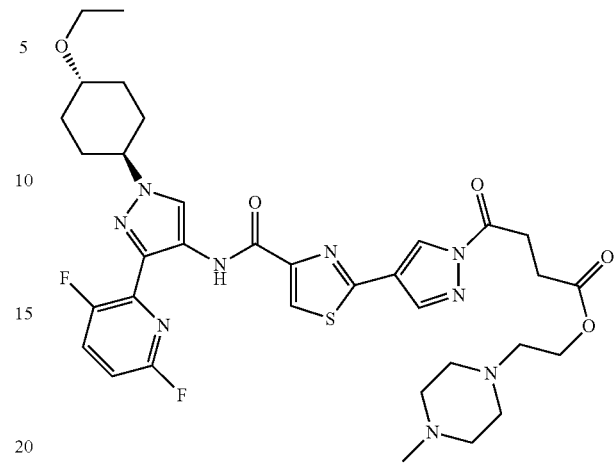
I-30
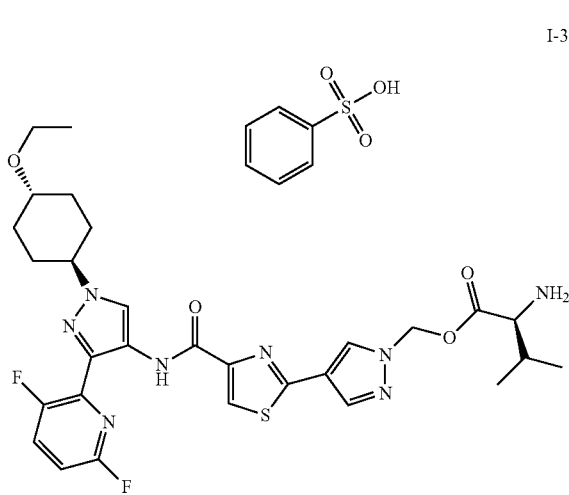
I-33
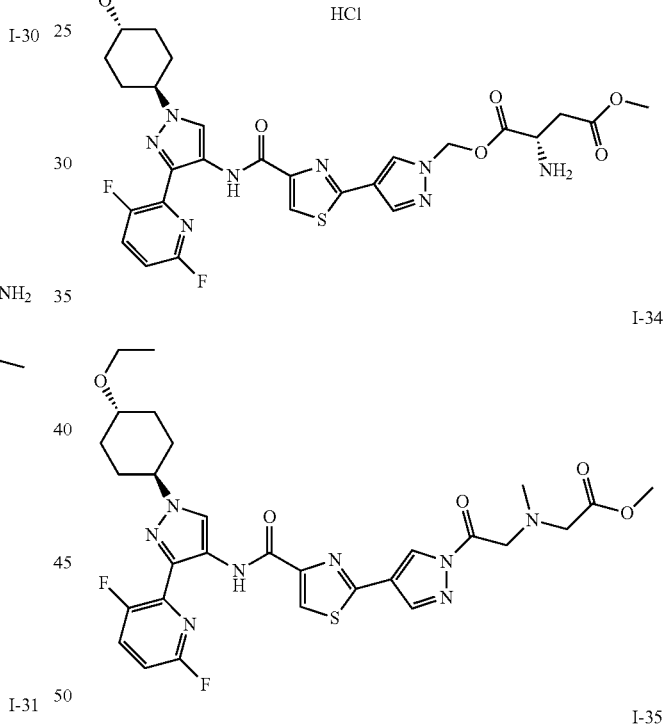
I-31
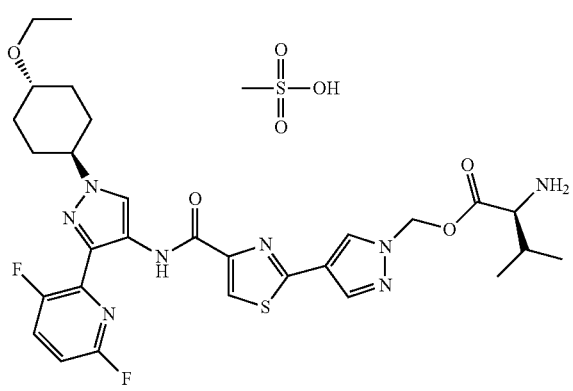
I-35
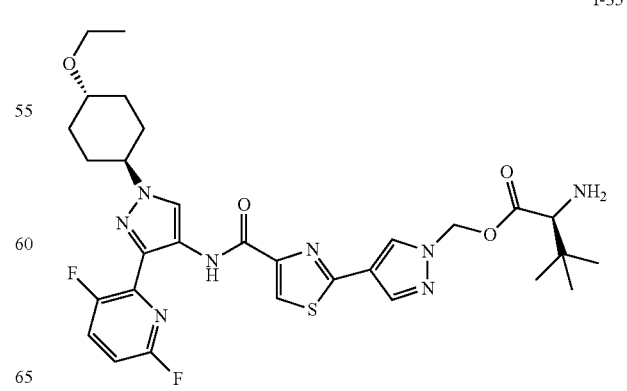

I-36
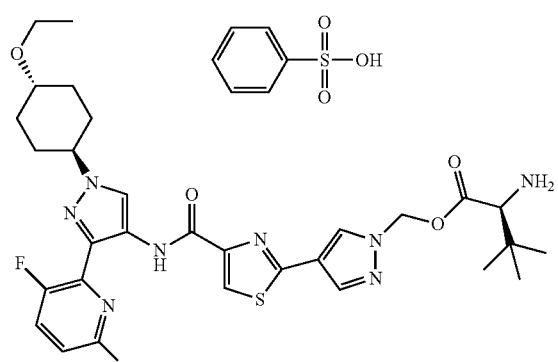
I-40
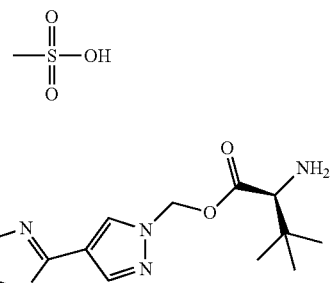
I-37
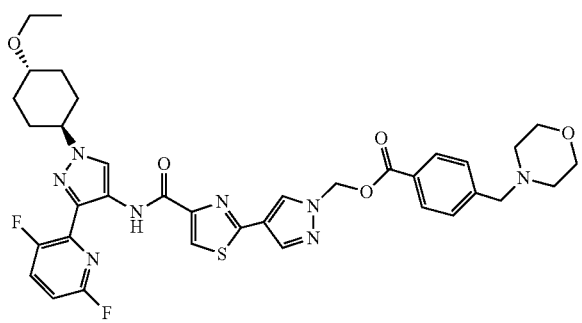
I-41
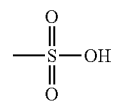
I-38
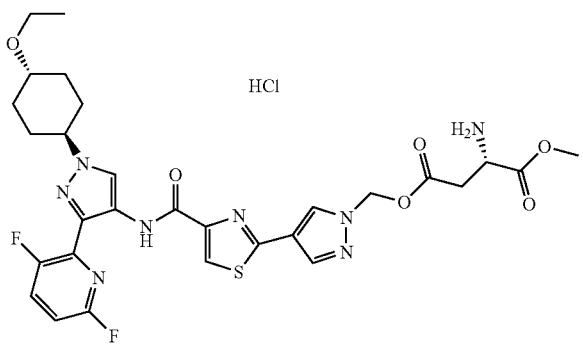
I-42
I-39
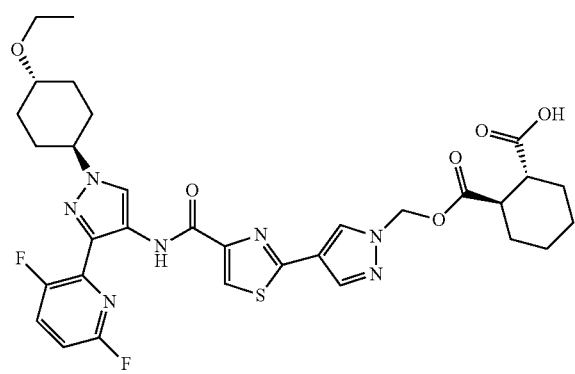
I-43
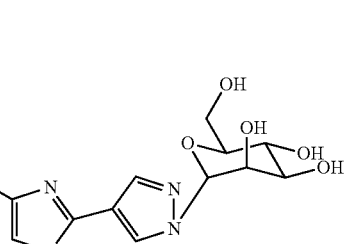

I-44
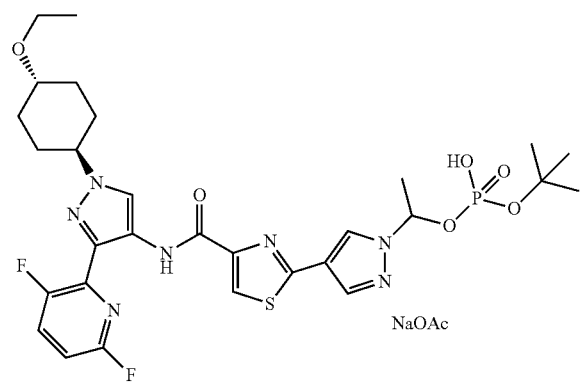
I-45
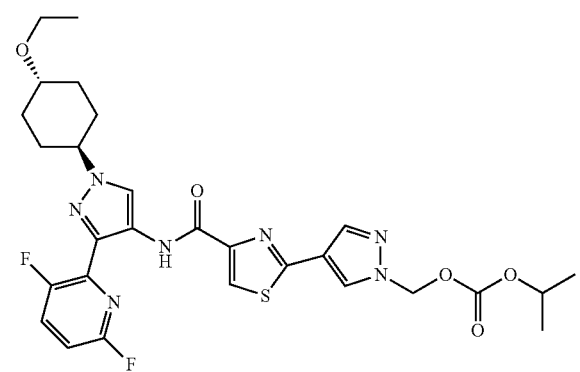
I-46
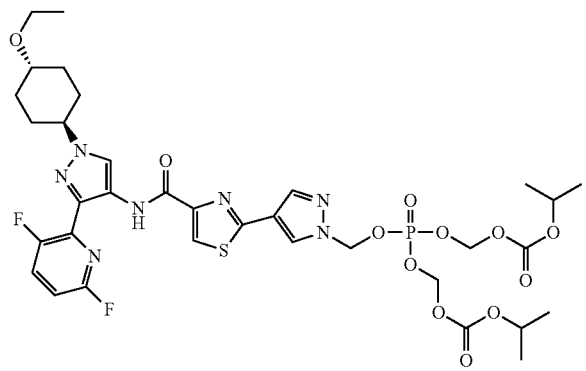
I-47
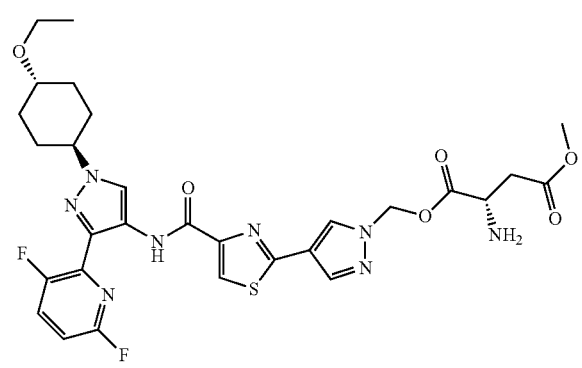
I-48
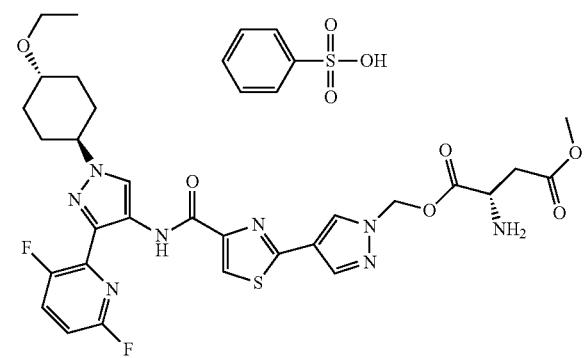
I-49
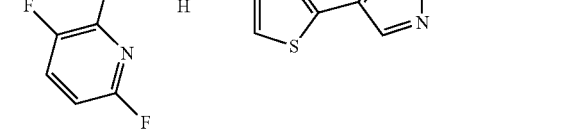
I-50
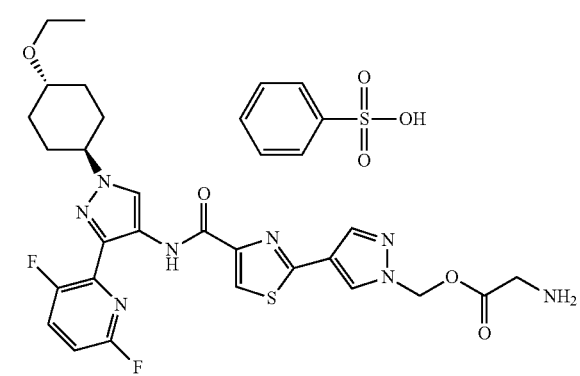

I-51
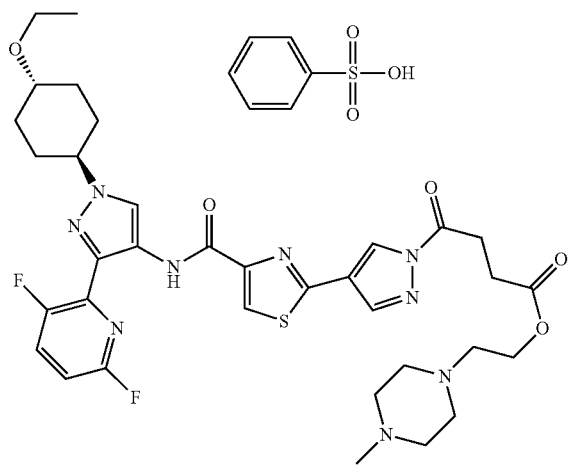
I-54
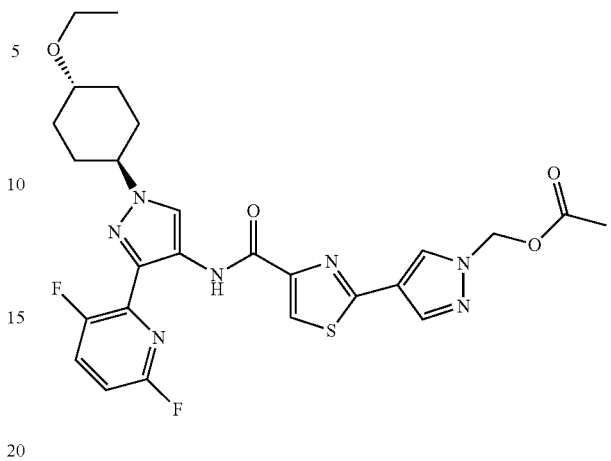
I-52
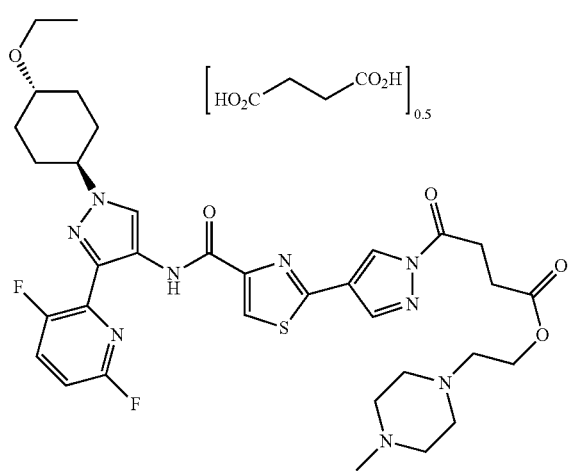
I-55
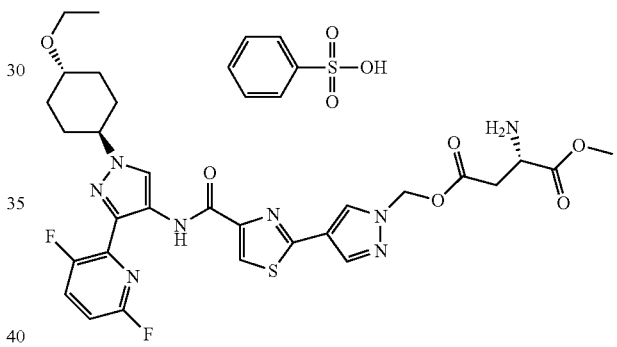
I-53
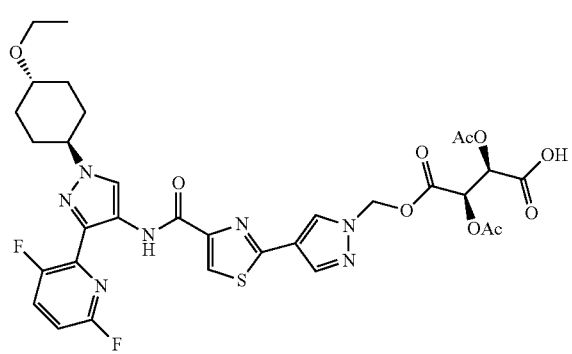
I-56
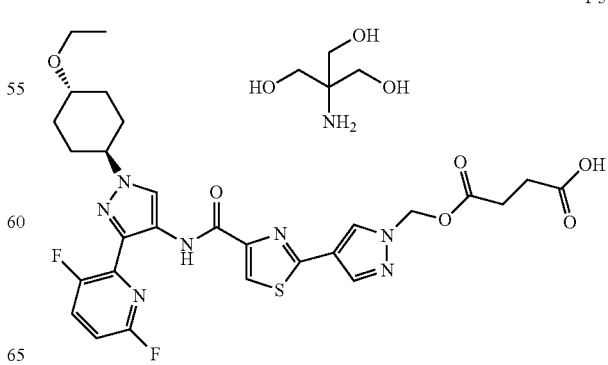

I-57
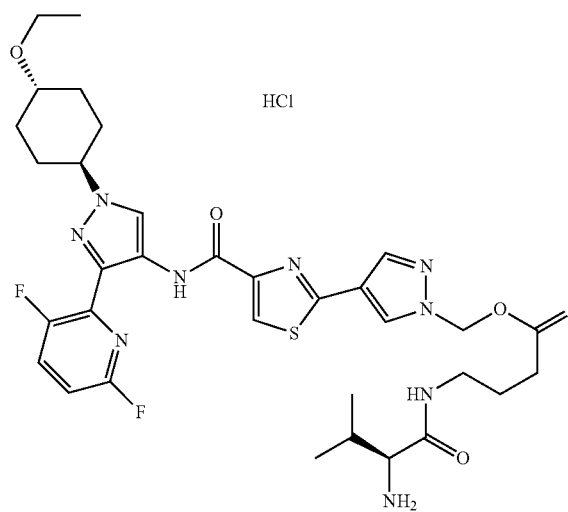
I-58
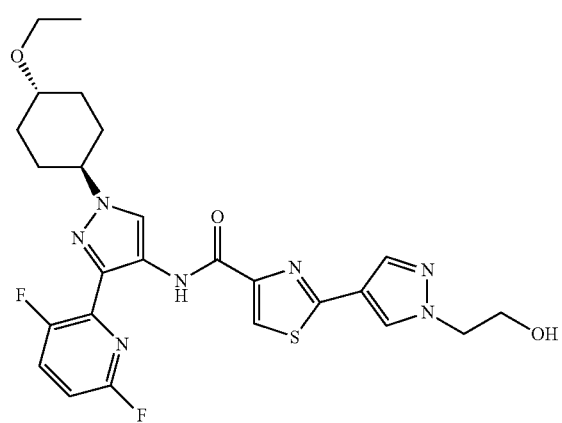
I-59
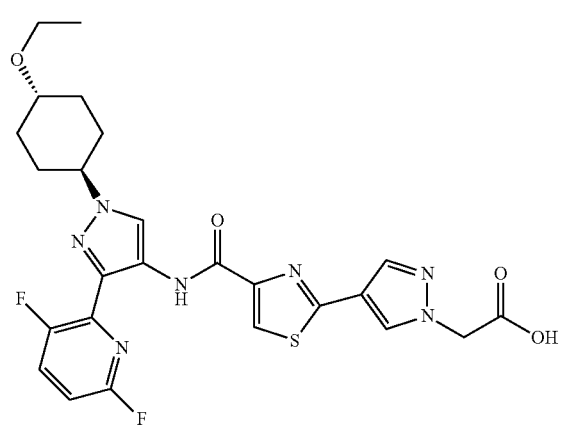
I-60
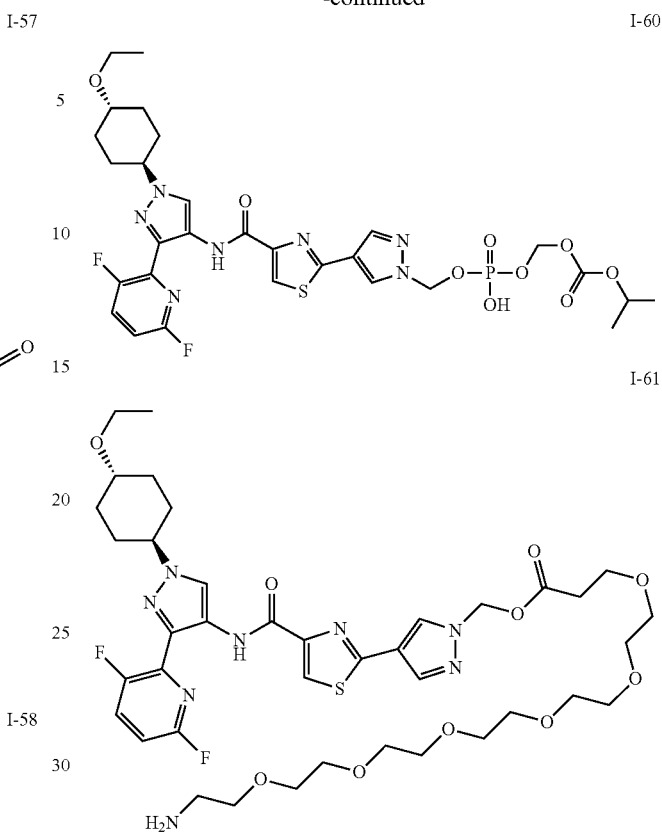
I-61
I-62
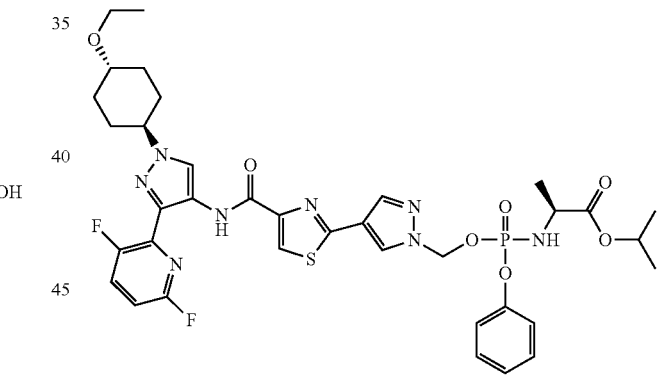
I-63
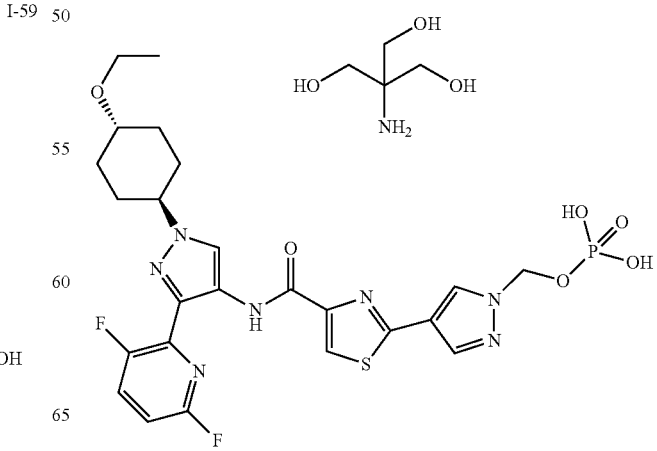

I-64
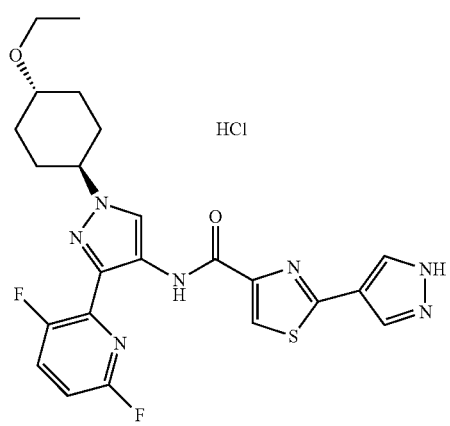
I-65
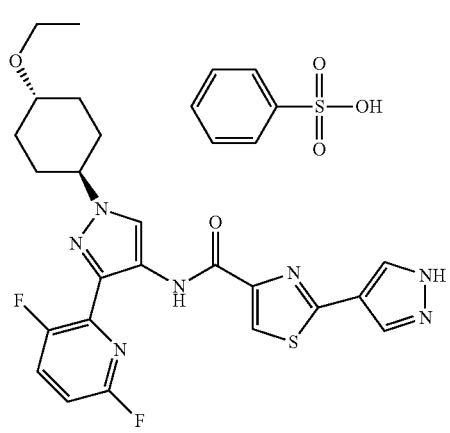
I-66
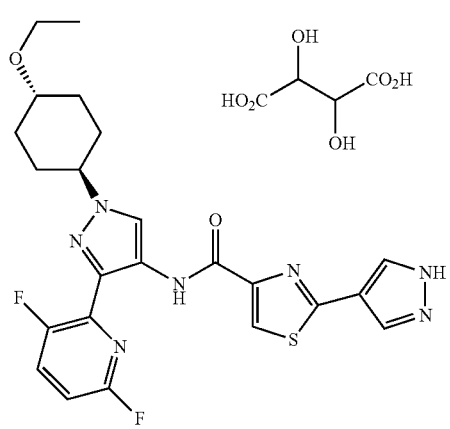
I-67
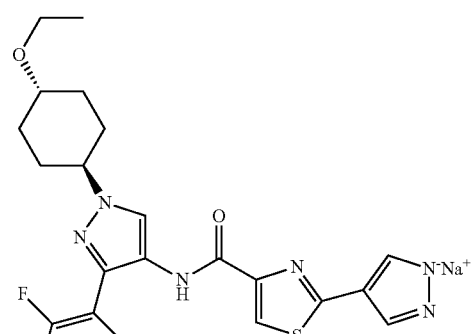
I-68
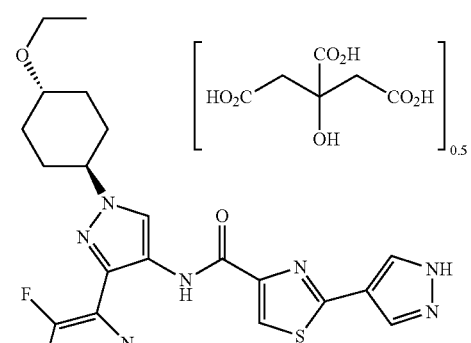
I-69
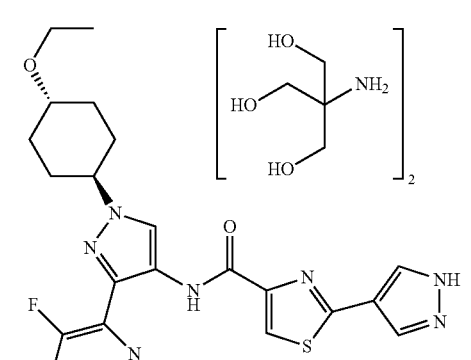
I-70
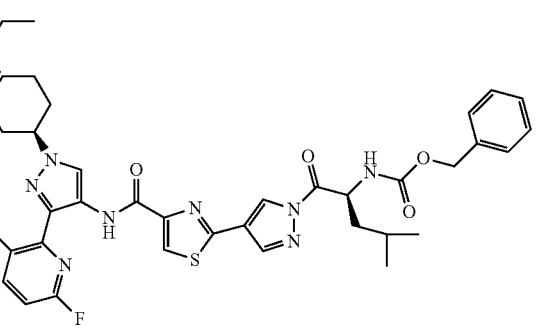

I-71
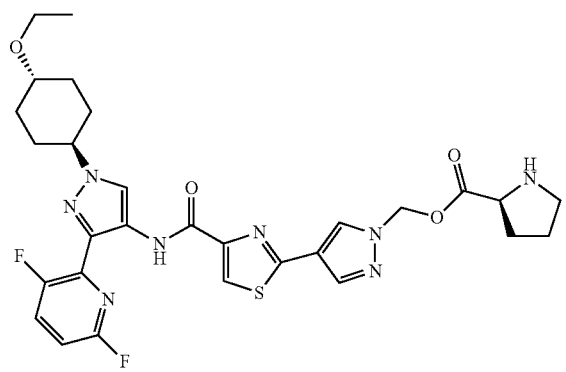
I-75
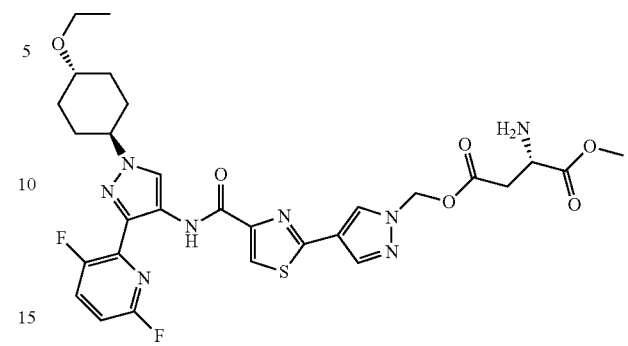
I-72
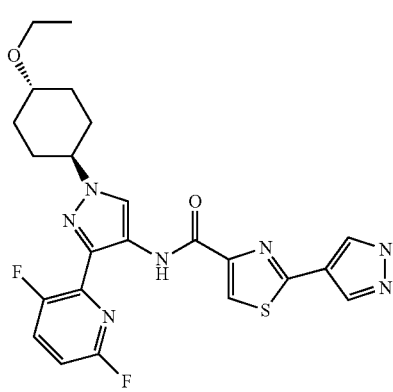
I-76
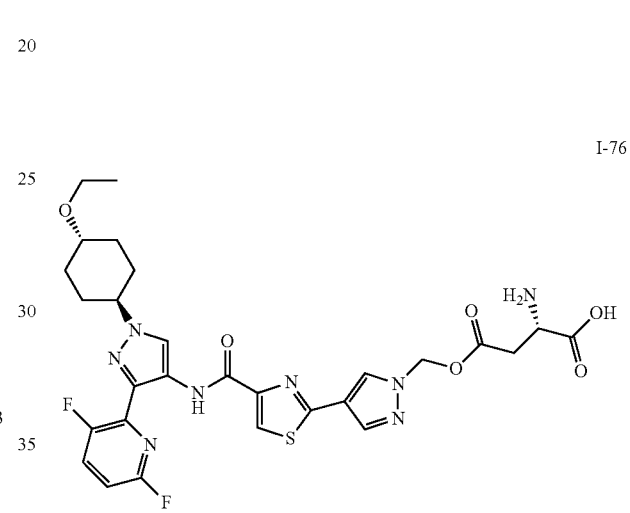
I-73
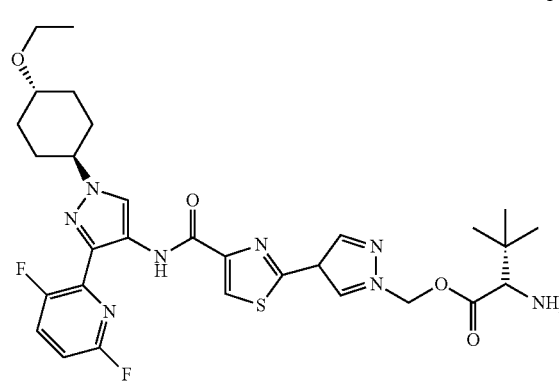
I-74
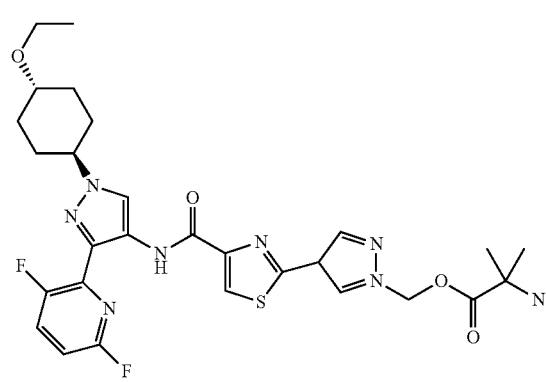
I-77
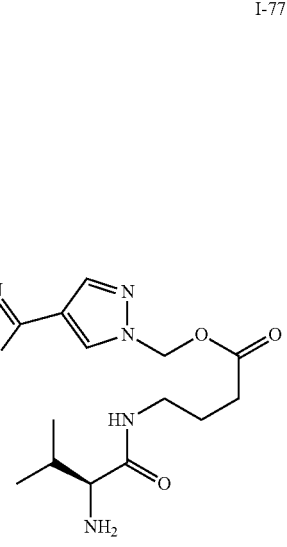

I-78
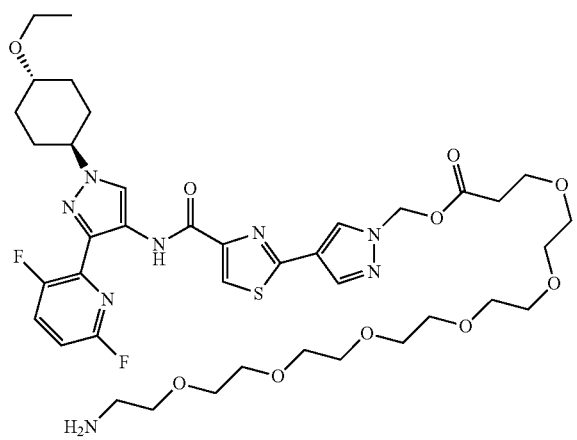
I-79
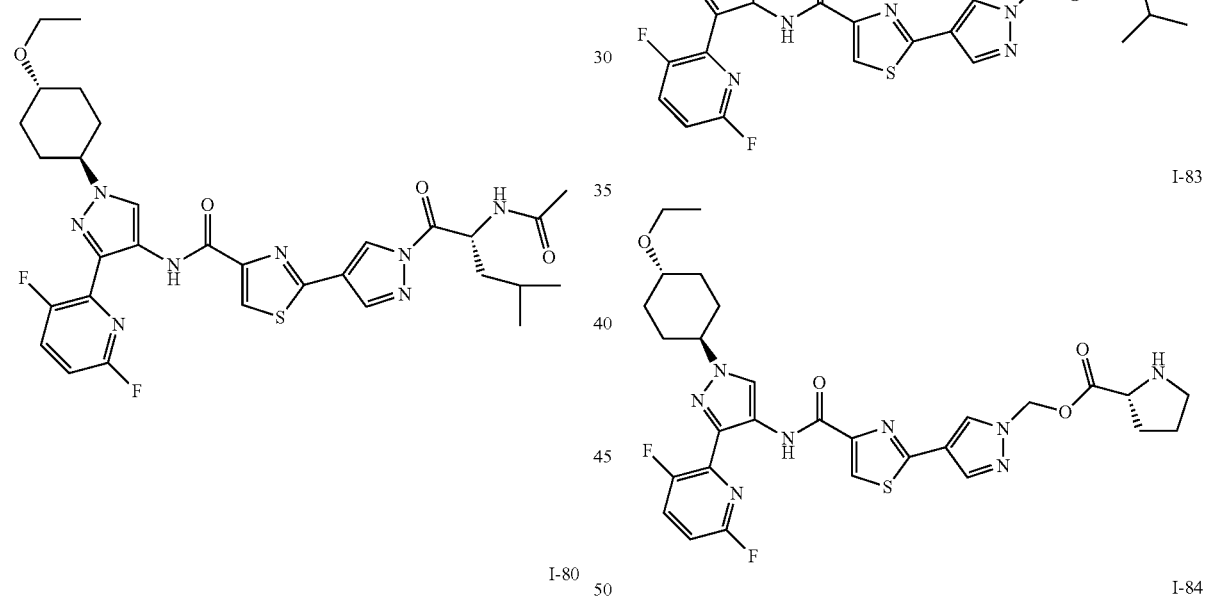
I-80
I-81
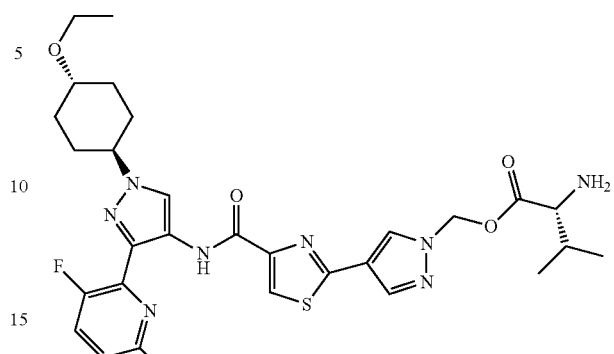
I-82
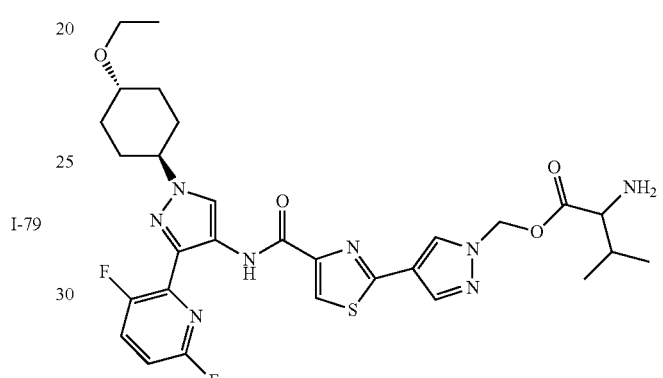
I-83
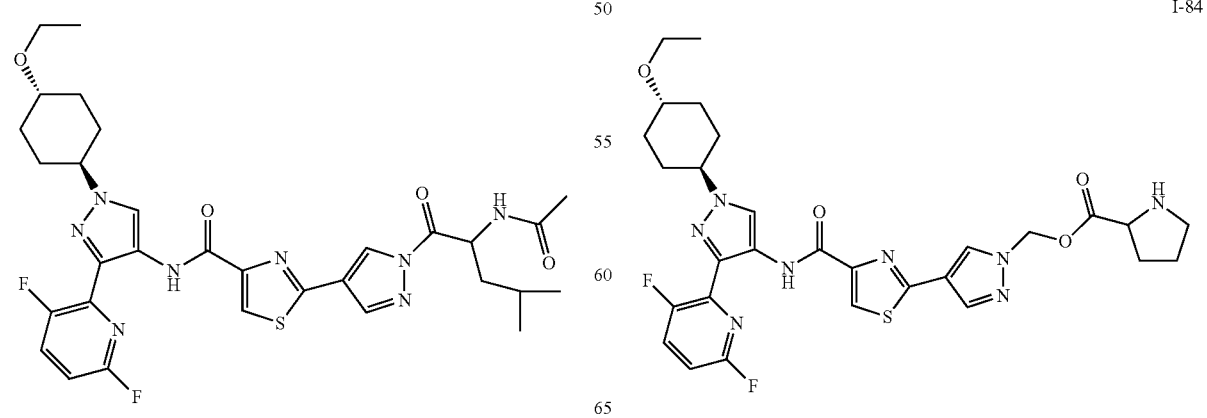
I-84

I-85
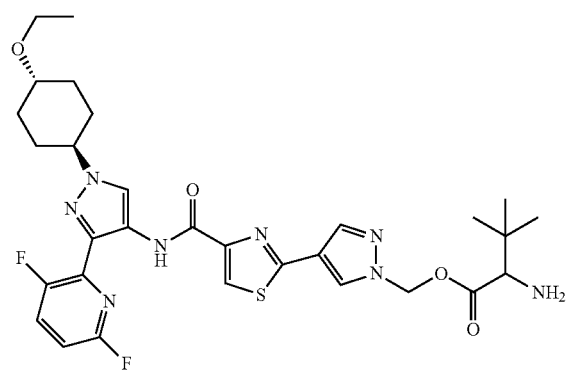
I-86
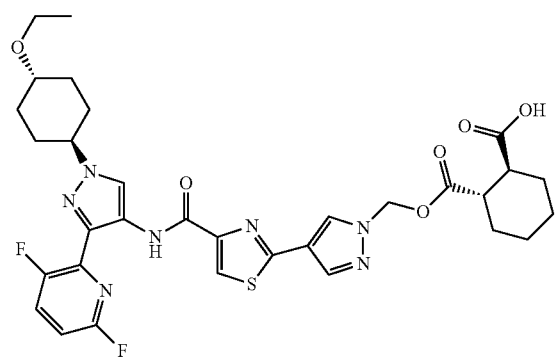
I-87
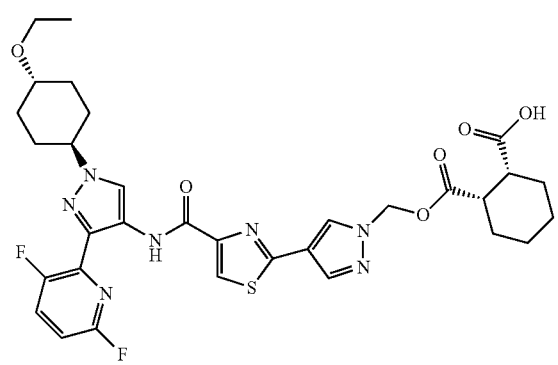
I-88
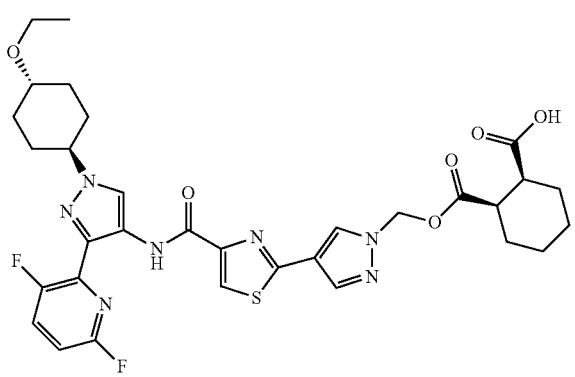
I-89
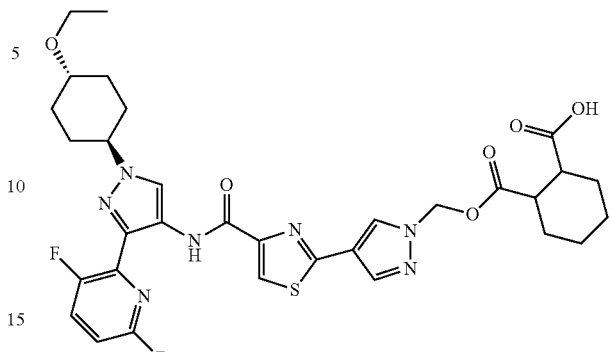
I-90
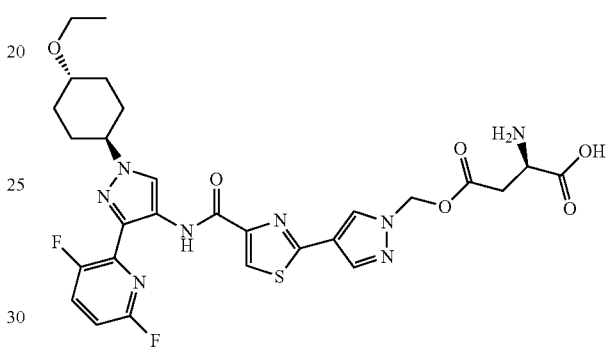
I-91
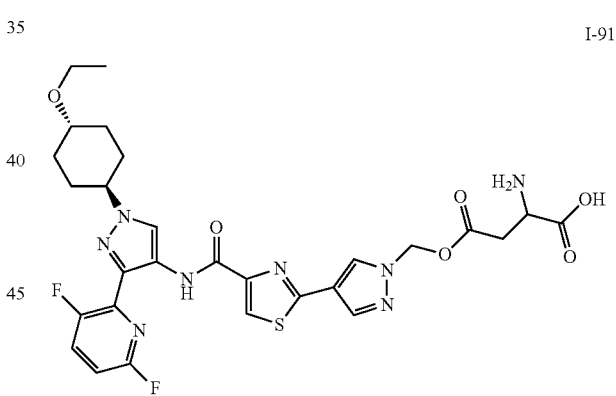
I-92
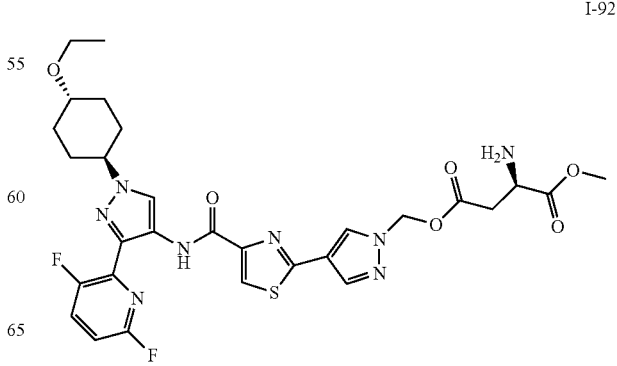

I-93
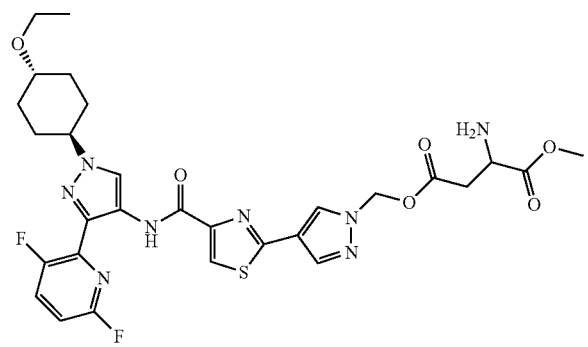
I-94
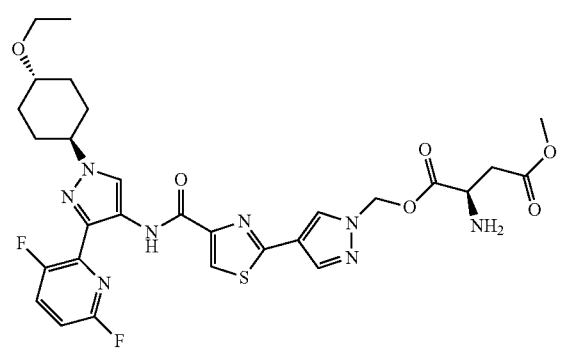
I-95
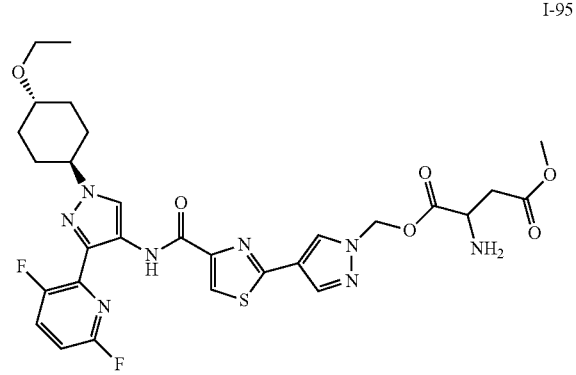
I-96
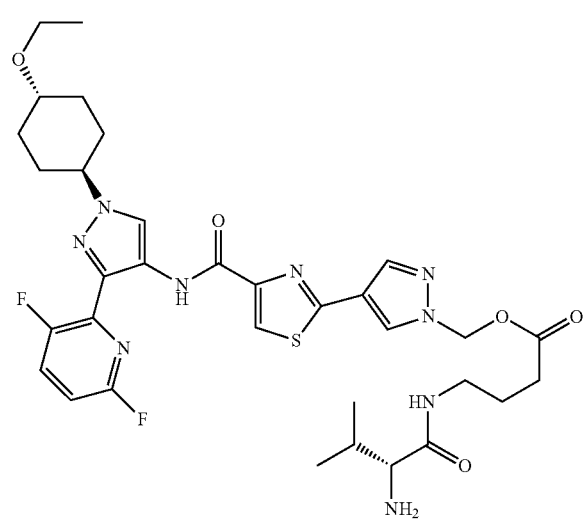
I-97
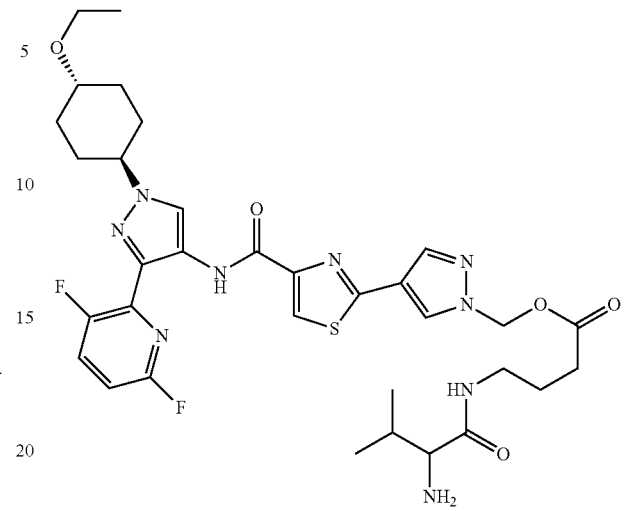
I-98
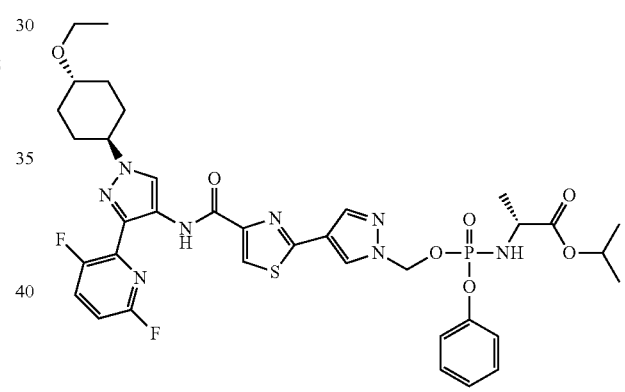
I-99
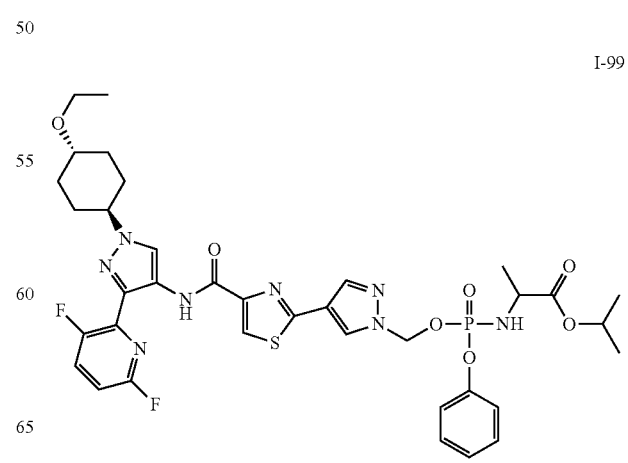

-continued
I-100
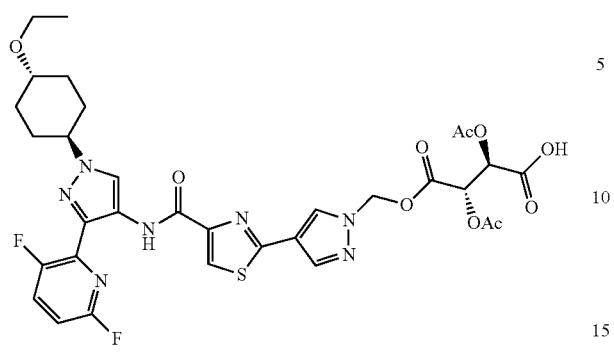
I-101
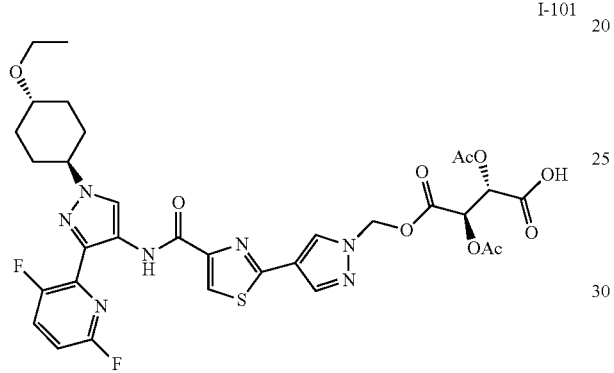
I-102
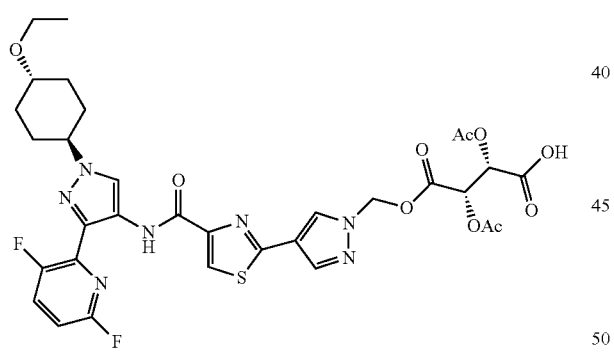
I-103
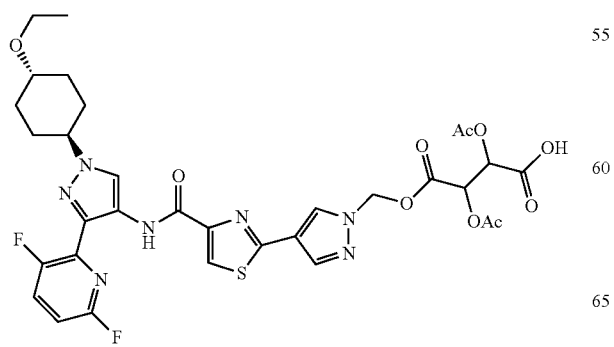
-continued
I-104
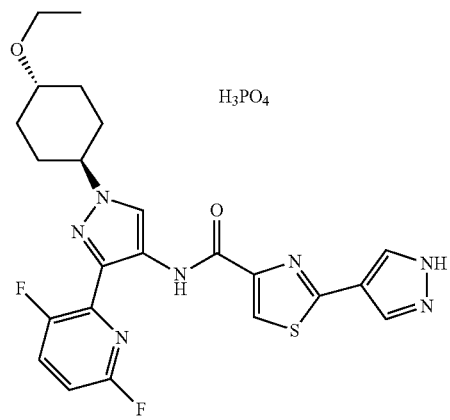
I-105
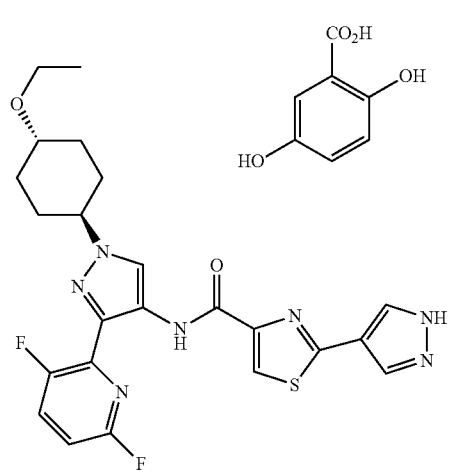
I-106
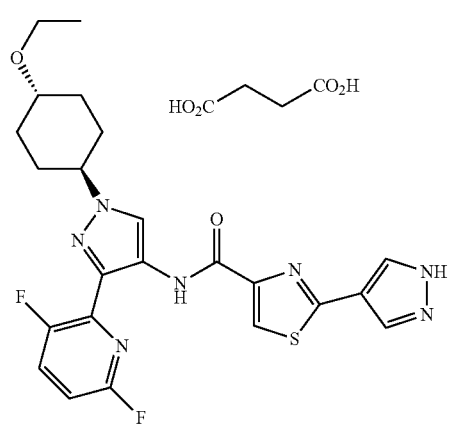

47
-continued
I-107
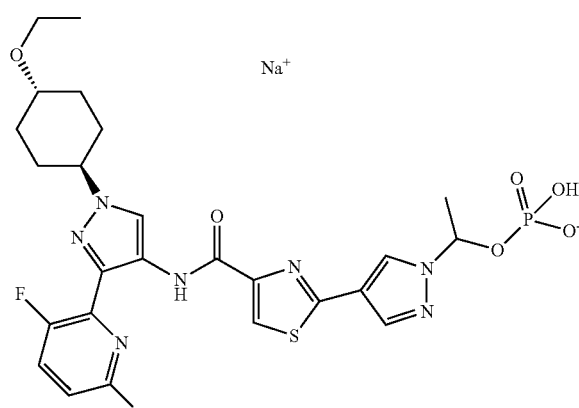
I-108
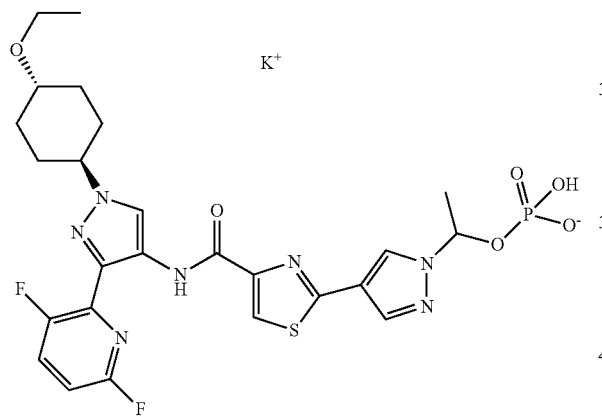
I-109
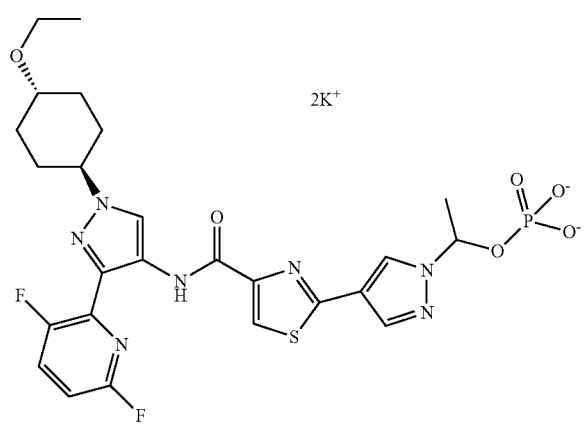
48
-continued
I-110
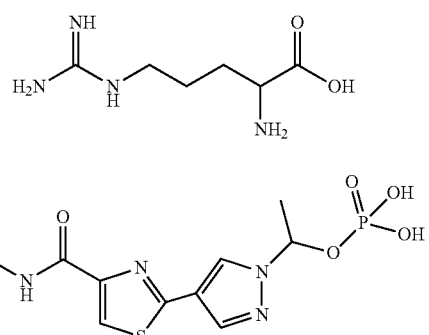
I-111
I-112

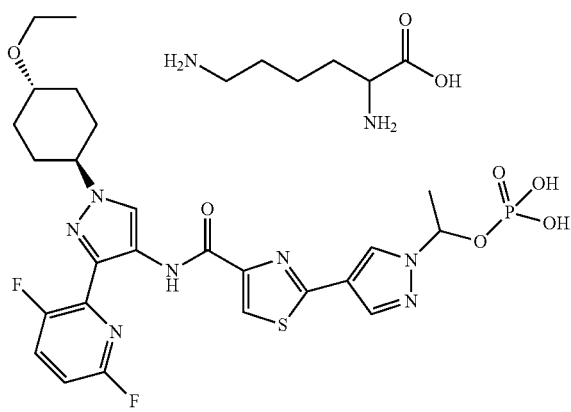

I-113

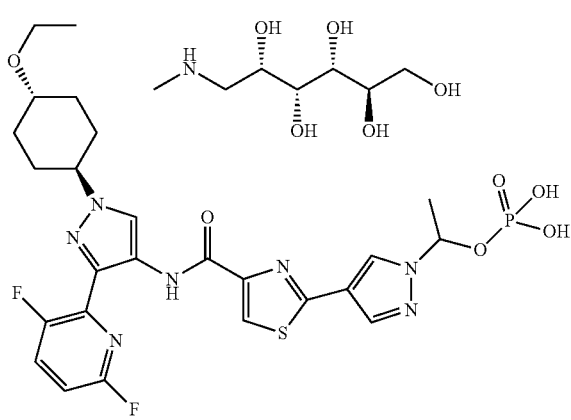

I-114

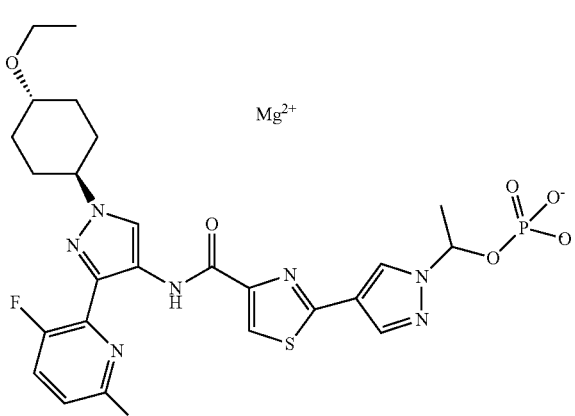

I-15

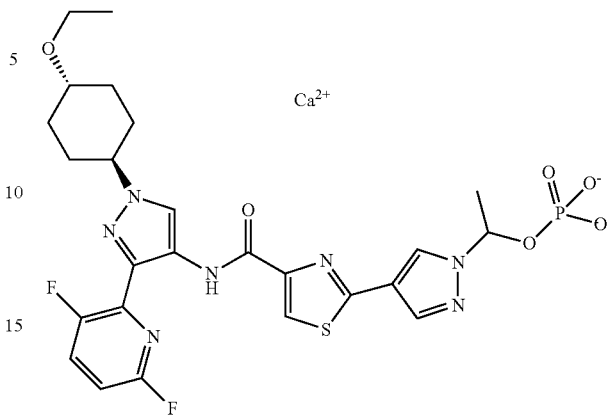

I-116

Exemplary compounds according to formula I include:

I-1: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide;

I-2: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl dihydrogen phosphate;

I-3: di-tert-butyl ((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) phosphate;

I-4: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl phosphate disodium salt;

I-5: N-(3-(3,6-difluoropyridin-2-yl)-1-((1r,4r)-4-ethoxycyclohexyl)-1H-pyrazol-4-yl)-2-(1-methyl-1H-pyrazol-4-yl)thiazole-4-carboxamide;

I-6: 2-(1-(acetyl-L-leucyl)-1H-pyrazol-4-yl)-N-(3-(3,6-difluoropyridin-2-yl)-1-((1r,4r)-4-ethoxycyclohexyl)-1H-pyrazol-4-yl)thiazole-4-carboxamide;

I-7: 1-methylcyclopropyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate;

I-8: 1-(isobutyryloxy)ethyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate;

I-9: N-(3-(3,6-difluoropyridin-2-yl)-1-((1r,4r)-4-ethoxycyclohexyl)-1H-pyrazol-4-yl)-2-(1-((5-methyl-2-oxo-1,3-dioxol-4-yl)methyl)-1H-pyrazol-4-yl)thiazole-4-carboxamide;

I-10: 2-morpholinoethyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate;

I-11: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide hemi-tartrate salt;

I-12: N-(3-(3,6-difluoropyridin-2-yl)-1-((1r,4r)-4-ethoxycyclohexyl)-1H-pyrazol-4-yl)-2-(1-(morpholine-4-carbonyl)-1H-pyrazol-4-yl)thiazole-4-carboxamide;

I-13: N-(3-(3,6-difluoropyridin-2-yl)-1-((1r,4r)-4-ethoxycyclohexyl)-1H-pyrazol-4-yl)-2-(1-((3-morpholinopropyl)carbamoyl)-1H-pyrazol-4-yl)thiazole-4-carboxamide;

I-14: N-(3-(3,6-difluoropyridin-2-yl)-1-((1r,4r)-4-ethoxycyclohexyl)-1H-pyrazol-4-yl)-2-(1-((3-(dimethylamino)propyl)carbamoyl)-1H-pyrazol-4-yl)thiazole-4-carboxamide;

I-15: 3-morpholinopropyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate;

I-16: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-valinate hydrochloride;

I-17: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-prolinate hydrochloride;

I-18: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate;

I-19: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl glycinate hydrochloride;

I-20: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl phosphate disodium salt;

I-21: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (S)-2-amino-3,3-dimethylbutanoate hydrochloride;

I-22: 2-(1-acetyl-1H-pyrazol-4-yl)-N-(3-(3,6-difluoropyridin-2-yl)-1-((1r,4r)-4-ethoxycyclohexyl)-1H-pyrazol-4-yl)thiazole-4-carboxamide;

I-23: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2-amino-2-methylpropanoate hydrochloride;

I-24: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-25: methyl 4-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)-4-oxobutanoate;

I-26: N-(3-(3,6-difluoropyridin-2-yl)-1-((1r,4r)-4-ethoxycyclohexyl)-1H-pyrazol-4-yl)-2-(1-(2-morpholinoacetyl)-1H-pyrazol-4-yl)thiazole-4-carboxamide;

I-27: N-(3-(3,6-difluoropyridin-2-yl)-1-((1r,4r)-4-ethoxycyclohexyl)-1H-pyrazol-4-yl)-2-(1-(2-hydroxy-3-morpholinopropyl)-1H-pyrazol-4-yl)thiazole-4-carboxamide;

I-28: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2-morpholinoacetate;

I-29: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-valinate;

I-30: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-valinate benzene sulfonate;

I-31: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-valinate mesylate;

I-32: 2-(4-methylpiperazin-1-yl)ethyl 4-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)-4-oxobutanoate;

I-33: 1-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 4-methyl L-aspartate hydrochloride;

I-34: methyl N-(2-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)-2-oxoethyl)-N-methylglycinate;

I-35: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (S)-2-amino-3,3-dimethylbutanoate;

I-36: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (S)-2-amino-3,3-dimethylbutanoate benzene sulfonate;

I-37: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-(morpholinomethyl)benzoate;

I-38: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 1-methyl L-aspartate hydrochloride;

I-39: (1R,2R)-2-(((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)carbonyl)cyclohexane-1-carboxylic acid;

I-40: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (S)-2-amino-3,3-dimethylbutanoate mesylate;

I-41: (S)-2-amino-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid hydrochloride;

I-42: N-(3-(3,6-difluoropyridin-2-yl)-1-((1r,4S)-4-ethoxycyclohexyl)-1H-pyrazol-4-yl)-2-(1-((2S,3S,4R,5R,6S)-3,4,5-trihydroxy-6-(hydroxymethyl)tetrahydro-2H-pyran-2-yl)-1H-pyrazol-4-yl)thiazole-4-carboxamide;

I-43: N-(3-(3,6-difluoropyridin-2-yl)-1-((1r,4R)-4-ethoxycyclohexyl)-1H-pyrazol-4-yl)-2-(1-((2R,3R,4R,5R,6S)-3,4,5-trihydroxy-6-(hydroxymethyl)tetrahydro-2H-pyran-2-yl)-1H-pyrazol-4-yl)thiazole-4-carboxamide;

I-44: tert-butyl (1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl) hydrogen phosphate sodium acetate salt;

I-45: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl isopropyl carbonate;

I-46: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl di(((isopropoxycarbonyl)oxy)methyl) phosphate;

I-47: 1-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 4-methyl L-aspartate;

I-48: 1-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 4-methyl L-aspartate benzene sulfonate;

I-49: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate tris salt;

I-50: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl glycinate benzene sulfonate;

I-51: 2-(4-methylpiperazin-1-yl)ethyl 4-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)-4-oxobutanoate benzene sulfonate;

I-52: 2-(4-methylpiperazin-1-yl)ethyl 4-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)-4-oxobutanoate succinate salt;

I-53: (2R,3R)-2,3-diacetoxy-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-54: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl acetate;

I-55: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 1-methyl L-aspartate benzene sulfonate;

I-56: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid tris salt;

I-57: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((S)-2-amino-3-methylbutanamido)butanoate hydrochloride;

I-58: N-(3-(3,6-difluoropyridin-2-yl)-1-((1r,4r)-4-ethoxycyclohexyl)-1H-pyrazol-4-yl)-2-(1-(2-hydroxyethyl)-1H-pyrazol-4-yl)thiazole-4-carboxamide;

I-59: 2-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)acetic acid;

I-60: ((((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)(hydroxy)phosphoryl)oxy)methyl isopropyl carbonate;

I-61: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 1-amino-3,6,9,12,15,18-hexaoxahenicosan-21-oate hydrochloride;

I-62: isopropyl (((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)(phenoxy)phosphoryl)-L-alaninate;

I-63: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl dihydrogen phosphate tris salt;

I-64: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide hydrochloride;

I-65: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide benzene sulfonate;

I-66: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide tartrate;

I-67: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide sodium salt;

I-68: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide hemicitrate;

I-69: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl dihydrogen phosphate ditris salt;

I-70: benzyl ((S)-1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)-4-methyl-1-oxopentan-2-yl)carbamate;

I-71: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-prolinate;

I-72: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl glycinate;

I-73: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (R)-2-amino-3,3-dimethylbutanoate;

I-74: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2-amino-2-methylpropanoate;

I-75: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 1-methyl L-aspartate;

I-76: (S)-2-amino-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-77: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((S)-2-amino-3-methylbutanamido)butanoate;

I-78: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 1-amino-3,6,9,12,15,18-hexaoxahenicosan-21-oate;

I-79: 2-(1-(acetyl-D-leucyl)-1H-pyrazol-4-yl)-N-(3-(3,6-difluoropyridin-2-yl)-1-((1r,4r)-4-ethoxycyclohexyl)-1H-pyrazol-4-yl)thiazole-4-carboxamide;

I-80: 2-(1-(acetylleucyl)-1H-pyrazol-4-yl)-N-(3-(3,6-difluoropyridin-2-yl)-1-((1r,4r)-4-ethoxycyclohexyl)-1H-pyrazol-4-yl)thiazole-4-carboxamide;

I-81: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl D-valinate;

I-82: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl valinate;

I-83: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl D-prolinate;

I-84: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl prolinate;

I-85: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2-amino-3,3-dimethylbutanoate;

I-86: (1S,2S)-2-(((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)carbonyl)cyclohexane-1-carboxylic acid;

I-87: (1R,2S)-2-(((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)carbonyl)cyclohexane-1-carboxylic acid;

I-88: (1S,2R)-2-(((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)carbonyl)cyclohexane-1-carboxylic acid;

I-89: 2-(((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)carbonyl)cyclohexane-1-carboxylic acid;

I-90: (R)-2-amino-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-91: 2-amino-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-92: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 1-methyl D-aspartate;

I-93: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 1-methyl aspartate;

I-94: 1-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 4-methyl D-aspartate;

I-95: 1-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl) 4-methyl aspartate;

I-96: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((R)-2-amino-3-methylbutanamido)butanoate;

I-97: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-(2-amino-3-methylbutanamido)butanoate;

I-98: isopropyl (((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)(phenoxy)phosphoryl)-D-alaninate;

I-99: isopropyl (((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)(phenoxy)phosphoryl)alaninate;

I-100: (2R,3S)-2,3-diacetoxy-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-101: (2S,3R)-2,3-diacetoxy-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-102: (2S,3S)-2,3-diacetoxy-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-103: 2,3-diacetoxy-4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid;

I-104: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide phosphate;

I-105: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide gentisate;

I-106: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide succinate;

I-107: sodium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl hydrogen phosphate;

I-108: potassium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl hydrogen phosphate;

I-109: potassium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl phosphate;

I-110: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate arginine salt;

I-111: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate choline salt;

I-112: ammonium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl hydrogen phosphate;

I-113: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate lysine salt;

I-114: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate meglumine salt;

I-115: magnesium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethylphosphate; or I-116: Calcium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethylphosphate.

III. Compositions and/or Combinations Comprising Pyrazole Compounds

A. Combinations with Other Therapeutic Agents

The pyrazole compounds of the present invention may be used alone, in combination with one another, or as an adjunct to, or in combination with, other established therapies. In another aspect, the compounds of the present invention may be used in combination with other therapeutic agents useful for the disorder or condition being treated. These compounds may be administered simultaneously, sequentially in any order, by the same route of administration, or by a different route.

In some embodiments, the second therapeutic agent is an analgesic, an antibiotic, an anticoagulant, an antibody, an anti-inflammatory agent, an immunosuppressant, a guanylate cyclase-C agonist, an intestinal secretagogue, an antiviral, anticancer, antifungal, a cell therapy, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhibitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present pyrazole compounds include proteasome inhibitors, such as bortezomib, carfilzomib, marizomib and the like.

Examples of cell therapies include, but are not limited to, cells expressing chimeric antigen receptors (CARs) and/or T cell receptors (TCRs). YESCARTA and KYMRIAH are two commercially available examples.

Examples of kinase inhibitors that are useful in combination with the presently disclosed compounds, particularly in treating malignancies, include Btk inhibitors, such as ibrutinib, CDK inhibitors, such as palbociclib, EGFR inhibitors, such as afatinib, erlotinib, gefitinib, lapatinib, osimertinib and vandetinib, Mek inhibitors, such as trametinib, Raf inhibitors, such as dabrafenib, sorafenib and vemurafenib, VEGFR inhibitors, such as axitinib, lenvatinib, nintedanib, pazopanib, BCR-Abl inhibitors, such as bosutinib, dasatinib, imatinib and nilotinib, Syk inhibitors, such as fostamatinib, and JAK inhibitors, such as ruxolitinib, In other embodiments, the second therapeutic agent may be selected from any of the following:

analgesics—morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics—aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (e.g., azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies—anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, cleneoliximab, clazakiumab, fezakinumab, fletikumab, mavrilimumab, ocrelizumab, sarilumab, secukinumab, toralizumab, zanolimumab;

anticoagulants—warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents—steroids, e.g., budesonide, nonsteroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants—mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues—for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

B. Compositions Comprising Pyrazole Compounds

The disclosed pyrazole compounds may be used alone, in any combination, and in combination with, or adjunctive to, at least one second therapeutic agent, and further the pyrazole compounds, and the at least one second therapeutic if present, may be used in combination with any suitable additive useful for forming compositions for administration to a subject. Additives can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. Typical additives include, by way of example and without limitation: pharmaceutically acceptable excipients; pharmaceutically acceptable carriers; and/or adjuvants, such as mono-, di-, and polysaccharides, sugar alcohols and other polyols, such as, lactose, glucose, raffinose, melezitose, lactitol, maltitol, trehalose, sucrose, mannitol, starch, or combinations thereof, surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose), gelatin, synthetic polymers (such as polyvinylpyrrolidone, polyalkylene gylcols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

IV. Method of Use

The present disclosure provides pyrazole compounds and combinations and/or compositions thereof, that may be useful to ameliorate, treat and/or prevent a variety of diseases and/or disorders. Certain disclosed compounds, referred to herein as active compounds, have activity as IRAK inhibitors and/or may be used to ameliorate, treat or prevent a disease and/or disorder when administered at a dose that provides a desired benefit to the subject but does not cause significant unwanted and/or harmful side effects to the subject. In some embodiments, the disease and/or disorder is one for which an IRAK inhibitor is indicated. The present disclosure also addresses the problem of administering and/or providing a biologically effective amount of such an active compound to a subject, such as a subject in need of an IRAK inhibitor. Certain embodiments concern pyrazole compounds that are useful to provide and/or deliver a biologically effective amount of an active compound to the subject. Such compounds may be a prodrug of the active compound, a salt of the active compound, or a combination thereof. Also disclosed are embodiments of a formulation comprising one or more of the pyrazole compounds that are useful for delivering the active compound, a prodrug and/or salt of the active compound, or a combination thereof. Certain embodiments of the composition concern a spray-dried formulation.

A. Diseases/Disorders

The disclosed pyrazole compounds, as well as combinations and/or compositions thereof, may be useful to ameliorate, treat and/or prevent a variety of diseases and/or disorders. In particular embodiments, the pyrazole compound, combinations of pyrazole compounds, and/or compositions thereof, may be useful for treating or preventing autoimmune diseases, inflammatory disorders, cardiovascular diseases, nerve disorders, neurodegenerative disorders, allergic disorders, asthma, pancreatitis, multi-organ failure, kidney diseases, platelet aggregation, cancer, transplantation, sperm motility, erythrocyte deficiency, graft rejection, lung injuries, respiratory diseases, ischemic conditions, cytokine release syndrome (CRS), and bacterial and viral infections.

In some embodiments, the pyrazole compound, combinations of pyrazole compounds, and/or compositions thereof, may be useful or treating or preventing allergic diseases, amyotrophic lateral sclerosis (ALS), systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy or asthma.

The pyrazole compound, combinations of pyrazole compounds, and/or compositions thereof, may also be useful for ameliorating, treating or preventing immune regulatory disorders related to bone marrow or organ transplant rejection or graft-versus-host disease. Examples of inflammatory and immune regulatory disorders that can be treated with the present compounds include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

In certain embodiments, the present compounds are useful for treating nerve pain, including neuropathic pain and inflammation induced pain.

In certain embodiments, the pyrazole compound, combinations of pyrazole compounds, and/or compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), Alzheimer's disease, or Parkinson's disease.

Proliferative diseases that may be treated by the pyrazole compound, combinations of pyrazole compounds, and/or compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, or intravascular large B-cell lymphoma). In particular, the presently disclosed compounds are useful for treating drug resistant malignancies, such as those resistant to JAK inhibitors, ibrutinib resistant malignancies, including ibrutinib resistant hematological malignancies, such as ibrutinib resistant CLL and ibrutinib resistant Waldenström's macroglobulinemia.

Examples of allergic disorders that may be treated using the pyrazole compound, combinations of pyrazole compounds, and/or compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, postnasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The pyrazole compound, combinations of pyrazole compounds, or compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration

Pharmaceutical compositions comprising the active compounds of the invention (or prodrugs thereof) may be manufactured by means of conventional mixing, dissolving, granulating, dragee-making, levigating, emulsifying, encapsulating, entrapping or lyophilization processes. The compositions may be formulated in conventional manner using one or more physiologically acceptable excipients, diluents, carriers, adjuvants or auxiliaries to provide preparations which can be used pharmaceutically.

The active compound or a prodrug thereof may be formulated in the pharmaceutical compositions per se, or in the form of a hydrate, solvate, N-oxide, co-crystal, or pharmaceutically acceptable salt. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), hydrate, solvate, N-oxide, co-crystal, or pharmaceutically acceptable salt and/or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the pyrazole compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the pyrazole compound(s) may be formulated as solutions (for retention enemas) suppositories or ointments containing conventional suppository bases, such as cocoa butter or other glycerides.

For nasal administration or administration by inhalation or insufflation, the active compound(s), hydrate, solvate, N-oxide, co-crystal, pharmaceutically acceptable salt and/or prodrug(s) can be conveniently delivered in the form of an aerosol spray from pressurized packs or a nebulizer with the use of a suitable propellant, e.g.) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5 to 20 mg/ml); benzalkonium chloride (0.1 to 0.2 mg/mL); polysorbate 80 (TWEEN® 80; 0.5 to 5 mg/ml); carboxymethylcellulose sodium or microcrystalline cellulose (1 to 15 mg/ml); phenylethanol (14 mg/ml); and dextrose (20 to 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL Compound or prodrug, 1% (v/v) Polysorbate 80 (TWEEN® 80), 50 mM citrate and/or 0.9% sodium chloride.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the pyrazole compound(s) can be formulated as a depot preparation for administration by implantation or intramuscular injection. The pyrazole compound maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver the pyrazole compound(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

I. Spray-Dried Formulation

Disclosed herein are embodiments of a spray-dried formulation comprising one or more compounds according to formula I. The spray-dried formulation may be a dispersion, such as a spray-dried dispersion of the compound(s) according to formula I in a carrier or matrix, such as a polymer matrix. Typically, the spray-dried formulation comprises a single phase, amorphous dispersion of the disclosed compound(s) in the carrier, such as a polymer matrix.

Embodiments of the spray-dried formulation comprise, consist essentially of, or consist of, an effective amount of one or more compounds according to formula I and an amount of the carrier sufficient to form the spray-dried formulation. A person of ordinary skill in the art will appreciate that an effective amount of the compound(s) may vary, but typically the effective amount is from 0.1% to 50% (w/w with respect to the carrier) or more, such as from 1% to 50%, from 5% to 40%, from 10% to 35%, from 15% to 30%, or from 15% to 25%. In particular embodiments, the spray-dried formulation comprises, consists essentially of, or consists of, 20% w/w of the disclosed compound(s) and 80% w/w carrier, such as a polymer matrix.

In some embodiments, the carrier is a polymer, such as a polymer that is suitable to form a spray-dried formulation with the disclosed compound(s). Suitable polymers include, but are not limited to, cellulose derivatives, such as hydroxypropylmethylcellulose acetate succinate (hypromellose acetate succinate; HPMCAS), hydroxypropyl methylcellulose phthalate (hypromellose phthalate; HPMCP) or hydroxypropyl methylcellulose (HPMC); vinyl polymers, such as poly(vinylpyrrolidone) (PVP), or poly(vinylpyrrolidone-co-vinyl acetate) (PVPVA); lactide polymers, such as polylactide (PLA) or polylactide-co-glycolide (PLGA); sugars, such as sucrose or trehalose; or any combination thereof. In certain embodiments, the carrier is HPMCAS. The polymer, such as HPMCAS, may be of any grade suitable to form the spray-dried formulation, such as grade L, grade M, or grade H. In particular embodiments, grade M is used. Additionally, the HPMCAS may be a fine grade (F) or a granular grade (G), and in certain embodiments, fine grade is used. And in certain working embodiments, the carrier is HPMCAS-MF.

In some embodiments, the spray-dried formulation has a suitable glass transition temperature. The glass transition temperature may be from 100° C. or less to 120° C. or more, such as from 105° C. to 110° C. or 107° C. to 110° C. In certain working embodiments, the glass transition temperature is from 108° C. to 109° C.

In some embodiments, the formulation may comprise additional components. Additional components can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. Typical additional components include, by way of example and without limitation: pharmaceutically acceptable excipients; pharmaceutically acceptable carriers; and/or adjuvants, such as mono-, di-, and polysaccharides, sugar alcohols and other polyols, such as, lactose, glucose, raffinose, melezitose, lactitol, maltitol, trehalose, sucrose, mannitol, starch, or combinations thereof, surfactants, such as sorbitols, diphosphatidyl choline, and lecithin; bulking agents; buffers, such as phosphate and citrate buffers; antiadherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose), gelatin, synthetic polymers (such as polyvinylpyrrolidone, polyalkylene gylcols); coatings (such as cellulose ethers, including hydroxypropylmethyl cellulose, shellac, corn protein zein, and gelatin); release aids (such as enteric coatings); disintegrants (such as crospovidone, cross-linked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

II. Method of Making a Spray-Dried Formulation

Embodiments of a method for making the spray-dried formulation are also disclosed herein. In some embodiments, one or more compounds according to formula I and the polymer are dissolved in a suitable solvent or mixture of solvents, and then spray-dried. Suitable solvent(s) include any solvent or mixture of solvents that dissolves the disclosed compound(s) and the carrier and is suitable for a spray-drying process. Exemplary solvents include, but are not limited to, alcohol, such as methanol, ethanol, isopropanol, n-propanol, and the like; chlorinated solvents, such as dichloromethane, chloroform. In some embodiments, the disclosed compound(s) is dissolved in the solvent or mixture of solvents, and the polymer is added to the mixture. However, in other embodiments, the polymer is dissolved first and the compound(s) is subsequently added, or the compound(s) and the polymer are mixed substantially simultaneously with the solvent or solvent mixture. Regardless of the order of addition, the mixture typically is mixed until the disclosed compound(s) and the polymer are dissolved, and/or the mixture has a uniform appearance. In some embodiments, the resulting mixture is stored at a reduced temperature, such as below 25° C., or from less than 25° C. to 0° C., from 15° C. to 0° C., from 10° C. to 0° C., or from 7° C. to 3° C., typically at about 5° C. The solution also may be protected from light, i.e. stored in a dark environment.

The solution is then spray-dried using a spray drying apparatus. Suitable spray-drying apparatuses are known to persons of ordinary skill in the art. In some embodiments, the parameters of the spray drying apparatus, such as feed temperature, inlet temperature, target outlet temperature and aspiration are set to values suitable for the disclosed compound(s) and the polymer, as understood by a person of ordinary skill in the art. In certain embodiments, the feed temperature is from 15° C. or less to 35° C. or more, such as from 20° C. to 25° C. The inlet temperature may be from 40° C. or less to 60° C. or more, such as from 45° C. to 55° C. The target outlet temperature may be from 30° C. or less to 45° C. or more, such as from 32° C. to 42° C. or from 34° C. to 40° C. And/or the aspirator may be from 50% or more to 100%, such as from 70% to 100% or from 80% to 100%.

The resulting spray-dried solid may be further dried at a temperature suitable to remove at least some, and may be substantially all, of any remaining solvent without substantially degrading the disclosed compound(s) and/or the carrier. In some embodiments, the solid is dried at a temperature of from 25° C. to 100° C. or more, such as from 30° C. to 75° C., or from 35° C. to 50° C. The dispersion may be dried until substantially all the remaining solvent has been removed, and/or until no further weight loss is achieved. The drying may continue for from 1 hour to 48 hours or more, such as from 6 hours to 36 hours, from 12 hours to 32 hours, or from 18 hours to 24 hours. The resulting solid formulation may be stored at a reduced temperature, such as such as below 25° C., or from less than 25° C. to 0° C., from 15° C. to 0° C., from 10° C. to 0° C., or from 7° C. to 3° C., typically at about 5° C. The solution also may be protected from light, i.e. stored in a dark environment, and/or stored under dry conditions, such as in the presence of a desiccant and/or under a dry atmosphere.

C. Dosages

The pyrazole compound or combinations of pyrazole compounds will generally be used in an amount effective to achieve an intended result, for example, in an amount effective to treat and/or prevent a particular disease or disorder. The pyrazole compound(s), or compositions thereof, can be administered therapeutically to achieve therapeutic benefit or prophylactically to achieve prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of pyrazole compounds will also depend on various factors, including the age, weight, general health, and severity of the condition of the patient or subject being treated. Dosage may also need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, and respiratory infections. Dosage, and frequency of administration of the disclosed pyrazole compound(s) or compositions thereof, will also depend on whether the pyrazole compound(s) are formulated for treatment of acute episodes of a condition or for the prophylactic treatment of a disorder. A person or ordinary skill in the art will be able to determine the optimal dose for a particular individual.

For prophylactic administration, the pyrazole compound, combinations of pyrazole compounds, or compositions thereof, can be administered to a patient or subject at risk of developing one of the previously described conditions. For example, if it is unknown whether a patient or subject is allergic to a particular drug, the pyrazole compound, combinations of pyrazole compounds, or compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a pyrazole compound(s), or composition thereof, can be administered to an allergy sufferer prior to expected exposure to the allergen. A pyrazole compound, combinations of pyrazole compounds, or compositions thereof, can also be administered prophylactically to healthy individuals who are repeatedly exposed to agents known to one of the above-described maladies to prevent the onset of the disorder. For example, a pyrazole compound, combinations of pyrazole compounds, or compositions thereof, can be administered to a healthy individual who is repeatedly exposed to an allergen known to induce allergies, such as latex, in an effort to prevent the individual from developing an allergy. Alternatively, a pyrazole compound, combinations of pyrazole compounds, or compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 µM, such as from greater than 0 to 10 µM, from greater than 0 to 5 µM, from greater than 0 to 1 µM, from greater than 0 to 0.5 µM, or from greater than 0 to 0.1 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

Dosage amounts of disclosed pyrazole compounds will typically be in the range of from greater than 0 mg/kg/day, such as 0.0001 mg/kg/day or 0.001 mg/kg/day or 0.01 mg/kg/day, up to at least 100 mg/kg/day. More typically, the dosage (or effective amount) may range from 0.0025 mg/kg to 1 mg/kg administered at least once per day, such as from 0.01 mg/kg to 0.5 mg/kg or from 0.05 mg/kg to 0.15 mg/kg. The total daily dosage typically ranges from 0.1 mg/kg to 5 mg/kg or to 20 mg/kg per day, such as from 0.5 mg/kg to 10 mg/kg per day or from 0.7 mg/kg per day to 2.5 mg/kg/day. Dosage amounts can be higher or lower depending upon, among other factors, the activity of the pyrazole compound, its bioavailability, the mode of administration, and various factors discussed above.

Dosage amount and dosage interval can be adjusted for individuals to provide plasma levels of the pyrazole compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Compositions comprising one or more of the disclosed pyrazole compounds typically comprise from greater than 0 up to 99% of the pyrazole compound, or compounds, and/or other therapeutic agent by total weight percent. More typically, compositions comprising one or more of the disclosed pyrazole compounds comprise from 1 to 20 total weight percent of the pyrazole compound and other therapeutic agent, and from 80 to 99 weight percent of a pharmaceutically acceptable additive.

Preferably, the pyrazole compound, combinations of pyrazole compounds, and/or compositions thereof, will provide therapeutic or prophylactic benefit without causing substantial toxicity. Toxicity of the pyrazole compound can be determined using standard pharmaceutical procedures. The dose ratio between toxic and therapeutic (or prophylactic) effect is the therapeutic index. Pyrazole compounds that exhibit high therapeutic indices are preferred.

IV. Working Examples

Example 1

Compound I-1 (8 g, 20% w/w) was slowly added to a mixture of methylene chloride (360 g) and methanol (40 g) while mixing, and the mixing was continued until compound I-1 dissolved. HPMCAS-MF (32 g) was then slowly added to the mixture while mixing, and resultant mixture was mixed until the HPMCAS-MF dissolved, and the solution was visually uniform. The solution was stored at 5° C. and protected from light.

A spray drier apparatus (Buchi B290) was prepared with a feed temperature of 25° C., an inlet temperature of 50° C., and a target outlet temperature of 38° C. During the spray drying, the outlet temperature varied from 34 to 40° C., the inlet temperature varied from 45 to 51° C. and the aspirator varied from 80 to 100%. The yield was 32 g, 90%.

The resulting solid dispersion was collected and further dried in an oven set at 40° C. for 24 hours. The resulting powder was stored at 5° C. in the presence of a desiccant. The yield after the secondary drying was 27 g, 67.5%. Table 1 provides stability data for the solid dispersion.

TABLE 1

Stability data

| Storage Temp | Storage Config | Storage Time | $T_g$ (° C.) | LOD, at 150° C. (% w/w) | Moisture uptake at 80% RH (% w/w) | Crystallinity by XRPD |
|---|---|---|---|---|---|---|
| 25° C. | Sealed | T = 0 | 108.3 | 1.1 | 5.8 | Amorphous |
|  |  | T = 1 m | 108.3 | 1.0 | 5.8 | Amorphous |
|  |  | T = 3 m | 108.7 | 1.1 | 5.8 | Amorphous |
| 40° C | Sealed | T = 0 | 108.3 | 1.1 | 5.8 | Amorphous |
|  |  | T = 1 m | — | 2.0 | — | Amorphous |
|  |  | T = 3 m | 107.5 | 1.2 | — | Amorphous |
|  | Open | T = 0 | 108.3 | 1.1 | 5.8 | Amorphous |
|  |  | T = 1 m | 108.4 | 2.7 | 4.9 | Amorphous |
|  |  | T = 3 m | 108.0 | 1.3 | — | Amorphous |

Figure 2:
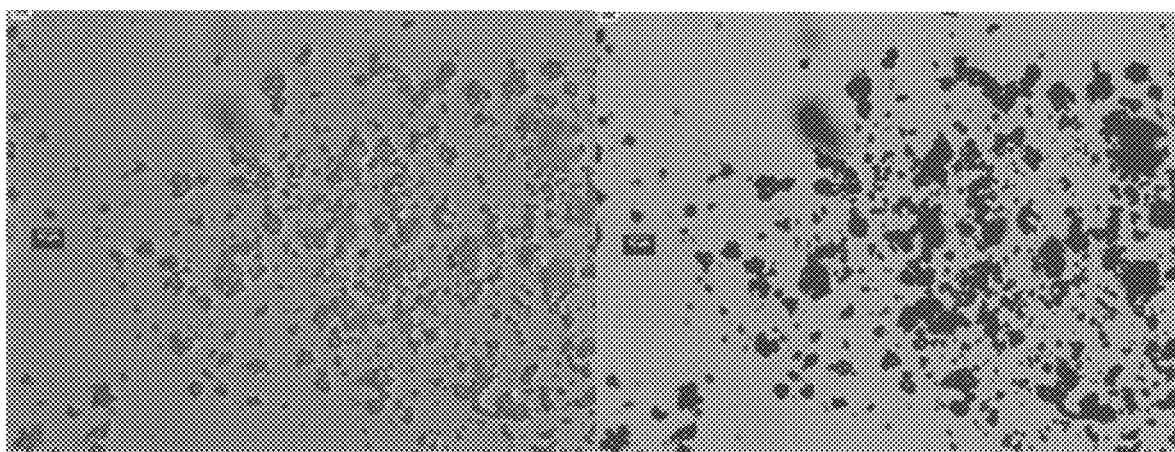
FIG. 2 is a digital image showing a polarized light microscopy (PLM) image of one embodiment of the disclosed spray-dried formulation at 400× magnification.
Figure 3:
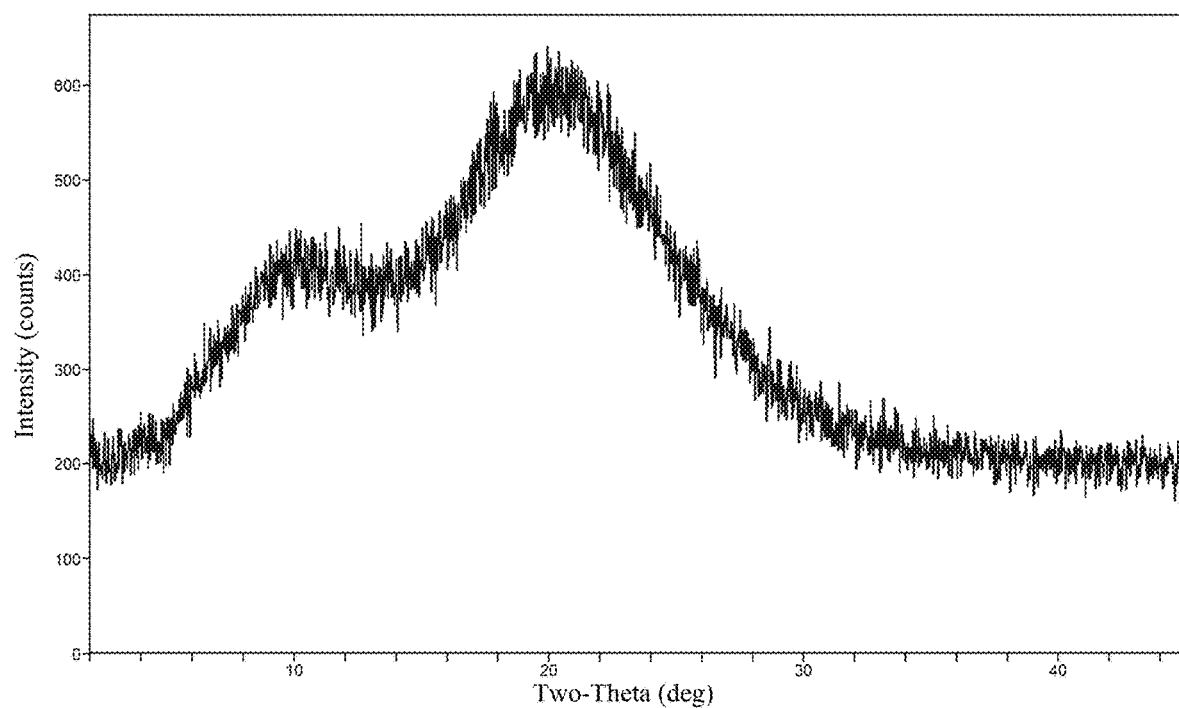
FIG. 3 is a graph of intensity versus scattering angle, illustrating the X-ray powder diffraction pattern of one embodiment of the disclosed spray-dried formulation.
Figure 4:
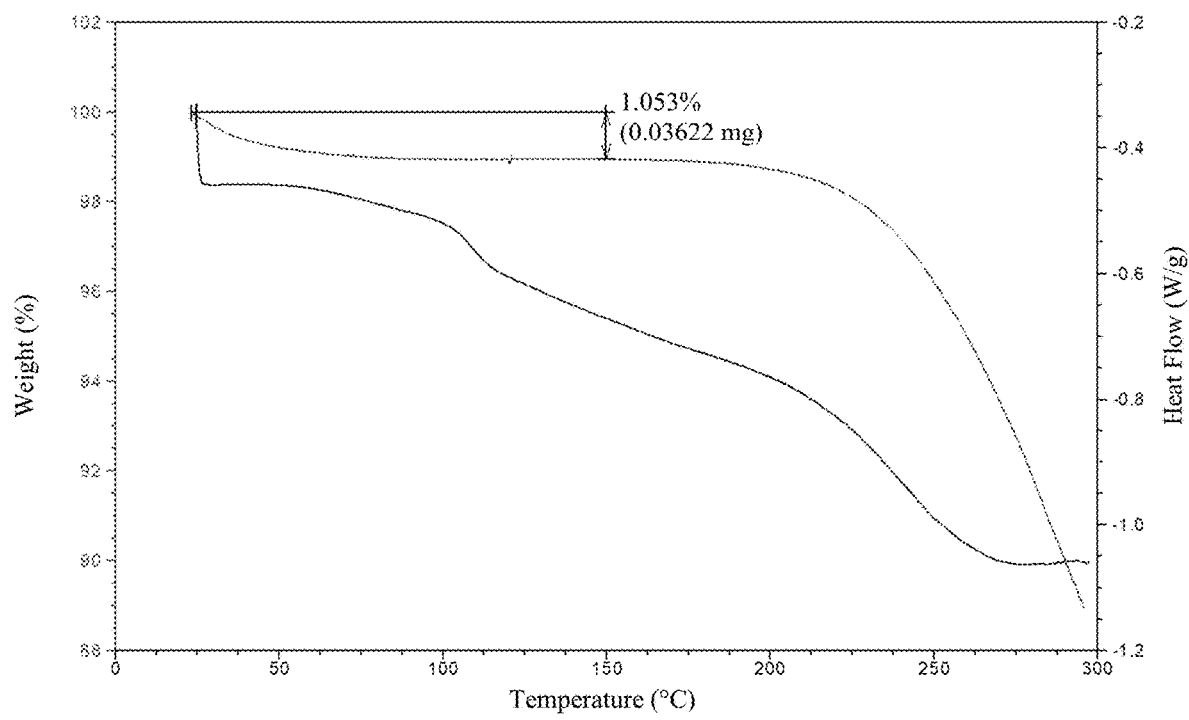
FIG. 4 is a graph of weight and heat flow versus temperature, providing both the thermogravimetry (TGA) and differential scanning calorimetry (DSC) plots for one embodiment of the spray-dried formulation, illustrating the weight change and heat flow of the dispersion at different temperatures.
Figure 5:
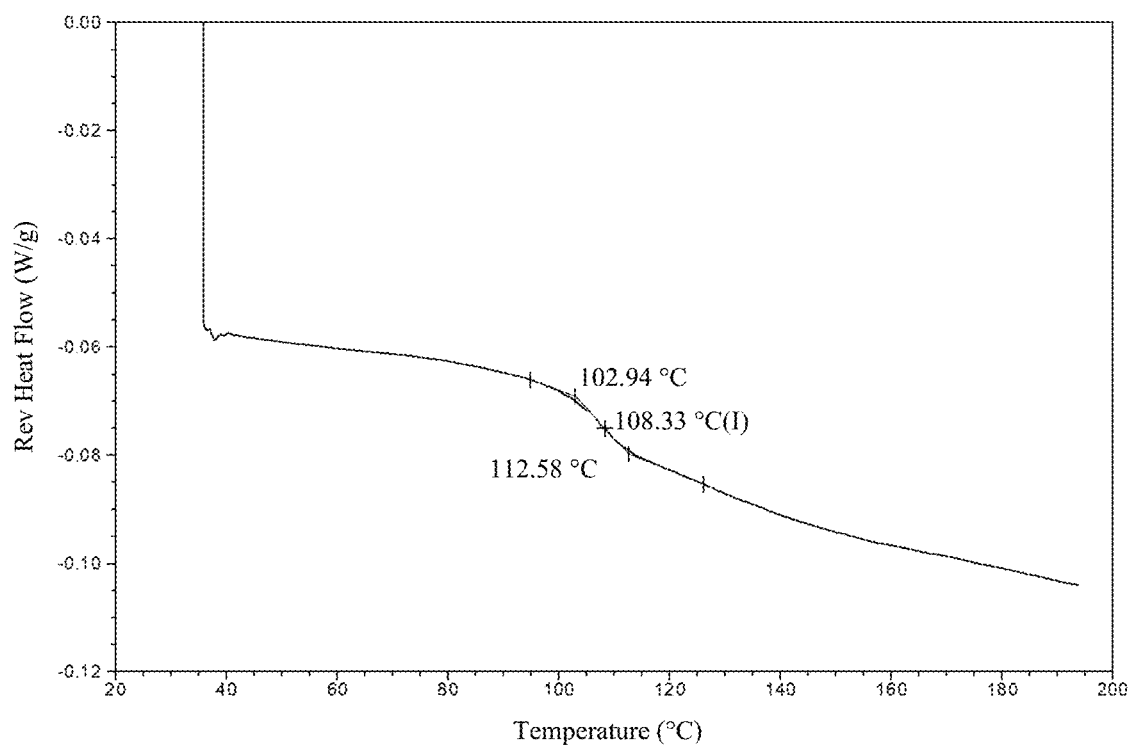
FIG. 5 is a modulated DSC (mDSC) plot of reversing heat flow versus temperature, illustrating the heat flow for one embodiment of the spray-dried formulation and showing that the glass transition temperature (Tg) for that embodiment is 108.3° C.
Figure 6:
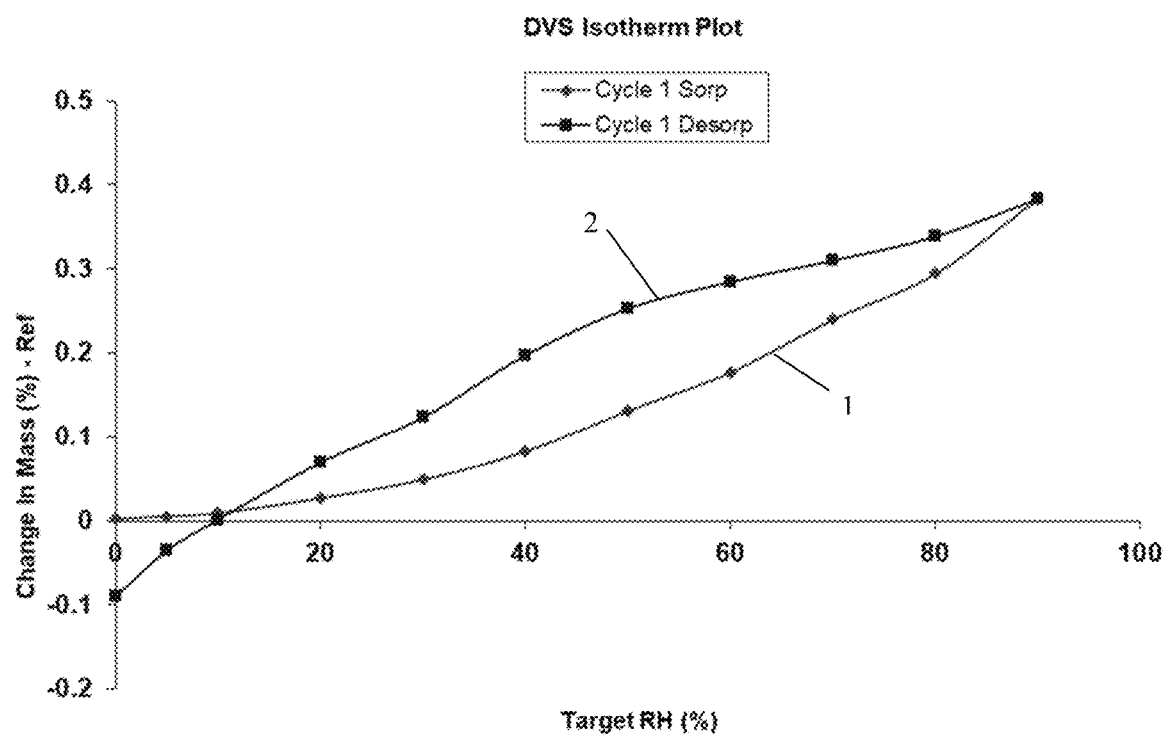
FIG. 6 is a DVS plot of percent change in mass versus target relative humidity, illustrating the change in mass of one embodiment of a crystalline sample of compound I-1 at 25° C. under various relative humidity conditions. The plot provides two isotherms: 1 is the sorption plot, illustrating the change in mass with increasing relative humidity steps; and 2 is the desorption plot, illustrating the change in mass with decreasing relative humidity steps.
Figure 7:
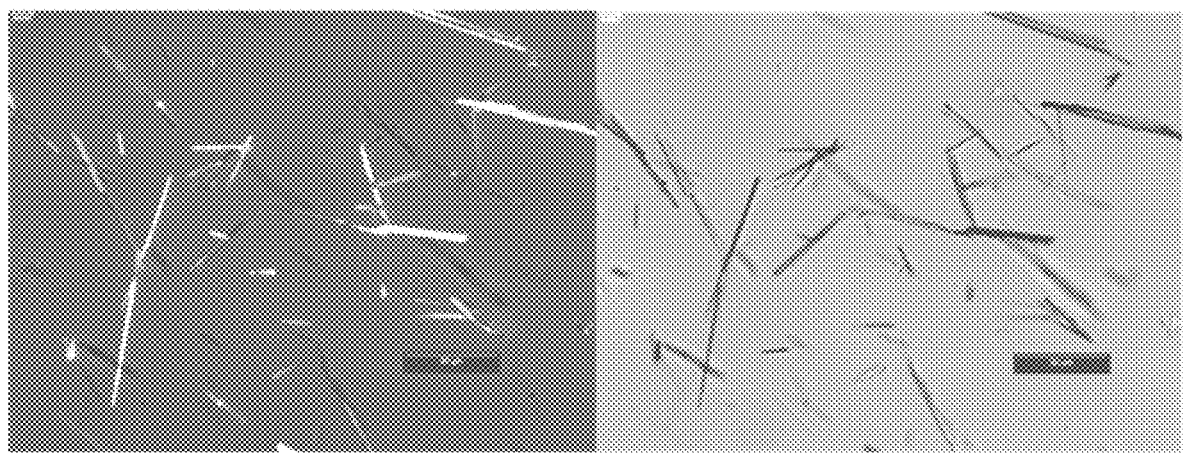
FIG. 7 is a digital image showing a PLM image of a crystalline sample of compound I-1 at 400× magnification.
Figure 8:
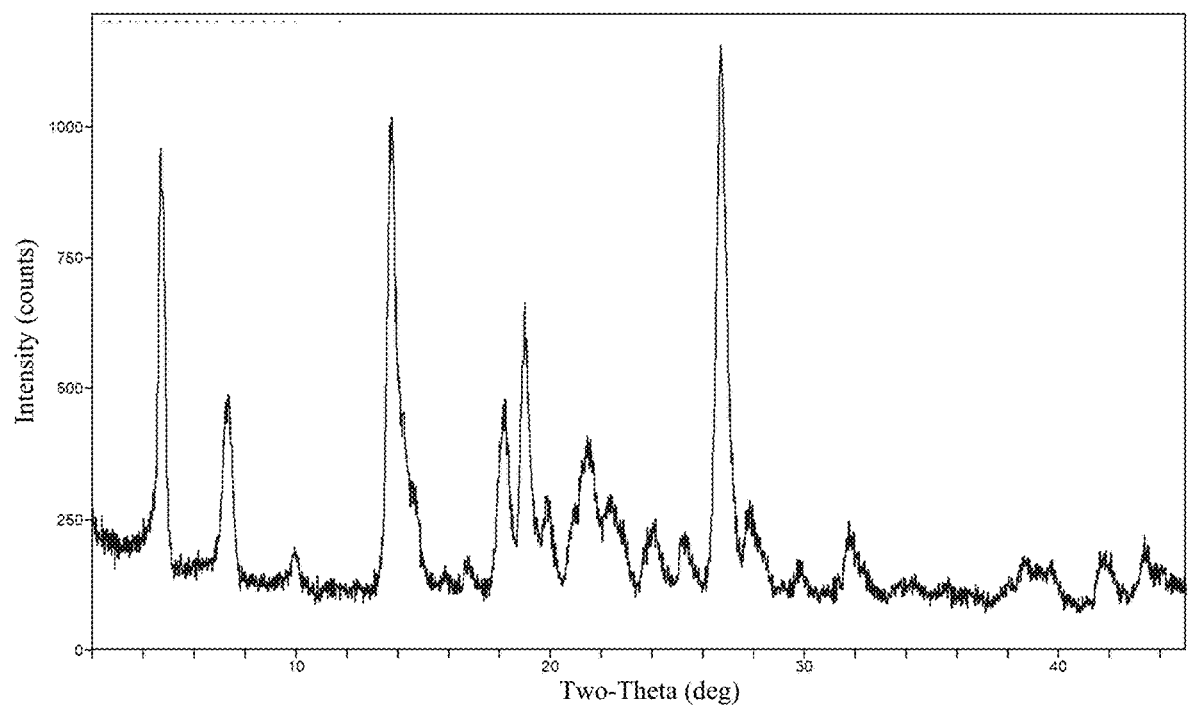
FIG. 8 is a graph of intensity versus scattering angle, illustrating the X-ray powder diffraction pattern of a crystalline sample of compound I-1.
Figure 9:
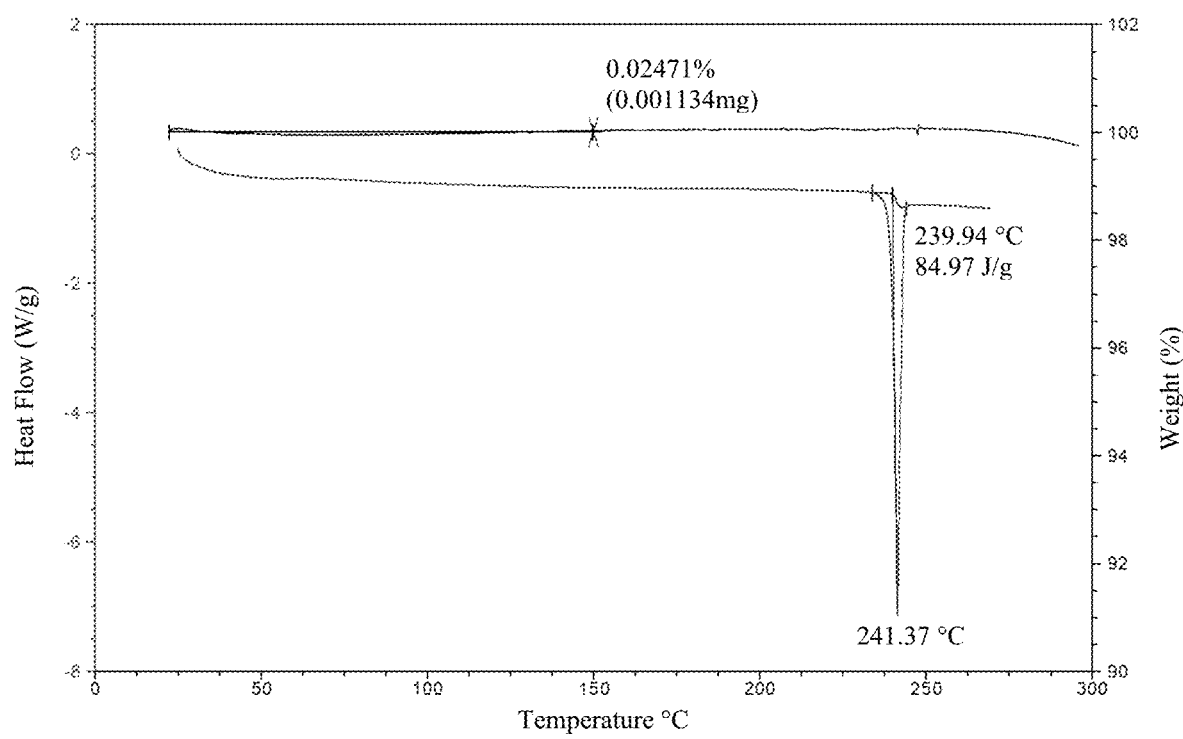
FIG. 9 is a graph of weight and heat flow versus temperature, providing both the thermogravimetry (TGA) and differential scanning calorimetry (DSC) plots for a crystalline sample of compound I-1, illustrating the weight change and heat flow of the formulation at different temperatures.
Figure 10:
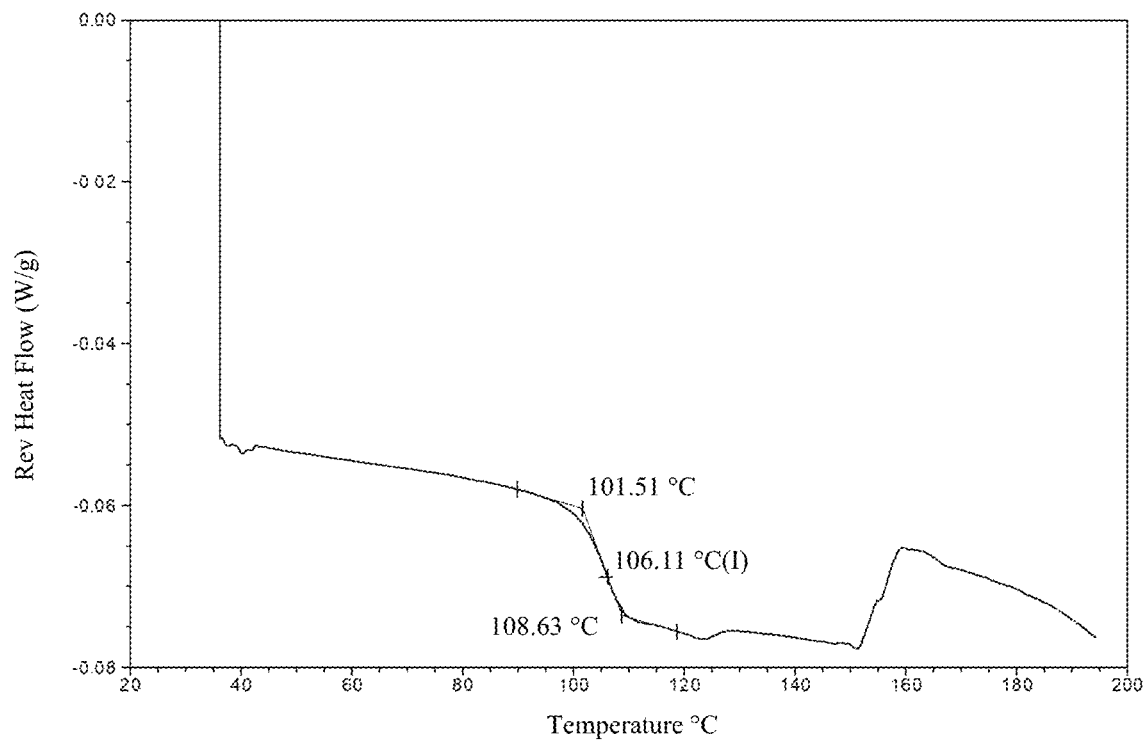
FIG. 10 is an mDSC plot of reversing heat flow versus temperature, illustrating the heat flow for a crystalline sample of compound I-1, and showing that the glass transition temperature (Tg) for the crystalline sample is 106.1° C.
Figure 11:
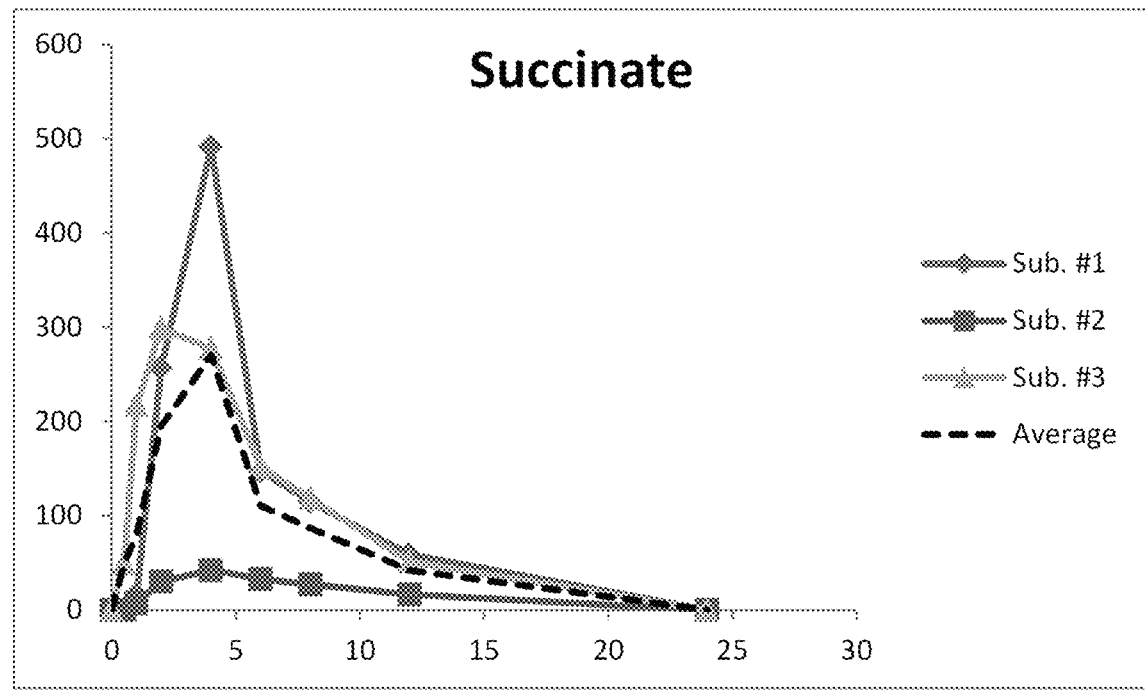
FIG. 11 is a graph of plasma concentration versus time in hours, illustrating the individual plasma concentrations and an average plasma concentration resulting from administering compound I-1 as a succinate co-crystal (compound I-106) to each of the three subjects, with the results normalized to a dose of 5 mg/kg of compound I-1.
Figure 12:
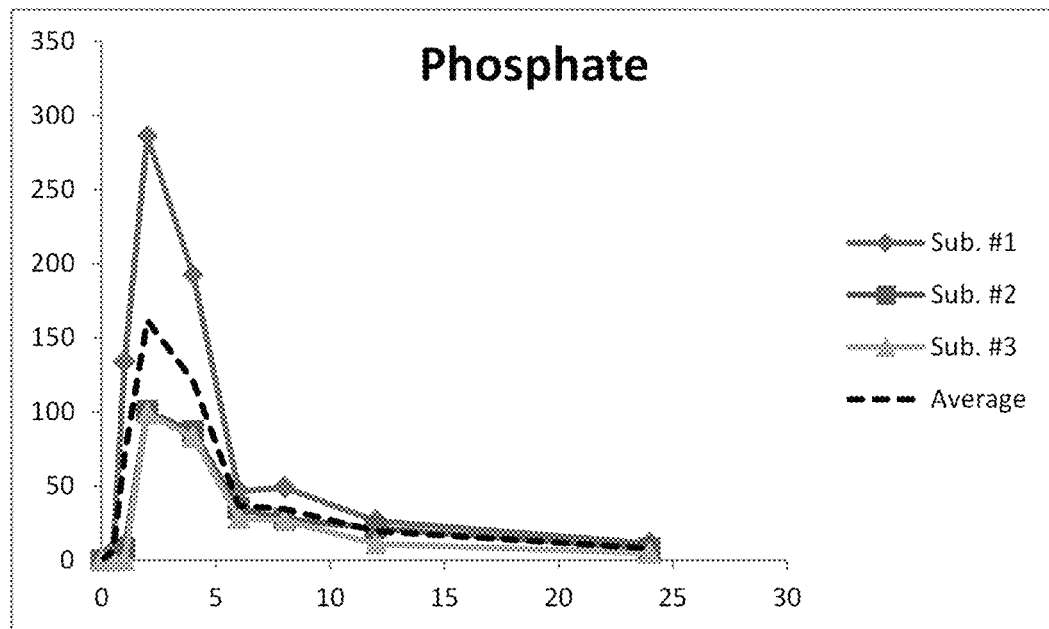
FIG. 12 is a graph of plasma concentration versus time in hours, illustrating the individual plasma concentrations and an average plasma concentration resulting from administering compound I-1 as a phosphate co-crystal (compound I-104) to each of the three subjects, with the results normalized to a dose of 5 mg/kg of compound I-1.
Figure 13:
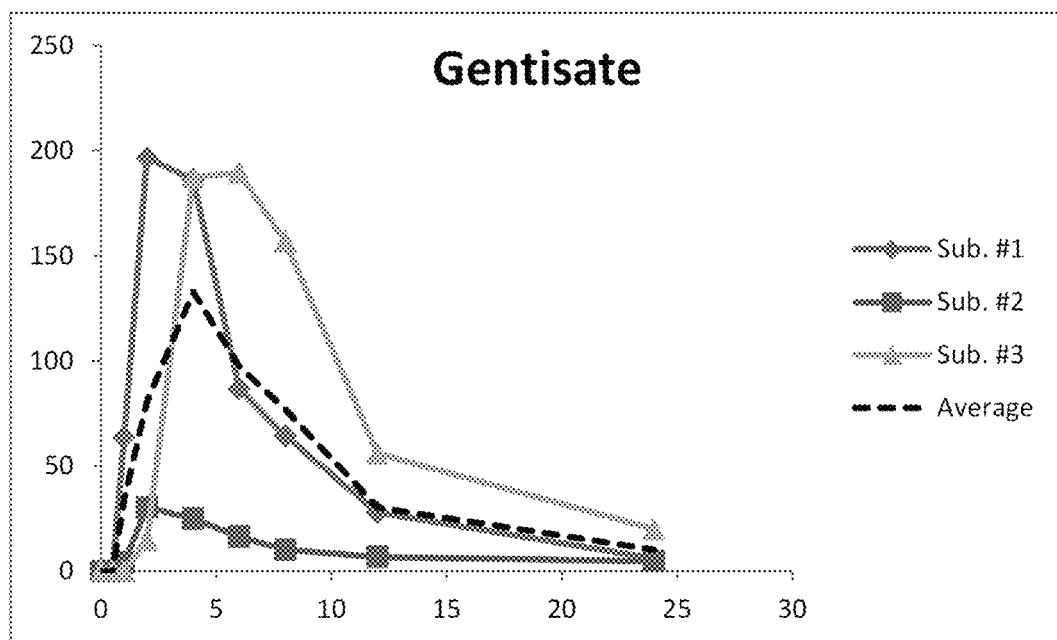
FIG. 13 is a graph of plasma concentration versus time in hours, illustrating the individual plasma concentrations and an average plasma concentration resulting from administering compound I-1 as a gentisate co-crystal (compound I-105) to each of the three subjects, with the results normalized to a dose of 5 mg/kg of compound I-1.
Figure 14:
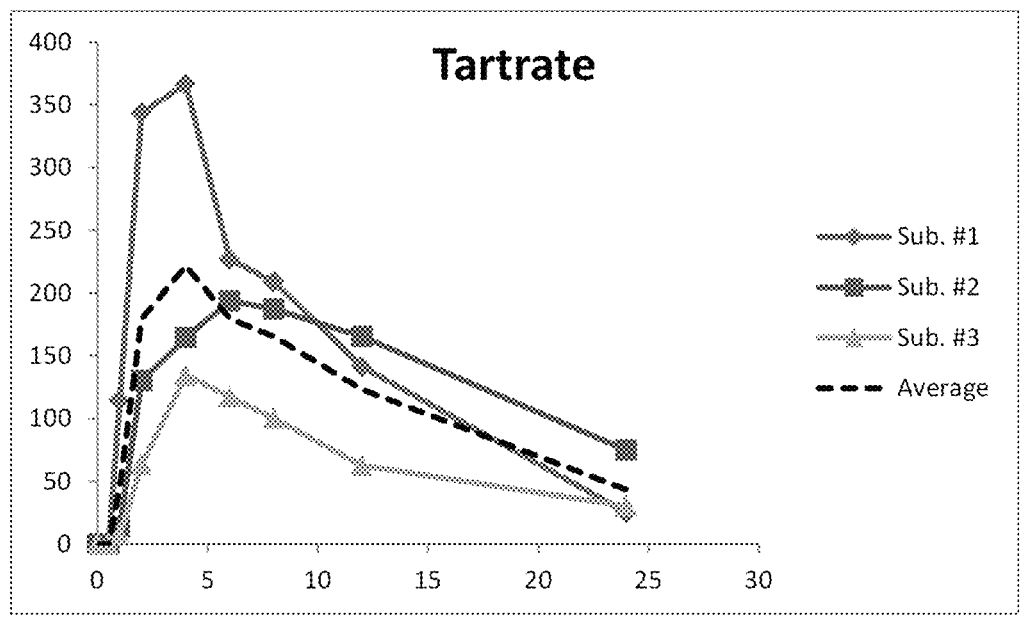
FIG. 14 is a graph of plasma concentration versus time in hours, illustrating the individual plasma concentrations and an average plasma concentration resulting from administering compound I-1 as a tartrate co-crystal (compound I-11) to each of the three subjects, with the results normalized to a dose of 5 mg/kg of compound I-1.
Figure 15:
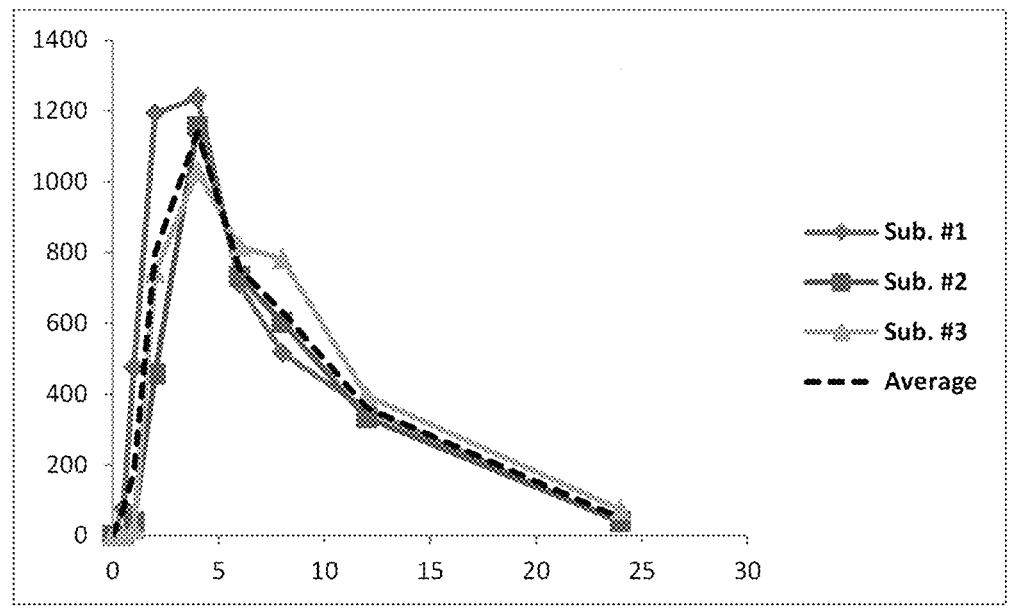
FIG. 15 is a graph of plasma concentration versus time, illustrating the plasma concentration of compound I-1 from each of three subjects, and an average plasma concentration, resulting from administering a dose of one embodiment of the disclosed spray-dried formulation sufficient to provide of a dose of 5 mg/kg of compound I-1.
Figure 16:
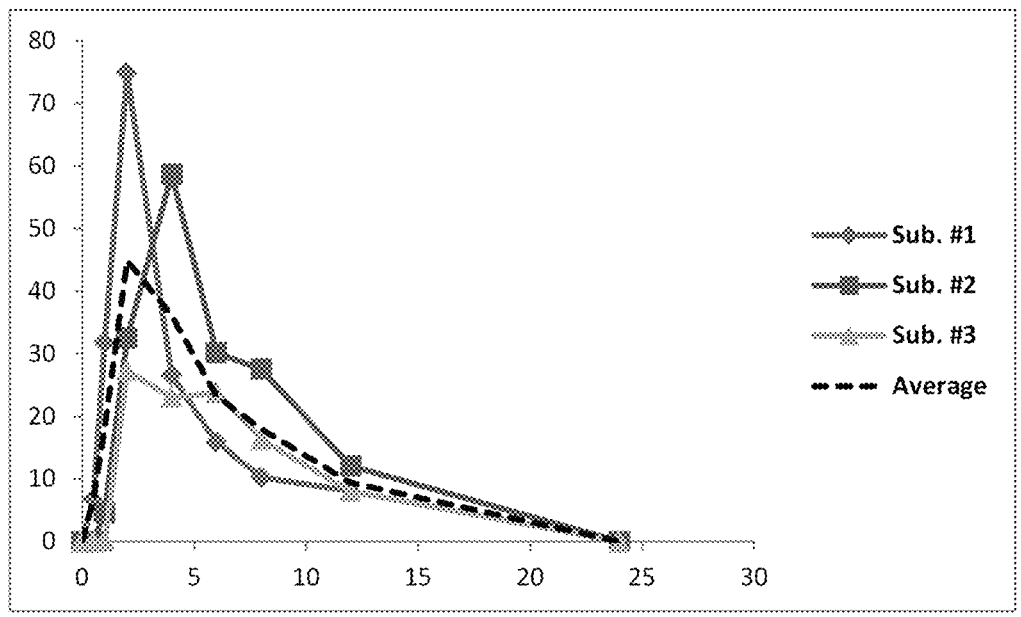
FIG. 16 is a graph of plasma concentration versus time, illustrating the plasma concentration of a metabolite of compound I-1 from each of three subjects, and an average plasma concentration, resulting from administering a dose of one embodiment of the disclosed spray-dried formulation sufficient to provide of a dose of 5 mg/kg of compound I-1.
Figure 17:
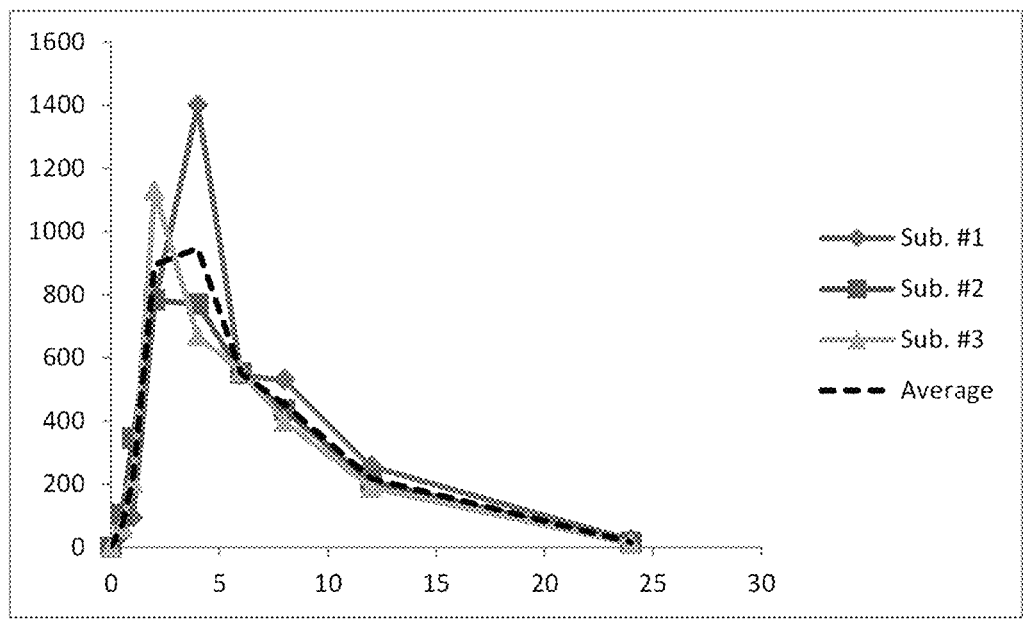
FIG. 17 is a graph of plasma concentration versus time, illustrating the plasma concentration of compound I-1 from each of three subjects, and an average plasma concentration, resulting from administering 5 mg/kg of compound I-1 as a stock solution diluted with orange juice.
Figure 18:
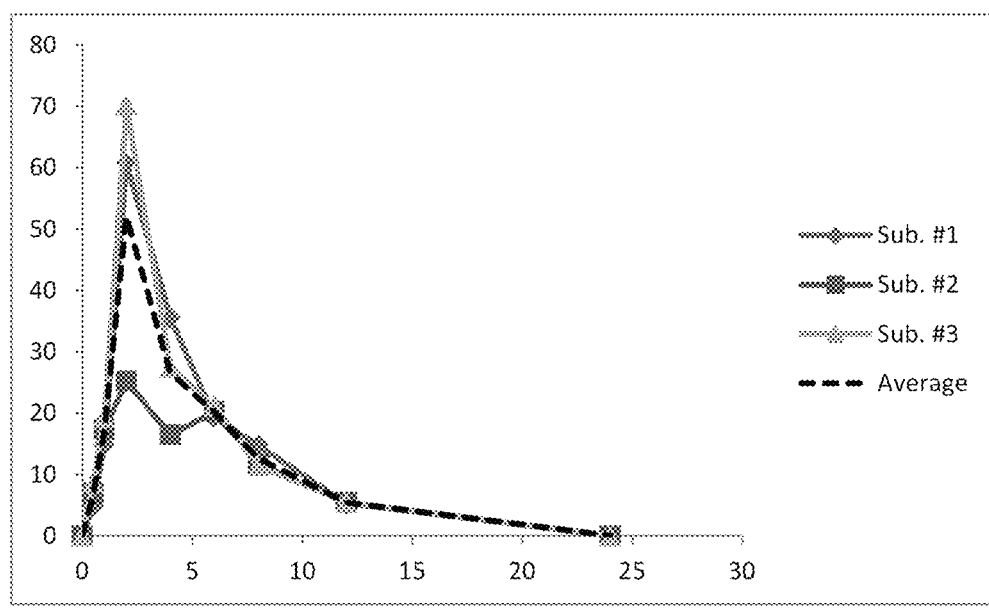
FIG. 18 is a graph of plasma concentration versus time, illustrating the plasma concentration of a metabolite of compound I-1 from each of the three subjects, and an average plasma concentration, resulting from administering 5 mg/kg of compound I-1 as a stock solution diluted with orange juice.

FIGS. 1-10 provide structural and stability data concerning the spray-dried formulation (FIGS. 1-5) and a crystalline sample of compound I-1 (FIGS. 6-10). FIGS. 1 and 6 provide DVS isotherm plots for the spray-dried formulation and crystalline compound, respectively. FIGS. 1 and 6 clearly show that the crystalline compound has a substantially smaller change in mass when exposed to higher relative humidity than the dispersion. FIGS. 2 and 3 demonstrate that the dispersion does not have a substantially crystalline structure, whereas FIGS. 7 and 8 clearly show that the compound I-1 has a crystalline structure.

Example 2

Two groups of male cynomolgus monkeys (n=3/group) were administered test articles in a 3-way crossover design as indicated in Table 2. The washout period between doses was 3-4 days. Test article capsules were prepared such that each capsule contained an equivalent of 25 mg of free base compound I-1. The organic stock solution of compound I-1 was prepared at a concentration of 5 mg/ml using TPGS/PEG400/PG, and was diluted with apple juice within 1 hour of dosing (PO) at 1 part stock solution to 3 parts apple juice.

TABLE 2

Study design

| Group | Phase | Test Article | Test article Description | Dose, mg of compound I-1 | Corrected dose, mg compound I-1/kg, Average/(range) |
|---|---|---|---|---|---|
| 1 | I | Capsule | Phosphate co-crystal | 25 | 5.99 |
|  | II | Capsule | Gentisate co-crystal | 25 | 5.96 |
|  | III | Capsule | Spray-dried Dispersion (SDD) | 25 | 5.90 |
| 2 | I | Capsule | Succinate co-crystal | 25 | 5 |
|  | II | Capsule | Tartrate co-crystal | 25 | 5.06 |
|  | III | Liquid | Organic stock in apple juice | — | 5 |

FIGS. 11-14 provide graphs of the plasma concentrations obtained from administering the co-crystal formulations of compound I-1 to monkeys. And Table 3 provides pharmacokinetic (PK) data for the co-crystal formulations, including the average area under the curve (AUC) and percent bioavailability.

TABLE 3

AUC and percent bioavailability (% F)

| Test Article | Average $AUC_{0-24h}$ ± SD (5 mg/kg basis) | % F |
|---|---|---|
| Phosphate co-crystal | 921 ± 446 | 7.9 |
| Succinate co-crystal | 1470 ± 1000 | 12.7 |
| Gentisate cocystal | 1140 ± 811 | 9.8 |
| Tartrate co-crystal | 2860 ± 1120 | 24.7 |

FIG. 19 provides PK data for one embodiment of the disclosed spray-dried formulation, and the organic/juice formulation. FIG. 19 demonstrates that administration of the spray-dried formulation resulted in 88% bioavailability of compound I-1.

Example 3

Rats were administered either compound I-1 or a potential prodrug form of compound I-1. Area under the curve (AUC) and percent bioavailability (% F) data concerning compound I-1 resulting from the prodrug administration were determined by standard techniques known to a person of ordinary skill in the art (Table 4).

TABLE 4

AUC and percent bioavailability (% F) of compound I-1 after administration of potential prodrugs of I-1

| Compound Code | Prodrug Type | Form | Dose I-1 equiv. | Rat AUC$_{last}$ | % F |
|---|---|---|---|---|---|
| I-1 | parent | | iv 1 mg/kg | 1051 | |
| I-18 | alpha-methyl, methylene-Phosphate | | | 1050 | 30 |
| I-20 | alpha-methyl, methylene-Phosphate | Disodium salt of I-18 | 3.73 mg/kg | 3790 | >100 |
| I-45 | | | | 319 | 10 |
| I-46 | Phosphate | | | 4510 | >100 |
| I-62 | Phosphate | | | 694 | 25 |
| I-21 | HCl salt of I-35, partially crystalline | | 3.68 mg/kg | 1850 | 56.6 |
| I-61 | Pegylated Ester | | | 2530 | 103 |
| I-32 | N-acetyl methylpiperazine | Free base, crystalline | 3.44 mg/kg | 2310 | 75 |

Example 4

Formation of N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide Benzenesulfonic Acid Salt (I-65)

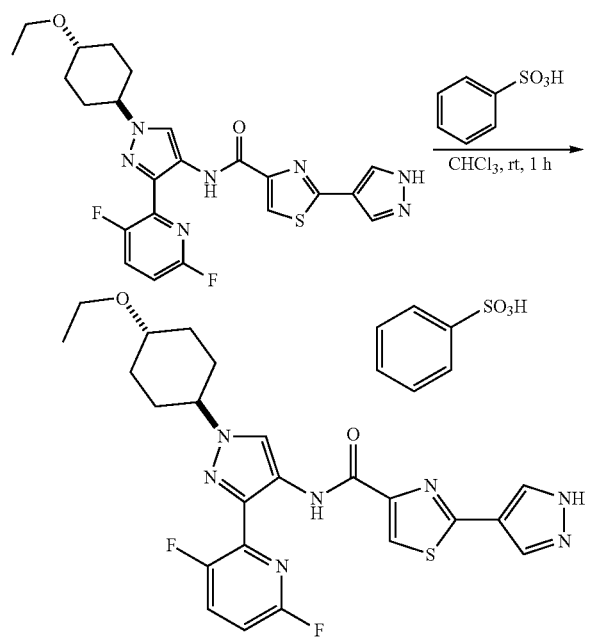

N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide (0.050 g, 0.100 mmol, 1.0 eq) was dissolved in chloroform (1.0 eq) to obtain a clear colorless solution. Benzenesulfonic acid (0.019 g, 0.120 mmol, 1.2 eq) was added and a precipitate formed over the next 15 minutes. The reaction was stirred at room temperature for 1 hour and the precipitate was isolated by filtration to obtain the title compound (0.038 g) as a white solid; $^1$H nmr (400 MHz, D$_6$-DMSO) δ 8.53 (1H, s, thiazoleH-5 or pyrazoleH-5), 8.30 (1H, s, 1H of thiazoleH-5 or pyrazoleH-5, pyrazoleH-3, H-5), 8.29 (1H, s, 1H of thiazoleH-5 or pyrazoleH-5, pyrazoleH-3, H-5), 8.28 (1H, s, 1H of thiazoleH-5 or pyrazoleH-5, pyrazoleH-3, H-5), 8.08 (1H, dt, J 9.0, 6.5 Hz, pyridineH-4 or H-5), 7.59-7.56 (2H, m, 2H of C$_6$H$_5$SO$_3$H), 7.32-7.27 (4H, m, pyridineH-4 or H-5, 3H of C$_6$H$_5$SO$_3$H), 4.33 (1H, tt, J 11.5, 3.5 Hz, cyclohexaneH-1 or H-4), 3.47 (2H, q, J 7.0 Hz, OCH$_2$CH$_3$), 3.34 (1H, tt, J 10.5, 3.5 Hz, cyclohexaneH-1 or H-4), 2.08 (4H, m, 4H of cyclohexaneH-2, H-3, H-5, H-6), 1.85 (2H, m, cyclohexaneH-2, H-3, H-5, H-6), 1.35 (2H, m, 2H of cyclohexaneH-2, H-3, H-5, H-6), 1.10 (3H, t, J 7.0 Hz, OCH$_2$CH$_3$); $^{19}$F nmr (380 MHz, D$_6$-DMSO) δ −73.0 (dd, 24.5, 2.5 Hz), −124.2 (ddd, J 26.0, 9.5, 1.5 Hz); m/z: 500 [M+H]$^+$.

Example 5

Formation of N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide Sodium Salt (I-67)

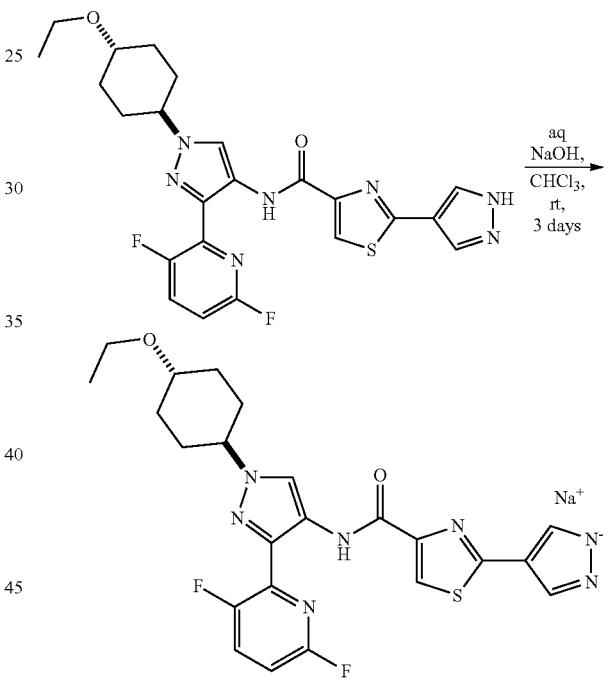

N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide (0.062 g, 0.124 mmol, 1.0 eq) was dissolved in chloroform (2.0 mL) to obtain a clear solution. Sodium hydroxide (0.05 mL of a 3M aqueous solution, 0.149 mmol, 1.2 eq) was added and the reaction was stirred at room temperature for 3 days. No precipitate was formed. The reaction was concentrated and further concentrated from acetonitrile (5 mL) to obtain the title compound as a white solid; $^1$H nmr (400 MHz, D$_6$-DMSO) δ 8.53 (1H, s, thiazoleH-5 or pyrazoleH-5), 8.13 (3H, br s, thiazoleH-5 or pyrazoleH-5, pyrazoleH-3, H-5), 8.08 (1H, dt, J 9.5, 6.5 Hz, pyridineH-4 or H-5), 7.28 (1H, ddd, J 9.0, 3.0, 2.5 Hz, pyridineH-4 or H-5), 4.33 (1H, tt, J 11.5, 3.0 Hz, cyclohexaneH-1 or H-4), 3.47 (2H, q, J 7.0 Hz, OCH$_2$CH$_3$), 3.35 (1H, tt, J 11.0, 3.5 Hz, cyclohexaneH-1 or H-4), 2.08 (4H, m, 4H of cyclohexaneH-2, H-3, H-5, H-6), 1.85 (2H, m, cyclohexaneH-2, H-3, H-5, H-6), 1.35 (2H, m, 2H of cyclohexaneH-2, H-3, H-5, H-6), 1.10 (3H, t, J 7.0 Hz, OCH$_2$CH$_3$); m/z: 500 [M+H]$^+$.

Example 6

Formation of N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide tartaric acid cocrystal (I-66)

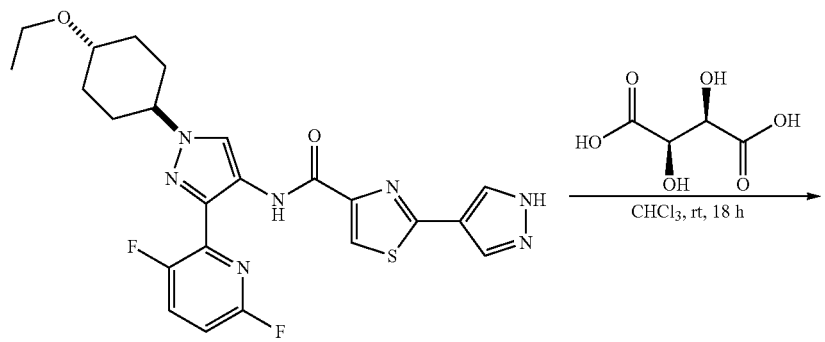

L-Tartaric acid (0.017 g, 0.110 mmol, 1.1 eq) was added to a solution of N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide (0.050 g 0.100 mmol, 1.0 eq) in chloroform (1.0 eq). A white solid slowly precipitated. The reaction was stirred at room temperature for 18 hours and the precipitate isolated by filtration to obtain the title compound (0.055 g, 85%) as a white solid; $^1$H nmr (400 MHz, D$_6$-DMSO) δ 8.53 (1H, s, thiazoleH-5 or pyrazoleH-5), 8.29 (3H, br s, thiazoleH-5 or pyrazoleH-5, pyrazoleH-3, H-5), 8.08 (1H, dt, J 9.5, 6.5 Hz, pyridineH-4 or H-5), 7.28 (1H, dt, J 9.0, 3.0 Hz, pyridineH-4 or H-5), 5.05 (2H, br s, 2×OH), 4.33 (1H, tt, J 11.5, 3.5 Hz, cyclohexaneH-1 or H-4), 4.29 (2H, s, COC$\underline{H}$(OH)C$\underline{H}$(OH)CO), 3.47 (2H, q, J 7.0 Hz, OC$\underline{H}_2$CH$_3$), 3.34 (1H, tt, J 10.5, 3.5 Hz, cyclohexaneH-1 or H-4), 2.08 (4H, m, 4H of cyclohexaneH-2, H-3, H-5, H-6), 1.85 (2H, m, cyclohexaneH-2, H-3, H-5, H-6), 1.35 (2H, m, 2H of cyclohexaneH-2, H-3, H-5, H-6), 1.09 (3H, t, J 7.0 Hz, OCH$_2$C$\underline{H}_3$); $^{13}$C nmr (100 MHz, D$_6$-DMSO) δ 173.5, 161.7, 157.7, 157.6 (d, J 236.0 Hz), 153.5 (dd, J 259.0, 4.0 Hz), 149.2, 138.2 (t, J 15.0 Hz), 132.6 (d, J 9.0 Hz), 131.9 (dd, J 22.5, 9.0 Hz), 123.5, 121.5, 120.2, 116.2, 109.2 (dd, J 43.0, 8.5 Hz), 76.0, 72.6, 63.0, 60.8, 30.9, 30.9, 16.1; $^{19}$F nmr (380 MHz, D$_6$-DMSO) δ −73.0-124.2; m/z: 500 [M+H]$^+$.

Example 7

Formation of N-(3-(3,6-difluoropyridin-2-yl)-1-(trans-4-ethoxycyclohexyl)-1H-pyrazol-4-yl)-2-(1H-pyrazol-4-yl)thiazole-4-carboxamide hemi((2R,3R)-2,3-dihydroxysuccinate) (I-11)

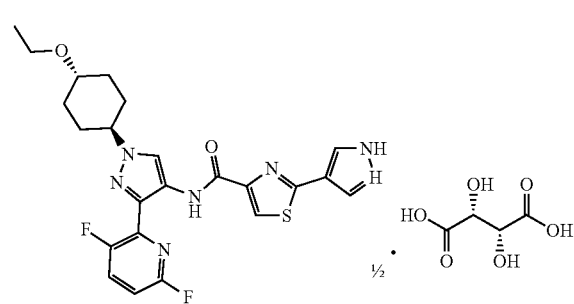

A MeOH (1.3 mL) solution of (L)-Tartaric Acid (750.5 mg, 5 mmol) was added dropwise to a CH$_2$Cl$_2$-MeOH (60 mL-5 mL) solution of N-(3-(3,6-difluoropyridin-2-yl)-1-(trans-4-ethoxycyclohexyl)-1H-pyrazol-4-yl)-2-(1H-pyrazol-4-yl)thiazole-4-carboxamide (5.0 g, 10 mmol) at 35° C., additional MeOH (5 mL) and CH$_2$Cl$_2$ (100 mL) were added after 15 minutes. The mixture was stirred at 35° C. for another 20 hours, and then cooled to room temperature. Solid was collected by filtration, washed with CH$_2$Cl$_2$, and was further dried in vacuo. The title compound was obtained as a white solid: 3.48 g (60.7% yield); $^1$H NMR (400 MHz, DMSO-d$_6$) δ 13.32 (br s, 1H), 12.74 (br s, 1H), 11.45 (s, 1H), 8.51 (s, 1H), 8.27 (s, 1H), 8.43-8.14 (m, 2H), 8.07 (ddd, J=9.8, 8.8, 6.3 Hz, 1H), 7.27 (ddd, J=8.8, 2.9, 2.9 Hz, 1H), 5.07 (br s, 1H), 4.31 (tt, partially overlapped, J=11.7, 3.2 Hz, 1H), 4.27 (s, 1H), 3.45 (q, J=7.0 Hz, 2H), 3.33 (tt, partially overlapped with H$_2$O, J=10.7, 3.6 Hz, 1H), 2.08-2.03 (m, 4H), 1.88-1.78 (m, 2H), 1.38-1.28 (m, 2H), 1.08 (t, J=7.0 Hz, 3H); $^{19}$F NMR (376 MHz, DMSO-d$_6$) δ −72.97 (ddd, J=28.1, 6.8, 3.8 Hz), −124.18 (ddd, J=28.1, 10.3, 3.2 Hz); LRMS (M+H) m/z 500.2.

A second crop (1.58 g, combined yield: 88%) of the same compound was obtained from the filtrate, after removal of the solvent in vacuo, and resuspended the solid in CH$_2$Cl$_2$-MeOH (25 mL-2 mL) at 35° C. overnight.

Example 8

Preparation of N-(3-(3,6-difluoropyridin-2-yl)-1-(trans-4-ethoxycyclohexyl)-1H-pyrazol-4-yl)-2-(1H-pyrazol-4-yl)thiazole-4-carboxamide (I-1)—Method 1

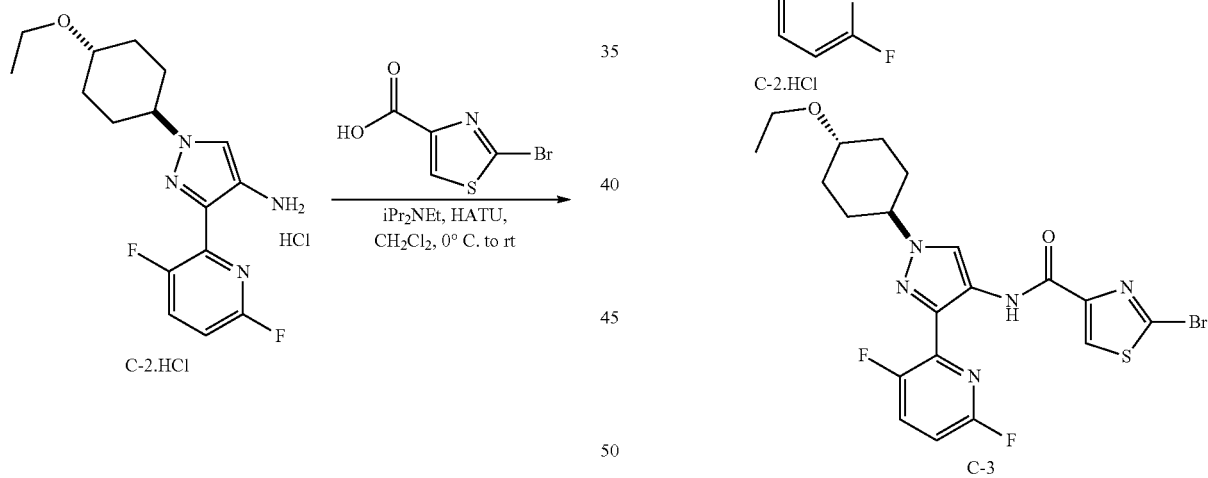

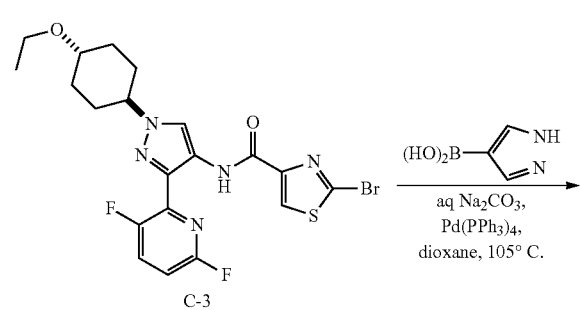

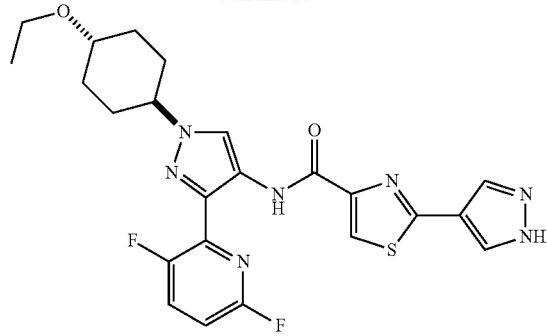

I. Preparation of 2-bromo-N-(3-(3,6-difluoropyridin-2-yl)-1-(trans-4-ethoxycyclohexyl)-1H-pyrazol-4-yl)thiazole-4-carboxamide C-3 from C2.HCl

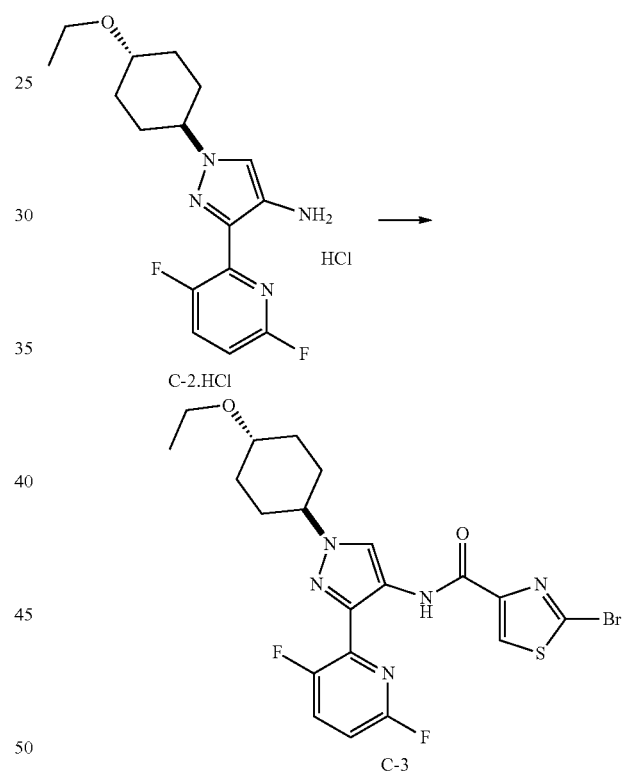

Diisopropylethylamine (8.5 mL, 48.95 mmol, 3.5 eq) was added to a mixture of the aminopyrazole C-2.HCl (5.00 g, 13.99 mmol, 1.0 eq) and bromothiazolecarboxylic acid (3.20 g, 15.38 mmol, 1.1 eq) in dichloromethane (50 mL) at 0° C. HATU (5.85 g, 15.38 mmol, 1.1 eq) added. The reaction was stirred at 0° C. for 10 minutes and then at room temperature for 4 hours. The reaction was diluted with CH$_2$Cl$_2$ (100 mL). The organics were washed with NaHCO$_3$ (150 mL), NH$_4$Cl (150 mL) and brine (100 mL), dried (Na$_2$SO$_4$) and concentrated under reduced pressure. The residue was suspended in EtOAc-hexane (1:1, 50 mL) and the resulting solid was isolated by filtration. The solid was suspended in NaHCO$_3$ (50 mL) for 1 hour to remove residual coupling agent before isolating by filtration and drying under vacuum to obtain C-3 (5.3 g, 74%) as an off-white solid; IR ν$_{max}$ (film) 3290, 3121, 2942, 2865, 1671, 1615, 1552, 1485, 1431, 1377, 1237, 1154, 1104, 1056, 1011, 819, 787, 731 cm$^{-1}$; $^1$H nmr (400 MHz, CDCl$_3$) δ 8.42 (1H, d, J 0.5 Hz, thiazoleH-5 or pyrazoleH-5), 8.09 (1H, s, thiazoleH-5 or pyrazoleH-5), 7.63 (1H, td, J 9.0, 6.0 Hz, pyridineH-4 or H-5), 6.85 (1H, ddd, J 9.0, 3.5, 2.5 Hz, pyridineH-4 or H-5), 4.26 (1H, tt, J 11.5, 4.0 Hz, cyclohexaneH-1 or H-4), 3.55 (2H, q, J 7.0 Hz, OCH$_2$CH$_3$), 3.36 (1H, tt, J 10.5, 4.0 Hz, cyclohexaneH-1 or H-4), 2.28 (2H, br d, J 13.0 Hz, 2H of cyclohexaneH-2, H-3, H-5, H-6), 2.21 (2H, m, 2H of cyclohexaneH-2, H-3, H-5, H-6), 1.91, 1.84 (2H, 2dd AB system, J 13.0, 3.5 Hz, 2H of cyclohexaneH-2, H-3, H-5, H-6), 1.46 (2H, m, 2H of cyclohexaneH-2, H-3, H-5, H-6), 1.22 (3H, t, J 7.0 Hz, OCH$_2$CH$_3$); $^{13}$C nmr (100 MHz, CDCl$_3$) δ 157.6 (d, J 238.0 Hz), 156.9, 153.3 (dd, J 260.0, 8.5 Hz), 150.0, 138.6 (t, J 14.0 Hz), 136.1, 133.1 (d, J 8.5 Hz), 129.8 (dd, J 23.0, 8.5 Hz), 126.7, 121.7, 119.2, 107.8 (dd, J 39.5, 5.5 Hz), 76.4, 63.6, 61.5, 31.1, 30.9, 15.7; $^{19}$F nmr (380 MHz, CDCl$_3$) δ −72.3, −124.9; m/z: 536, 534 [M+Na]$^+$, 514, 512 [M+H]$^+$. The filtrate from the initial trituration was purified by column chromatography (20→80% EtOAc-hexane) to obtain further C-3 (0.8 g, 9%) as a pink foam.

II. Preparation of N-(3-(3,6-difluoropyridin-2-yl)-1-(trans-4-ethoxycyclohexyl)-1H-pyrazol-4-yl)-2-(1H-pyrazol-4-yl)thiazole-4-carboxamide (I-1)

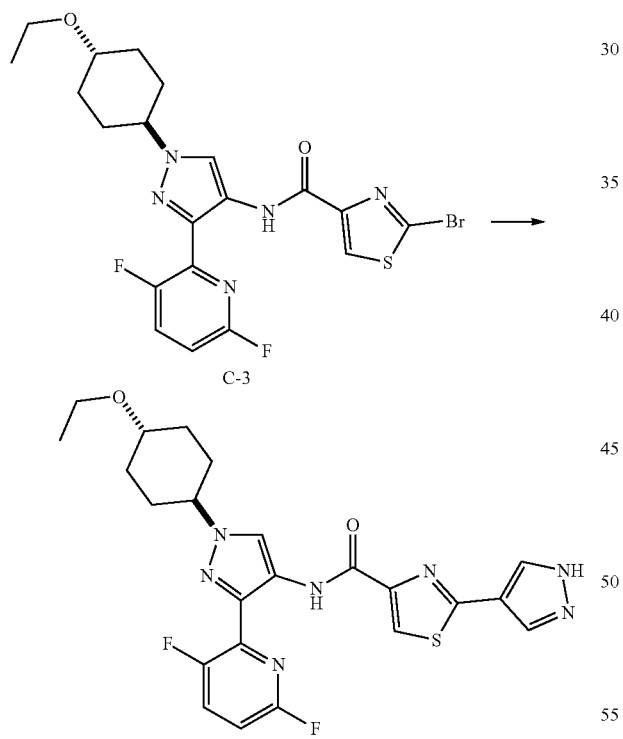

Dioxane (400 mL) was added to a mixture of the bromothiazole C-3 (25.0 g, 48.8 mmol, 1.0 eq) and pyrazole-4-boronic acid (8.2 g, 73.2 mmol, 1.5 eq) followed by aqueous solution of sodium carbonate (73.3 mL of a 2M solution, 146.5 mmol, 3.0 eq). The reaction mixture was degassed by bubbling argon through for five minutes.

Tetrakis(triphenylphosphine)palladium (1.4 g, 1.2 mmol, 0.025 eq) was added and the reaction further degassed before heating to 105° C. for 6 hours. The reaction was filtered through Celite® while hot, eluting with EtOAc (200 mL). The filtrate was concentrated to approximately 150 mL, upon which a precipitate formed. The precipitate was isolated by filtration. The filtrate was concentrated to remove the remaining organics, filtered to remove more precipitate, diluted with water-brine (1:2, 300 mL) and extracted with EtOAc (3×200 mL). The combined organics were combined, dried (Na$_2$SO$_4$) and concentrated under reduced pressure. The combined precipitates and extracts were loaded onto silica. Column chromatography (silica, 0→10% MeOH—CH$_2$Cl$_2$) yielded the title compound (16.5 g, 68%) as a white solid; IR ν$_{max}$(film) 3229, 2938, 2861, 1663, 1615, 1589, 1549, 1482, 1425, 1377, 1237, 1104, 1055, 972, 930, 903, 875, 820, 786, 715, 664 cm$^{-1}$; $^1$H nmr (400 MHz, CDCl$_3$) δ 8.52 (1H, s, thiazoleH-5 or pyrazoleH-5), 8.24 (2H, s, NHpyrazoleH-3, H-5), 8.07 (1H, s, thiazoleH-5 or pyrazoleH-5), 7.41 (1H, td, J 9.0, 6.0 Hz, pyridineH-4 or H-5), 6.86 (1H, ddd, J 9.0, 3.5, 2.5 Hz, pyridineH-4 or H-5), 4.28 (1H, tt, J 11.5, 4.0 Hz, cyclohexaneH-1 or H-4), 3.57 (2H, q, J 7.0 Hz, OCH$_2$CH$_3$), 3.37 (1H, tt, J 11.0, 4.0 Hz, cyclohexaneH-1 or H-4), 2.26 (4H, m, 4H of cyclohexaneH-2, H-3, H-5, H-6), 1.92, 1.86 (2H, 2dd AB system, J 13.0, 3.5 Hz, 2H of cyclohexaneH-2, H-3, H-5, H-6), 1.50, 1.44 (2H, 2dd AB system, J 13.0, 3.5 Hz, 2H of cyclohexaneH-2, H-3, H-5, H-6), 1.23 (3H, t, J 7.0 Hz, OCH$_2$CH$_3$); $^{13}$C nmr (100 MHz, CDCl$_3$) δ 160.6, 158.6, 158.3, 156.3, 154.8, 152.2, 150.2, 138.9, 133.0 (d, J 9.0 Hz), 129.9 (dd, J 23.5, 9.0 Hz), 122.0, 121.6, 119.4, 117.2, 107.5 (dd, J 40.5, 5.0 Hz), 76.4, 63.7, 61.5, 31.1, 30.9, 15.7; $^{19}$F nmr (380 MHz, CDCl$_3$) δ −72.7 (dddd, J 27.0, 9.5, 5.5, 4.0 Hz), −124.3 (ddd, J 27.5, 9.5, 3.0 Hz); m/z: 500 [M+H]$^+$ (found [M+H]$^+$, 500.1687, C$_{23}$H$_{23}$F$_2$N$_7$O$_2$S requires [M+H]$^+$ 500.1675).

Example 9

Preparation of N-(3-(3,6-difluoropyridin-2-yl)-1-(trans-4-ethoxycyclohexyl)-1H-pyrazol-4-yl)-2-(1H-pyrazol-4-yl)thiazole-4-carboxamide (I-1)—Method 2

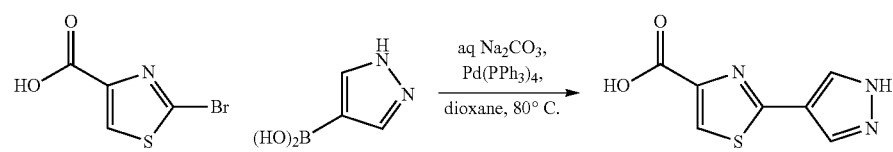

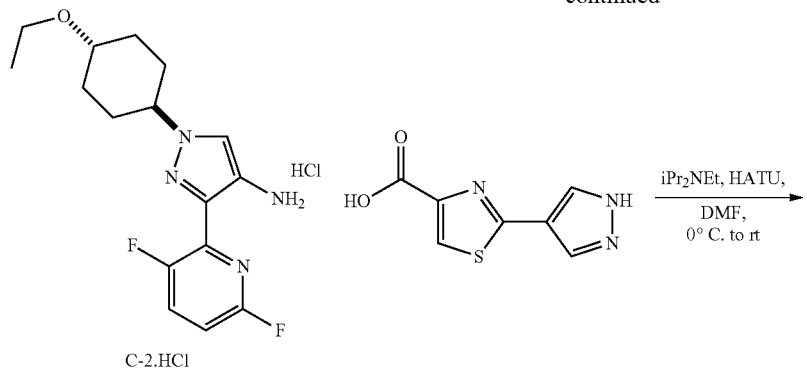

I. Formation of 2-(1H-pyrazol-4-yl)thiazole-4-carboxylic acid

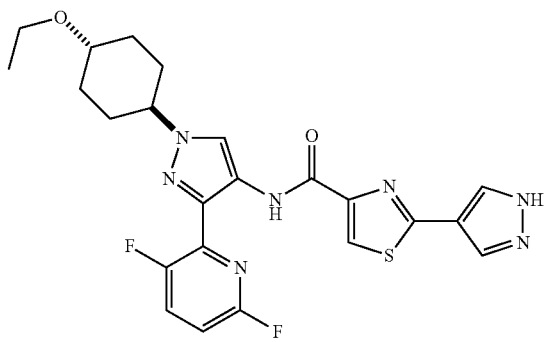

A 1,4-Dioxane-H₂O (32 mL-8 mL) solution of 2-bromothiazole-4-carboxylic acid (2.08 g, 10 mmol, 1.0 eq), (1H-pyrazol-4-yl)boronic acid (3.36 g, 30 mmol, 3.0 eq), tetrakis(triphenylphosphine)palladium (0.23 g, 0.2 mmol, 0.02 eq) and sodium carbonate (3.18 g, 30 mmol, 3.0 eq) was degassed, backed-filled with nitrogen gas, three times. The cloudy solution was stirred at 60° C. for 2 hours (by LC-MS, starting material:product≠1:1), then at 100° C. for a further 3 hours, until the reaction went to completion as monitored by LC-MS. After removal of organic solvent under reduced pressure, the crude mixture was diluted with water (100 mL) and mixed well. The aqueous solution was passed through a Celite® pad, and washed with water. While stirring, the filtrate with acidified with 6M HCl aq. solution (about 11 mL) until pH=1-2. The precipitate was collected by filtration, washed with water and further dried in vacuo to obtain the title compound (1.79 g 92% yield) as a light tan color solid; ¹H nmr (400 MHz, D₆-DMSO) δ 13.11 (2H, br s, NH, OH), 8.28 (1H, s, thiazoleH-4), 8.17 (2H, br s, pyrazoleH-3, H-5); m/z: 196 [M+H]⁺.

II. Preparation of N-(3-(3,6-difluoropyridin-2-yl)-1-(trans-4-ethoxycyclohexyl)-1H-pyrazol-4-yl)-2-(1H-pyrazol-4-yl)thiazole-4-carboxamide (I-1)

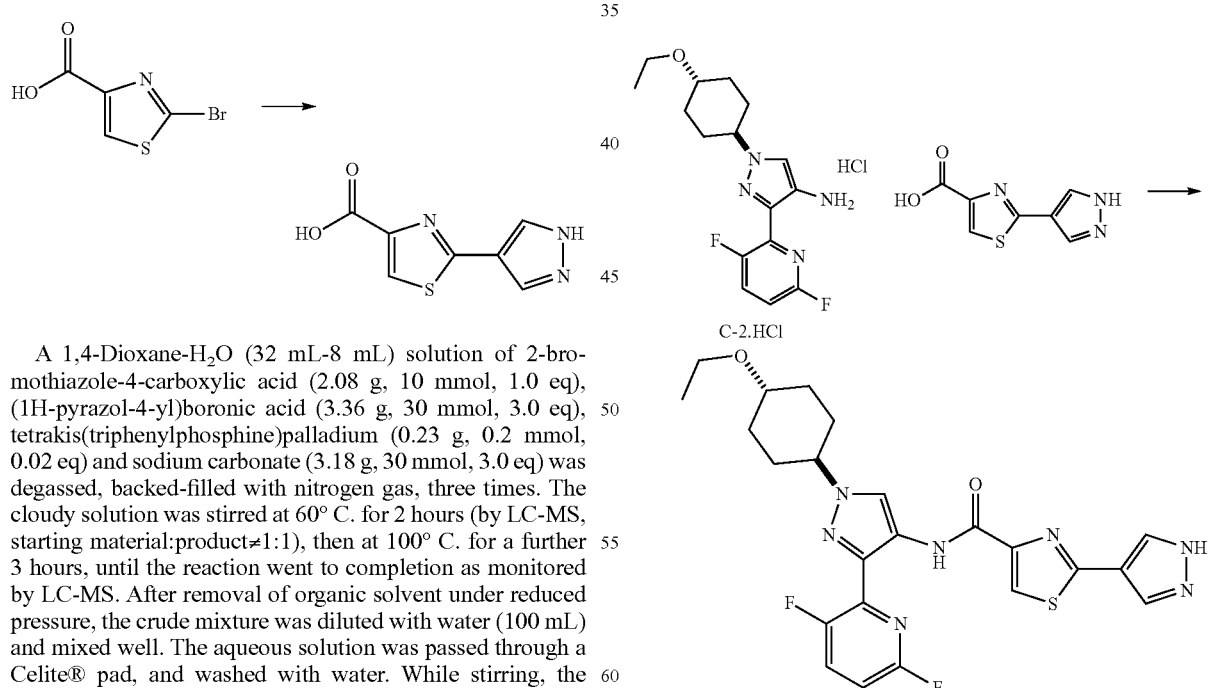

A mixture of the C2.HCl aminopyrazole hydrochloride (1.00 g, 2.80 mmol, 1.0 eq) and 2-(1H-pyrazol-4-yl)thiazole-4-carboxylic acid (0.65 g, 3.36 mmol, 1.2 eq) in dimethylformamide (14 mL) was cooled to 0° C. and diisopropylethylamine (1.22 mL, 6.99 mmol, 2.5 eq) added. A solution resulted to which was added HATU (1.17 g, 3.08 mmol, 1.1 eq). The solution was stirred at 0° C. for 15 minutes and room temperature for 1 hour, before adding the reaction to water (75 mL). A solid formed that collapsed to a gum. The liquid was decanted isolating any solid by filtration. The gum and solid were dissolved in EtOAc-MeOH (4:1, 100 mL), combined and concentrated under reduced pressure. The resulting solid was triturated from 10% EtOH-EtOAc (4 mL) to obtain the title compound I-1 as an off-white solid (0.76 g, 55%). The filtrate was concentrated and loaded onto silica. Column chromatography (0→10% MeOH—CH$_2$Cl$_2$) yielded a pale yellow solid, which was stirred with NaHCO$_3$ (15 mL). The liquid was decanted and the residue triturated with 10% EtOH-EtOAc (4 mL) to obtain further product as an off-white solid (0.226 g, 16%). Total yield 0.99 g, 71%; data agreed with that stated above.

Example 10

Exemplary Synthesis of Alkyl Phosphate Compounds

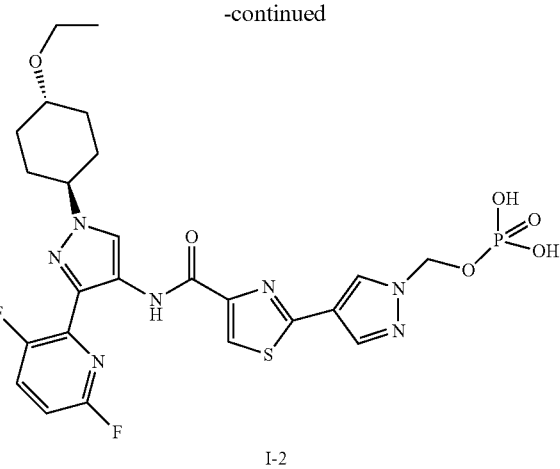

I. Preparation of di-tert-butyl ((4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)methyl) phosphate (I-3)

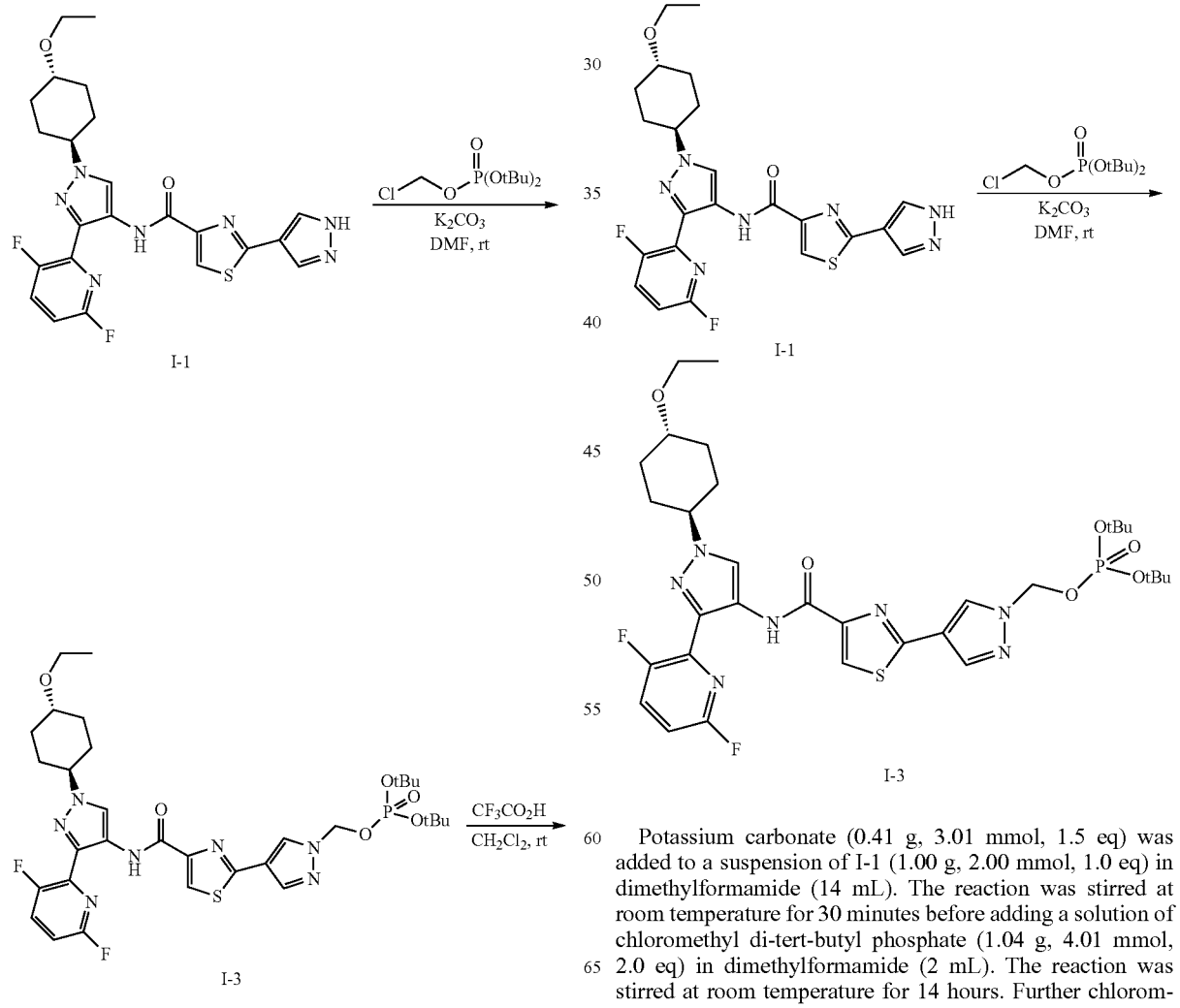

Potassium carbonate (0.41 g, 3.01 mmol, 1.5 eq) was added to a suspension of I-1 (1.00 g, 2.00 mmol, 1.0 eq) in dimethylformamide (14 mL). The reaction was stirred at room temperature for 30 minutes before adding a solution of chloromethyl di-tert-butyl phosphate (1.04 g, 4.01 mmol, 2.0 eq) in dimethylformamide (2 mL). The reaction was stirred at room temperature for 14 hours. Further chloromethyl di-tert-butyl phosphate (0.52 g, 2.00 mmol, 1.0 eq) and potassium carbonate (0.21 g, 1.50 mmol, 0.75 eq) was added and the reaction stirred for a further 24 hours. The reaction was cooled to 0° C. and water (25 mL) added dropwise over 45 minutes. A sticky solid resulted which was isolated by decanting the liquid. The liquid was added to water (40 mL) and stirred to obtain more solid, which was isolated by filtration. The solid was dried under vacuum and used without further purification (1.76 g, quantitative-theoretical yield 1.44 g); IR $v_{max}$ (film) 3308, 2979, 2978, 2864, 1668, 1615, 1592, 1549, 1482, 1374, 1266, 1234, 1104, 998, 965, 822, 787, 714, 666 cm$^{-1}$; $^1$H nmr (400 MHz, CDCl$_3$) δ 8.50 (1H, s, pyrazoleH-5, thiazoleH-5), 8.34 (1H, s, 1H of pyrazoleH-3, H-5), 8.21 (1H, s, 1H of pyrazoleH-3, H-5), 8.06 (1H, s 1H of pyrazoleH-5, thiazoleH-5), 7.65 (1H, td, J 9.0, 6.0 Hz, pyridineH-4 or H-5), 6.88 (1H, ddd, J 9.0, 3.0, 2.5 Hz, pyridineH-4 or H-5), 5.93 (2H, d, J 12.5 Hz, NCH$_2$OP), 4.27 (1H, tt, J 12.0, 4.0 Hz, cyclohexaneH-1 or H-4), 3.56 (2H, q, J 7.0 Hz, OC$\underline{H}_2$CH$_3$), 3.37 (1H, tt, J 10.5, 4.0 Hz, cyclohexaneH-1 or H-4), 2.29 (2H, br d, J 12.5 Hz, 2H of cyclohexaneH-2, H-3, H-5, H-6), 2.22 (2H, br d, J 11.0 Hz, 2H of cyclohexaneH-2, H-3, H-5, H-6), 1.89 (2H, m, 2H of cyclohexaneH-2, H-3, H-5, H-6), 1.50 (2H, m, 2H of cyclohexaneH-2, H-3, H-5, H-6), 1.45 (18H, s, 2×OC(CH$_3$)$_3$), 1.22 (3H, t, J 7.0 Hz, OCH$_2$C$\underline{H}_3$); $^{13}$C nmr (100 MHz, CDCl$_3$) δ 160.0, 158.2, 157.5 (d, J 236.5 Hz), 153.5 (dd, J 260.0, 5.0 Hz), 150.2, 139.5 (d, J 6.0 Hz), 138.9 (t, J 15.0 Hz), 133.0 (d, J 9.0 Hz), 130.0 (d, J 4.5 Hz), 129.8 (d, J 9.0 Hz), 122.0, 121.8, 119.4, 118.6, 107.6 (dd, J 40.5, 5.0 Hz), 83.9, 83.8, 77.2, 76.4, 63.6, 61.5, 31.1, 30.9, 29.8, 29.7, 15.7; 31P nmr (162 MHz, CDCl$_3$) δ −11.1; $^{19}$F nmr (380 MHz, CDCl$_3$) δ −72.4 (dt, J 27.0, 5.5 Hz), −124.5 (dd, J 27.5, 9.5 Hz); m/z: 744 [M+Na]$^+$.

II. Preparation of (4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)methyl dihydrogen phosphate (I-2)

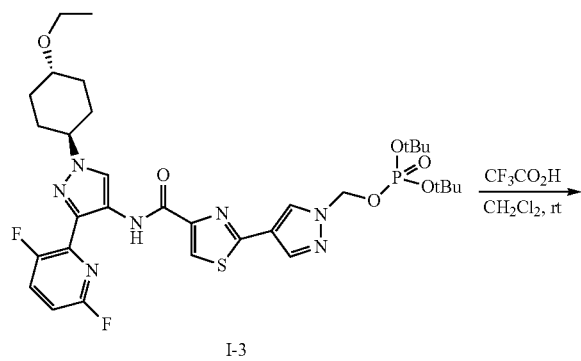

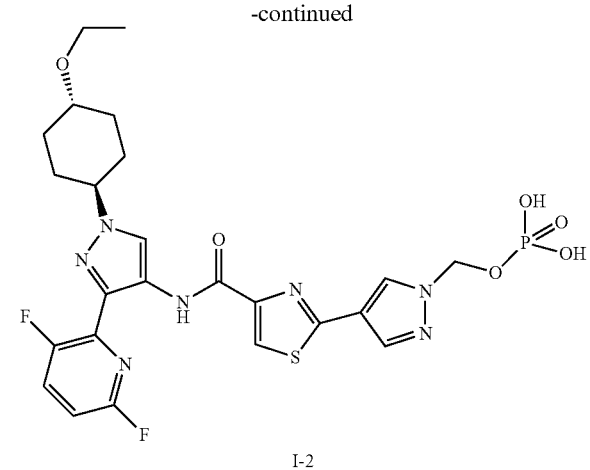

To a solution of I-3 (1.58 g crude mass, 1.80 mmol, 1.0 eq) in dichloromethane (8.0 mL) was added trifluoroacetic acid (0.99 mL, 12.80 mmol, 7.1 eq). The reaction was stirred at room temperature for 20 hours, during which time a precipitate formed. After 20 hours the precipitate was isolated by filtration. The solid was washed with CH$_2$Cl$_2$ (2×8 mL) to obtain a white solid. The solid was stirred with dioxane-water (10:1, 11 mL) for 5 hours and filtered, washing with dioxane-water (10:1, 11 mL) to obtain I-2 (0.60 g, 55% over two steps) as a white solid. The filtrate was concentrated and stirred in dioxane-water (10:1, 11 mL) for 18 hours before isolating by filtration. The solid was washed with dioxane-water (10:1, 2×5.5 mL) to obtain further product (0.12 g, total 0.72 g, 66%) as a white solid; $^1$H nmr (400 MHz, D$_6$-DMSO) δ 8.59 (1H, s, 1H of pyrazoleH-3, H-5), 8.52 (1H, s, 1H of pyrazoleH-3, H-5), 8.34 (1H, s, 1H of pyrazoleH-5, thiazoleH-5), 8.19 (1H, s, 1H of pyrazoleH-5, thiazoleH-5), 8.08 (1H, td, J 9.5, 6.5 Hz, pyridineH-4 or H-5), 6.88 (1H, ddd, J 9.0, 3.0, 2.5 Hz, pyridineH-4 or H-5), 5.83 (2H, d, J 12.5 Hz, NCH$_2$OP), 4.33 (1H, tt, J 12.0, 3.0 Hz, cyclohexaneH-1 or H-4), 3.47 (2H, q, J 7.0 Hz, OC$\underline{H}_2$CH$_3$), 3.35 (1H, tt, J 10.5, 3.5 Hz, cyclohexaneH-1 or H-4), 2.29 (4H, br d, J 11.0 Hz, 4H of cyclohexaneH-2, H-3, H-5, H-6), 1.85 (2H, m, 2H of cyclohexaneH-2, H-3, H-5, H-6), 1.35 (2H, m, 2H of cyclohexaneH-2, H-3, H-5, H-6), 1.10 (3H, t, J 7.0 Hz, OCH$_2$C$\underline{H}_3$); $^{13}$C nmr (100 MHz, CDCl$_3$) δ 160.6, 157.6, 157.6 (d, J 234.5 Hz), 154.3 (dd, J 259.5, 4.0 Hz), 149.4, 137.7 (d, J 7.0 Hz), 138.2, 132.6 (d, J 9.0 Hz), 131.9 (dd, J 22.0, 9.0 Hz), 131.4, 124.1, 121.4, 120.2, 117.7, 109.2 (d, 38.0 Hz), 76.0, 75.2, 63.0, 60.8, 30.9 (2C), 16.1; $^{31}$P nmr (162 MHz, D$_6$-DMSO) δ −2.7; $^{19}$F nmr (380 MHz, D$_6$-DMSO) δ −72.8, −124.2 (ddd, J 27.0, 9.5, 3.0 Hz); m/z: 610 [M+H]$^+$ (found [M+H]$^+$, 610.1451, C$_{24}$H$_{26}$F$_2$N$_7$O$_6$PS requires [M+H]$^+$ 610.1444).

Other phosphate compounds were made by similar methods

Example 11

Exemplary Synthesis of Carbamates and Ureas as Potential IRAK ProDrugs

I. Formation of 2-morpholinoethyl (4-nitrophenyl) carbonate

II. Formation of 3-morpholinopropyl (4-nitrophenyl) carbonate

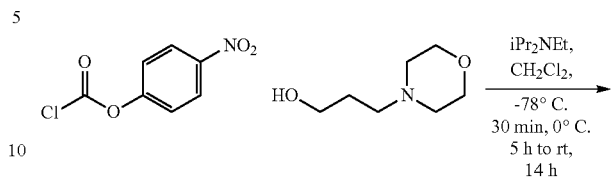

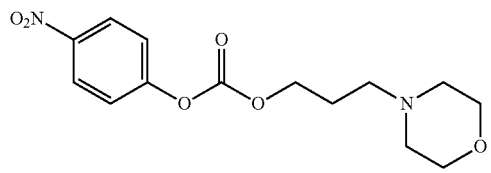

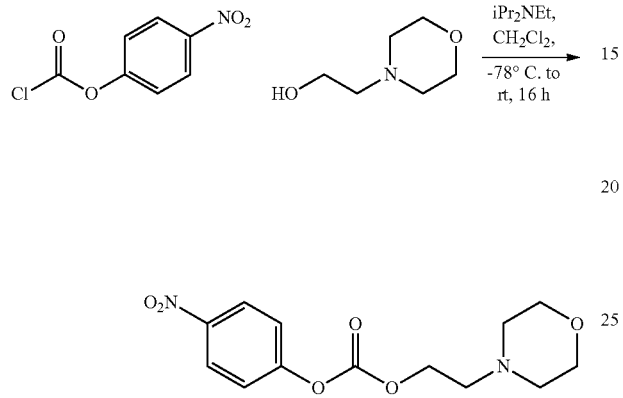

A solution of 4-nitrophenol chloroformate (0.500 g, 2.48 mmol, 1.0 eq) in dichloromethane (20 mL) was cooled to −78° C. Diisopropylethylamine (0.65 mL, 3.72 mmol, 1.5 eq) was added followed by 4-(2-hydroxyethyl)morpholine (0.30 mL, 2.48 mmol, 1.0 eq) and the reaction was stirred between −78° C. and room temperature over 16 hours. The reaction was diluted with dichloromethane (40 mL) and washed with NaHCO$_3$ (60 mL) and brine (60 mL), dried (Na$_2$SO$_4$) and concentrated under reduced pressure to obtain the title compound as an orange oil; $^1$H nmr (400 MHz, CDCl$_3$) δ 8.27 (2H, d, J 9.5 Hz, 2H of C$_6$H$_4$NO$_2$), 7.37 (2H, d, J 9.0 Hz, 2H of C$_6$H$_4$NO$_2$), 4.39 (2H, t, J 5.5 Hz, 2H of COOCH$_2$CH$_2$N), 3.72, 3.71 (4H, 2d AB system, J 4.5 Hz, 4H of morpholine), 2.72 (2H, t, J 5.5 Hz, 2H of COCH$_2$CH$_2$N), 2.54, 2.53 (4H, 2d AB system, J 4.5 Hz, 4H of morpholine).

Diisopropylethylamine (0.65 mL, 3.72 mmol, 1.5 eq) was added to a solution of 4-nitrophenyl chloroformate (0.500 g, 2.48 mmol, 1.0 eq) in dichloromethane (20 mL) at −78° C. 3-(Hydroxypropyl)morpholine (0.34 mL, 2.48 mmol, 1.0 eq) was added dropwise and the reaction stirred at −78° C. for 30 minutes. The reaction froze and was warmed to 0° C. After stirred at 0° C. for 5 hours the reaction was allowed to warm to room temperature over 16 hours. The reaction was diluted with dichloromethane (20 mL) and washed with NaHCO$_3$ (3×40 mL). The organics were dried (Na$_2$SO$_4$) and concentrated under reduced pressure to obtain the title compound as a pale yellow oil; $^1$H nmr (400 MHz, CDCl$_3$) δ 8.26 (2H, d, J 9.5 Hz, 2H of C$_6$H$_4$NO$_2$), 7.36 (2H, d, J 9.0 Hz, 2H of C$_6$H$_4$NO$_2$), 4.36 (2H, t, J 6.5 Hz, OCH$_2$CH$_2$CH$_2$N), 3.70 3.69 (4H, 2d AB system, J 4.5 Hz, 4H of morpholine), 2.49-2.43 (6H, m, 4H of morpholine, OCH$_2$CH$_2$CH$_2$N), 1.93 (pentet, J 6.5 Hz, OCH$_2$CH$_2$CH$_2$N).

III. Formation of 2-morpholinoethyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate (I-10)

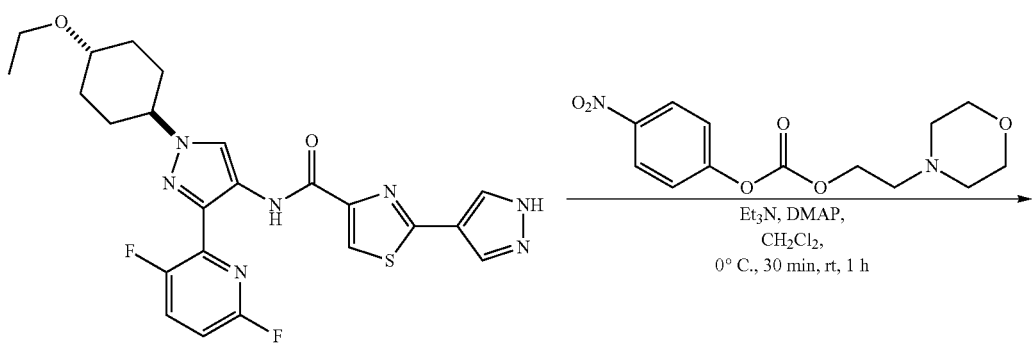

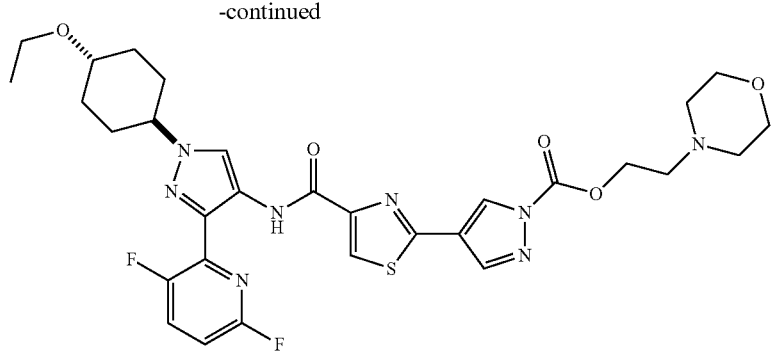

To the nitrophenyl carbonate (0.050 g, 0.169 mmol, 1.5 eq) in dichloromethane (1.0 mL) at 0° C. was added N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide (0.056 g, 0.113 mmol, 1.0 eq) and dimethylaminopyridine (0.001 g, 0.011 mmol, 0.1 eq). Triethylamine (0.023 mL, 0.169 mmol, 1.5 eq) was added and the reaction stirred at 0° C. for 30 minutes and room temperature for 1 hour. The reaction was partitioned between $CH_2Cl_2$ (30 mL) and $NaHCO_3$ (30 mL). The aqueous phase was extracted with $CH_2Cl_2$ (2×30 mL). The combined organics were dried ($Na_2SO_4$) and concentrated under reduced pressure. MPLC (20→80% acetone-hexane, 0.1% triethylamine) yielded the title compound as a white solid; $^1$H nmr (400 MHz, $CDCl_3$) δ 8.75 (1H, s, 1H of thiazoleH-5, pyrazoleH-5, pyrazoleH-3, H-5), 8.49 (1H, s, 1H of thiazoleH-5, pyrazoleH-5, pyrazoleH-3, H-5), 8.35 (1H, s, 1H of thiazoleH-5, pyrazoleH-5, pyrazoleH-3, H-5), 8.13 (1H, s, 1H of thiazoleH-5, pyrazoleH-5, pyrazoleH-3, H-5), 7.64 (1H, td, J 9.0, 6.0 Hz, pyridineH-4 or H-5), 6.86 (1H, dt, J 8.5, 3.5, 2.5 Hz, pyridineH-4 or H-5), 4.63 (2H, t, J 6.0 Hz, $COOCH_2CH_2N$), 4.26 (1H, tt, J 11.5, 4.0 Hz, cyclohexaneH-1 or H-4), 3.70, 3.68 (4H, 2d AB system, J 4.5 Hz, 4H of morpholine), 3.55 (2H, q, J 7.0 Hz, $OCH_2CH_3$), 3.36 (1H, tt, J 10.5, 4.0 Hz, cyclohexaneH-1 or H-4), 2.84 (2H, t, J 6.0 Hz, $COOCH_2CH_2N$), 2.58, 2.57 (4H, 2d AB system, J 4.5 Hz, 4H of morpholine), 2.28 (2H, m, 2H of cyclohexaneH-2, H-3, H-5, H-6), 2.20 (2H, m, 2H of cyclohexaneH-2, H-3, H-5, H-6), 1.88 (2H, m, 2H of cyclohexaneH-2, H-3, H-5, H-6), 1.45 (2H, m, 2H of cyclohexaneH-2, H-3, H-5, H-6), 1.21 (3H, t, J 7.0 Hz, $OCH_2CH_3$); $^{19}$F nmr (380 MHz, $CDCl_3$) δ −72.7 (ddd, J 27.0, 5.5, 4.0 Hz), −124.3 (ddd, 27.0, 11.0, 9.5 Hz); m/z: 657 [M+H]$^+$.

IV. Formation of 3-morpholinopropyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate (I-15)

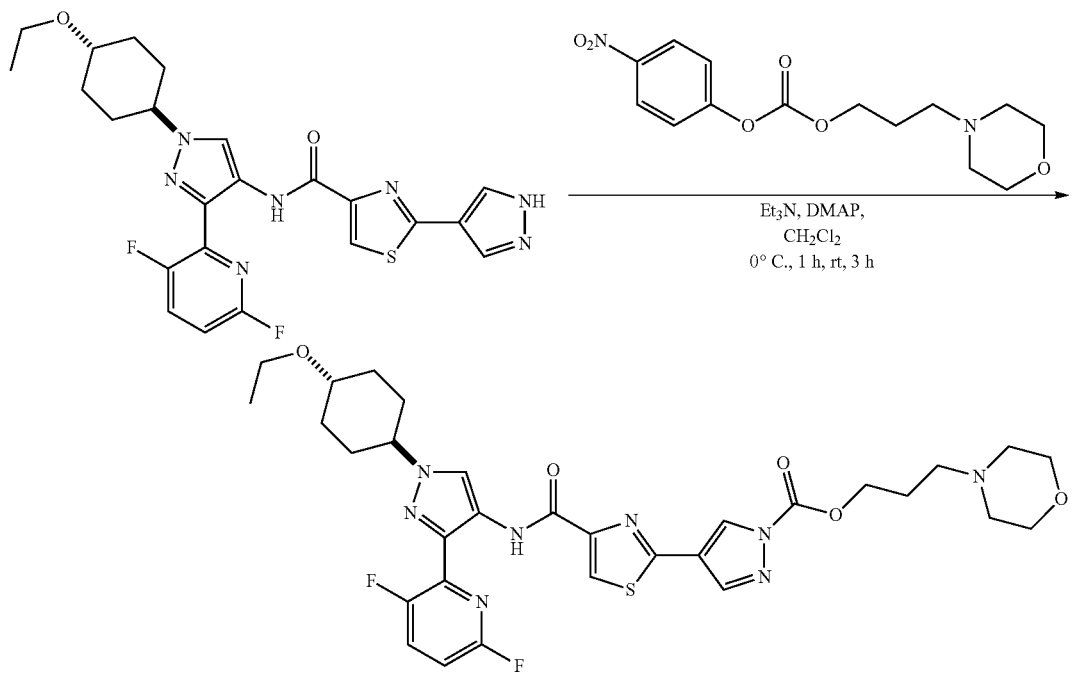

To a mixture of the nitrophenyl carbonate (0.068 g, 0.220 mmol, 1.1 eq) and N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide (0.100 g, 0.200 mmol, 1.0 eq) in dichloromethane (2.0 mL) at 0° C. was added triethylamine (0.031 mL, 0.220 mmol, 1.1 eq) and dimethylaminopyridine (0.002 g, 0.020 mmol, 0.1 eq). The reaction stirred at 0° C. for 1 hour and then at room temperature for 3 hours, resulting an almost clear solution. The reaction was partitioned between $CH_2Cl_2$ (30 mL) and $NaHCO_3$ (30 mL). The aqueous phase was extracted with $CH_2Cl_2$ (2×30 mL). The combined organics were dried ($Na_2SO_4$) and concentrated under reduced pressure. MPLC (40→100% acetone-hexane, 0.1% triethylamine) yielded the title compound (0.077 g, 57%) as a white solid; $^1H$ nmr (400 MHz, $CDCl_3$) δ 8.75 (1H, s, pyrazoleH-5, thiazoleH-5, pyrazoleH-3 or H-5), 8.49 (1H, s, pyrazoleH-5, thiazoleH-5, pyrazoleH-3 or H-5), 8.34 (1H, s, pyrazoleH-5, thiazoleH-5, pyrazoleH-3 or H-5), 8.12 (1H, s, pyrazoleH-5, thiazoleH-5, pyrazoleH-3 or H-5), 7.64 (1H, td, J 9.0, 6.0 Hz, pyridineH-4 or H-5), 6.87 (1H, ddd, J 9.0, 3.5, 2.5 Hz, pyridineH-4 or H-5), 4.61 (2H, 6.5 Hz, 2H of $OCH_2CH_2CH_2N$), 4.26 (1H, tt, J 11.5, 4.0 Hz, cyclohexaneH-1 or H-4), 3.66, 3.65 (4H, 2d AB system, J 4.5 Hz, 4H of morpholine), 3.55 (2H, q, J 7.0 Hz, $OCH_2CH_3$), 3.35 (1H, tt, J 10.5, 4.0 Hz, cyclohexaneH-1 or H-4), 2.52 (2H, J 7.0 Hz, 2H of $OCH_2CH_2CH_2N$), 2.44 (4H, m, 4H of morpholine), 2.30-2.24 (2H, m, 2H of cyclohexaneH-2, H-3, H-5, H-6), 2.24-2.17 (2H, m, 2H of cyclohexaneH-2, H-3, H-5, H-6), 2.05 (2H, pentet, J 6.5 Hz, $OCH_2CH_2CH_2N$), 1.93-1.83 (2H, m, 2H of cyclohexaneH-2, H-3, H-5, H-6), 1.51-1.41 (2H, m, 2H of cyclohexaneH-2, H-3, H-5, H-6), 1.21 (3H, t, J 7.0 Hz, $OCH_2CH_3$); $^{19}F$ nmr (380 MHz, $CDCl_3$) δ −72.7 (ddd, J 28.5, 5.5, 4.0 Hz), −124.3 (ddd, J 28.0, 9.5, 2.5 Hz); m/z: 671 $[M+H]^+$ (found $[M+H]^+$, 671.2560, $C_{31}H_{36}F_2N_8O_5S$ requires $[M+H]^+$ 671.2570).

A person of ordinary skill in the art will understand that the above methods also can be used to make the corresponding urea compounds, such as I-13 and I-14, by using an amine in place of the starting hydroxy compound. An exemplary scheme to synthesis urea compound I-13 is provided below.

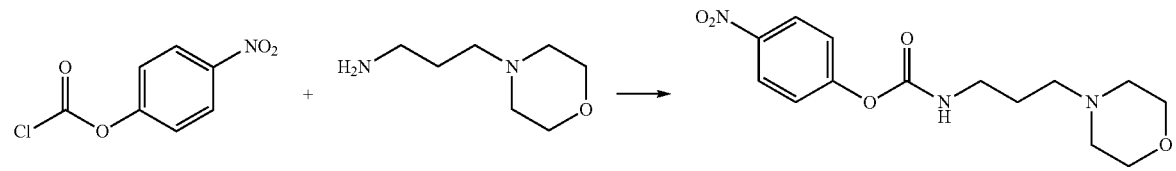

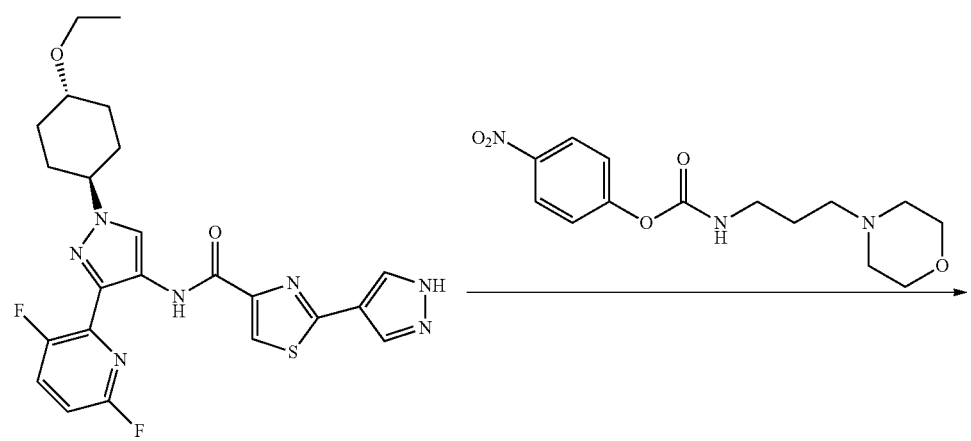

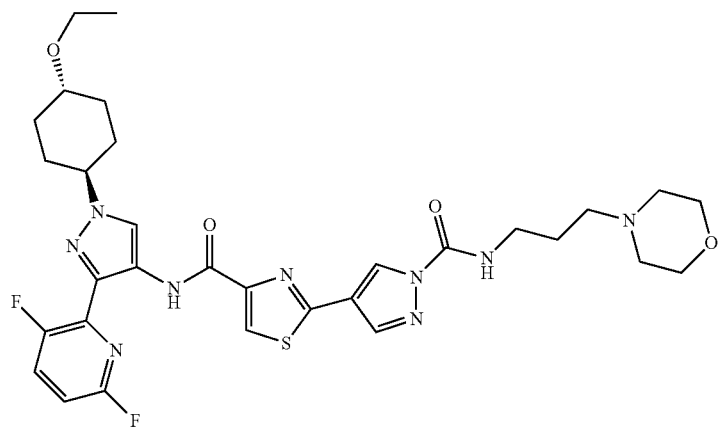

Example 12
Exemplary Synthesis of Amino Acid Esters
Synthesis of (4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)methyl L-valinate hydrochloride (I-16)
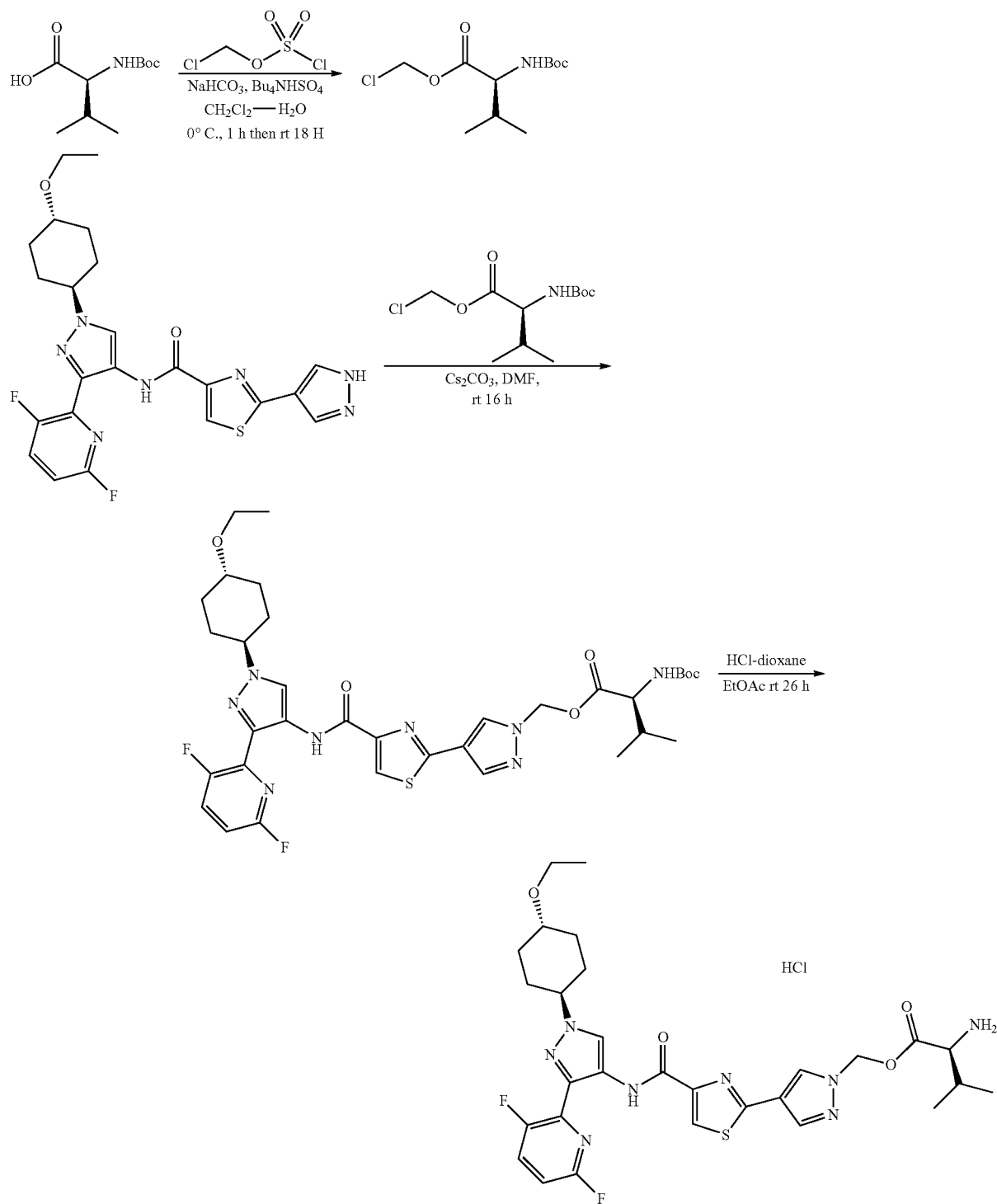

I. Preparation of chloromethyl (tert-butoxycarbonyl)-L-valinate

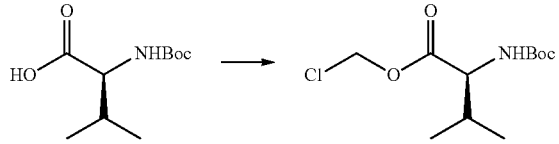 [SMILES: CC(C)[C@H](NC(=O)OC(C)(C)C)C(=O)O ; CC(C)[C@H](NC(=O)OC(C)(C)C)C(=O)OCCl]

To a solution of N-Boc-valine (5.00 g, 23.0 mmol, 1.0 eq) in dichloromethane (100 mL) was added sodium bicarbonate (7.74 g, 92.2 mmol, 4.0 eq) and tetrabutylammonium hydrogen sulfate (0.78 g, 2.3 mmol, 0.1 eq) followed by water (100 mL). The mixture was stirred for 10 minutes to allow for dissolution before cooling to 0° C. and adding a solution of chloromethyl chlorosulfate (3.0 mL, 29.0 mmol, 1.3 eq) in dichloromethane (20 mL) dropwise over 20 minutes. The reaction was stirred at 0° C. for 1 hour and then at room temperature for 18 hours. The reaction was partitioned and the aqueous phase was extracted with $CH_2Cl_2$ (20 mL). The combined organic phases were washed with water (3×100 mL) and brine (100 mL), dried ($Na_2SO_4$) and concentrated under reduced pressure to obtain the title compound (6.10 g, quantitative) as a colourless oil; $^1H$ nmr (400 MHz, $CDCl_3$) δ 5.87 (1H, d, J 6.0 Hz, 1H of $OCH_2C$), 5.61 (1H, d, J 6.0 Hz, 1H of $OCH_2C$), 4.97 (1H, br d, J 7.0 Hz, NH), 4.27 (1H, dd, J 9.0, 4.5 Hz, $COCHNH$), 2.22-2.17 (1H, m, $CHCH(CH_3)_2$), 1.44 (9H, s, $C(CH_3)_3$), 0.99 (3H, d, J 6.5 Hz, 1×$CH_3$ of $CH(CH_3)_2$), 0.92 (3H, d, J 7.0 Hz, 1×$CH_3$ of $CH(CH_3)_2$).

II. Preparation of (4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)methyl (tert-butoxycarbonyl)-L-valinate

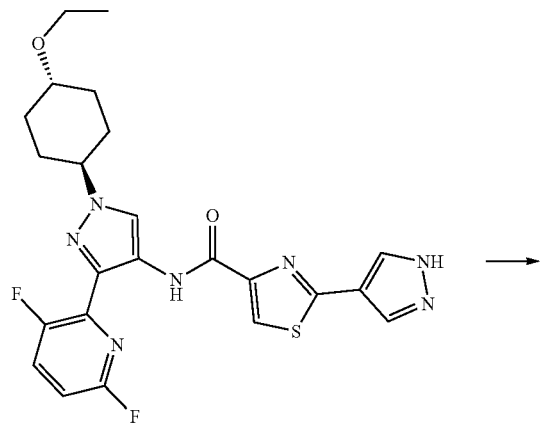

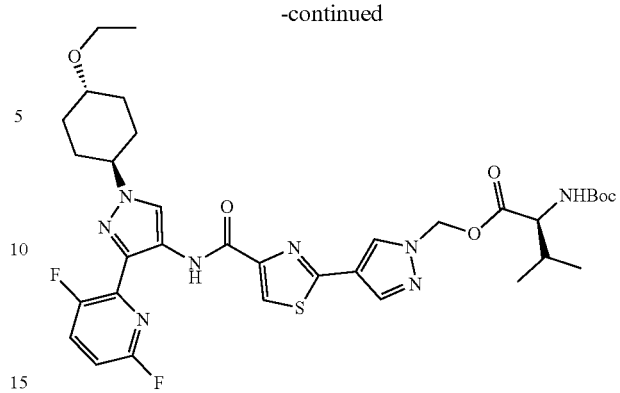

To a mixture of I-1 (5.00 g, 10.0 mmol, 1.0 eq) and N-Boc-valine chloromethyl ester (2.93 g, 11.0 mmol, 1.1 eq) was added dimethylformamide (50 mL). Caesium carbonate (3.92 g, 12.0 mmol, 1.2 eq) was added and the reaction stirred at room temperature for 16 hours. The reaction was partitioned between EtOAc (150 mL) and water (150 mL). The organics were washed with brine (100 mL). The combined organics were back-extracted with EtOAc (75 mL). The combined organics were washed with water (200 mL) and brine (150 mL), dried ($Na_2SO_4$) and concentrated under reduced pressure. MPLC (50→100% EtOAc-hexane) yielded the title compound (6.51 g, 89%) as a white solid; $^1H$ nmr (400 MHz, $CDCl_3$) δ 8.48 (1H, s, pyrazoleH-5, thiazoleH-5, pyrazoleH-3 or H-5), 8.29 (1H, s, pyrazoleH-5, thiazoleH-5, pyrazoleH-3 or H-5), 8.14 (1H, s, pyrazoleH-5, thiazoleH-5, pyrazoleH-3 or H-5), 8.04 (1H, s, pyrazoleH-5, thiazoleH-5, pyrazoleH-3 or H-5), 7.63 (1H, td, J 9.0, 6.0 Hz, pyridineH-4 or H-5), 6.87 (1H, ddd, J 9.0, 3.5, 2.5 Hz, pyridineH-4 or H-5), 6.21, 6.02 (2H, 2d AB system, J 10.5 Hz, $NCH_2O$), 4.94 (1H, d, J 9.0 Hz, NHBoc), 4.28-4.21 (2H, m, cyclohexaneH-1 or H-4, $COCHNH$), 3.54 (2H, q, J 7.0 Hz, $OCH_2CH_3$), 3.43 (1H, tt, J 10.5, 4.0 Hz, cyclohexaneH-1 or H-4), 2.30-2.24 (2H, m, 2H of cyclohexaneH-2, H-3, H-5, H-6), 2.23-2.16 (2H, m, 2H of cyclohexaneH-2, H-3, H-5, H-6), 2.13-2.04 (1H, m, $CHCH(CH_3)_2$), 1.92-1.82 (2H, m, 2H of cyclohexaneH-2, H-3, H-5, H-6), 1.49-1.40 (2H, m, 2H of cyclohexaneH-2, H-3, H-5, H-6), 1.40 (9H, s, $C(CH_3)_3$), 1.20 (3H, t, J 7.0 Hz, $OCH_2CH_3$), 0.86 (3H, d, J 6.5 Hz, 1×$CH_3$ of $CH(CH_3)_2$), 0.77 (3H, d, J 6.5 Hz, 1×$CH_3$ of $CH(CH_3)_2$); $^{13}C$ nmr (100 MHz, $CDCl_3$) δ 171.9, 159.7, 158.2, 15x (d, J 236.5 Hz), 155.6, 153.x (dd, J 260.5, 4.5 Hz), 150.2, 139.8 (d, J 5.0 Hz), 138.9 (t, J 14.5 Hz), 133.0 (d, J 8.5 Hz), 130.5 (d, J 5.0 Hz), 129.9 (dd, J 22.5, 9.0 Hz), 122.0, 121.8, 119.4, 118.6, 107.6 (dd, J 40.5, 5.5 Hz), 80.1, 77.2, 76.4, 72.6, 63.6, 61.5, 58.4, 31.1, 31.0, 30.9, 28.3, 18.8, 17.4, 15.7; $^{19}F$ nmr (380 MHz, $CDCl_3$) δ −72.6, −124.4; m/z: 751 $[M+H]^+$, 673 $[M+H−C_4H_8]^+$, 629 $[M+H−C_4H_8−CO_2]^+$.

III. Preparation of (4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)methyl L-valinate hydrochloride, I-16

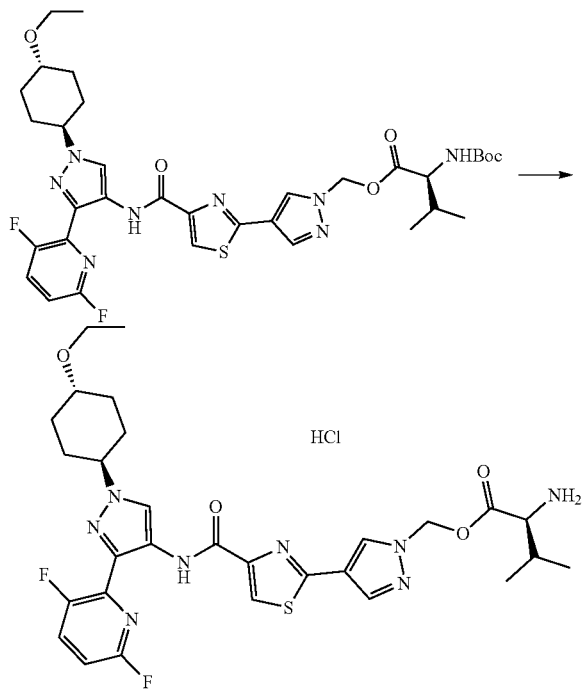

To a solution/suspension of the Boc-protected valine methylene ester (1.73 g, 2.38 mmol, 1.0 eq) in ethyl acetate (25 mL) was added hydrogen chloride 5.94 mL of a 4M solution in dioxane, 23.76 mmol, 10.0 eq). The reaction was stirred at room temperature for 18 hours. Further hydrogen chloride 3.0 mL of a 4M solution in dioxane, 11.88 mmol, 5.0 eq) was added and the reaction stirred for a further 8 hours before concentrating under reduced pressure. The residue was concentrated from EtOAc (2×30 ml) and dried under vacuum to yield the title compound (1.50 g, quantitative) as a white solid; $^1$H nmr (400 MHz, D$_6$-DMSO) δ 8.66 (1H, s, pyrazoleH-5, thiazoleH-5, pyrazoleH-3 or H-5), 8.51 (1H, s, pyrazoleH-5, thiazoleH-5, pyrazoleH-3 or H-5), 8.35 (1H, s, pyrazoleH-5, thiazoleH-5, pyrazoleH-3 or H-5), 8.22 (1H, s, pyrazoleH-5, thiazoleH-5, pyrazoleH-3 or H-5), 8.07 (1H, td, J 9.0, 6.0 Hz, pyridineH-4 or H-5), 7.25 (1H, ddd, J 8.5, 3.0, 2.5 Hz, pyridineH-4 or H-5), 6.2x, 6.2x (2d, AB system, J Hz, NCH$_2$OCO), 4.32 (1H, tt, J 11.5, 3.0 Hz, cyclohexaneH-1 or H-4), 3.90 (1H, d, J 4.0 Hz, COCHNH$_2$), 3.45 (2H, q, J 7.0 Hz, OCH$_2$CH$_3$), 3.30 (1H, tt, J 11.0, 4.0 Hz, cyclohexaneH-1 or H-4), 2.12-2.00 (5H, m, 4H of cyclohexaneH-2, H-3, H-5, H-6, CH(CH$_3$)$_2$), 1.88-1.80 (2H, m, 2H of cyclohexaneH-2, H-3, H-5, H-6), 1.38-1.29 (2H, m, 2H of cyclohexaneH-2, H-3, H-5, H-6), 1.08 (3H, t, J 7.0 Hz, OCH$_2$CH$_3$), 0.87 (3H, d, J 7.0 Hz, 3H of CH(CH$_3$)$_2$), 0.83 (3H, d, J 7.0 Hz, 3H of CH(CH$_3$)$_2$); $^{19}$F nmr (380 MHz, D$_6$-DMSO) δ −73.0 (d, J 28.5 Hz), −124.1 (dd, J 27.0, 9.5 Hz); m/z: 629 [M+H]$^+$ (found [M+H]$^+$, 629.2477, C$_{29}$H$_{34}$F$_2$N$_8$O$_4$S requires [M+H]$^+$ 629.2465).

A person of ordinary skill in the art will understand that this method is generally applicable to any amino acid, particularly a naturally occurring amino acid, as disclosed herein.

Example 13

Synthesis of 1-(4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)ethyl dihydrogen phosphate (I-18)

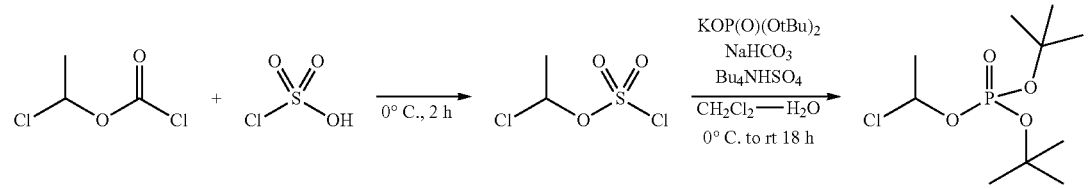

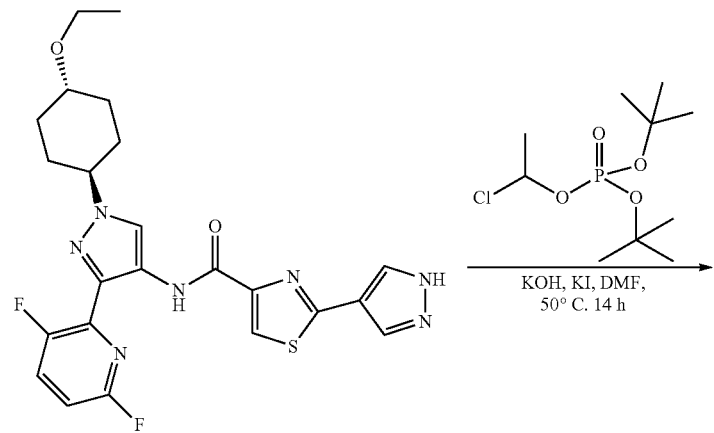

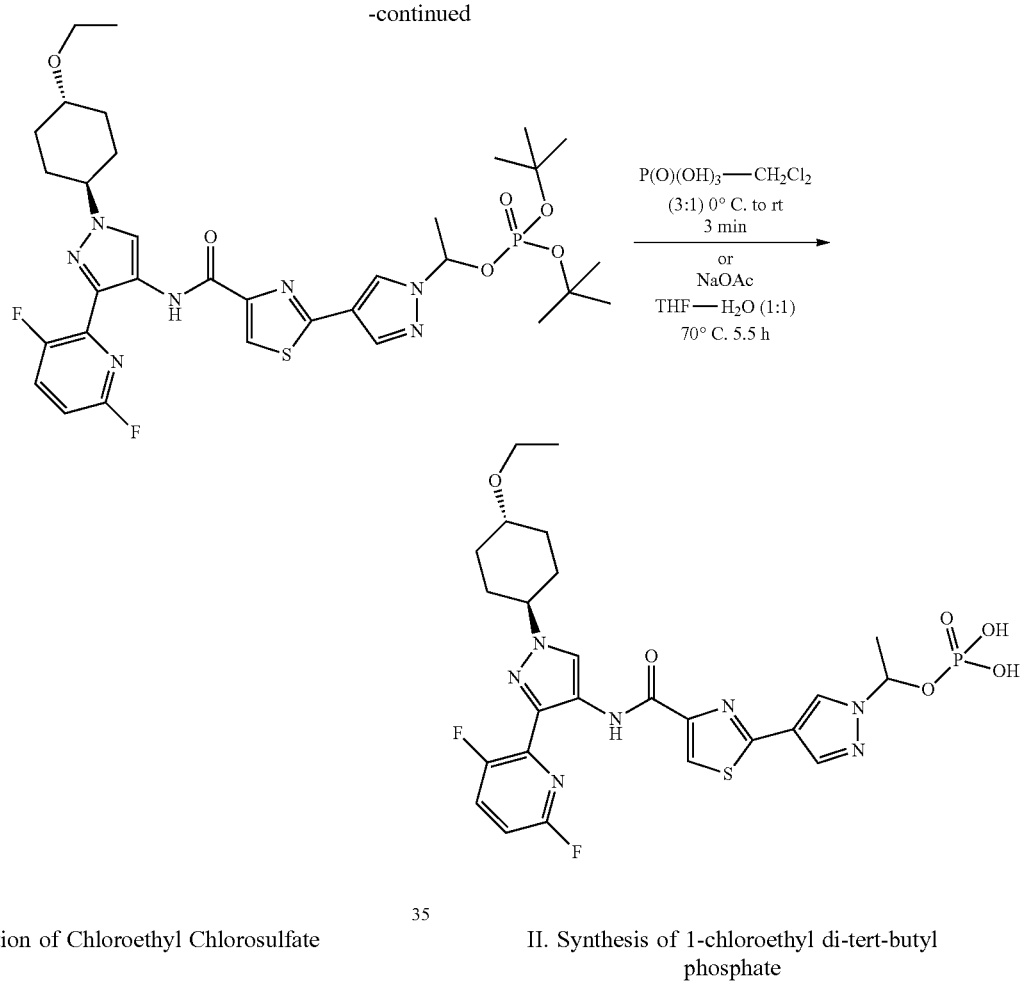

I. Preparation of Chloroethyl Chlorosulfate

II. Synthesis of 1-chloroethyl di-tert-butyl phosphate

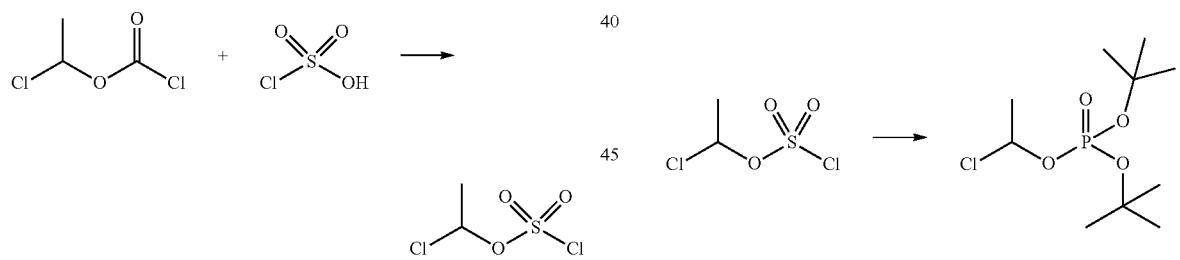

Chlorosulfonic acid (4.90 mL, 73.7 mmol, 1.46 eq) was added dropwise to chloroethyl chloroformate (5.44 mL, 50.4 mmol, 1.0 eq) at 0° C. over 20 minutes. The reaction was stirred at 0° C. for 2 hours and then at room temperature for 10 minutes (during which time the solution temperature rose to 5° C.). Dichloromethane (50 mL) was added followed carefully by ice (2 g), and the mixture stirred rapidly to ensure mixing. Some bubbling was observed and the yellow solution became green-black. The mixture was washed with NaHCO$_3$ (2×40 mL) to ensure the organics are not acidic. The organics were washed with brine (40 mL), dried (Na$_2$SO$_4$) to obtain a clear solution, which was concentrated under reduced pressure to obtain the title compound (4.72 g, 52%) as a black-brown oil; $^1$H nmr (400 MHz, CDCl$_3$) δ 6.46 (1H, q, J 6.0 Hz, ClCH(CH$_3$)O), 1.97 (3H, d, J 5.5 Hz, CHCH$_3$).

Potassium di-tert-butyl phosphate (5.44 g, 21.97 mmol, 1.0 eq) was dissolved in dichloromethane-water (200 mL, 1:1) and cooled to 0° C. Sodium bicarbonate (7.37 g, 87.74 mmol, 4.0 eq) and tetrabutylammonium hydrogen phosphate (0.74 g, 2.19 mmol, 0.1 eq) were added and the reaction was stirred at 0° C. for 10 minutes. Chloroethyl chlorosulfate (4.72 g as a solution in 20 mL of dichloromethane, 26.37 mmol, 1.2 eq) was then added dropwise over 30 minutes at 0° C. The resulting mixture was stirred rapidly at room temperature for 18 hours and partitioned. The organics were washed with water (3×100 mL) and brine (100 mL), dried (Na$_2$SO$_4$) and concentrated under reduced pressure to obtain the title compound (2.35 g, 39%) as a pale brown oil; $^1$H nmr (400 MHz, CDCl$_3$) δ 6.19 (1H, dq, J 8.5, 5.5 Hz, ClCH(CH$_3$)O), 1.79 (3H, dd, J 5.5, 1.0 Hz, CHCH$_3$), 1.49 (9H, s, 1×OC(CH$_3$)$_3$), 1.48 (9H, s, 1×OC(CH$_3$)$_3$); $^{32}$P nmr (380 MHz, CDCl$_3$) δ −13.0.

III. Preparation of di-tert-butyl(1-(4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)ethyl) phosphate

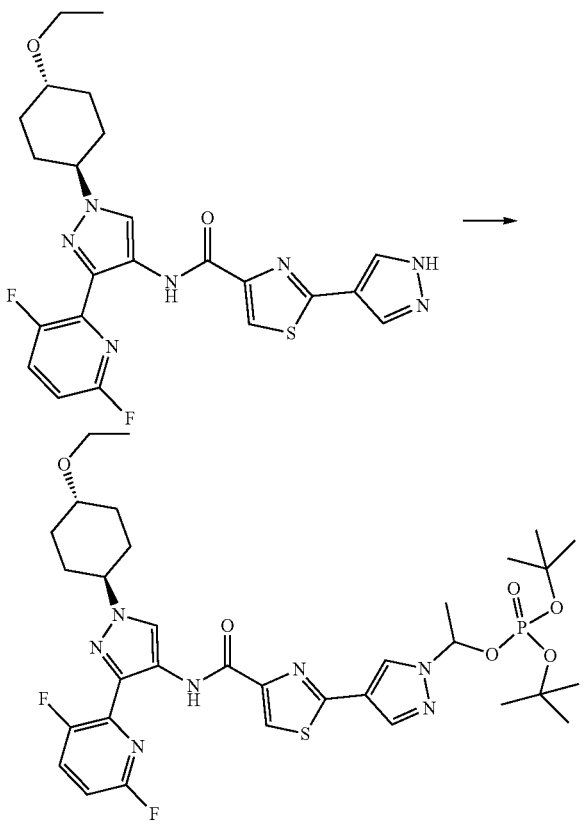

To a suspension of I-1 (2.00 g, 4.01 mmol, 1.0 eq) in degassed dimethylformamide (15 mL) was added potassium iodide (0.07 g, 0.40 mmol, 0.1 eq) and potassium hydroxide (0.90 g, 16.03 mmol, 4.0 eq) as small flakes. Chloroethyl di-tert-butyl phosphate (1.64 g as a solution in 5 mL of dimethylformamide, 6.01 mmol, 1.5 eq) was added dropwise over 10 minutes. The resulting mixture was heated to 50° C. for 14 hours before cooling and diluting with EtOAc (50 mL). The reaction was partitioned between EtOAc (100 mL) and water (150 mL). The organics were washed with brine (100 mL), water (150 mL) and brine (100 mL), dried (Na$_2$SO$_4$) and concentrated under reduced pressure. Column chromatography (silica, 50→100% EtOAc-hexane) yielded the title compound as a white solid; $^1$H nmr (400 MHz, CDCl$_3$) δ 11.73 (1H, s, NH), 8.51 (1H, s, pyrazoleH-5, thiazoleH-5, pyrazoleH-3 or H-5), 8.33 (1H, s, pyrazoleH-5, thiazoleH-5, pyrazoleH-3 or H-5), 8.16 (1H, s, pyrazoleH-5, thiazoleH-5, pyrazoleH-3 or H-5), 8.05 (1H, s pyrazoleH-5, thiazoleH-5, pyrazoleH-3 or H-5), 7.65 (1H, td, J 9.0, 6.5 Hz, pyridineH-4 or H-5), 6.88 (1H, ddd, J 8.0, 3.0, 2.5 Hz, pyridineH-4 or H-5), 6.39 (1H, dq, J 7.5, 6.5 Hz, NCH(CH$_3$)O), 4.27 (1H, tt, J 11.5, 3.5 Hz, cyclohexaneH-1 or H-4), 3.56 (2H, q, J 7.0 Hz, OCH$_2$CH$_3$), 3.37 (1H, tt, J 10.5, 4.5 Hz, cyclohexaneH-1 or H-4), 2.32-2.26 (2H, m, 2H of cyclohexaneH-2, H-3, H-5, H-6), 2.26-1.90 (2H, m, 2H of cyclohexaneH-2, H-3, H-5, H-6), 1.94 (3H, d, J 6.5 Hz, NCH(CH$_3$)O), 1.93-1.84 (2H, m, 2H of cyclohexaneH-2, H-3, H-5, H-6), 1.52-1.42 (11H, m, 2H of cyclohexaneH-2, H-3, H-5, H-6, 1×C(CH$_3$)$_3$), 1.37 (9H, s, 1×C(CH$_3$)$_3$), 1.23 (3H, t, J 7.0 Hz, OCH$_2$CH$_3$); $^{19}$F nmr (380 MHz, CDCl$_3$) δ −72.3, −124.5; $^{32}$P nmr (380 MHz, CDCl$_3$) δ −11.9; m/z: 758 [M+Na]$^+$.

Alternative synthesis of di-tert-butyl (1-(4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)ethyl) phosphate To a mixture of I-1 (7.00 g, 14.0 mmol, 1.0 eq) and potassium iodide (0.23 g, 1.4 mmol, 0.1 eq) was added dioxane (48 mL) followed by cesium carbonate (9.15 g, 28.1 mmol, 2.0 eq). The resulting suspension was stirred at room temperature and chloroethyl di-tert-butyl phosphate (4.20 g as a solution in 8 mL of dioxane, 15.4 mmol, 1.1 eq) was added. The reaction was heated to 70° C. for 30 hours before cooling and partitioning between EtOAc (100 mL) and NH$_4$Cl-water (1:1, 100 mL). The organics were dried (Na$_2$SO$_4$) and concentrated under reduced pressure. On standing in the fridge a solid formed along with some liquid thought to be water. The liquid did not contain any product and was decanted. EtOAc (7.5 mL) was added and the solid isolated by filtration, washing with EtOAc (7.5 mL and 5 mL). The solid was dried under vacuum to obtain the title compound (5.20 g, 50%) as an off white solid; $^1$H nmr (400 MHz, CDCl$_3$) δ 11.73 (1H, s, NH), 8.51 (1H, s, pyrazoleH-5, thiazoleH-5, pyrazoleH-3 or H-5), 8.33 (1H, s, pyrazoleH-5, thiazoleH-5, pyrazoleH-3 or H-5), 8.16 (1H, s, pyrazoleH-5, thiazoleH-5, pyrazoleH-3 or H-5), 8.05 (1H, s pyrazoleH-5, thiazoleH-5, pyrazoleH-3 or H-5), 7.65 (1H, td, J 9.0, 6.5 Hz, pyridineH-4 or H-5), 6.88 (1H, ddd, J 8.0, 3.0, 2.5 Hz, pyridineH-4 or H-5), 6.39 (1H, dq, J 7.5, 6.5 Hz, NCH(CH$_3$)O), 4.27 (1H, tt, J 11.5, 3.5 Hz, cyclohexaneH-1 or H-4), 3.56 (2H, q, J 7.0 Hz, OCH$_2$CH$_3$), 3.37 (1H, tt, J 10.5, 4.5 Hz, cyclohexaneH-1 or H-4), 2.32-2.26 (2H, m, 2H of cyclohexaneH-2, H-3, H-5, H-6),2.26-1.90 (2H, m, 2H of cyclohexaneH-2, H-3, H-5, H-6), 1.94 (3H, d, J 6.5 Hz, NCH(CH$_3$)O), 1.93-1.84 (2H, m, 2H of cyclohexaneH-2, H-3, H-5, H-6), 1.52-1.42 (11H, m, 2H of cyclohexaneH-2, H-3, H-5, H-6, 1×C(CH$_3$)$_3$), 1.37 (9H, s, 1×C(CH$_3$)$_3$), 1.23 (3H, t, J 7.0 Hz, OCH$_2$CH$_3$); $^{19}$F nmr (380 MHz, CDCl$_3$) δ −72.3, −124.5; $^{32}$P nmr (162 MHz, CDCl$_3$) δ −11.9; m/z: 758 [M+Na]$^+$. The filtrate contains further product.

IV. Preparation of 1-(4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)ethyl dihydrogen phosphate

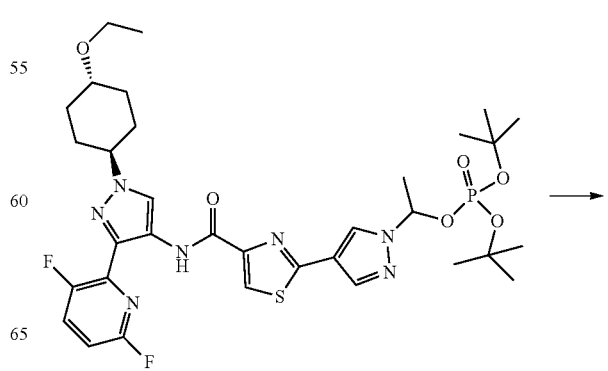

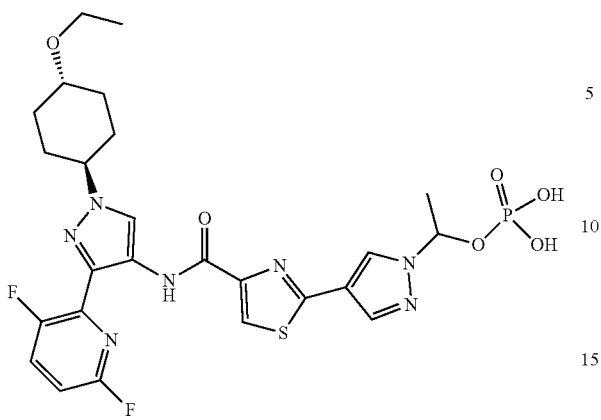

A solution of the di-tert-butyl phosphate (0.202 g, 0.275 mmol) in dichloromethane (3 mL) was cooled to 0° C. and phosphoric acid (85%, 9 mL) was added. The reaction was stirred at room temperature for 3 minutes before adding to water (60 mL). The organics were extracted with EtOAc (3×40 mL). The combined organics were dried (Na$_2$SO$_4$) and concentrated under reduced pressure to approximately 7 mL. A precipitate formed, which was isolated by filtration to obtain the title compound (0.082 g, 48%) as a pink solid; $^1$H nmr (400 MHz, D$_6$-DMSO) δ 11.45 (1H, s, NH), 8.55 (1H, s, pyrazoleH-5, thiazoleH-5, pyrazoleH-3 or H-5), 8.50 (1H, s, pyrazoleH-5, thiazoleH-5, pyrazoleH-3 or H-5), 8.30 (1H, s, pyrazoleH-5, thiazoleH-5, pyrazoleH-3 or H-5), 8.13 (1H, s pyrazoleH-5, thiazoleH-5, pyrazoleH-3 or H-5), 8.06 (1H, td, J 9.5, 6.5 Hz, pyridineH-4 or H-5), 7.24 (1H, dt, J 9.0, 2.5 Hz, pyridineH-4 or H-5), 6.28-6.21 (1H, m, NCH(CH$_3$)O), 4.31 (1H, brt, J 11.5 Hz, cyclohexaneH-1 or H-4), 3.46 (2H, q, J 7.0 Hz, OCH$_2$CH$_3$), 3.30 (1H, brt, J 10.5 Hz, cyclohexaneH-1 or H-4), 2.10-2.03 (4H, m, 4H of cyclohexaneH-2, H-3, H-5, H-6), 1.88-1.78 (2H, m, 2H of cyclohexaneH-2, H-3, H-5, H-6), 1.77 (3H, d, J 6.0 Hz, NCH(CH$_3$)O), 1.38-1.29 (2H, m, 2H of cyclohexaneH-2, H-3, H-5, H-6), 1.08 (3H, t, J 7.0 Hz, OCH$_2$CH$_3$); $^{19}$F nmr (380 MHz, D$_6$-DMSO) δ -72.8, -124.2; $^{32}$P nmr (380 MHz, D$_6$-DMSO) δ -3.3; m/z: 624 [M+H]$^+$ (found [M+H]$^+$, 624.1610, C$_{25}$H$_{28}$F$_2$N$_7$O$_6$PS requires [M+H]$^+$ 624.1600).

To a suspension of the di-tert-butyl phosphate (0.100 g, 0.136 mmol, 1.0 eq) in tetrahydrofuran (0.8 mL) water (0.8 mL, distilled, deionized, 18MΩ) was added sodium acetate (0.008 g, 0.010 mmol, 0.75 eq). The reaction was sealed and stirred at 70° C. for 5.5 hours before cooling and adding acetone (20 mL). A precipitate resulted, which was isolated by filtration to obtain the title compound (0.055 g, 65%) as a white solid; data agrees with that stated above.

V. Preparation of sodium 1-(4-(4-((3-(3,6-difluoro-pyridin-2-yl)-1-(trans-4-ethoxycyclohexyl)-1H-pyrazol-4-yl)carbamoyl)thiazol-2-yl)-1H-pyrazol-1-yl) ethyl phosphate (I-20)

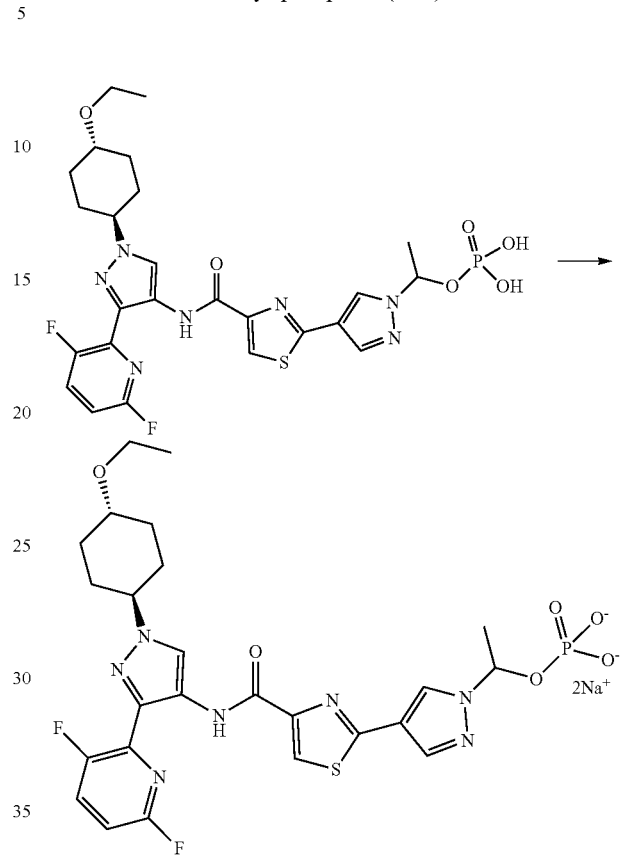

A suspension of the phosphate (I-18) (2.34 g, 3.75 mmol, 1.0 eq) in acetonitrile (15 mL) and water (20 mL) was cooled to 0° C. and sodium hydroxide (0.27 g in 5 mL of water, 6.76 mmol, 1.8 eq) was added dropwise over 30 minutes (approximately 4 mL of solution added, reaction mixture pH about 9). The reaction was stirred at 0° C. for a further 15 minutes before water (10 mL) was added. The mixture was stirred for 15 minutes at 0° C. and filtered (filter paper). The filtrate was frozen and dried by lyophylisation to obtain the title compound (2.40 g, 96%) as a white powder; $^1$H nmr (400 MHz, D$_2$O) δ 8.05 (1H, s, pyrazoleH-5, thiazoleH-5, pyrazoleH-3 or H-5), 7.86 (1H, s, pyrazoleH-5, thiazoleH-5, pyrazoleH-3 or H-5), 7.55 (1H, s, pyrazoleH-5, thiazoleH-5, pyrazoleH-3 or H-5), 7.52 (1H, s pyrazoleH-5, thiazoleH-5, pyrazoleH-3 or H-5), 7.37 (1H, m, pyridineH-4 or H-5), 6.59 (1H, m, pyridineH-4 or H-5), 6.00 (1H, t, J 7.5 Hz, NCH(CH$_3$)O), 3.94 (1H, m, cyclohexaneH-1 or H-4), 3.56 (2H, q, J 7.0 Hz, OCH$_2$CH$_3$), 3.43 (1H, m, cyclohexaneH-1 or H-4), 2.16-2.08 (2H, m, 2H of cyclohexaneH-2, H-3, H-5, H-6), 2.07-2.00 (2H, m, 2H of cyclohexaneH-2, H-3, H-5, H-6), 1.69 (3H, d, J 6.0 Hz, NCH(CH$_3$)O), 1.68-1.60 (2H, m, 2H of cyclohexaneH-2, H-3, H-5, H-6), 1.36-1.25 (2H, m, 2H of cyclohexaneH-2, H-3, H-5, H-6), 1.10 (3H, t, J 7.0 Hz, OCH$_2$CH$_3$); $^{13}$C nmr (100 MHz, D$_2$O) δ 160.4, 157.9, 156.8 (d, J 237 Hz), 152.4 (d, J 256.5 Hz), 147.5, 137.2 (d, J 10.5 Hz), 135.9 (t, J 14.5 Hz), 132.0 (d, J 9.0 Hz), 130.2 (dd, J 25.0, 8.5 Hz), 128.0, 122.7, 120.4, 119.2, 116.0, 108.6 (d, J 41.0 Hz), 82.1, 76.7, 63.8, 60.7, 30.5, 30.2, 22.1, 14.5;

$^{19}$F nmr (380 MHz, D$_2$O) δ −72.8, −124.8; $^{32}$P nmr (162 MHz, D$_2$O) δ 1.2; m/z: 624 [M+H]$^+$.

VI. Preparation of sodium 1-(4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)ethyl hydrogen phosphate (I-107)

VII. Preparation of potassium 1-(4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)ethyl hydrogen phosphate

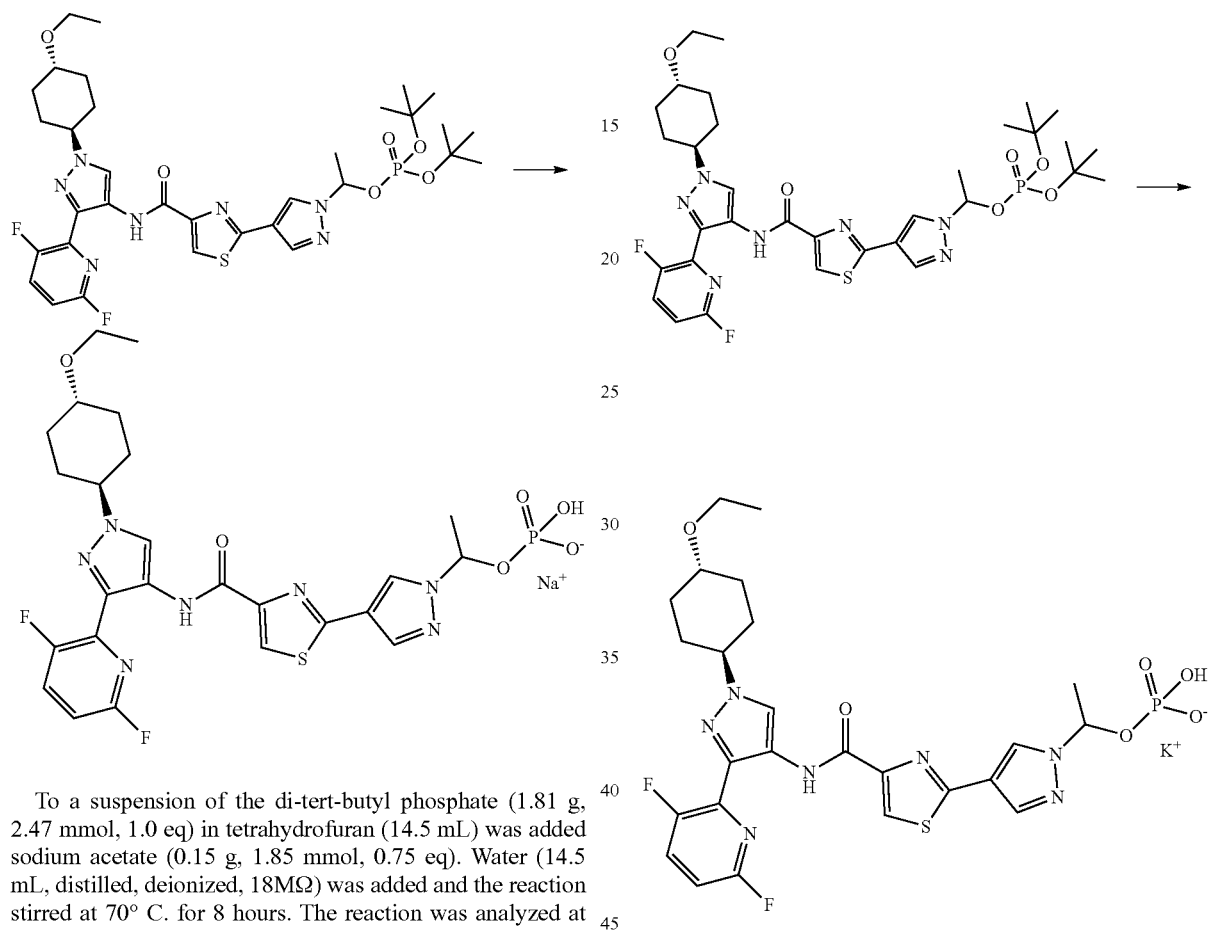

To a suspension of the di-tert-butyl phosphate (1.81 g, 2.47 mmol, 1.0 eq) in tetrahydrofuran (14.5 mL) was added sodium acetate (0.15 g, 1.85 mmol, 0.75 eq). Water (14.5 mL, distilled, deionized, 18MΩ) was added and the reaction stirred at 70° C. for 8 hours. The reaction was analyzed at hourly intervals from 4 hours and heating continued until the profile showed approximately 10% of the monophosphate and 70% product (prolonged heating may result in product decomposition). The reaction was cooled and added to acetone (75 mL) resulting in a precipitate, which was isolated by filtration to obtain the title compound (1.04 g, 67%) as a white solid; IR ν$_{max}$ (film) 3427, 2935, 2869, 1660, 1593, 1556, 1490, 1372, 1333, 1229, 1103, 1092, 1022, 963, 823, 784, 713, 665, 647 cm$^{-1}$; $^1$H nmr (400 MHz, D$_6$-DMSO) δ 11.43 (1H, s, NH), 8.42 (1H, s, 1H of pyrazoleH-5, thiazoleH-5, pyrazoleH-3, H-5), 8.47 (1H, s, 1H of pyrazoleH-5, thiazoleH-5, pyrazoleH-3, H-5), 8.23 (1H, s, 1H of pyrazoleH-5, thiazoleH-5, pyrazoleH-3, H-5), 8.04 (1H, dt, J 9.5, 6.5 Hz, pyridineH-4 or H-5), 8.03 (1H, s, 1H of pyrazoleH-5, thiazoleH-5, pyrazoleH-3, H-5), 7.27 (1H, dt, J 8.5, 2.5 Hz, 1H of pyridineH-4 or H-5), 6.11 (1H, dq, J 3.5, 6.0 Hz, NCH(CH$_3$)O), 4.31 (1H, tt, J 11.5, 3.5 Hz, cyclohexaneH-1 or H-4), 3.47 (2H, q, J 7.0 Hz, OCH$_2$CH$_3$), 3.35 (1H, tt, J 10.5, 3.5 Hz, cyclohexaneH-1 or H-4), 2.12-2.05 (4H, m, 4H of cyclohexaneH-2, H-3, H-5, H-6), 1.90-1.80 (2H, m, 2H of cyclohexaneH-2, H-3, H-5, H-6), 1.63 (3H, d, J 6.0 Hz, CHCH$_3$), 1.41-1.30 (2H, m, 2H of cyclohexaneH-2, H-3, H-5, H-6), 1.10 (3H, t, J 7.0 Hz, OCH$_2$CH$_3$); m/z: 624 [M+H]$^+$.

A similar procedure was used to the procedure provided above for the sodium salt but using potassium acetate instead of sodium acetate, and the reaction may take longer to reach completion. $^1$H nmr (400 MHz, D$_6$-DMSO) δ 11.43 (1H, s, NH), 8.47 (1H, s, 1H of pyrazoleH-5, thiazoleH-5, pyrazoleH-3, H-5), 8.46 (1H, s, 1H of pyrazoleH-5, thiazoleH-5, pyrazoleH-3, H-5), 8.22 (1H, s, 1H of pyrazoleH-5, thiazoleH-5, pyrazoleH-3, H-5), 8.07-8.00 (1H, m, pyridineH-4 or H-5), 8.02 (1H, s, 1H of pyrazoleH-5, thiazoleH-5, pyrazoleH-3, H-5), 7.25 (1H, d, J 8.5 Hz, 1H of pyridineH-4 or H-5), 6.10 (1H, dq, J 9.0, 6.0 Hz, NCH(CH$_3$)O), 4.30 (1H, br t, J 11.5 Hz, cyclohexaneH-1 or H-4), 3.47 (2H, q, J 7.0 Hz, OCH$_2$CH$_3$), 3.34 (1H, br t, J 10.5 Hz, cyclohexaneH-1 or H-4), 2.12-2.03 (4H, m, 4H of cyclohexaneH-2, H-3, H-5, H-6), 2.00-1.78 (2H, m, 2H of cyclohexaneH-2, H-3, H-5, H-6), 1.63 (3H, d, J 6.0 Hz, CHCH$_3$), 1.39-1.29 (2H, m, 2H of cyclohexaneH-2, H-3, H-5, H-6), 1.09 (3H, t, J 7.0 Hz, OCH$_2$CH$_3$); $^{32}$P nmr (162 MHz, D$_6$-DMSO) δ −2.0; $^{19}$F nmr (380 MHz, D$_6$-DMSO) δ −72.5 (d, J 27.5 Hz), −124.4 (dd, J 30.5, 11.0 Hz); m/z: 624 [M+H]$^+$.

VIII. Preparation of 2-amino-2-(hydroxymethyl) propane-1,3-diol 1-(4-(4-((3-(3,6-difluoropyridin-2-yl)-1-(trans-4-ethoxycyclohexyl)-1H-pyrazol-4-yl)carbamoyl)thiazol-2-yl)-1H-pyrazol-1-yl)ethyl hydrogen phosphate (I-49)

Example 14

Synthesis of (4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methyl Isopropyl Carbonate (I-45)

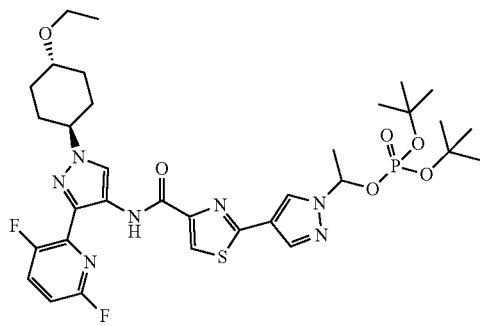

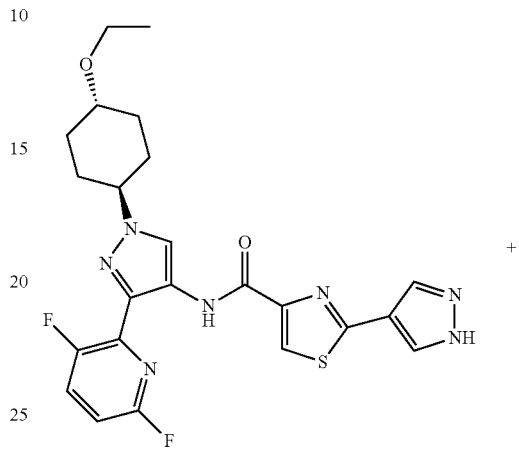

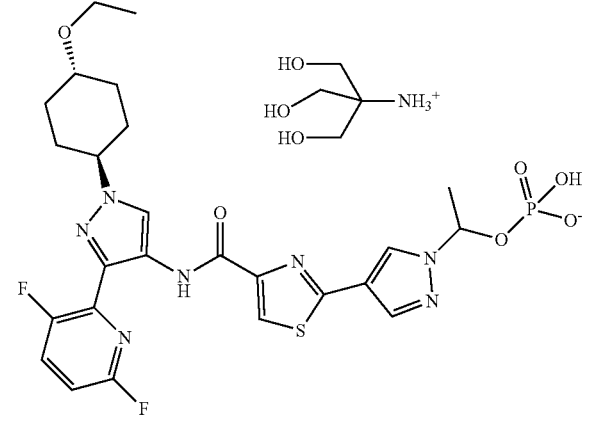

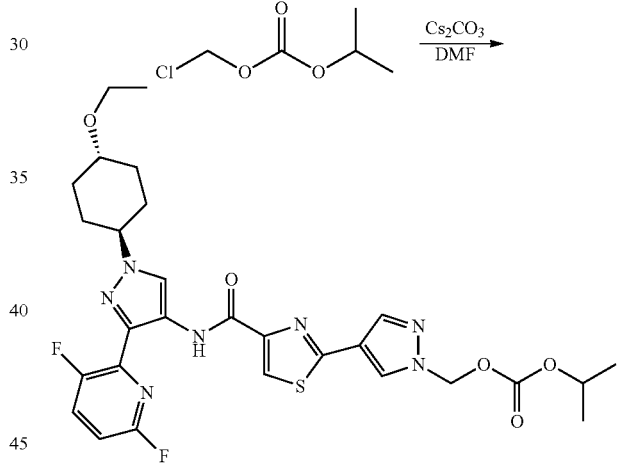

A similar procedure was used to the procedure provided above for the sodium salt but using tris(hydroxymethyl) aminomethane. $^1$H nmr (400 MHz, D$_6$-DMSO) δ 11.45 (1H, s, NH), 8.49 (1H, s, 1H of pyrazoleH-5, thiazoleH-5, pyrazoleH-3, H-5), 8.47 (1H, s, 1H of pyrazoleH-5, thiazoleH-5, pyrazoleH-3, H-5), 8.25 (1H, s, 1H of pyrazoleH-5, thiazoleH-5, pyrazoleH-3, H-5), 8.08-8.02 (1H, m Hz, pyridineH-4 or H-5), 8.05 (1H, s, 1H of pyrazoleH-5, thiazoleH-5, pyrazoleH-3, H-5), 7.27 (1H, br d, J 8.5 Hz, 1H of pyridineH-4 or H-5), 6.11 (1H, dq, J 9.0, 6.0 Hz, NCH(CH$_3$)O), 4.31 (1H, br t, J 11.5 Hz, cyclohexaneH-1 or H-4), 3.46 (2H, q, J 7.0 Hz, OCH$_2$CH$_3$), 3.40 (6H, s, NH$_2$C(CH$_2$OH)$_3$), 3.34 (1H, br t, J 10.0 Hz, cyclohexaneH-1 or H-4), 2.12-2.04 (4H, m, 4H of cyclohexaneH-2, H-3, H-5, H-6), 1.89-1.79 (2H, m, 2H of cyclohexaneH-2, H-3, H-5, H-6), 1.65 (3H, d, J 6.0 Hz, CHCH$_3$), 1.39-1.29 (2H, m, 2H of cyclohexaneH-2, H-3, H-5, H-6), 1.09 (3H, t, J 7.0 Hz, OCH$_2$CH$_3$); $^{32}$P nmr (162 MHz, D$_6$-DMSO) δ −1.7; $^{19}$F nmr (380 MHz, D$_6$-DMSO) δ −72.5 (d, J 27.5 Hz), −124.4 (dd, J 30.5, 11.0 Hz); m/z: 624 [M+H]$^+$.

To a solution of N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide (50 mg, 0.1 mmol) and chloromethyl isopropyl carbonate (20 mg, 0.13 mmol) in anhydrous DMF (1 mL) was added cesium carbonate (40 mg, 0.12 mmol). The resulting reaction mixture was then allowed to stir at ambient temperature overnight and then diluted with water (50 mL) to provide upon filtration and drying (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl isopropyl carbonate as a white solid, wt. 49 mg (80%). $^1$H NMR (400 MHz, CD$_3$OD) δ 11.73 (s, 1H), 8.55-8.47 (m, 2H), 8.26-8.15 (m, 2H), 7.88 (ddd, J=9.7, 8.8, 6.2 Hz, 1H), 7.14-7.06 (m, 1H), 6.11 (d, J=4.3 Hz, 2H), 4.96-4.88 (m, 1H), 4.36-4.25 (m, 1H), 3.60 (qd, J=7.0, 1.4 Hz, 2H), 3.52-3.42 (m, 1H), 2.31-2.18 (m, 4H), 1.97 (q, J=11.5 Hz, 2H), 1.54-1.41 (m, 2H), 1.29 (d, J=6.3 Hz, 6H), 1.21 (t, J=7.0 Hz, 3H). MS m/e: Calculated 615.21; Found 616.2 (M+H)$^+$.

Example 15
Synthesis of (4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((S)-2-amino-3-methylbutanamido)butanoate Hydrochloride (I-57)
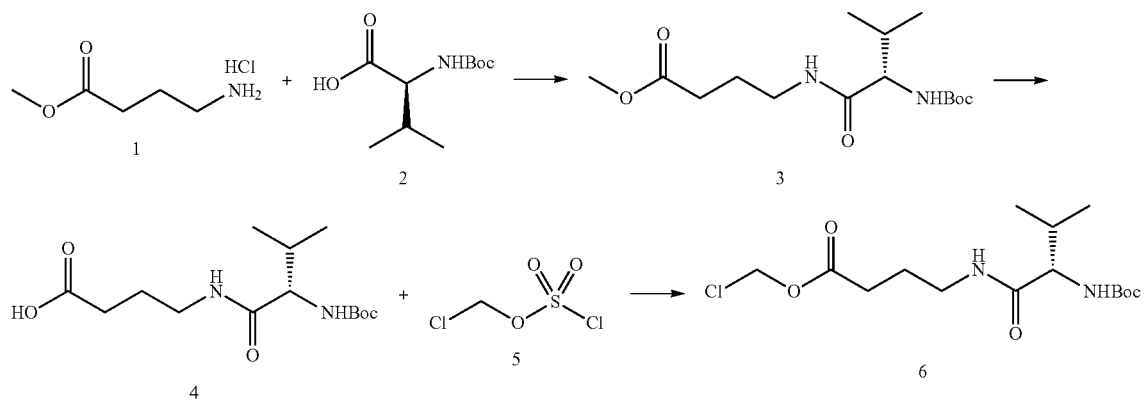
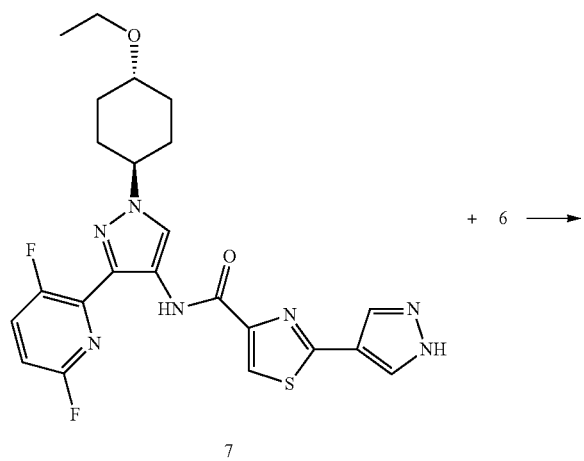
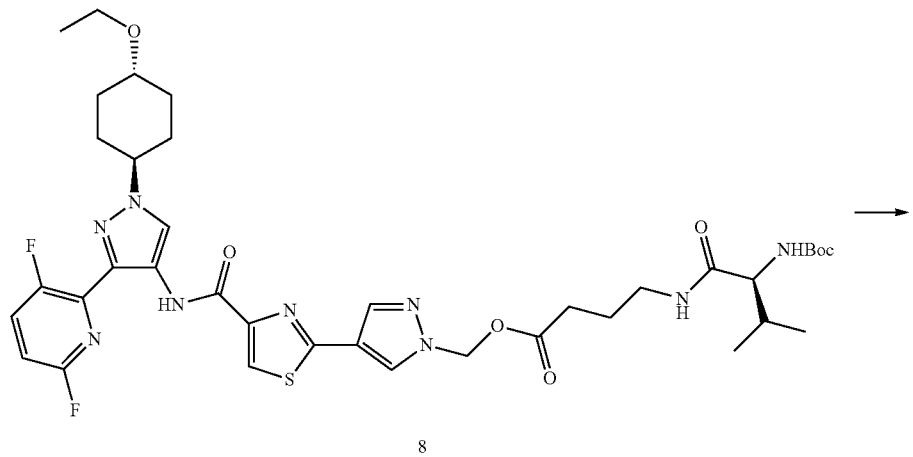

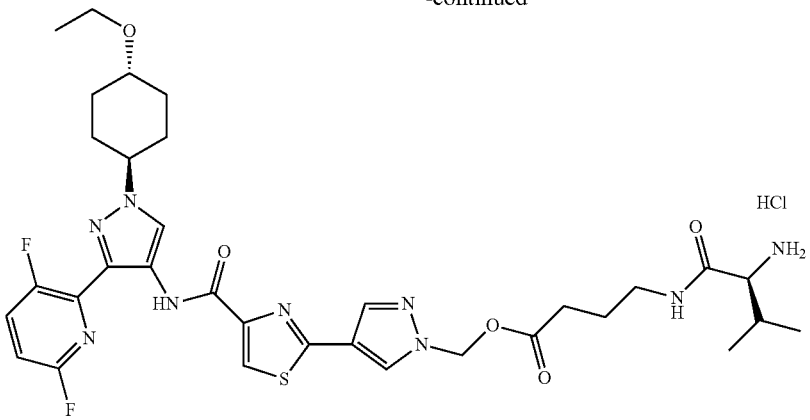

-continued

I. Synthesis of Methyl (S)-4-(2-((tert-Butoxycarbonyl)amino)-3-methylbutanamido)butanoate (3)

To a solution of methyl 4-aminobutanoate hydrogen chloride salt 1 (306 mg, 2.0 mmol) and (tert-butoxycarbonyl)-L-valine 2 (433 mg, 2.0 mmol) in anhydrous DMF (5 mL) was added diisopropylethylamine (568 mg, 0.76 mL, 4.4 mmol). The mixture was then cooled down to 0° C. and HATU (835 mg, 2.2 mmol) was added and the resulting solution was allowed to warm up to ambient temperature and stirred for 17 hours. Water (50 mL) and ethyl acetate (100 mL) were then added and the organic layer was separated, washed with water (3×30 mL), brine (30 mL), dried over anhydrous magnesium sulfate, filtered and concentrated under reduced pressure. The residue obtained was purified by chromatography using 0 to 100% ethyl acetate in hexane gradient to afford methyl (S)-4-(2-((tert-butoxycarbonyl)amino)-3-methylbutanamido)butanoate 3 (591 mg, 94%) as a pale sticky oil. MS m/e: Calculated 316.20; Found 261.1 [M−$^t$Bu+H]$^+$.

II. Synthesis of (S)-4-(2-((tert-Butoxycarbonyl)amino)-3-methylbutanamido)butanoic Acid (4)

To a solution of methyl (S)-4-(2-((tert-butoxycarbonyl)amino)-3-methylbutanamido)butanoate 3 (583 mg, 1.85 mmol) in a mixture of THF (4 mL) and MeOH (1 mL) was added NaOH aqueous solution (1 mL, 4N, 4 mmol). The resulting solution was stirred at ambient temperature for 15 hours. Most of the solvent mixture was removed under reduced pressure and water (50 mL) was added to the obtained residue. The aqueous layer was then washed with ethyl ether (50 mL), acidified with aqueous HCl (5 mL, 1N) to pH 4 and extracted with ethyl acetate (3×40 mL). Combined organic layer was washed with brine (20 mL), dried over anhydrous magnesium sulfate, filtered and concentrated under reduced pressure to afford (S)-4-(2-((tert-butoxycarbonyl)amino)-3-methylbutanamido)butanoic acid 4 (480 mg, 86%) as a white solid. MS m/e: Calculated 302.18; Found 247.2 [M−$^t$Bu+H]$^+$.

III. Synthesis of Chloromethyl (S)-4-(2-((tert-butoxycarbonyl)amino)-3-methylbutanamido)butanoate (6)

To a solution of (S)-4-(2-((tert-butoxycarbonyl)amino)-3-methylbutanamido)butanoic acid 4 (370 mg, 1.23 mmol) in a mixture of dichloromethane (7 mL) and water (7 mL), were added sodium bicarbonate (412 mg, 4.90 mmol) and tetrabutylammonium bisulfate (42 mg, 0.123 mmol), followed by chloromethyl chlorosulfate 5 (233 mg, 143 µL, 1.41 mmol). The resulting solution was stirred at ambient temperature for 2 days and dichloromethane (80 mL) and water (30 mL) were added. The organic layer was separated, and the aqueous layer was extracted with dichloromethane (30 mL). The combined organic layers were dried over anhydrous magnesium sulfate, filtered and concentrated under reduced pressure to afford crude product which was further purified by chromatography using 0 to 100% ethyl acetate in hexane gradient to afford chloromethyl (S)-4-(2-((tert-butoxycarbonyl)amino)-3-methylbutanamido)butanoate 6 (369 mg, 86%) as a colorless oil. MS m/e: Calculated 350.16; Found 251.1 [M−Boc+H]$^+$.

IV. Synthesis of (4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((S)-2-((tert-butoxycarbonyl)amino)-3-methylbutanamido)butanoate (8)

To a solution of chloromethyl (S)-4-(2-((tert-butoxycarbonyl)amino)-3-methylbutanamido) butanoate 6 (45 mg, 0.128 mmol) in anhydrous DMF (1 mL) was added diisopropylethylamine (33.2 mg, 45 µL, 0.128 mmol) followed by N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide 7 (64 mg, 0.128 mmol). The resulting solution was stirred at ambient temperature for 2 days, then water (20 mL) was added and the aqueous solution was extracted with ethyl acetate (2×40 mL). The combined organic layers were then washed with brine (20 mL), dried over anhydrous magnesium sulfate, filtered and concentrated under reduced pressure. The resulting crude product was purified by reverse phase HPLC (40 to 100% acetonitrile in water buffered with 0.1% formic acid). Desired fractions were combined and lyophilized to afford (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((S)-2-((tert-butoxycarbonyl)amino)-3-methylbutanamido) butanoate 8 (26 mg, 25%) as a white foam. MS m/e: Calculated 813.34; Found 814.3 [M+H]$^+$.

V. Synthesis of (4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((S)-2-amino-3-methylbutanamido)butanoate Hydrochloride (I-57)

To a suspension of (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((S)-2-((tert-butoxycarbonyl)amino)-3-methylbutanamido)butanoate 8 (26 mg, 0.032 mmol) in ethyl acetate was added HCl (0.31 mL, 4M in dioxane). The resulting solution was stirred at ambient temperature for 19 hours. A cloudy solution was obtained, filtered and the resulting solid was washed with ethyl acetate and hexanes and dried under high vacuum to afford (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-((S)-2-amino-3-methylbutanamido)butanoate hydrogen chloride (21.4 mg, 89%) as a white solid. $^1$H NMR (400 MHz, CD$_3$OD) δ 8.51-8.48 (m, 2H), 8.22 (d, J=0.7 Hz, 1H), 8.20 (s, 1H), 7.89 (td, J=9.2, 6.2 Hz, 1H), 7.09 (ddd, J=8.8, 3.4, 2.6 Hz, 1H), 6.15 (s, 2H), 4.31 (ddd, J=11.7, 8.4, 3.7 Hz, 1H), 3.61 (q, J=7.0 Hz, 2H), 3.53 (d, J=5.9 Hz, 1H), 3.50-3.40 (m, 1H), 3.27 (dt, J=6.9, 3.4 Hz, 2H), 2.48 (t, J=7.4 Hz, 2H), 2.30-2.17 (m, 4H), 2.11 (dq, J=13.4, 6.4 Hz, 1H), 2.05-1.91 (m, 2H), 1.86 (p, J=7.2 Hz, 2H), 1.47 (q, J=11.8 Hz, 2H), 1.21 (t, J=7.0 Hz, 3H), 1.01 (dd, J=6.9, 5.4 Hz, 6H). MS m/e: Calculated 713.29; Found 714.3 [M+H]$^+$.

Example 16

Synthesis of (4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methyl 1-Amino-3,6,9,12,15,18-hexaoxahenicosan-21-oate Hydrochloride (I-61)

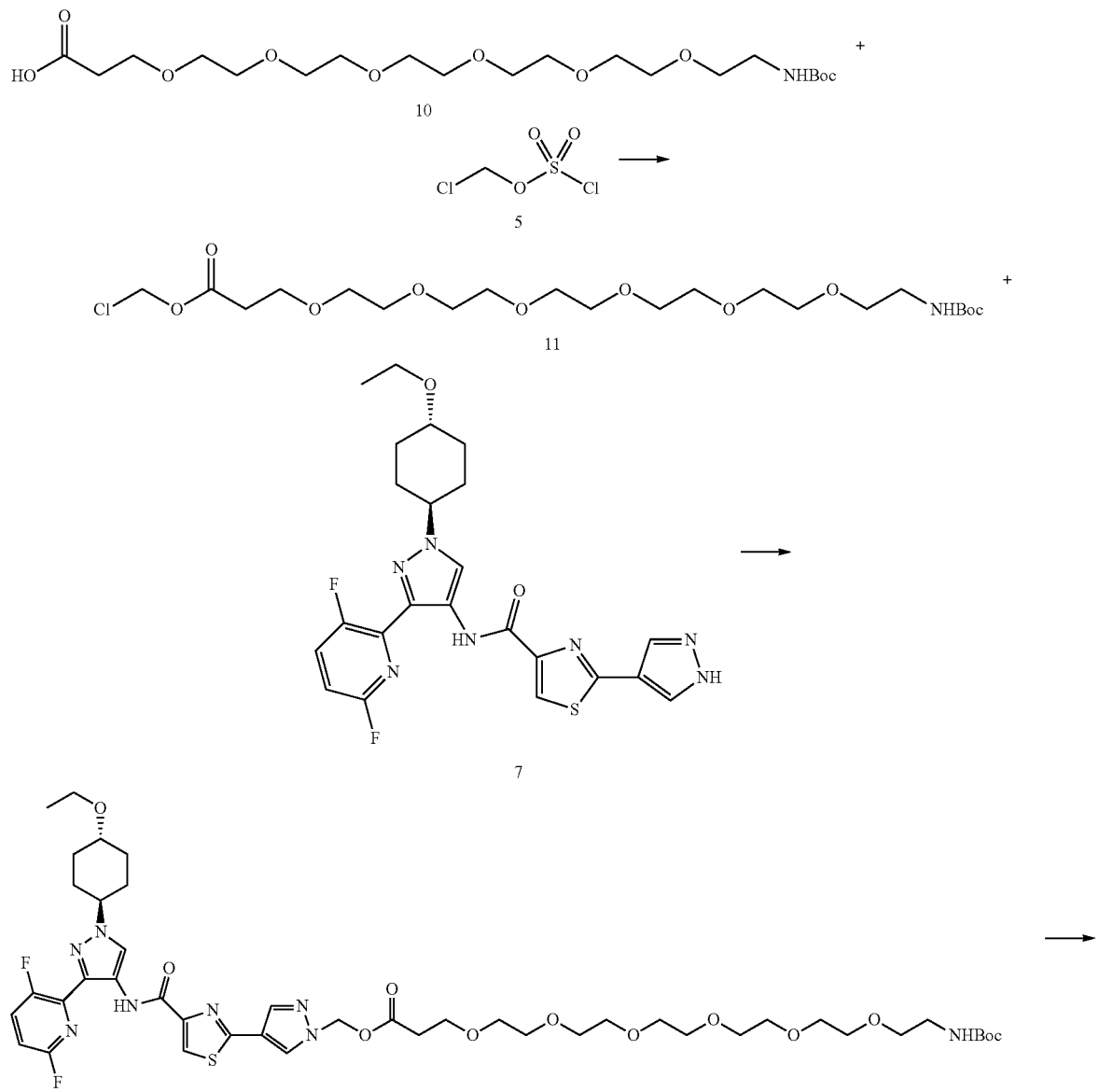

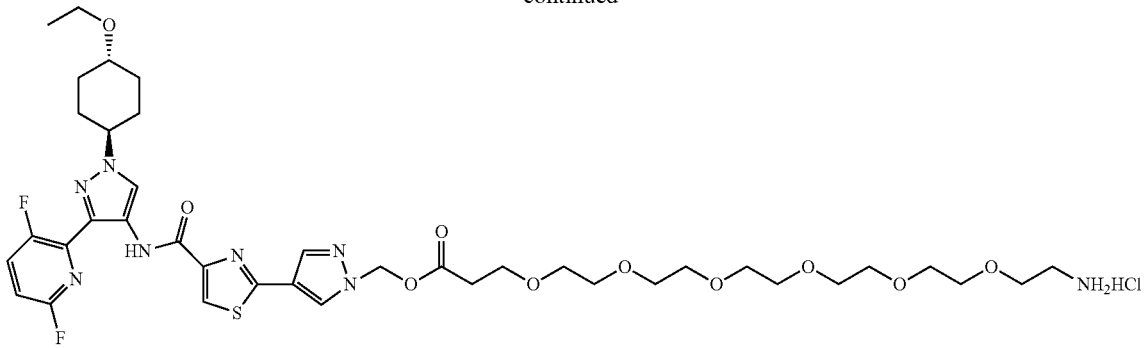

I. Synthesis of Chloromethyl 2,2-Dimethyl-4-oxo-3,8,11,14,17,20,23-heptaoxa-5-azahexacosan-26-oate (11)

To a solution of 2,2-dimethyl-4-oxo-3,8,11,14,17,20,23-heptaoxa-5-azahexacosan-26-oic acid (250 mg, 0.551 mmol) 10 in the mixture of dichloromethane (5.2 mL) and water (5.2 mL) were added sodium bicarbonate (185 mg, 2.21 mmol) and tetrabutylammonium bisulfate (18.7 mg, 0.0551 mmol). Chloromethyl chlorosulfate 5 (105 mg, 64 µL, 0.634 mmol) was then added and the resulting solution was stirred at ambient temperature for 18 hours. Water (10 mL) was then added, and the resulting aqueous solution was extracted with dichloromethane (3×30 mL). The combined organic layers were washed with brine (20 mL), dried over anhydrous magnesium sulfate, filtered and concentrated under reduced pressure to afford crude product of chloromethyl 2,2-dimethyl-4-oxo-3,8,11,14,17,20,23-heptaoxa-5-azahexacosan-26-oate 11 (303 mg, 100%) with 91% purity. The crude product was directly used in next step without further purification. MS m/e: Calculated 501.23; Found 402.1 [M-Boc+H]$^+$.

II. Synthesis of (4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2,2-dimethyl-4-oxo-3,8,11,14,17,20,23-heptaoxa-5-azahexacosan-26-oate (12)

To a solution of chloromethyl 2,2-dimethyl-4-oxo-3,8,11,14,17,20,23-heptaoxa-5-azahexacosan-26-oate 11 (51.8 mg, 0.103 mmol) and N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide 7 (51.5 mg, 0.103 mmol) in anhydrous DMF (1 mL) was added anhydrous cesium carbonate (37 mg, 0.113 mmol). The resulting reaction mixture was stirred at ambient temperature for 16 hours. Water (20 mL) and ethyl acetate (100 mL) were then added, and the organic layer was separated, washed with brine, dried over anhydrous magnesium sulfate, filtered and concentrated under reduced pressure. The residue obtained was purified by reverse phase HPLC (30 to 100% acetonitrile in water buffered with 0.1% formic acid). The desired fractions were combined, lyophilized to afford (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2,2-dimethyl-4-oxo-3,8,11,14,17,20,23-heptaoxa-5-azahexacosan-26-oate 12 (57.4 mg, 58%) as a colorless sticky oil. MS m/e: Calculated 964.42; Found 865.3[M-Boc+H]$^+$.

III. Synthesis of (4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methyl 1-Amino-3,6,9,12,15,18-hexaoxahenicosan-21-oate Hydrochloride (I-61)

To a solution of (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2,2-dimethyl-4-oxo-3,8,11,14,17,20,23-heptaoxa-5-azahexacosan-26-oate 12 (57.4 mg, 0.0595 mmol) in ethyl acetate (5 mL) was added HCl (2.4 mL, 1M in ethyl ether, 2.4 mmol). The resulting solution was stirred at ambient temperature for 2 days. All solvents were removed under reduced pressure and the residue obtained was purified by reverse phase HPLC (0 to 70% acetonitrile in water buffered with 0.1% formic acid). The desired fractions were combined and HCl solution (65 µL, 1N) was added and lyophilized to afford (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 1-amino-3,6,9,12,15,18-hexaoxahenicosan-21-oate hydrochloride (19 mg, 35%) as a sticky pale yellow solid. $^1$H NMR (400 MHz, CD$_3$OD) δ 11.71 (s, 1H), 8.50 (s, 2H), 8.28-8.16 (m, 2H), 7.90 (td, J=9.2, 6.1 Hz, 1H), 7.21-7.00 (m, 1H), 6.17 (s, 2H), 4.31 (ddd, J=11.8, 8.3, 3.7 Hz, 1H), 3.76 (t, J=5.9 Hz, 2H), 3.72-3.48 (m, 24H), 3.06 (t, J=5.1 Hz, 2H), 2.70 (t, J=5.9 Hz, 2H), 2.66 (s, 1H), 2.30-2.17 (m, 4H), 1.97 (dt, J=13.7, 11.2 Hz, 2H), 1.56-1.41 (m, 2H), 1.29 (s, 3H), 1.21 (t, J=7.0 Hz, 3H). MS m/e: Calculated 864.37; Found 865.3 [M+H]$^+$.

Example 17

Synthesis of Isopropyl (((4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)(phenoxy)phosphoryl)-L-alaninate (I-62)

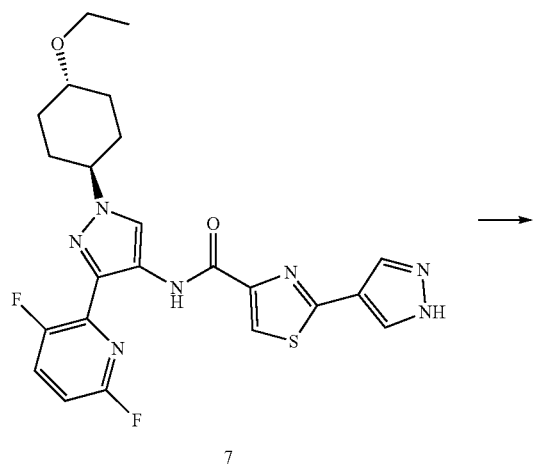

7

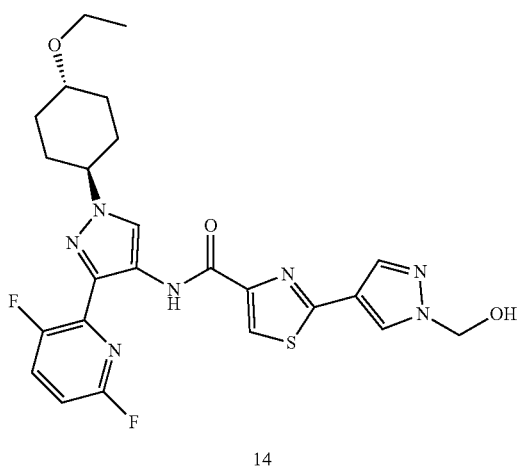

14

+

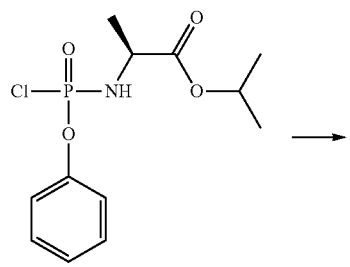

15

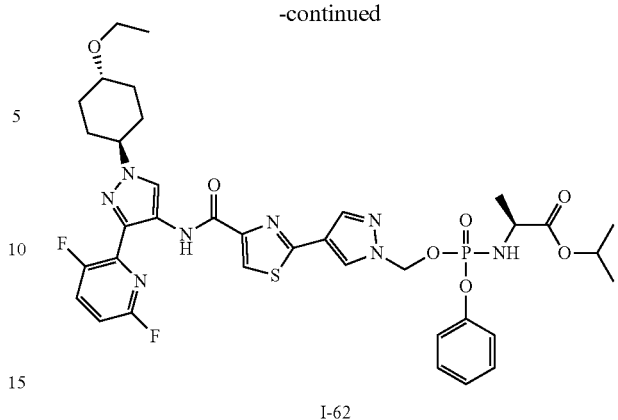

I-62

I. Synthesis of N-(3-(3,6-Difluoropyridin-2-yl)-1-((1r,4r)-4-ethoxycyclohexyl)-1H-pyrazol-4-yl)-2-(1-(hydroxymethyl)-1H-pyrazol-4-yl)thiazole-4-carboxamide (14)

To a solution of N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide 7 (501 mg, 1 mmol) in absolute ethanol (3 mL) was added formaldehyde aqueous solution (162 mg, 0.15 mL, 37% wt., 2 mmol). The resulting solution was heated at 50° C. for 18 hours, and the resulting cloudy reaction mixture was filtered, washed with absolute ethanol and hexanes. The white solid obtained was placed under high vacuum to afford N-(3-(3,6-difluoropyridin-2-yl)-1-((1r,4r)-4-ethoxycyclohexyl)-1H-pyrazol-4-yl)-2-(1-(hydroxymethyl)-1H-pyrazol-4-yl)thiazole-4-carboxamide 14 (385 mg, 73%). $^1$H NMR (400 MHz, DMSO-$d_6$) δ 11.47 (s, 1H), 8.52 (d, J=8.5 Hz, 2H), 8.31 (s, 1H), 8.10 (d, J=15.2 Hz, 2H), 7.28 (s, 1H), 6.99 (s, 1H), 5.43 (d, J=7.7 Hz, 2H), 4.33 (s, 1H), 3.47 (d, J=7.4 Hz, 2H), 2.08 (d, J=11.9 Hz, 4H), 1.86 (d, J=13.4 Hz, 2H), 1.35 (d, J=12.3 Hz, 2H), 1.10 (t, J=7.0 Hz, 3H). MS m/e: Calculated 529.17; Found 530.1[M+H]$^+$.

II. Synthesis of Isopropyl (((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)(phenoxy)phosphoryl)-L-alaninate (I-62)

To a solution of N-(3-(3,6-difluoropyridin-2-yl)-1-((1r,4r)-4-ethoxycyclohexyl)-1H-pyrazol-4-yl)-2-(1-(hydroxymethyl)-1H-pyrazol-4-yl)thiazole-4-carboxamide 14 (57.3 mg, 0.108 mmol) in anhydrous dichloromethane (2 mL), diisopropylethylamine (28 mg, 38 μL, 0.217 mmol) was added followed by isopropyl (chloro(phenoxy)phosphoryl)-L-alaninate 15 (36.4 mg, 30 μL, 0.119 mmol). The resulting solution was stirred at ambient temperature for 2 days and then concentrated under reduced pressure. The residue obtained was purified by reverse phase HPLC (50 to 100% acetonitrile in water buffered with 0.1% formic acid) and the desired fractions were combined and lyophilized to afford isopropyl (((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)(phenoxy)phosphoryl)-L-alaninate (16 mg, 19%) as a white solid. $^1$H NMR (400 MHz, CD$_3$OD) δ 8.51 (s, 1H), 8.48 (d, J=14.4 Hz, 1H), 8.24 (d, J=4.5 Hz, 1H), 8.22 (s, 1H), 7.87 (ddd, J=9.7, 8.8, 6.2 Hz, 1H), 7.33-7.25 (m, 2H), 7.21-7.01 (m, 4H), 6.11 (d, J=11.8 Hz, 1H), 6.06 (dd, J=11.6, 2.3 Hz, 1H), 4.95 (pd, J=6.3, 5.3 Hz, 1H), 4.38-4.25 (m, 1H), 3.99-3.81 (m, 1H), 3.60 (q, J=7.0 Hz, 2H), 3.51-3.39 (m, 1H), 2.32-2.14 (m, 4H), 1.98 (q, J=12.1, 11.6 Hz, 2H), 1.47 (q, J=12.1 Hz, 2H), 1.32 (ddd, J=8.8, 7.2, 1.2 Hz, 3H), 1.26-1.09 (m, 9H). MS m/e: Calculated 798.25; Found 799.2 [M+H]$^+$.

Example 18

Synthesis of (((((4-(4-((3-(3,6-Difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)(hydroxy)phosphoryl)oxy)methyl isopropyl carbonate (I-60)

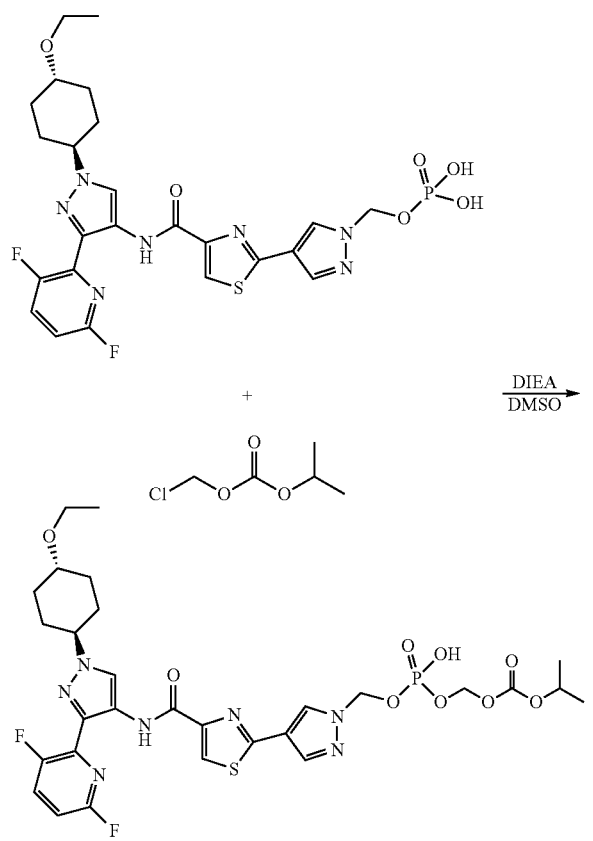

To a solution of (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl dihydrogen phosphate (1.00 g, 1.64 mmol, 1.0 eq) in dimethyl sulfoxide (10 mL) was added chloromethyl isopropyl carbonate (2.17 mL, 16.4 mmol, 10 eq) and diisopropylethylamine (2.71 mL, 16.4 mmol, 10 eq). The solution was stirred at room temperature for 2 days. The reaction mixture was purified by reverse phase HPLC (C-18, water/acetonitrile with 0.1% formic acid) to give the title compound (309 mg, 26%) as a white solid. $^1$H NMR (400 MHz, CDCl$_3$) δ 11.6 (s, 1H), 8.37 (s, 1H), 8.25 (s, 1H), 8.03 (s, 1H), 7.95 (s, 1H), 7.57-7.51 (m, 1H), 6.81-6.79 (m, 1H), 5.97 (d, J=10.8 Hz, 2H), 5.65 (d, J=10.8 Hz, 2H), 4.93-4.87 (m, 1H), 4.27-4.21 (m, 1H), 3.57 (q, J=7.2, 6.8 Hz, 2H), 3.41-3.35 (m, 1H), 2.32-2.22 (m, 4H), 1.93-1.84 (m, 2H), 1.52-1.43 (m, 2H), 1.33-1.24 (m, 9H). MS m/e: Calculated 725.18; Found 726.2 (M+H)$^+$.

The following exemplary compounds were prepared using the methods of Examples 4-18. Characterization data for these additional compounds are provided below.

I-6: 2-(1-(acetyl-L-leucyl)-1H-pyrazol-4-yl)-N-(3-(3,6-difluoropyridin-2-yl)-1-((1r,4r)-4-ethoxycyclohexyl)-1H-pyrazol-4-yl)thiazole-4-carboxamide

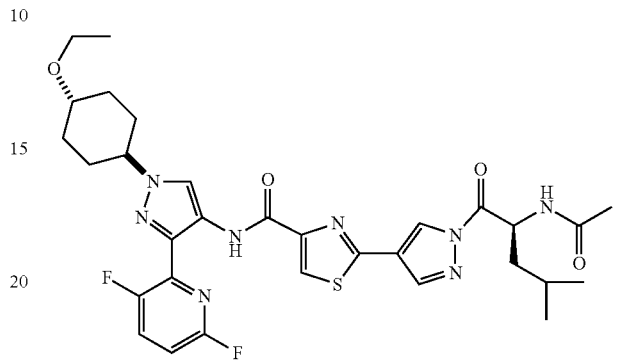

$^1$H nmr (400 MHz, CDCl$_3$) δ 8.78 (1H, s, pyrazoleH-3 or H-5), 8.50 (1H, s, thiazoleH-5 or pyrazoleH-5), 8.36 (1H, s, pyrazoleH-3 or H-5), 8.14 (1H, s, thiazoleH-5 or pyrazoleH-5), 7.65 (1H, td, J 9.0, 6.0 Hz, pyridineH-4 or H-5), 6.91 (1H, ddd, J 9.0, 3.5, 2.5 Hz, pyridineH-4 or H-5), 6.11 (1H, d, J 9.0 Hz, NHCOCH$_3$), 5.88 (1H, m, COCHNHCO), 4.27 (1H, tt, J 11.5, 4.0 Hz, cyclohexaneH-1 or H-4), 3.56 (2H, q, J 7.0 Hz, OCH$_2$CH$_3$), 3.37 (1H, tt, J 10.5, 4.0 Hz, cyclohexaneH-1 or H-4), 2.30 (2H, m, 2H of cyclohexaneH-2, H-3, H-5, H-6), 2.22 (2H, m, 2H of cyclohexaneH-2, H-3, H-5, H-6), 2.08 (3H, s, COCH$_3$), 1.89 (2H, m, 2H of cyclohexaneH-2, H-3, H-5, H-6), 1.86-1.76 (2H, m, 2H of CHCH$_2$CH(CH$_3$)$_2$), 1.65 (1H, m, 1H of CHCH$_2$CH(CH$_3$)$_2$), 1.33 (2H, m, 2H of cyclohexaneH-2, H-3, H-5, H-6), 1.22 (3H, t, J 7.0 Hz, OCH$_2$CH$_3$), 1.07 (3H, d, J 6.0 Hz, 1×CH$_3$ of CH(CH$_3$)$_2$), 0.97 (3H, d, J 6.5 Hz, 1×CH$_3$ of CH(CH$_3$)$_2$); m/z: 677 [M+Na]$^+$, 655 [M+H]$^+$ (found [M+H]$^+$, 655.2623, C$_{31}$H$_{36}$F$_2$N$_8$O$_4$S requires [M+H]$^+$ 655.2621).

I-7: 1-methylcyclopropyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate

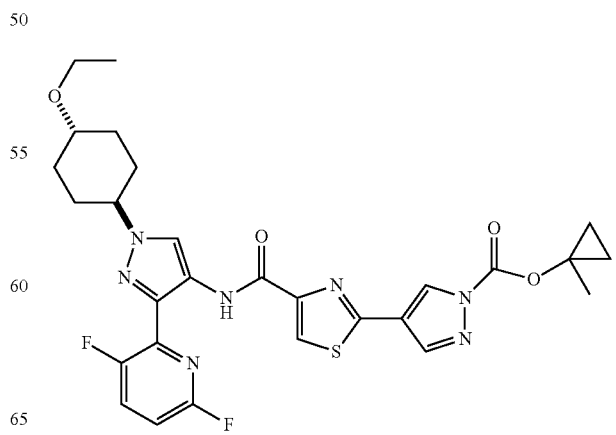

¹H nmr (400 MHz, CDCl₃) δ 8.73 (1H, s, 1H of thiazoleH-5, pyrazoleH-5 or pyrazoleH-3, H-5), 8.50 (1H, s, 1H of thiazoleH-5, pyrazoleH-5 or pyrazoleH-3, H-5), 8.33 (1H, s, 1H of thiazoleH-5, pyrazoleH-5 or pyrazoleH-3, H-5), 8.13 (1H, s, 1H of thiazoleH-5, pyrazoleH-5 or pyrazoleH-3, H-5), 7.66 (1H, td, J 9.0, 6.0 Hz, pyridineH-4 or H-5), 6.88 (1H, ddd, J 9.0, 3.5, 2.5 Hz, pyridineH-4 or H-5), 4.28 (1H, tt, J 11.5, 4.0 Hz, cyclohexaneH-1 or H-4), 3.56 (2H, q, J 7.0 Hz, OCH₂CH₃), 3.37 (1H, tt, J 10.5, 4.0 Hz, cyclohexaneH-1 or H-4), 2.30 (2H, br t, J 11.5 Hz, 2H of cyclohexaneH-2, H-3, H-5, H-6), 2.22 (2H, m, 2H of cyclohexaneH-2, H-3, H-5, H-6), 1.89 (2H, m, 2H of cyclohexaneH-2, H-3, H-5, H-6), 1.76 (3H, s, CH₃), 1.47 (2H, m, 2H of cyclohexaneH-2, H-3, H-5, H-6), 1.24 (2H, m, 2H of cPrH-2, H-3), 1.23 (3H, t, J 7.0 Hz, OCH₂CH₃), 0.86 (2H, m, 2H of cPrH-2, H-3); ¹⁹F nmr (380 MHz, CDCl₃) δ −72.6, −124.3; m/z: 598 [M+H]⁺ (found [M+H]⁺, 598.2035, C₂₈H₂₉F₂N₇O₄S requires [M+H]⁺ 598.2043).

I-8: 1-(isobutyryloxy)ethyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate

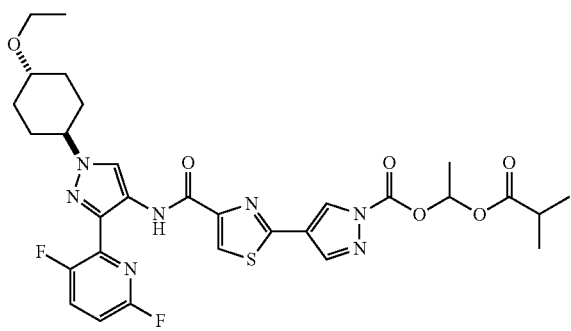

¹H nmr (400 MHz, CDCl₃) δ 8.76 (1H, s, 1H of thiazoleH-5, pyrazoleH-5, pyrazoleH-3, H-5), 8.51 (1H, s, 1H of thiazoleH-5, pyrazoleH-5, pyrazoleH-3, H-5), 8.38 (1H, s, 1H of thiazoleH-5, pyrazoleH-5, pyrazoleH-3, H-5), 8.14 (1H, s, 1H of thiazoleH-5, pyrazoleH-5, pyrazoleH-3, H-5), 7.66 (1H, td, J 9.0, 6.0 Hz, pyridineH-4 or H-5), 7.15 (1H, q, J 5.5 Hz, OCH(CH₃)O), 6.87 (1H, ddd, J 9.0, 3.5, 2.5 Hz, pyridineH-4 or H-5), 4.28 (1H, tt, J 11.5, 4.0 Hz, cyclohexaneH-1 or H-4), 3.57 (2H, q, J 7.0 Hz, OCH₂CH₃), 3.37 (1H, tt, J 10.5, 4.0 Hz, cyclohexaneH-1 or H-4), 2.63 (1H, heptet, J 7.0 Hz, COCH(CH₃)₂), 2.30 (2H, m, 2H of cyclohexaneH-2, H-3, H-5, H-6), 2.22 (2H, m, 2H of cyclohexaneH-2, H-3, H-5, H-6), 1.90 (2H, m, 2H of cyclohexaneH-2, H-3, H-5, H-6), 1.74 (3H, d, J 5.5 Hz, OCH(CH₃)O), 1.47 (2H, m, 2H of cyclohexaneH-2, H-3, H-5, H-6), 1.23 (3H, t, J 7.0 Hz, OCH₂CH₃), 1.21 (3H, d, J 7.0 Hz, 1×CH₃ of (CH(CH₃)₂), 1.21 (3H, d, J 6.5 Hz, 1×CH₃ of CH(CH₃)₂); ¹⁹F nmr (380 MHz, CDCl₃) δ −72.6 (ddd, J 27.0, 5.5, 4.0 Hz), −124.3 (ddd, 27.0, 9.5, 2.5 Hz); m/z: 658 [M+H]⁺ (found [M+H]⁺, 658.2553, C₃₀H₃₃F₂N₇O₆S requires [M+H]⁺ 658.2254).

I-9: N-(3-(3,6-difluoropyridin-2-yl)-1-((1r,4r)-4-ethoxycyclohexyl)-1H-pyrazol-4-yl)-2-(1-((5-methyl-2-oxo-1,3-dioxol-4-yl)methyl)-1H-pyrazol-4-yl)thiazole-4-carboxamide

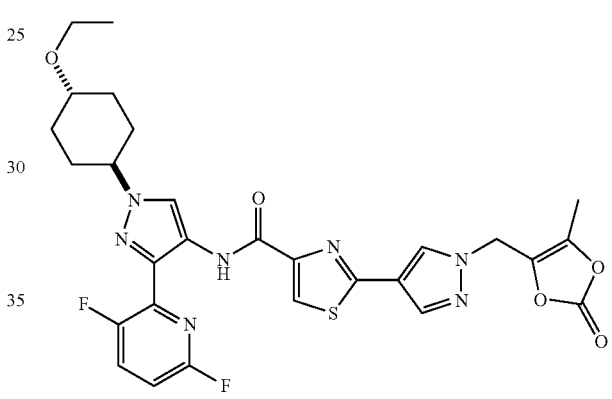

¹H nmr (400 MHz, CDCl₃) δ 8.50 (1H, s, 1H of thiazoleH-5, pyrazoleH-5, pyrazoleH-3, H-5), 8.49 (1H, s, 1H of thiazoleH-5, pyrazoleH-5, pyrazoleH-3, H-5), 8.11 (1H, s, 1H of thiazoleH-5, pyrazoleH-5, pyrazoleH-3, H-5), 8.09 (1H, s, 1H of thiazoleH-5, pyrazoleH-5, pyrazoleH-3, H-5), 7.67 (1H, td, J 9.0, 6.5 Hz, pyridineH-4 or H-5), 6.92 (1H, dt, J 9.0, 3.0 Hz, pyridineH-4 or H-5), 5.19 (1H, d, J 4.5 Hz, 1H of NCH₂C), 4.73 (1H, d, J 4.5 Hz, 1H of NCH₂C), 4.28 (1H, tt, J 11.5, 4.0 Hz, cyclohexaneH-1 or H-4), 3.57 (2H, q, J 7.0 Hz, OCH₂CH₃), 3.38 (1H, tt, J 10.5, 4.0 Hz, cyclohexaneH-1 or H-4), 2.36 (3H, s, CCH₃), 2.30 (2H, m, 2H of cyclohexaneH-2, H-3, H-5, H-6), 2.23 (2H, m, 2H of cyclohexaneH-2, H-3, H-5, H-6), 1.90 (2H, m, 2H of cyclohexaneH-2, H-3, H-5, H-6), 1.48 (2H, m, 2H of cyclohexaneH-2, H-3, H-5, H-6), 1.23 (3H, t, J 7.0 Hz, OCH₂CH₃); ¹⁹F nmr (380 MHz, CDCl₃) δ −73.5, −124.1 (ddd, 27.0, 9.5, 3.0 Hz); m/z: 612 [M+H]⁺ (found [M+H]⁺, 612.1835, C₂₈H₂₇F₂N₇O₅S requires [M+H]⁺ 612.1857).

I-10: 2-morpholinoethyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate

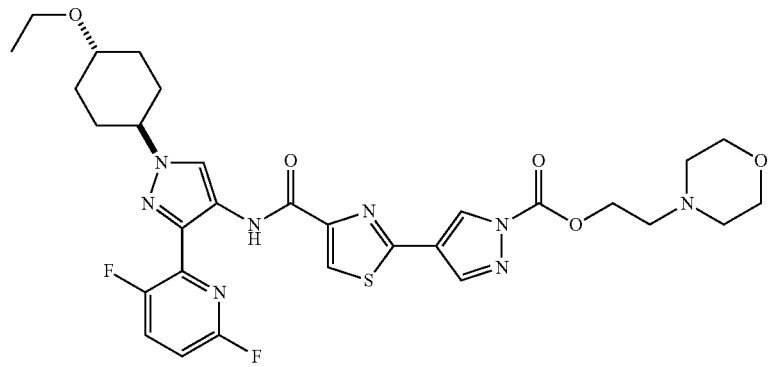

¹H nmr (400 MHz, CDCl₃) δ 8.75 (1H, s, 1H of thiazoleH-5, pyrazoleH-5, pyrazoleH-3, H-5), 8.49 (1H, s, 1H of thiazoleH-5, pyrazoleH-5, pyrazoleH-3, H-5), 8.35 (1H, s, 1H of thiazoleH-5, pyrazoleH-5, pyrazoleH-3, H-5), 8.13 (1H, s, 1H of thiazoleH-5, pyrazoleH-5, pyrazoleH-3, H-5), 7.64 (1H, td, J 9.0, 6.0 Hz, pyridineH-4 or H-5), 6.86 (1H, dt, J 8.5, 3.5, 2.5 Hz, pyridineH-4 or H-5), 4.63 (2H, t, J 6.0 Hz, COOC$\underline{H}_2$CH₂N), 4.26 (1H, tt, J 11.5, 4.0 Hz, cyclohexaneH-1 or H-4), 3.70, 3.68 (4H, 2d AB system, J 4.5 Hz, 4H of morpholine), 3.55 (2H, q, J 7.0 Hz, OC$\underline{H}_2$CH₃), 3.36 (1H, tt, J 10.5, 4.0 Hz, cyclohexaneH-1 or H-4), 2.84 (2H, t, J 6.0 Hz, COOCH2C$\underline{H}$2N), 2.58, 2.57 (4H, 2d AB system, J 4.5 Hz, 4H of morpholine), 2.28 (2H, m, 2H of cyclohexaneH-2, H-3, H-5, H-6), 2.20 (2H, m, 2H of cyclohexaneH-2, H-3, H-5, H-6), 1.88 (2H, m, 2H of cyclohexaneH-2, H-3, H-5, H-6), 1.45 (2H, m, 2H of cyclohexaneH-2, H-3, H-5, H-6), 1.21 (3H, t, J 7.0 Hz, OCH₂C$\underline{H}_3$); ¹⁹F nmr (380 MHz, CDCl₃) δ −72.7 (ddd, J 27.0, 5.5, 4.0 Hz), −124.3 (ddd, 27.0, 11.0, 9.5 Hz); m/z: 657 [M+H]⁺.

I-12: N-(3-(3,6-difluoropyridin-2-yl)-1-((1r,4r)-4-ethoxycyclohexyl)-1H-pyrazol-4-yl)-2-(1-(morpholine-4-carbonyl)-1H-pyrazol-4-yl)thiazole-4-carboxamide

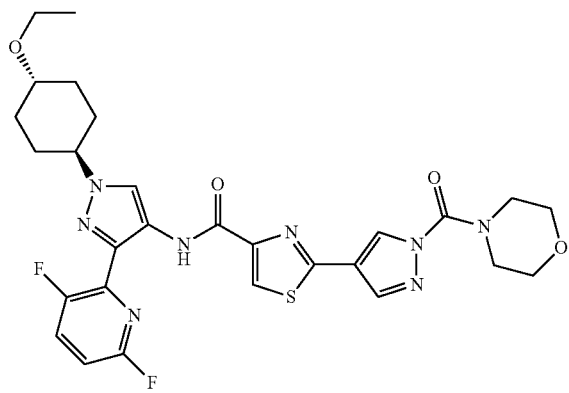 [SMILES: CCO[C@H]1CC[C@H](n2cc(NC(=O)c3csc(-c4cnn(C(=O)N5CCOCC5)c4)n3)c(-c3nc(F)ccc3F)n2)CC1]

¹H nmr (400 MHz, CDCl₃) δ 8.71 (1H, s, pyrazoleH-5, thiazoleH-5, pyrazoleH-3 or H-5), 8.50 (1H, s, pyrazoleH-5, thiazoleH-5, pyrazoleH-3 or H-5), 8.26 (1H, d, J 0.5 Hz), 8.10 (1H, s, pyrazoleH-5, thiazoleH-5, pyrazoleH-3 or H-5), 7.64 (1H, td, J 9.0, 6.0 Hz, pyridineH-4 or H-5), 6.90 (1H, ddd, J 9.0, 3.5, 2.5 Hz, pyridineH-4 or H-5), 4.27 (1H, tt, J 11.5, 4.0 3.83, 3.82 (4H, 2d AB system, J 4.0 Hz, 4H of morpholine), 3.56 (2H, q, J 7.0 Hz, OC$\underline{H}_2$CH₃), 3.36 (1H, tt, J 11.0, 4.0 Hz, cyclohexaneH-1 or H-4), Hz, cyclohexaneH-1 or H-4), 3.94 (4H, br s, 4H of morpholine), 2.33-2.25 (2H, m, 2H of cyclohexaneH-2, H-3, H-5, H-6), 2.55-1.90 (2H, m, 2H of cyclohexaneH-2, H-3, H-5, H-6), 1.94-1.84 (2H, m, 2H of cyclohexaneH-2, H-3, H-5, H-6), 1.52-1.41 (2H, m, 2H of cyclohexaneH-2, H-3, H-5, H-6), 1.22 (3H, t, J 7.0 Hz, OCH₂C$\underline{H}_3$); ¹⁹F nmr (380 MHz, CDCl₃) δ −72.5, −124.4; m/z: 613 [M+H]⁺ (found [M+H]⁺, 613.2163, C₂₈H₃₀F₂N₈O₄S requires [M+H]⁺ 613.2152).

I-13: N-(3-(3,6-difluoropyridin-2-yl)-1-((1r,4r)-4-ethoxycyclohexyl)-1H-pyrazol-4-yl)-2-(1-((3-morpholinopropyl)carbamoyl)-1H-pyrazol-4-yl)thiazole-4-carboxamide

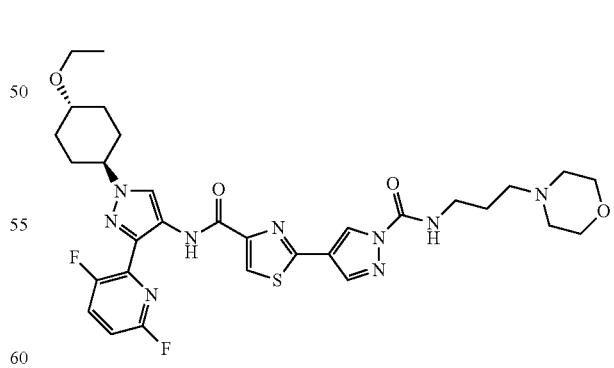

¹H nmr (400 MHz, CDCl₃) δ 8.85 (1H, t, J 5.0 Hz, CON$\underline{H}$CH₂), 8.79 (1H, s, pyrazoleH-5, thiazoleH-5, pyrazoleH-3 or H-5), 8.49 (1H, s, pyrazoleH-5, thiazoleH-5, pyrazoleH-3 or H-5), 8.25 (1H, s, pyrazoleH-5, thiazoleH-5, pyrazoleH-3 or H-5), 8.08 (1H, s, pyrazoleH-5, thiazoleH-5, pyrazoleH-3 or H-5), 7.36 (1H, td, J 9.0, 6.0 Hz, pyridineH-4 or H-5), 6.90 (1H, ddd, J 9.0, 3.5, 2.5 Hz, pyridineH-4 or H-5), 4.26 (1H, tt, J 12.0, 4.0 Hz, cyclohexaneH-1 or H-4), 3.85, 3.84 (4H, 2d AB system, J 4.5 Hz, 4H of morpholine), 3.60-3.56 (2H, m, CONHCH₂CH₂CH₂N), 3.55 (2H, q, J 7.0 Hz, OCH₂CH₃), 3.36 (1H, tt, J 10.5, 4.0 Hz, cyclohexaneH-1 or H-4), 2.57-2.54 (2H, m, CONHCH₂CH₂CH₂N), 2.51 (4H, br s, 4H of morpholine), 2.30-2.26 (2H, m, 2H of cyclohexaneH-2, H-3, H-5, H-6), 2.23-2.18 (2H, m, 2H of cyclohexaneH-2, H-3, H-5, H-6), 1.93-1.84 (2H, m, 2H of cyclohexaneH-2, H-3, H-5, H-6), 1.84-1.78 (2H, m, CONHCH₂CH₂CH₂N), 1.51-1.41 (2H, m, 2H of cyclohexaneH-2, H-3, H-5, H-6), 1.21 (3H, t, J 7.0 Hz, OCH₂CH₃); $^{19}$F nmr (380 MHz, CDCl₃) δ −72.6 (ddd, J 27.0, 5.5, 4.0 Hz), −124.5 (ddd, J 27.0, 9.5, 2.5 Hz); m/z: 670 [M+H]⁺.

I-14: N-(3-(3,6-difluoropyridin-2-yl)-1-((1r,4r)-4-ethoxycyclohexyl)-1H-pyrazol-4-yl)-2-(1-((3-(dimethylamino)propyl)carbamoyl)-1H-pyrazol-4-yl)thiazole-4-carboxamide

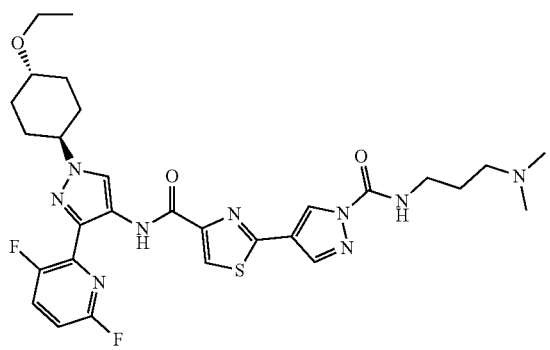 [SMILES: CCO[C@H]1CC[C@H](n2cc(NC(=O)c3csc(-c4cnn(C(=O)NCCCN(C)C)c4)n3)c(-c3nc(F)ccc3F)n2)CC1]

$^1$H nmr (400 MHz, CDCl₃) δ 8.80 (1H, s, pyrazoleH-5, thiazoleH-5, pyrazoleH-3 or H-5), 8.49 (1H, s pyrazoleH-5, thiazoleH-5, pyrazoleH-3 or H-5), 8.36 (1H, t, J 5.5 Hz, pyrazoleCONH), 8.20 (1H, d, J 0.5 Hz, pyrazoleH-5, thiazoleH-5, pyrazoleH-3 or H-5), 8.08 (1H, s, pyrazoleH-5, thiazoleH-5, pyrazoleH-3 or H-5), 7.63 (1H, td, J 9.0, 6.0 Hz, pyridineH-4 or H-5), 6.89 (1H, ddd, J 9.0, 3.5, 2.5 Hz, pyridineH-4 or H-5), 4.26 (1H, tt, J 11.5, 4.0 Hz, cyclohexaneH-1 or H-4), 3.58-3.52 (4H, m, OCH₂CH₃, pyrazoleCONHCH₂), 3.36 (1H, tt, J 10.5, 4.0 Hz, cyclohexaneH-1 or H-4), 2.44 (2H, t, J 6.5 Hz, CH₂N(CH₃)₂), 2.26 (6H, s, N(CH₃)₂), 2.30-2.18 (4H, m, 4H of cyclohexaneH-2, H-3, H-5, H-6), 1.93-1.83 (2H, m, 2H of cyclohexaneH-2, H-3, H-5, H-6), 1.79 (2H, pentet, J 6.5 Hz, NCH₂CH₂CH₂N(CH₃)₂), 1.51-1.41 (2H, m, 2H of cyclohexaneH-2, H-3, H-5, H-6), 1.21 (3H, t, J 7.0 Hz, OCH₂CH₃); $^{19}$F nmr (380 MHz, CDCl₃) δ −72.6, −124.5; m/z: 628 [M+H]⁺ (found [M+H]⁺, 628.2628, C₂₉H₃₅F₂N₉O₃S requires [M+H]⁺ 628.2624).

I-15: 3-morpholinopropyl 4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazole-1-carboxylate

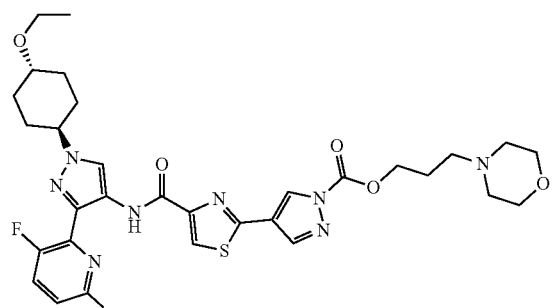

$^1$H nmr (400 MHz, CDCl₃) δ 8.75 (1H, s, pyrazoleH-5, thiazoleH-5, pyrazoleH-3 or H-5), 8.49 (1H, s, pyrazoleH-5, thiazoleH-5, pyrazoleH-3 or H-5), 8.34 (1H, s, pyrazoleH-5, thiazoleH-5, pyrazoleH-3 or H-5), 8.12 (1H, s, pyrazoleH-5, thiazoleH-5, pyrazoleH-3 or H-5), 7.64 (1H, td, J 9.0, 6.0 Hz, pyridineH-4 or H-5), 6.87 (1H, ddd, J 9.0, 3.5, 2.5 Hz, pyridineH-4 or H-5), 4.61 (2H, 6.5 Hz, 2H of OCH₂CH₂CH₂N), 4.26 (1H, tt, J 11.5, 4.0 Hz, cyclohexaneH-1 or H-4), 3.66, 3.65 (4H, 2d AB system, J 4.5 Hz, 4H of morpholine), 3.55 (2H, q, J 7.0 Hz, OCH₂CH₃), 3.35 (1H, tt, J 10.5, 4.0 Hz, cyclohexaneH-1 or H-4), 2.52 (2H, J 7.0 Hz, 2H of OCH₂CH₂CH₂N), 2.44 (4H, m, 4H of morpholine), 2.30-2.24 (2H, m, 2H of cyclohexaneH-2, H-3, H-5, H-6), 2.24-2.17 (2H, m, 2H of cyclohexaneH-2, H-3, H-5, H-6), 2.05 (2H, pentet, J 6.5 Hz, OCH₂CH₂CH₂N), 1.93-1.83 (2H, m, 2H of cyclohexaneH-2, H-3, H-5, H-6), 1.51-1.41 (2H, m, 2H of cyclohexaneH-2, H-3, H-5, H-6), 1.21 (3H, t, J 7.0 Hz, OCH₂CH₃); $^{19}$F nmr (380 MHz, CDCl₃) δ −72.7 (ddd, J 28.5, 5.5, 4.0 Hz), −124.3 (ddd, J 28.0, 9.5, 2.5 Hz); m/z: 671 [M+H]⁺ (found [M+H]⁺, 671.2560, C₃₁H₃₆F₂N₈O₅S requires [M+H]⁺ 671.2570).

I-16: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-valinate hydrogen chloride salt

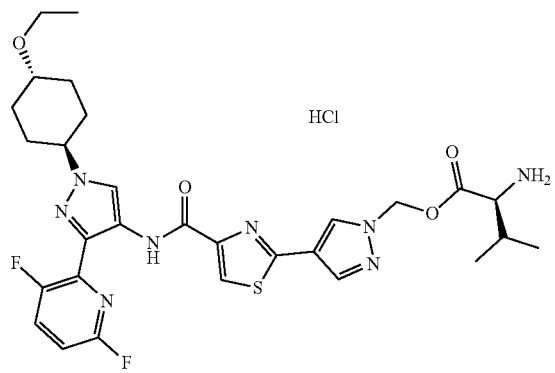 [SMILES: CCO[C@H]1CC[C@H](n2cc(NC(=O)c3csc(-c4cnn(COC(=O)[C@@H](N)C(C)C)c4)n3)c(-c3nc(F)ccc3F)n2)CC1 ; Cl]

$^1$H nmr (400 MHz, D₆-DMSO) δ 8.66 (1H, s, pyrazoleH-5, thiazoleH-5, pyrazoleH-3 or H-5), 8.51 (1H, s, pyrazoleH-5, thiazoleH-5, pyrazoleH-3 or H-5), 8.35 (1H, s, pyrazoleH-5, thiazoleH-5, pyrazoleH-3 or H-5), 8.22 (1H, s, pyrazoleH- 5, thiazoleH-5, pyrazoleH-3 or H-5), 8.07 (1H, td, J 9.0, 6.0 Hz, pyridineH-4 or H-5), 7.25 (1H, ddd, J 8.5, 3.0, 2.5 Hz, pyridineH-4 or H-5), 6.2x, 6.2x (2d, AB system, J Hz, NCH$_2$OCO), 4.32 (1H, tt, J 11.5, 3.0 Hz, cyclohexaneH-1 or H-4), 3.90 (1H, d, J 4.0 Hz, COCHNH$_2$), 3.45 (2H, q, J 7.0 Hz, OCH$_2$CH$_3$), 3.30 (1H, tt, J 11.0, 4.0 Hz, cyclohexaneH-1 or H-4), 2.12-2.00 (5H, m, 4H of cyclohexaneH-2, H-3, H-5, H-6, CH(CH$_3$)$_2$), 1.88-1.80 (2H, m, 2H of cyclohexaneH-2, H-3, H-5, H-6), 1.38-1.29 (2H, m, 2H of cyclohexaneH-2, H-3, H-5, H-6), 1.08 (3H, t, J 7.0 Hz, OCH$_2$CH$_3$), 0.87 (3H, d, J 7.0 Hz, 3H of CH(CH$_3$)$_2$), 0.83 (3H, d, J 7.0 Hz, 3H of CH(CH$_3$)$_2$); $^{13}$C nmr (100 MHz, D$_6$-DMSO) δ 168.8, 160.2, 157.6, 157.5 (d, J 236.0 Hz), 153.5 (dd, J 259.0, 4.5 Hz), 149.4, 139.5 (d, 6.5 Hz), 138.2 (t, J 14.5 Hz), 132.6 (d, 8.5 Hz), 132.3, 131.9 (dd, 22.5, 9.5 Hz), 124.4, 121.4, 120.3, 117.8, 109.2 (br d, J 34.0 Hz), 76.0, 73.6, 63.0, 60.8, 57.4, 30.9 (2C), 29.8, 18.6, 17.7, 16.1; $^{19}$F nmr (380 MHz, D$_6$-DMSO) δ −73.0 (d, J 28.5 Hz), −124.1 (dd, J 27.0, 9.5 Hz); m/z: 629 [M+H]$^+$ (found [M+H]$^+$, 629.2477, C$_{29}$H$_{34}$F$_2$N$_8$O$_4$S requires [M+H]$^+$ 629.2465).

I-17: (4-(4-((3-(3,6-difluoropyridin-2-yl)-1-((1r,4r)-4-ethoxycyclohexyl)-1H-pyrazol-4-yl)carbamoyl) thiazol-2-yl)-1H-pyrazol-1-yl)methyl L-prolinate hydrogen chloride salt

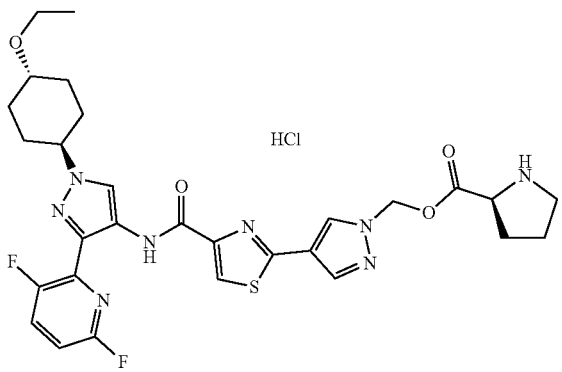 [SMILES: CCO[C@H]1CC[C@H](n2cc(NC(=O)c3csc(-c4cnn(COC(=O)[C@@H]5CCCN5)c4)n3)c(-c3nc(F)ccc3F)n2)CC1 ; Cl]

$^1$H nmr (400 MHz, D$_6$-DMSO) δ 11.48 (1H, s, 1×NH), 9.32 (1H, br s, 1×NH), 8.66 (1H, pyrazoleH-5, thiazoleH-5, pyrazoleH-3 or H-5), 8.51 (1H, s, pyrazoleH-5, thiazoleH-5, pyrazoleH-3 or H-5), 8.35 (1H, s, pyrazoleH-5, thiazoleH-5, pyrazoleH-3 or H-5), 8.22 (1H, s, pyrazoleH-5, thiazoleH-5, pyrazoleH-3 or H-5), 8.07 (1H, td, J 9.5, 6.5 Hz, pyridineH-4 or H-5), 7.26 (1H, dt, J 8.5, 2.5 Hz, pyridineH-4 or H-5), 6.24 (2H, s, NCH$_2$OCOCHN), 4.42 (1H, tt, J 8.5, 3.5 Hz, cyclohexaneH-1 or H-4), 3.45 (2H, q, J 7.0 Hz, OCH$_2$CH$_3$), 3.33 (1H, tt, J 10.0, 4.0 Hz, cyclohexaneH-1 or H-4), 3.23-3.11 (2H, m, COCHNHCH$_2$), 2.27-2.19 (1H, m, 1H of COCH(NH)CH$_2$), 2.10-2.04 (4H, m, 4H of cyclohexaneH-2, H-3, H-5, H-6), 1.98-1.80 (5H, m, 2H of cyclohexaneH-2, H-3, H-5, H-6, 3H of COCH(NH)CH$_2$CH$_2$), 1.38-1.29 (2H, m, 2H of cyclohexaneH-2, H-3, H-5, H-6), 1.08 (3H, t, J 7.0 Hz, OCH$_2$CH$_3$); $^{19}$F nmr (380 MHz, D$_6$-DMSO) δ −73.0 (d, J 27.0 Hz), −124.1 (dd, J 27.0, 9.5 Hz); m/z: 627 [M+H]$^+$.

I-18: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate

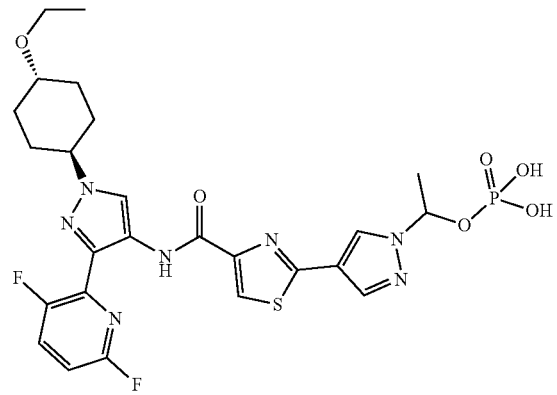 [SMILES: CCO[C@H]1CC[C@H](n2cc(NC(=O)c3csc(-c4cnn(C(C)OP(=O)(O)O)c4)n3)c(-c3nc(F)ccc3F)n2)CC1]

$^1$H nmr (400 MHz, D$_6$-DMSO) δ 11.45 (1H, s, NH), 8.55 (1H, s, pyrazoleH-5, thiazoleH-5, pyrazoleH-3 or H-5), 8.50 (1H, s, pyrazoleH-5, thiazoleH-5, pyrazoleH-3 or H-5), 8.30 (1H, s, pyrazoleH-5, thiazoleH-5, pyrazoleH-3 or H-5), 8.13 (1H, s pyrazoleH-5, thiazoleH-5, pyrazoleH-3 or H-5), 8.06 (1H, td, J 9.5, 6.5 Hz, pyridineH-4 or H-5), 7.24 (1H, dt, J 9.0, 2.5 Hz, pyridineH-4 or H-5), 6.28-6.21 (1H, m, NCH(CH$_3$)O), 4.31 (1H, brt, J 11.5 Hz, cyclohexaneH-1 or H-4), 3.46 (2H, q, J 7.0 Hz, OCH$_2$CH$_3$), 3.30 (1H, brt, J 10.5 Hz, cyclohexaneH-1 or H-4), 2.10-2.03 (4H, m, 4H of cyclohexaneH-2, H-3, H-5, H-6), 1.88-1.78 (2H, m, 2H of cyclohexaneH-2, H-3, H-5, H-6), 1.77 (3H, d, J 6.0 Hz, NCH(CH$_3$)O), 1.38-1.29 (2H, m, 2H of cyclohexaneH-2, H-3, H-5, H-6), 1.08 (3H, t, J 7.0 Hz, OCH$_2$CH$_3$); $^{19}$F nmr (380 MHz, D$_6$-DMSO) δ −72.8, −124.2; $^{32}$P nmr (380 MHz, D$_6$-DMSO) δ −3.3; m/z: 624 [M+H]$^+$ (found [M+H]$^+$, 624.1610, C$_{25}$H$_{28}$F$_2$N$_7$O$_6$PS requires [M+H]$^+$ 624.1600).

I-19: (4-(4-((3-(3,6-difluoropyridin-2-yl)-1-((1r,4r)-4-ethoxycyclohexyl)-1H-pyrazol-4-yl)carbamoyl) thiazol-2-yl)-1H-pyrazol-1-yl)methyl glycinate hydrogen chloride salt

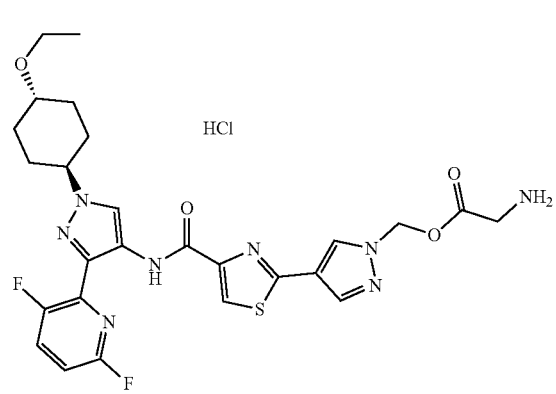 [SMILES: CCO[C@H]1CC[C@H](n2cc(NC(=O)c3csc(-c4cnn(COC(=O)CN)c4)n3)c(-c3nc(F)ccc3F)n2)CC1 ; Cl]

$^1$H nmr (400 MHz, D$_6$-DMSO) δ 11.47 (1H, s, NH), 8.67 (1H, s, 1H of pyrazoleH-5, thiazoleH-5, pyrazoleH-3 or H-5), 8.52 (1H, s, 1H of pyrazoleH-5, thiazoleH-5, pyrazoleH-3 or H-5), 8.37 (1H, s, 1H of pyrazoleH-5, thiazoleH- 5, pyrazoleH-3 or H-5), 8.34 (2H, br s, NH$_2$), 8.23 (1H, s, 1H of pyrazoleH-5, thiazoleH-5, pyrazoleH-3 or H-5), 8.09 (1H, td, J 9.5, 6.5 Hz, pyridineH-4 or H-5), 7.27 (1H, dt, J 8.5, 2.5 Hz, pyridineH-4 or H-5), 6.25 (2H, s, NCH$_2$O or COCH$_2$NH$_2$), 4.33 (1H, tt, J 11.5, 3.5 Hz, cyclohexaneH-1 or H-4), 3.89 (2H, s, NCH$_2$O or COCH$_2$NH$_2$), 3.47 (2H, q, J 7.0 Hz, OCH$_2$CH$_3$), 3.34 (1H, tt, J 11.0, 3.5 Hz, cyclohexaneH-1 or H-4), 2.12-2.04 (4H, m, 4H of cyclohexaneH-2, H-3, H-5, H-6), 1.91-1.80 (2H, m, 2H of cyclohexaneH-2, H-3, H-5, H-6), 1.41-1.29 (2H, m, 2H of cyclohexaneH-2, H-3, H-5, H-6), 1.10 (3H, t, J 7.0 Hz, OCH$_2$CH$_3$); $^{19}$F nmr (380 MHz, D$_6$-DMSO) δ −72.9, −124.1; m/z: 587 [M+H]$^+$ (found [M+H]$^+$, 587.1996, C$_{26}$H$_{28}$F$_2$N$_8$O$_4$S requires [M+H]$^+$ 587.1995).

I-20: sodium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl phosphate

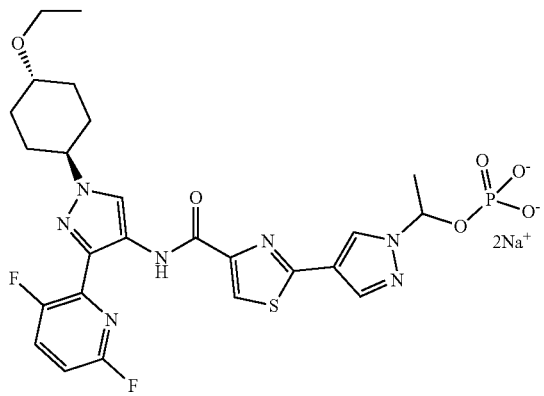 [SMILES: CCO[C@H]1CC[C@H](n2cc(NC(=O)c3csc(-c4cnn(C(C)OP(=O)([O-])[O-])c4)n3)c(-c3nc(F)ccc3F)n2)CC1]

$^1$H nmr (400 MHz, D$_2$O) δ 8.05 (1H, s, pyrazoleH-5, thiazoleH-5, pyrazoleH-3 or H-5), 7.86 (1H, s, pyrazoleH-5, thiazoleH-5, pyrazoleH-3 or H-5), 7.55 (1H, s, pyrazoleH-5, thiazoleH-5, pyrazoleH-3 or H-5), 7.52 (1H, s pyrazoleH-5, thiazoleH-5, pyrazoleH-3 or H-5), 7.37 (1H, m, pyridineH-4 or H-5), 6.59 (1H, m, pyridineH-4 or H-5), 6.00 (1H, t, J 7.5 Hz, NCH(CH$_3$)O), 3.94 (1H, m, cyclohexaneH-1 or H-4), 3.56 (2H, q, J 7.0 Hz, OCH$_2$CH$_3$), 3.43 (1H, m, cyclohexaneH-1 or H-4), 2.16-2.08 (2H, m, 2H of cyclohexaneH-2, H-3, H-5, H-6), 2.07-2.00 (2H, m, 2H of cyclohexaneH-2, H-3, H-5, H-6), 1.69 (3H, d, J 6.0 Hz, NCH(CH$_3$)O), 1.68-1.60 (2H, m, 2H of cyclohexaneH-2, H-3, H-5, H-6), 1.36-1.25 (2H, m, 2H of cyclohexaneH-2, H-3, H-5, H-6), 1.10 (3H, t, J 7.0 Hz, OCH$_2$CH$_3$); $^{19}$F nmr (380 MHz, D$_2$O) δ −72.8, −124.8; $^{32}$P nmr (380 MHz, D$_2$O) δ 1.2; m/z: 624 [M+H]$^+$.

I-21: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (S)-2-amino-3,3-dimethylbutanoate hydrogen chloride salt

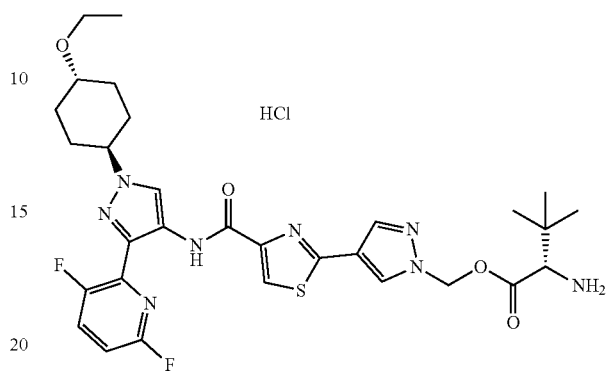

$^1$H nmr (400 MHz, D$_6$-DMSO) δ 11.47 (1H, s, NH), 8.68 (1H, s, 1H of pyrazoleH-5, thiazoleH-5, pyrazoleH-3 or H-5), 8.52 (1H, s, 1H of pyrazoleH-5, thiazoleH-5, pyrazoleH-3 or H-5), 8.43 (2H, br s, NH$_2$), 8.37 (1H, s, 1H of pyrazoleH-5, thiazoleH-5, pyrazoleH-3 or H-5), 8.24 (1H, s, 1H of pyrazoleH-5, thiazoleH-5, pyrazoleH-3 or H-5), 8.09 (1H, td, J 9.5, 6.5 Hz, pyridineH-4 or H-5), 7.26 (1H, br d, J 8.5 Hz, pyridineH-4 or H-5), 6.34, 6.24 (2H, 2d AB system, J 11.0 Hz, NCH$_2$O), 4.33 (1H, br t, J 11.5, Hz, cyclohexaneH-1 or H-4), 3.86 (1H, s, COCH(tBu)NH$_2$), 3.47 (2H, q, J 7.0 Hz, OCH$_2$CH$_3$), 3.38-3.30 (1H, m, cyclohexaneH-1 or H-4), 2.12-2.05 (4H, m, 4H of cyclohexaneH-2, H-3, H-5, H-6), 1.91-1.81 (2H, m, 2H of cyclohexaneH-2, H-3, H-5, H-6), 1.40-1.30 (2H, m, 2H of cyclohexaneH-2, H-3, H-5, H-6), 1.10 (3H, t, J 7.0 Hz, OCH$_2$CH$_3$), 0.93 (9H, s, C(CH$_3$)$_3$); $^{19}$F nmr (380 MHz, D$_6$-DMSO) δ −72.9, −124.1; m/z: 643 [M+H]$^+$ (found [M+H]$^+$, 643.2607, C$_{30}$H$_{36}$F$_2$N$_8$O$_4$S requires [M+H]$^+$ 643.2621).

I-23: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2-amino-2-methylpropanoate hydrogen chloride salt

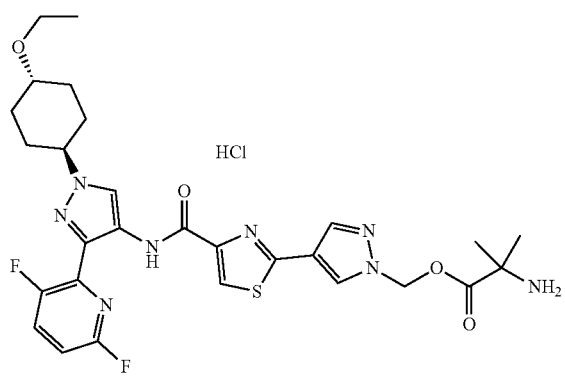 [SMILES: CCO[C@H]1CC[C@H](n2cc(NC(=O)c3csc(-c4cnn(COC(=O)C(C)(C)N)c4)n3)c(-c3nc(F)ccc3F)n2)CC1 ; Cl]

$^1$H nmr (400 MHz, D$_6$-DMSO) δ 8.68 (1H, s, 1H of pyrazoleH-5, thiazoleH-5, pyrazoleH-3 or H-5), 8.52 (2H, br s, 2×NH), 8.52 (1H, s, 1H of pyrazoleH-5, thiazoleH-5, pyrazoleH-3 or H-5), 8.37 (1H, s, 1H of pyrazoleH-5, thiazoleH-5, pyrazoleH-3 or H-5), 8.24 (1H, s, 1H of pyrazoleH-5, thiazoleH-5, pyrazoleH-3 or H-5), 8.09 (1H, td, J 9.0, 6.5 Hz, pyridineH-4 or H-5), 7.26 (1H, dt, J 9.0, 3.0 Hz, pyridineH-4 or H-5), 6.26 (2H, s, NCH$_2$O), 4.33 (1H, br t, J 12.0 Hz, cyclohexaneH-1 or H-4), 3.47 (2H, q, J 7.0 Hz, OCH$_2$CH$_3$), 3.34 (1H, tt, J 10.5, 3.5 Hz, cyclohexaneH-1 or H-4), 2.11-2.04 (4H, m, 4H of cyclohexaneH-2, H-3, H-5, H-6), 1.91-1.80 (2H, m, 2H of cyclohexaneH-2, H-3, H-5, H-6), 1.43 (6H, s, C(CH$_3$)$_2$), 1.41-1.30 (2H, m, 2H of cyclohexaneH-2, H-3, H-5, H-6), 1.10 (3H, t, J 7.0 Hz, OCH$_2$CH$_3$); $^{19}$F nmr (380 MHz, D$_6$-DMSO) δ −72.9, −124.1; m/z: 615 [M+H]$^+$ (found [M+H]$^+$, 615.2343, C$_{28}$H$_{32}$F$_2$N$_8$O$_4$S requires [M+H]$^+$ 615.2309).

I-24: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid

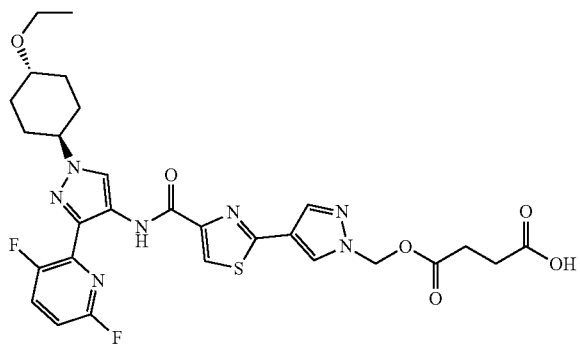 [SMILES: CCO[C@H]1CC[C@H](n2cc(NC(=O)c3csc(-c4cnn(COC(=O)CCC(=O)O)c4)n3)c(-c3nc(F)ccc3F)n2)CC1]

$^1$H nmr (400 MHz, CDCl$_3$) δ 11.71 (1H, s, NH), 8.48 (1H, s, 1H of pyrazoleH-5, thiazoleH-5, pyrazoleH-3 or H-5), 8.29 (1H, s, 1H of pyrazoleH-5, thiazoleH-5, pyrazoleH-3 or H-5), 8.14 (1H, s, 1H of pyrazoleH-5, thiazoleH-5, pyrazoleH-3 or H-5), 8.06 (1H, s, 1H of pyrazoleH-5, thiazoleH-5, pyrazoleH-3 or H-5), 7.63 (1H, td, J 9.0, 6.5 Hz, pyridineH-4 or H-5), 6.88 (1H, ddd, J 8.5, 3.5, 2.5 Hz, pyridineH-4 or H-5), 6.11 (2H, s, OCH$_2$O), 4.26 (1H, tt, J 11.5, 4.0 Hz, cyclohexaneH-1 or H-4), 3.56 (2H, q, J 7.0 Hz, OCH$_2$CH$_3$), 3.37 (1H, tt, J 10.5, 4.0 Hz, cyclohexaneH-1 or H-4), 2.69 (4H, br s, COCH$_2$CH$_2$CO), 2.32-2.2.18 (4H, m, 4H of cyclohexaneH-2, H-3, H-5, H-6), 1.94-1.83 (2H, m, 2H of cyclohexaneH-2, H-3, H-5, H-6), 1.52-1.42 (2H, m, 2H of cyclohexaneH-2, H-3, H-5, H-6), 1.22 (3H, t, J 7.0 Hz, OCH$_2$CH$_3$); $^{13}$C nmr (100 MHz, CDCl$_3$) δ 175.8, 171.6, 159.8, 158.2, 157.5 (d, J 237.5 Hz), 153.4 (dd, J 260.5, 4.5 Hz), 150.1, 139.7 (d, J 5.0 Hz), 138.7 (t, J 14.5 Hz), 133.0 (d, J 8.5 Hz), 130.4 (d, J 5.0 Hz), 129.9 (dd, J 22.5, 9.0 Hz), 122.0, 121.8, 119.4, 118.6, 107.6 (dd, J 40.5, 5.5 Hz), 76.4, 72.4, 63.7, 61.5, 31.0, 30.9, 28.7, 28.5, 15.7; $^{19}$F nmr (380 MHz, CDCl$_3$) δ −72.5 dd, J 27.5, 9.5 Hz), −124.4 (ddd, J 28.5, 9.5, 2.5 Hz); m/z: 630 [M+H]$^+$ (found [M+H]$^+$, 630.1927, C$_{28}$H$_{29}$F$_2$N$_7$O$_6$S requires [M+H]$^+$ 630.1941).

I-28: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 2-morpholinoacetate

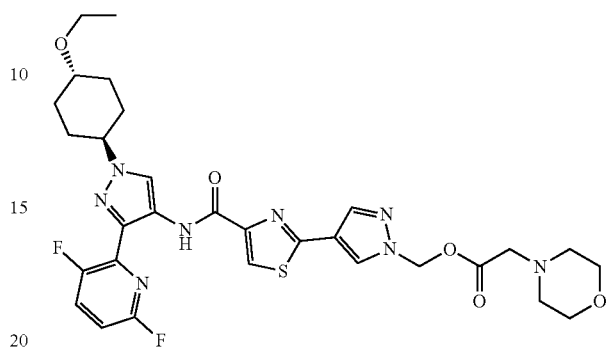

$^1$H nmr (400 MHz, CDCl$_3$) δ 8.50 (1H, s, 1H of pyrazoleH-5, thiazoleH-5, pyrazoleH-3 or H-5), 8.31 (1H, s, 1H of pyrazoleH-5, thiazoleH-5, pyrazoleH-3 or H-5), 8.17 (1H, s, 1H of pyrazoleH-5, thiazoleH-5, pyrazoleH-3 or H-5), 8.06 (1H, s, 1H of pyrazoleH-5, thiazoleH-5, pyrazoleH-3 or H-5), 7.65 (1H, td, J 9.0, 6.0 Hz, pyridineH-4 or H-5), 6.89 (1H, ddd, J 8.5, 3.0, 2.5 Hz, pyridineH-4 or H-5), 6.13 (2H, s, NCH$_2$O), 4.27 (1H, tt, J 11.5, 3.5 Hz, cyclohexaneH-1 or H-4), 3.73, 3.72 (4H, 2d AB system, J 4.5 Hz, 4H of morpholine), 3.56 (2H, q, J 7.0 Hz, OCH$_2$CH$_3$), 3.37 (1H, tt, J 10.5, 4.0 Hz, cyclohexaneH-1 or H-4), 3.29 (2H, s, COCH$_2$N), 2.57, 2.56 (4H, 2d AB system, J Hz, 4H of morpholine), 2.32-2.26 (2H, m, 2H of cyclohexaneH-2, H-3, H-5, H-6), 2.26-2.18 (2H, m, 2H of cyclohexaneH-2, H-3, H-5, H-6), 1.94-1.84 (2H, m, 2H of cyclohexaneH-2, H-3, H-5, H-6), 1.52-1.42 (2H, m, 2H of cyclohexaneH-2, H-3, H-5, H-6), 1.22 (3H, t, J 7.0 Hz, OCH$_2$CH$_3$); $^{19}$F nmr (380 MHz, CDCl$_3$) δ −72.6 (ddd, J 27.0, 7.0, 2.5 Hz), −124.4 ((ddd, J 27.0, 9.5, 2.5 Hz); m/z: 657 [M+H]$^+$ (found [M+H]$^+$, 657.2432, C$_{30}$H$_{34}$F$_2$N$_8$O$_5$S requires [M+H]$^+$ 657.2414).

I-29: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-valinate

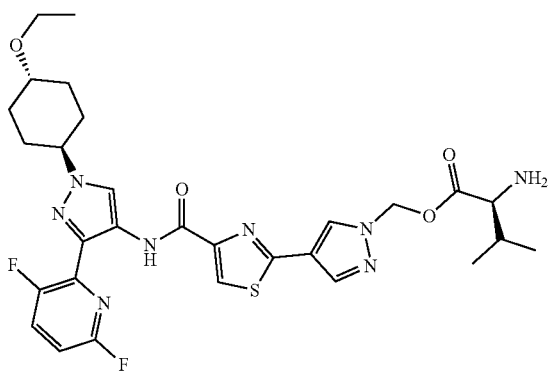 [SMILES: CCO[C@H]1CC[C@H](n2cc(NC(=O)c3csc(-c4cnn(COC(=O)[C@@H](N)C(C)C)c4)n3)c(-c3nc(F)ccc3F)n2)CC1]

$^1$H nmr (400 MHz, CDCl$_3$) δ 11.72 (1H, s, NH), 8.49 (1H, s, 1H of pyrazoleH-5, thiazoleH-5, pyrazoleH-3 or H-5), 8.31 (1H, s, 1H of pyrazoleH-5, thiazoleH-5, pyrazoleH-3 or H-5), 8.16 (1H, s, 1H of pyrazoleH-5, thiazoleH-5, pyrazoleH-3 or H-5), 8.05 (1H, s, 1H of pyrazoleH-5, thiazoleH-5, pyrazoleH-3 or H-5), 7.65 (1H, td, J 9.0, 6.5 Hz, pyridineH-4 or H-5), 6.88 (1H, dt, J 8.5, 3.0 Hz, pyridineH-4 or H-5), 6.14, 6.10 (2H, 2d AB system, J 10.5 Hz, NCH$_2$O), 4.26 (1H, tt, J 11.5, 4.0 Hz, cyclohexaneH-1 or H-4), 3.45 (2H, q, J 7.0 Hz, OCH$_2$CH$_3$), 3.40-3.32 (2H, m, cyclohexaneH-1 or H-4, COCHNH$_2$), 2.33-2.25 (2H, m, 2H of cyclohexaneH-2, H-3, H-5, H-6), 2.23-2.17 (2H, m, 2H of cyclohexaneH-2, H-3, H-5, H-6), 2.05-2.01 (1H, m, CHCH(CH$_3$)2), 1.94-1.83 (2H, m, 2H of cyclohexaneH-2, H-3, H-5, H-6), 1.51-1.41 (2H, m, 2H of cyclohexaneH-2, H-3, H-5, H-6), 1.22 (3H, t, J 7.0 Hz, OCH$_2$CH$_3$), 0.91 (3H, d, J 7.0 Hz, 1×CH$_3$ of CH(CH$_3$)$_2$), 0.82 (3H, d, J 6.5 Hz, 1×CH$_3$ of CH(CH$_3$)$_2$); $^{19}$F nmr (380 MHz, CDCl$_3$) δ -72.7, -124.4; m/z: 629 [M+H]$^+$ (found [M+H]$^+$, 629.2474, C$_{29}$H$_{34}$F$_2$N$_8$O$_4$S requires [M+H]$^+$ 629.2465).

I-30: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-valinate benzenesulfonic acid

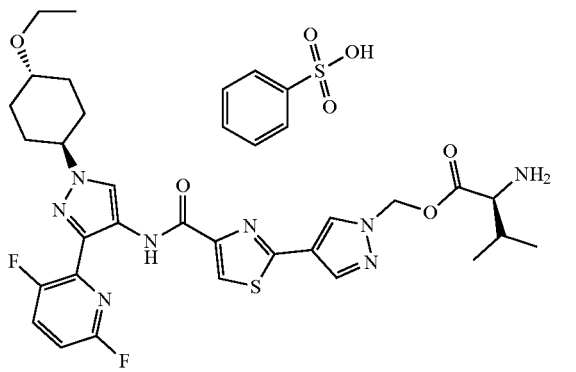 [SMILES: CCO[C@H]1CC[C@H](n2cc(NC(=O)c3csc(-c4cnn(COC(=O)[C@@H](N)C(C)C)c4)n3)c(-c3nc(F)ccc3F)n2)CC1 ; O=S(=O)(O)c1ccccc1]

$^1$H nmr (400 MHz, D$_6$-DMSO) δ 11.47 (1H, s, NH), 8.68 (1H, s, 1H of pyrazoleH-5, thiazoleH-5, pyrazoleH-3 or H-5), 8.53 (1H, s, 1H of pyrazoleH-5, thiazoleH-5, pyrazoleH-3 or H-5), 8.37 (1H, s, 1H of pyrazoleH-5, thiazoleH-5, pyrazoleH-3 or H-5), 8.27 (2H, br s, NH$_2$), 8.24 (1H, s, 1H of pyrazoleH-5, thiazoleH-5, pyrazoleH-3 or H-5), 8.09 (1H, td, J 9.5, 6.5 Hz, pyridineH-4 or H-5), 7.69-7.56 (2H, m, 2H of C$_6$H$_5$SO$_3$H), 7.32-7.24 (4H, m, 3H of C$_6$H$_5$SO$_3$H, pyridineH-4 or H-5), 6.34, 6.25 (2H, 2d AB system, J 11.0 Hz, NCH$_2$O), 4.33 (1H, tt, J 11.5, 3.5 Hz, cyclohexaneH-1 or H-4), 4.03 (1H, d, J 4.5 Hz, COCHNH$_2$), 3.47 (2H, q, J 7.0 Hz, OCH$_2$CH$_3$), 3.34 (1H, tt, J 10.5, 4.0 Hz, cyclohexaneH-1 or H-4), 2.14-2.06 (5H, m, CHCH(CH$_3$)$_2$, 4H of cyclohexaneH-2, H-3, H-5, H-6), 1.90-1.80 (2H, m, 2H of cyclohexaneH-2, H-3, H-5, H-6), 1.41-1.30 (2H, m, 2H of cyclohexaneH-2, H-3, H-5, H-6), 1.10 (3H, t, J 7.0 Hz, OCH$_2$CH$_3$), 0.89 (3H, d, J 6.5 Hz, 1×CH$_3$ of CH(CH$_3$)$_2$), 0.86 (3H, d, J 7.0 Hz, 1×CH$_3$ of CH(CH$_3$)$_2$); $^{19}$F nmr (380 MHz, D$_6$-DMSO) δ -72.6, -124.5; m/z: 629 [M+H]$^+$.

I-31: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl L-valinate methanesulfonic acid salt

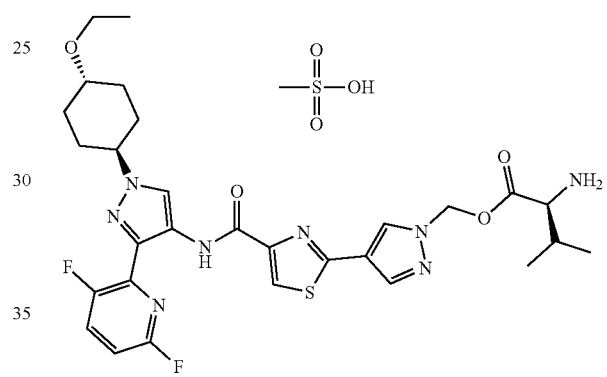

$^1$H nmr (400 MHz, D$_6$-DMSO) δ 8.68 (1H, s, 1H of pyrazoleH-5, thiazoleH-5, pyrazoleH-3 or H-5), 8.53 (1H, s, 1H of pyrazoleH-5, thiazoleH-5, pyrazoleH-3 or H-5), 8.37 (1H, s, 1H of pyrazoleH-5, thiazoleH-5, pyrazoleH-3 or H-5), 8.34 (2H, br s, NH$_2$), 8.24 (1H, s, 1H of pyrazoleH-5, thiazoleH-5, pyrazoleH-3 or H-5), 8.09 (1H, dt, J 9.0, 6.5 Hz, pyridineH-4 or H-5), 7.26 (1H, ddd, J 9.0, 3.0, 2.5 Hz, pyridineH-4 or H-5), 6.34, 6.25 (2H, 2d AB system, J 11.0 Hz, NCH$_2$O), 4.33 (1H, tt, J 11.5, 3.0 Hz, cyclohexaneH-1 or H-4), 4.04 (1H, t, J 5.0 Hz, COCHNH$_2$), 3.47 (2H, q, J 7.0 Hz, OCH$_2$CH$_3$), 3.38-3.30 (1H, m, cyclohexaneH-1 or H-4), 2.31 (3H, s, CH$_3$SO$_3$H), 2.16-2.04 (5H, m, 4H of cyclohexaneH-2, H-3, H-5, H-6, CHCH(CH$_3$)$_2$), 1.91-1.80 (2H, m, 2H of cyclohexaneH-2, H-3, H-5, H-6), 1.40-1.30 (2H, m, 2H of cyclohexaneH-2, H-3, H-5, H-6), 1.10 (3H, t, J 7.0 Hz, OCH$_2$CH$_3$), 0.90 (3H, d, J 7.0 Hz, 1×CH$_3$ of CH(CH$_3$)$_2$), 0.86 (3H, d, J 7.0 Hz, 1×CH$_3$ of CH(CH$_3$)$_2$); $^{19}$F nmr (380 MHz, D$_6$-DMSO) δ -73.0, -124.1; m/z: 629 [M+H]$^+$.

I-35: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (S)-2-amino-3,3-dimethylbutanoate

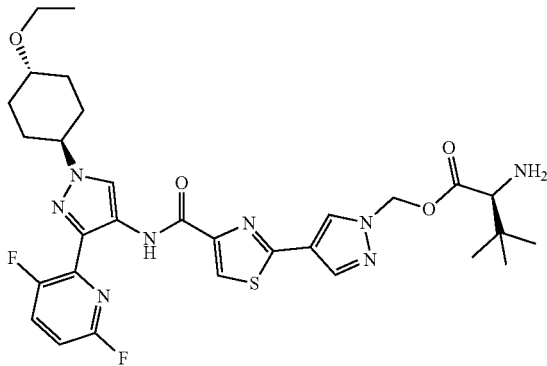 [SMILES: CCO[C@H]1CC[C@H](n2cc(NC(=O)c3csc(-c4cnn(COC(=O)[C@@H](N)C(C)(C)C)c4)n3)c(-c3nc(F)ccc3F)n2)CC1]

$^1$H nmr (400 MHz, CDCl$_3$) δ 11.70 (1H, s, NH), 8.48 (1H, s, 1H of pyrazoleH-5, thiazoleH-5, pyrazoleH-3, H-5), 8.29 (1H, s, 1H of pyrazoleH-5, thiazoleH-5, pyrazoleH-3, H-5), 8.15 (1H, s, 1H of pyrazoleH-5, thiazoleH-5, pyrazoleH-3, H-5), 8.04 (1H, s, 1H of pyrazoleH-5, thiazoleH-5, pyrazoleH-3, H-5), 7.63 (1H, td, J 9.0, 6.5 Hz, pyridineH-4 or H-5), 6.86 (1H, ddd, J 9.0, 3.0, 2.5 Hz, pyridineH-4 or H-5), 6.13, 6.08 (2H, 2d AB system, J 10.5 Hz, NCH$_2$CO), 4.25 (1H, tt, J 11.5, 4.0 Hz, cyclohexaneH-1 or H-4), 3.54 (2H, q, J 7.0 Hz, OCH$_2$CH$_3$), 3.35 (1H, tt, J 11.0, 4.0 Hz, cyclohexaneH-1 or H-4), 3.20 (1H, s, COCH(C(CH$_3$)$_3$)NH$_2$), 2.32-2.24 (2H, m, 2H of cyclohexaneH-2, H-3, H-5, H-6), 2.24-2.16 (2H, m, 2H of cyclohexaneH-2, H-3, H-5, H-6), 1.93-1.82 (2H, m, 2H of cyclohexaneH-2, H-3, H-5, H-6), 1.50-1.40 (2H, m, 2H of cyclohexaneH-2, H-3, H-5, H-6), 1.20 (3H, t, J 7.0 Hz, OCH$_2$CH$_3$), 0.89 (9H, s, C(CH$_3$)$_3$); $^{19}$F nmr (380 MHz, CDCl$_3$) δ −72.6, −124.4; m/z: 643 [M+H]$^+$ (found [M+H]$^+$, 643.2595, C$_{30}$H$_{37}$F$_2$N$_8$O$_4$S requires [M+H]$^+$ 643.2621).

I-36: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (S)-2-amino-3,3-dimethylbutanoate benzenesulfonic acid

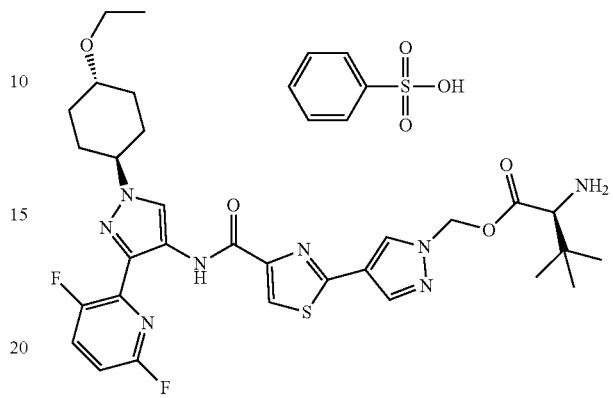

$^1$H nmr (400 MHz, D$_6$-DMSO) δ 11.74 (1H, s, NH), 8.68 (1H, s, 1H of pyrazoleH-5, thiazoleH-5, pyrazoleH-3, H-5), 8.53 (1H, s, 1H of pyrazoleH-5, thiazoleH-5, pyrazoleH-3, H-5), 8.37 (1H, s, 1H of pyrazoleH-5, thiazoleH-5, pyrazoleH-3, H-5), 8.29 (2H, m, 2×NH$_2$), 8.25 (1H, s, 1H of pyrazoleH-5, thiazoleH-5, pyrazoleH-3, H-5), 8.09 (1H, dt, J 9.5, 6.5 Hz, pyridineH-4 or H-5), 7.59-7.56 (2H, m, 2H of C$_6$H$_5$SO$_3$H), 7.32-7.23 (4H, m, 3H of C$_6$H$_5$SO$_3$H, pyridineH-4 or H-5), 6.34, 6.26 (2H, 2d AB system, J 11.0 Hz, NCH$_2$CO), 4.33 (tt, J 11.5, 3.5 Hz, cyclohexaneH-1 or H-4), 3.91 (1H, br s, COCH(C(CH$_3$)$_3$)NH$_2$), 3.47 (2H, q, J 7.0 Hz, OCH$_2$CH$_3$), 3.34 (1H, tt, J 10.5, 3.5 Hz, cyclohexaneH-1 or H-4), 2.12-2.05 (4H, m, 4H of cyclohexaneH-2, H-3, H-5, H-6), 1.92-1.80 (2H, m, 2H of cyclohexaneH-2, H-3, H-5, H-6), 1.41-1.30 (2H, m, 2H of cyclohexaneH-2, H-3, H-5, H-6), 1.10 (3H, t, J 7.0 Hz, OCH$_2$CH$_3$), 0.93 (9H, s, C(CH$_3$)$_3$); $^{13}$C nmr (100 MHz, D$_6$-DMSO) δ 168.5, 160.2, 157.5 (d, J 234.0 Hz), 157.5, 153.5 (d, J 258.0 Hz), 149.4, 148.9, 139.6 (d, J 7.5 Hz), 138.1 (d, J 14.5 Hz), 132.6 (d, J 9.0 Hz), 132.4 (d, J 3.0 Hz), 128.7, 128.0, 125.9, 124.4, 121.4, 120.3, 117.9, 76.0, 73.7, 63.0, 60.8, 33.7, 30.9 (2C), 26.4, 16.1; $^{19}$F nmr (380 MHz, D$_6$-DMSO) δ −72.9, −124.1; m/z: 643 [M+H]$^+$.

I-37: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl 4-(morpholinomethyl)benzoate

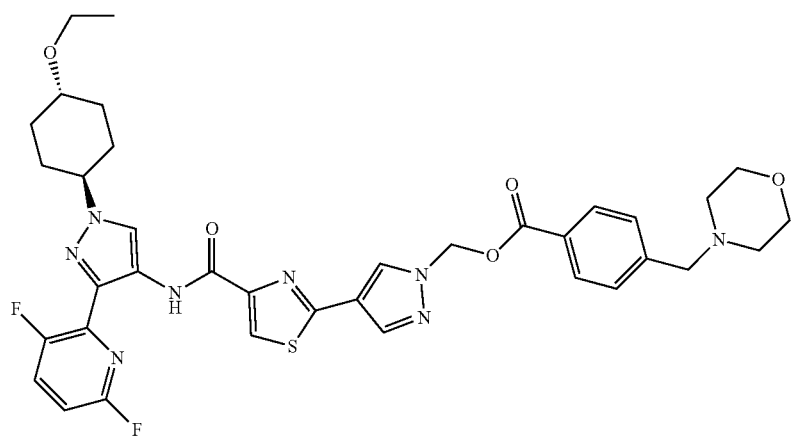 [SMILES: CCO[C@H]1CC[C@H](n2cc(NC(=O)c3csc(-c4cnn(COC(=O)c5ccc(CN6CCOCC6)cc5)c4)n3)c(-c3nc(F)ccc3F)n2)CC1]

¹H nmr (400 MHz, CDCl₃) δ 11.73 (1H, s, NH), 8.50 (1H, s, 1H of pyrazoleH-5, thiazoleH-5, pyrazoleH-3, H-5), 8.42 (1H, s, 1H of pyrazoleH-5, thiazoleH-5, pyrazoleH-3, H-5), 8.18 (1H, s, 1H of pyrazoleH-5, thiazoleH-5, pyrazoleH-3, H-5), 8.06 (1H, 1H of pyrazoleH-5, thiazoleH-5, pyrazoleH-3, H-5), 8.02 (2H, d, J 8.0 Hz, 2H of C₆H₄), 7.64 (1H, dt, J 9.0, 6.5 Hz, pyridineH-4 or H-5), 7.42 (1H, d, J 8.0 Hz, 2H of C₆H₄), 6.85 (1H, m, pyridineH-4 or H-5), 6.34 (2H, s, NCH₂CO), 4.27 (1H, tdd, J 11.5, 4.0, 3.5 Hz, cyclohexaneH-1 or H-4), 3.70, 3.69 (4H, 2d AB system, J 4.5 Hz, 4H of morpholine), 3.56 (2H, q, J 7.0 Hz, OCH₂CH₃), 3.54 (2H, s, C₆H₄CH₂N), 3.37 (1H, tt, J 10.5, 4.0 Hz, cyclohexaneH-1 or H-4), 2.42 (4H, br s, 4H of morpholine), 2.32-2.26 (2H, m, 2H of cyclohexaneH-2, H-3, H-5, H-6), 2.26-2.18 (2H, m, 2H of cyclohexaneH-2, H-3, H-5, H-6), 1.94-1.84 (2H, m, 2H of cyclohexaneH-2, H-3, H-5, H-6), 1.52-1.42 (2H, m, 2H of cyclohexaneH-2, H-3, H-5, H-6), 1.22 (3H, t, J 7.0 Hz, OCH₂CH₃); ¹⁹F nmr (380 MHz, CDCl₃) δ −72.5, −124.4; m/z: 733 [M+H]⁺.

I-39: (1R,2R)-2-(((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)carbonyl)cyclohexane-1-carboxylic acid

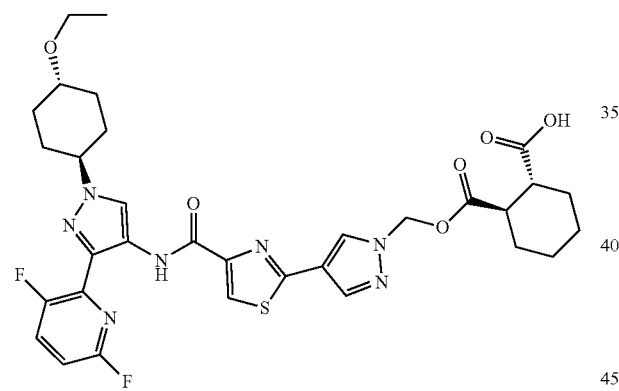

¹H nmr (400 MHz, D₆-DMSO) δ 12.25 (1H, br s, OH), 11.47 (1H, s, NH), 8.57 (1H, s, 1H of pyrazoleH-5, thiazoleH-5, pyrazoleH-3, H-5), 8.52 (1H, s, 1H of pyrazoleH-5, thiazoleH-5, pyrazoleH-3, H-5), 8.34 (1H, 1H of pyrazoleH-5, thiazoleH-5, pyrazoleH-3, H-5), 8.19 (1H, s, 1H of pyrazoleH-5, thiazoleH-5, pyrazoleH-3, H-5), 8.08 (1H, dt, J 9.0, 6.5 Hz, pyridineH-4 or H-5), 7.27 (1H, dt, J 8.5, 2.5 Hz, pyridineH-4 or H-5), 6.13, 6.05 (2H, 2d AB system, J 11.0 Hz, NCH₂), 4.33 (1H, tt, J 11.5, 3.5 Hz, cyclohexaneH-1 or H-4), 3.47 (2H, q, J 7.0 Hz, OCH₂CH₃), 3.35 (1H, tt, J 11.0, 3.5 Hz, cyclohexaneH-1 or H-4), 2.78-2.40 (1H, m, cyclohexane dicarboxylic acid H-1 or H-2), 2.12-2.04 (4H, m, 4H of cyclohexaneH-2, H-3, H-5, H-6), 1.97-1.82 (1H, m, 1H of cyclohexane dicarboxylic acid H-1 or H-2), 1.90-1.81 (4H, m, 2H of cyclohexaneH-2, H-3, H-5, H-6, 2H of cyclohexane dicarboxylic acid H-3, H-4, H-5, H-6), 1.65 (2H, br s, cyclohexane dicarboxylic acid H-3, H-4, H-5, H-6), 1.39-1.30 (2H, m, 2H of cyclohexaneH-2, H-3, H-5, H-6), 1.27-1.17 (4H, m, 4H of cyclohexane dicarboxylic acid H-3, H-4, H-5, H-6), 1.10 (3H, t, J 7.0 Hz, OCH₂CH₃); ¹⁹F nmr (380 MHz, D₆-DMSO) δ −72.8, −124.2; m/z: 684 [M+H]⁺ (found [M+H]⁺, 684.2416, C₃₂H₃₅F₂N₇O₆S requires [M+H]⁺ 684.2410).

I-40: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl (S)-2-amino-3,3-dimethylbutanoate methanesulfonic acid salt

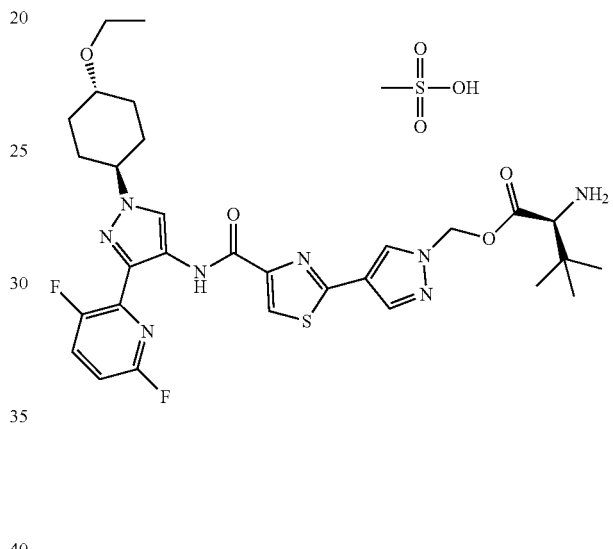

¹H nmr (400 MHz, D₆-DMSO) δ 12.47 (1H, br s, NH), 8.68 (1H, s, 1H of pyrazoleH-5, thiazoleH-5, pyrazoleH-3, H-5), 8.53 (1H, s, 1H of pyrazoleH-5, thiazoleH-5, pyrazoleH-3, H-5), 8.37 (1H, 1H of pyrazoleH-5, thiazoleH-5, pyrazoleH-3, H-5), 8.30 (2H, br s, NH₂), 8.25 (1H, s, 1H of pyrazoleH-5, thiazoleH-5, pyrazoleH-3, H-5), 8.09 (1H, dt, J 9.5, 6.5 Hz, pyridineH-4 or H-5), 7.27 (1H, dt, J 8.5, 2.5 Hz, pyridineH-4 or H-5), 6.34, 6.26 (2H, 2d AB system, J 11.0 Hz, NCH₂O), 4.33 (1H, tt, J 11.5, 3.5 Hz, 1H of cyclohexaneH-1 or H-4), 3.90 (1H, d, J 4.5 Hz, COCH(C(CH₃)₃)NH₂), 3.47 (2H, q, J 7.0 Hz, OCH₂CH₃), 3.39-3.31 (1H, m, cyclohexaneH-1 or H-4), 2.30 (3H, s, CH₃SO₃H), 2.12-2.04 (4H, m, 4H of cyclohexaneH-2, H-3, H-5, H-6), 1.90-1.80 (2H, m, 2H of cyclohexaneH-2, H-3, H-5, H-6), 1.40-1.30 (2H, m, 2H of cyclohexaneH-2, H-3, H-5, H-6), 1.10 (3H, t, J 7.0 Hz, OCH₂CH₃), 0.93 (9H, s, C(CH₃)₃); ¹³C nmr (100 MHz, D₆-DMSO) δ 168.5, 160.2, 157.6, 157.5 (d, J 236.0 Hz), 155.7 (dd, J 260.0, 4.5 Hz), 149.4, 139.5 (d, J 6.5 Hz), 138.2 (t, J 14.0 Hz), 132.6 (d, J 8.5 Hz), 132.4, 124.4, 121.4, 120.3, 117.9, 76.0, 73.7, 65.4, 63.0, 60.8, 33.7, 30.9 (2C), 26.4, 16.1; ¹⁹F nmr (380 MHz, D₆-DMSO) δ −72.9, −124.0; m/z: 643 [M+H]⁺.

I-42: N-(3-(3,6-difluoropyridin-2-yl)-1-((1r,4S)-4-ethoxycyclohexyl)-1H-pyrazol-4-yl)-2-(1-((2S,3S,4R,5R,6S)-3,4,5-trihydroxy-6-(hydroxymethyl)tetrahydro-2H-pyran-2-yl)-1H-pyrazol-4-yl)thiazole-4-carboxamide

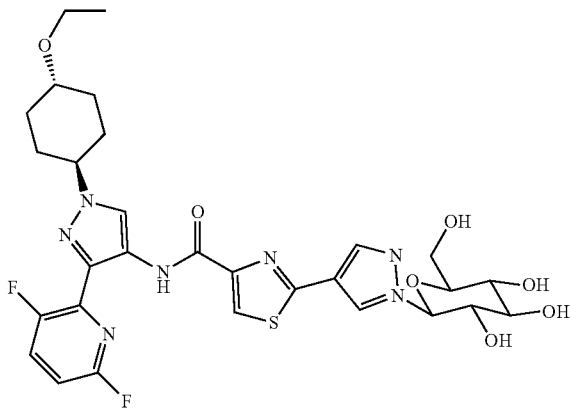

$^1$H nmr (400 MHz, D$_6$-DMSO) δ 11.47 (1H, s, NH), 8.66 (1H, s, 1H of pyrazoleH-5, thiazoleH-5, pyrazoleH-3, H-5), 8.53 (1H, s, 1H of pyrazoleH-5, thiazoleH-5, pyrazoleH-3, H-5), 8.32 (1H, s, 1H of pyrazoleH-5, thiazoleH-5, pyrazoleH-3, H-5), 8.14 (1H, s, 1H of pyrazoleH-5, thiazoleH-5, pyrazoleH-3, H-5), 8.08 (1H, td, J 9.5, 6.5 Hz, pyridineH-4 or H-5), 7.26 (1H, dt, J 8.5, 2.5 Hz, pyridineH-4 or H-5), 5.30 (1H, d, J 6.0 Hz, OH-2), 5.23-5.21 (2H, m, H-1, OH-3), 5.09 (1H, d, J 5.5 Hz, OH-4), 4.61 (1H, t, J 5.5 Hz, OH-6), 4.33 (1H, br t, J 11.5 Hz, cHexH-1 or H-4), 3.79 (1H, td, J 9.0, 6.0 Hz, H-2), 3.70 (1H, dd, J 11.0, 5.5 Hz, 1×H-6), 3.47 (2H, q, J 7.0 Hz, OCH$_2$CH$_3$), 3.45-3.32 (3H, m, cHexH-1 or H-4, H-3, 1×H-6), 3.24-3.21 (1H, m, H-4), 2.12-2.04 (4H, m, 4H of cHexH-2, H-3, H-5, H-6), 1.91-1.81 (1H, m, 2H of cHexH-2, H-3, H-5, H-6), 1.40-1.31 (2H, m, 2H of cHexH-2, H-3, H-5, H-6), 1.10 (3H, t, J 7.0 Hz, OCH$_2$CH$_3$); $^{19}$F nmr (380 MHz, D$_6$-DMSO) δ −72.8, −124.2; m/z: 662 [M+H]$^+$ (found [M+H]$^+$, 662.2219, C$_{29}$H$_{33}$F$_2$N$_7$O$_7$S requires [M+H]$^+$ 662.2203).

I-43: N-(3-(3,6-difluoropyridin-2-yl)-1-((1r,4R)-4-ethoxycyclohexyl)-1H-pyrazol-4-yl)-2-(1-((2R,3R,4R,5R,6S)-3,4,5-trihydroxy-6-(hydroxymethyl)tetrahydro-2H-pyran-2-yl)-1H-pyrazol-4-yl)thiazole-4-carboxamide

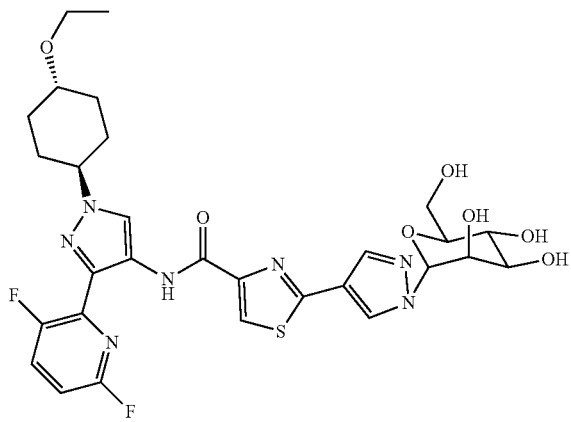 [SMILES: CCO[C@H]1CC[C@H](n2cc(NC(=O)c3csc(-c4cnn(C5OC(CO)C(O)C(O)C5O)c4)n3)c(-c3nc(F)ccc3F)n2)CC1]

$^1$H nmr (400 MHz, D$_6$-DMSO) δ 11.49 (1H, s, NH), 8.59 (1H, s, 1H of pyrazoleH-5, thiazoleH-5, pyrazoleH-3, H-5), 8.53 (1H, s, 1H of pyrazoleH-5, thiazoleH-5, pyrazoleH-3, H-5), 8.33 (1H, s, 1H of pyrazoleH-5, thiazoleH-5, pyrazoleH-3, H-5), 8.17 (1H, s, 1H of pyrazoleH-5, thiazoleH-5, pyrazoleH-3, H-5), 8.09 (1H, td, J 9.5, 6.0 Hz, pyridineH-4 or H-5), 7.28 (1H, dt, J 8.5, 2.5 Hz, pyridineH-4 or H-5), 5.70 (1H, d, J 4.0 Hz, H-1), 5.15 (1H, br s, 1×OH), 4.93 (2H, br m, 2×OH), 4.54 (1H, br s, 1×OH), 4.39 (1H, t, J 3.5 Hz, H-2), 4.33 (1H, br t, J 11.5 Hz, cHexH-1 or H-4), 3.91 (1H, dd, J 7.0, 3.0 Hz, H-3), 3.63 (1H, d, J 10.0 Hz, 1×H-6), 3.58-3.52 (2H, m, H-4, 1×H-6), 3.47 (2H, q, J 7.0 Hz, OCH$_2$CH$_3$), 3.45-3.42 (1H, m, H-5), 3.35 (1H, m, cHexH-1 or H-4), 2.12-2.04 (4H, m, 4H of cHexH-2, H-3, H-5, H-6), 1.92-1.81 (2H, m, 2H of cHexH-2, H-3, H-5, H-6), 1.40-1.31 (2H, m, 2H of cHexH-2, H-3, H-5, H-6), 1.10 (3H, t, J 7.0 Hz, OCH$_2$CH$_3$); $^{19}$F nmr (380 MHz, D$_6$-DMSO) δ −72.7, −124.2; m/z: 662 [M+H]$^+$ (found [M+H]$^+$, 662.2195, C$_{29}$H$_{33}$F$_2$N$_7$O$_7$S requires [M+H]$^+$ 662.2203).

I-49: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl hydrogen phosphate tris salt

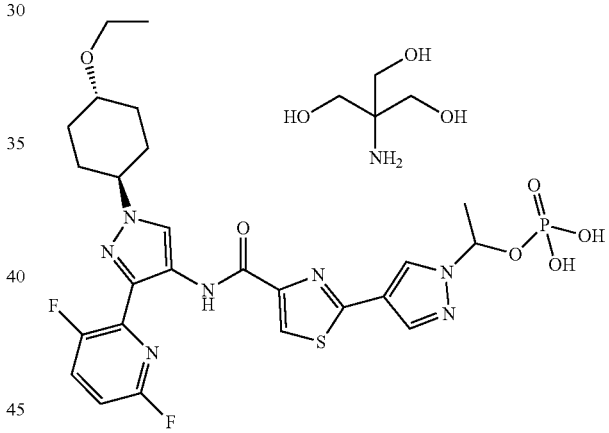

$^1$H nmr (400 MHz, D$_6$-DMSO) δ 11.46 (1H, s, NH), 8.51 (1H, s, 1H of pyrazoleH-5, thiazoleH-5, pyrazoleH-3, H-5), 8.49 (1H, s, 1H of pyrazoleH-5, thiazoleH-5, pyrazoleH-3, H-5), 8.28 (1H, s, 1H of pyrazoleH-5, thiazoleH-5, pyrazoleH-3, H-5), 8.07 (1H, s, 1H of pyrazoleH-5, thiazoleH-5, pyrazoleH-3, H-5), 8.06 (1H, dt, J 10.0, 6.5 Hz, pyridineH-4 or H-5), 7.28 (1H, dt, J 8.5, 2.5 Hz, pyridineH-4 or H-5), 6.12 (1H, dq, J 9.0, 6.0 Hz, NCH(CH$_3$)OP), 4.32 (1H, br t, J 11.5 Hz, cyclohexaneH-1 or H-4), 3.47 (2H, q, J 7.0 Hz, OCH$_2$CH$_3$), 3.44 (6H, s, C(CH$_2$OH)$_3$), 3.35 (1H, tt, J 10.5, 3.5 Hz, cyclohexaneH-1 or H-4), 2.12-2.05 (4H, m, 4H of cyclohexaneH-2, H-3, H-5, H-6), 1.91-1.81 (2H, m, 2H of cyclohexaneH-2, H-3, H-5, H-6), 1.66 (3H, d, J 6.0 Hz, NCH(CH$_3$)OP), 1.40-1.30 (2H, m, 2H of cyclohexaneH-2, H-3, H-5, H-6), 1.10 (3H, t, J 7.0 Hz, OCH$_2$CH$_3$); $^{32}$P nmr (380 MHz, D$_6$-DMSO) δ 0.2; $^{19}$F nmr (380 MHz, D$_6$-DMSO) δ −72.6, −124.4; m/z: 624 [M+H]$^+$.

I-50: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl glycinate benzenesulfonic acid salt

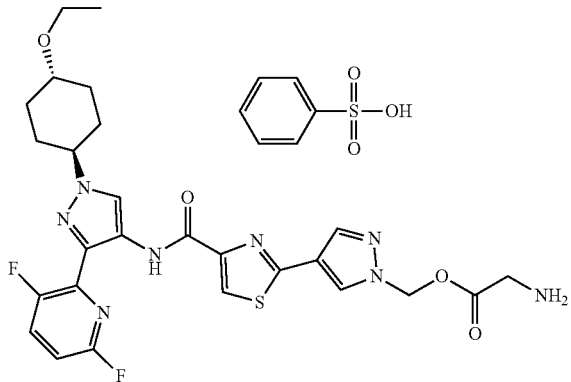 [SMILES: CCO[C@H]1CC[C@H](n2cc(NC(=O)c3csc(-c4cnn(COC(=O)CN)c4)n3)c(-c3nc(F)ccc3F)n2)CC1 ; O=S(=O)(O)c1ccccc1]

¹H nmr (400 MHz, D₆-DMSO) δ 11.47 (1H, s, NH), 8.67 (1H, s, 1H of pyrazoleH-5, thiazoleH-5, pyrazoleH-3, H-5), 8.53 (1H, s, 1H of pyrazoleH-5, thiazoleH-5, pyrazoleH-3, H-5), 8.37 (1H, s, 1H of pyrazoleH-5, thiazoleH-5, pyrazoleH-3, H-5), 8.24 (1H, s, 1H of pyrazoleH-5, thiazoleH-5, pyrazoleH-3, H-5), 8.23 (2H, br s, NH₂), 8.09 (1H, dt, J 9.5, 6.5 Hz, pyridineH-4 or H-5), 7.59-7.56 (2H, m, 2H of C₆H₅SO₃H), 7.32-7.25 (4H, m, 3H of C₆H₅SO₃H, pyridineH-4 or H-5), 6.26 (2H, s, NCH₂CO), 4.34 (1H, tt, J 11.5, 3.5 Hz, cyclohexaneH-1 or H-4), 3.92 (2H, br s, COCH₂NH₂), 3.47 (2H, q, J 7.0 Hz, OCH₂CH₃), 3.39-3.33 (1H, m, cyclohexaneH-1 or H-4), 2.12-2.05 (4H, m, 4H of cyclohexaneH-2, H-3, H-5, H-6), 1.91-1.80 (2H, m, 2H of cyclohexaneH-2, H-3, H-5, H-6), 1.41-1.30 (2H, m, 2H of cyclohexaneH-2, H-3, H-5, H-6), 1.10 (3H, t, J 7.0 Hz, OCH₂CH₃); ¹⁹F nmr (380 MHz, D₆-DMSO) δ −73.0, −124.1; m/z: 587 [M+H]⁺.

I-56: 4-((4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methoxy)-4-oxobutanoic acid tris salt

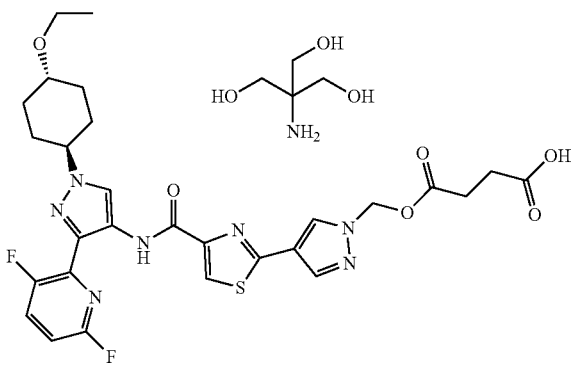 [SMILES: CCO[C@H]1CC[C@H](n2cc(NC(=O)c3csc(-c4cnn(COC(=O)CCC(=O)O)c4)n3)c(-c3nc(F)ccc3F)n2)CC1 ; NC(CO)(CO)CO]

¹H nmr (400 MHz, D₂O) δ 7.52 (1H, s, 1H of pyrazoleH-5, thiazoleH-5, pyrazoleH-3, H-5), 7.49 (1H, s, 1H of pyrazoleH-5, thiazoleH-5, pyrazoleH-3, H-5), 7.16 (1H, s, 1H of pyrazoleH-5, thiazoleH-5, pyrazoleH-3, H-5), 7.13 (1H, s, 1H of pyrazoleH-5, thiazoleH-5, pyrazoleH-3, H-5), 7.13-7.07 (1H, m, pyridineH-4 or H-5), 6.24 (1H, br d, J 8.0 Hz, pyridineH-4 or H-5), 5.69 (2H, s, NCH₂O), 7.39 (1H, br t, J 11.5 Hz, cyclohexaneH-1 or H-4), 3.59 (6H, s, 3×CCH₂OH), 3.55 (2H, q, J 7.0 Hz, OCH₂CH₃), 3.37 (1H, brt, J 10.5 Hz, cyclohexaneH-1 or H-4), 2.54 (2H, t, J 6.5 Hz, 2H of COCH₂CH₂CO), 2.39 (2H, t, J 6.5 Hz, 2H of COCH₂CH₂CO), 2.12-2.04 (2H, m, 2H of cyclohexaneH-2, H-3, H-5, H-6), 2.15-1.98 (2H, m, 2H of cyclohexaneH-2, H-3, H-5, H-6), 1.55-1.44 (2H, m, 2H of cyclohexaneH-2, H-3, H-5, H-6), 1.32-1.21 (2H, m, 2H of cyclohexaneH-2, H-3, H-5, H-6), 1.10 (3H, t, J 7.0 Hz, OCH₂CH₃); ¹⁹F nmr (380 MHz, D₂O) δ −73.4, −124.7; m/z: 630 [+MH]⁺.

I-68: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide citric acid cocrystal

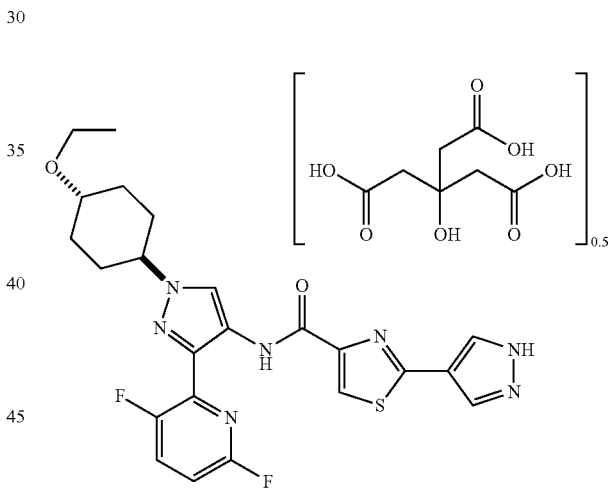

¹H nmr (400 MHz, D₆-DMSO) δ 8.53 (1H, s, thiazoleH-5 or pyrazoleH-5), 8.29 (3H, s, pyrazoleH-3, H-5, thiazoleH-5 or pyrazoleH-5), 8.08 (1H, td, J 9.0, 6.0 Hz, pyridineH-4 or H-5), 7.29 (1H, ddd, J 9.0, 3.0, 2.5 Hz, pyridineH-4 or H-5), 5.14 (0.5H, br s, COH), 4.33 (1H, tt, J 11.5, 3.5 Hz, cyclohexaneH-1 or H-4), 3.47 (2H, q, J 7.0 Hz, OCH₂CH₃), 3.35 (1H, m, cyclohexaneH-1 or H-4), 2.74, 2.64 (3H, 2d AB system, J 15.5 Hz, 3×0.5 OCH₂CO₂H), 2.08 (4H, m, 4H of cyclohexaneH-2, H-3, H-5, H-6), 1.85 (2H, m, 2H of cyclohexaneH-2, H-3, H-5, H-6), 1.35 (2H, m, 2H of cyclohexaneH-2, H-3, H-5, H-6), 1.10 (3H, t, J 7.0 Hz, OCH₂CH₃); ¹⁹F nmr (380 MHz, D₆-DMSO) δ −73.0, −124.2; m/z: 500 [M+H]⁺.

I-69: (4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)methyl dihydrogen phosphate bis(tris(hydroxymethyl)aminomethane) salt

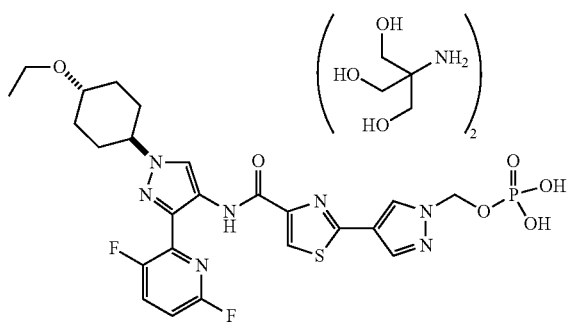

$^1$H nmr (400 MHz, D$_2$O) δ 7.89 (1H, s, thiazoleH-5 or pyrazoleH-5), 7.80 (1H, s, thiazoleH-5 or pyrazoleH-5), 7.45 (1H, s, pyrazoleH-3 or H-5), 7.44 (1H, s, pyrazoleH-3 or H-5), 7.33 (1H, m, pyridineH-4 or H-5), 6.53 (1H, d, J 9.0 Hz, pyridineH-4 or H-5), 5.51 (1H, d, J 6.5 Hz, NCH$_2$OP), 3.93 (1H, tt, J 12.0, 3.0 Hz, cyclohexaneH-1 or H-4), 3.58 (2H, q, J 7.0 Hz, OCH$_2$CH$_3$), 3.57 (12H, s, 2×H$_2$NC(CH$_2$OH)$_3$), 3.45 (1H, m, cyclohexaneH-1 or H-4), 2.14 (2H, br d, J 10.5 Hz, 2H of cyclohexaneH-2, H-3, H-5, H-6), 2.03 (2H, br d, J 12.0 Hz, cyclohexaneH-2, H-3, H-5, H-6), 1.63 (2H, m, 2H of cyclohexaneH-2, H-3, H-5, H-6), 1.32 (2H, m, 2H of cyclohexaneH-2, H-3, H-5, H-6), 1.11 (3H, t, J 7.0 Hz, OCH$_2$CH$_3$); $^{31}$P nmr (162 MHz, D$_2$O) δ 1.05; $^{19}$F nmr (380 MHz, D$_2$O) δ −72.8 (d, 26.0 Hz), −124.7 (dd, J 27.0, 9.5 Hz); m/z: 610 [M+H]$^+$ (found [M+H]$^+$, 610.1432, C$_{24}$H$_{26}$F$_2$N$_7$O$_6$PS requires [M+H]$^+$ 610.1444).

I-70: benzyl ((S)-1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)-4-methyl-1-oxopentan-2-yl)carbamate

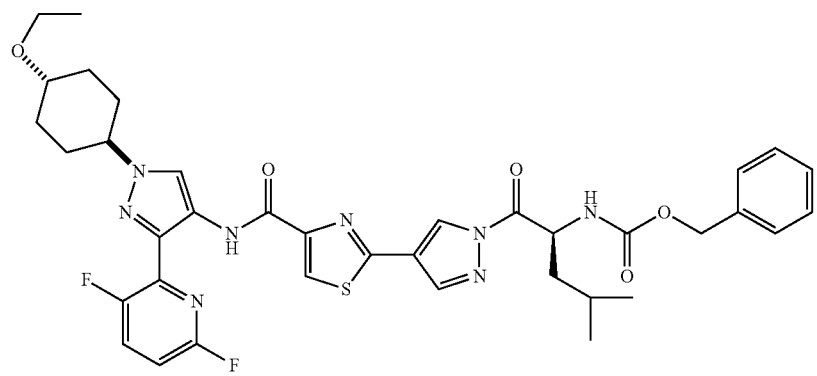 [SMILES: CCO[C@H]1CC[C@H](n2cc(NC(=O)c3csc(-c4cnn(C(=O)[C@H](CC(C)C)NC(=O)OCc5ccccc5)c4)n3)c(-c3nc(F)ccc3F)n2)CC1]

$^1$H nmr (400 MHz, CDCl$_3$) δ 8.78 (1H, s, 1H of pyrazoleH-3, H-5), 8.50 (1H, s, thiazoleH-5 or pyrazoleH-5), 8.35 (1H, s, 1H of pyrazoleH-3, H-5), 8.14 (1H, s, thiazoleH-5 or pyrazoleH-5), 7.65 (1H, td, J 9.0, 6.0 Hz, pyridineH-4 or H-5), 7.35-7.30 (5H, m, C$_6$H$_5$), 6.90 (1H, ddd, J 9.0, 3.0, 2.5 Hz, pyridineH-4 or H-5), 5.66 (1H, m, NCHCO), 5.50 (1H, d, J 9.0 Hz, NH), 5.14, 5.11 (2H, 2d AB system, J 12.5 Hz, OCH$_2$C$_6$H$_5$), 4.27 (1H, tt, J 11.5, 4.0 Hz, cyclohexaneH-1 or H-4), 3.56 (2H, q, J 7.0 Hz, OCH$_2$CH$_3$), 3.37 (1H, tt, J 10.5, 4.0 Hz, cyclohexaneH-1 or H-4), 2.29 (2H, br d, J 12.0 Hz, 2H of cyclohexaneH-2, H-3, H-5, H-6), 2.22 (2H, m, 2H of cyclohexaneH-2, H-3, H-5, H-6), 1.89 (2H, m, 2H of cyclohexaneH-2, H-3, H-5, H-6), 1.82 (2H, m, CHCH$_2$CH(CH$_3$)$_2$), 1.65 (1H, m, CHCH$_2$CH(CH$_3$)$_2$), 1.47 (2H, m, 2H of cyclohexaneH-2, H-3, H-5, H-6), 1.22 (3H, t, J 7.0 Hz, OCH$_2$CH$_3$), 1.07 (2H, br d, J 5.5 Hz, 1×CH(CH$_3$)$_2$), 0.96 (3H, d, J 6.0 Hz, 1×CH(CH$_3$)$_2$); $^{19}$F nmr (380 MHz, CDCl$_3$) δ −72.5 (d, J 27.5 Hz), −124.4 (dd, J 27.0, 9.5 Hz); m/z: 769 [M+Na]$^+$, 747 [M+H]$^+$ (found [M+H]$^+$, 747.2885, C$_{37}$H$_{40}$F$_2$N$_8$O$_5$S requires [M+H]$^+$ 747.2883).

Example 19

The purpose of the project was to evaluate several salts of compound I-18. Salts were prepared using 10 bases (two charge ratios for NaOH and KOH). Suitable solvents include, but are not limited to, methanol, DMSO/acetone (1:4 or 4:1), ethyl acetate, THF/water (9:1) or a combination thereof. The salts were isolated by centrifugation and dried under vacuum. Optionally, the salts also may be heated to dry and/or remove at least a portion of residual solvent.

1) A disodium salt was obtained by mixing 1 equivalent of I-18 with 2 equivalents of NaOH in a solvent at room temperature.
2) A dipotassium salt was obtained by mixing 1 equivalent of I-18 with 2 equivalents of KOH in a solvent at room temperature.
3) A magnesium salt was obtained by mixing equimolar amounts of I-18 and magnesium hydroxide in a solvent at room temperature.
4) A calcium salt was obtained by mixing equimolar amounts of I-18 and calcium hydroxide in a solvent at room temperature.
5) An ammonium salt was obtained by mixing equimolar amounts of I-18 and ammonium hydroxide in a solvent at room temperature.
6) An arginine salt was obtained by mixing equimolar amounts of I-18 and arginine in a solvent at room temperature.
7) A lysine salt was obtained by mixing equimolar amounts of I-18 and lysine in a solvent at room temperature.
8) A choline salt was obtained by mixing equimolar amounts of I-18 and choline in a solvent at room temperature.

9) A tris salt was obtained by mixing equimolar amounts of I-18 and tromethamine in a solvent at room temperature.
10) A meglumine salt was obtained by mixing equimolar amounts of I-18 and meglumine in a solvent at room temperature.
11) A monopotassium salt was obtained by mixing equimolar amounts of I-18 and KOH in a solvent at room temperature.
12) A monosodium salt was obtained by mixing equimolar amounts of I-18 and NaOH in a solvent at room temperature.

All salt hits were characterized by XRPD, TGA and DSC. The stoichiometric ratio was determined by 1H NMR or HPLC/IC. Characterization results of salt hits and freeform forms were listed in Table 5.

Hygroscopicity Evaluation

Figure 20:
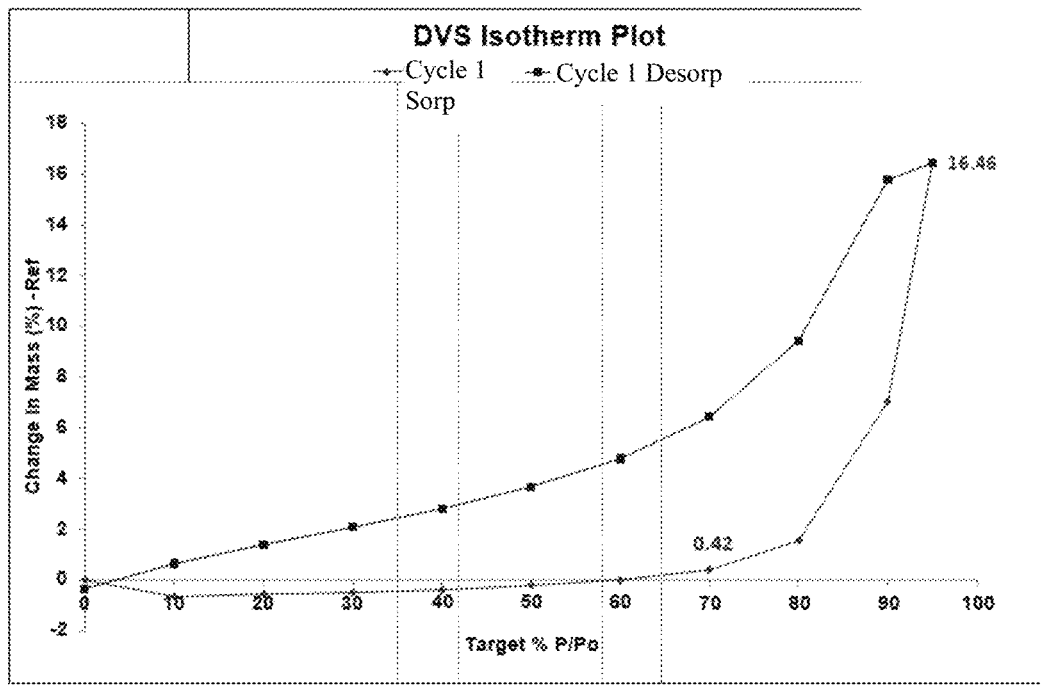
FIG. 20 is a DVS isotherm plot for a potassium salt of compound I-18.
Figure 21:
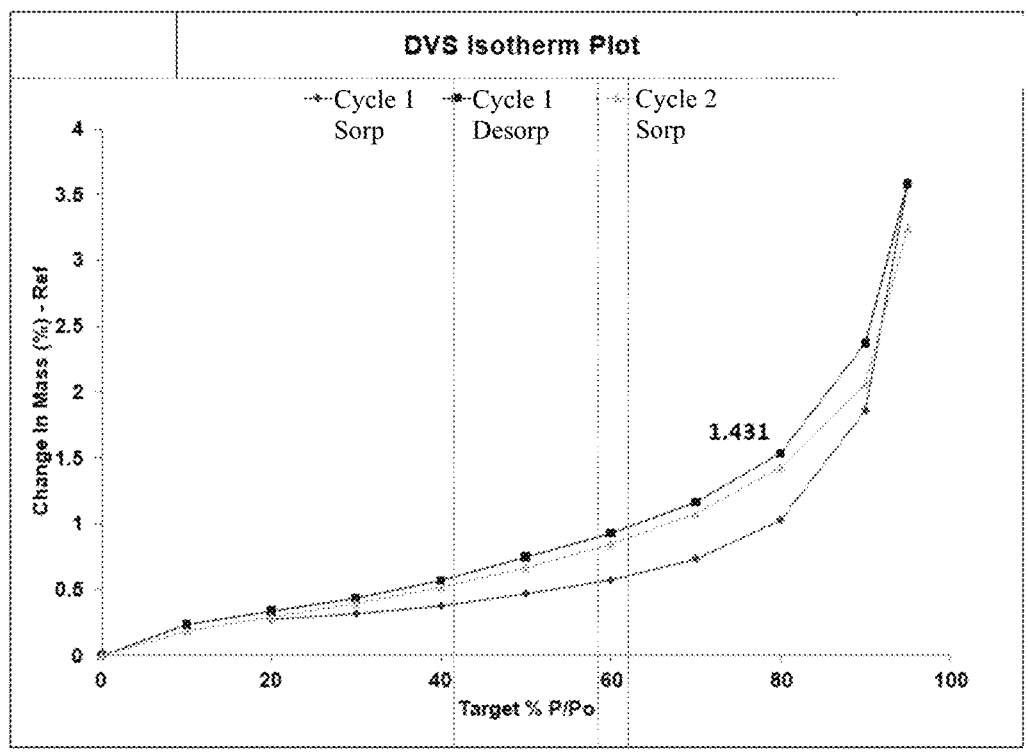
FIG. 21 is a DVS isotherm plot for a arginine salt of compound I-18.
Figure 22:
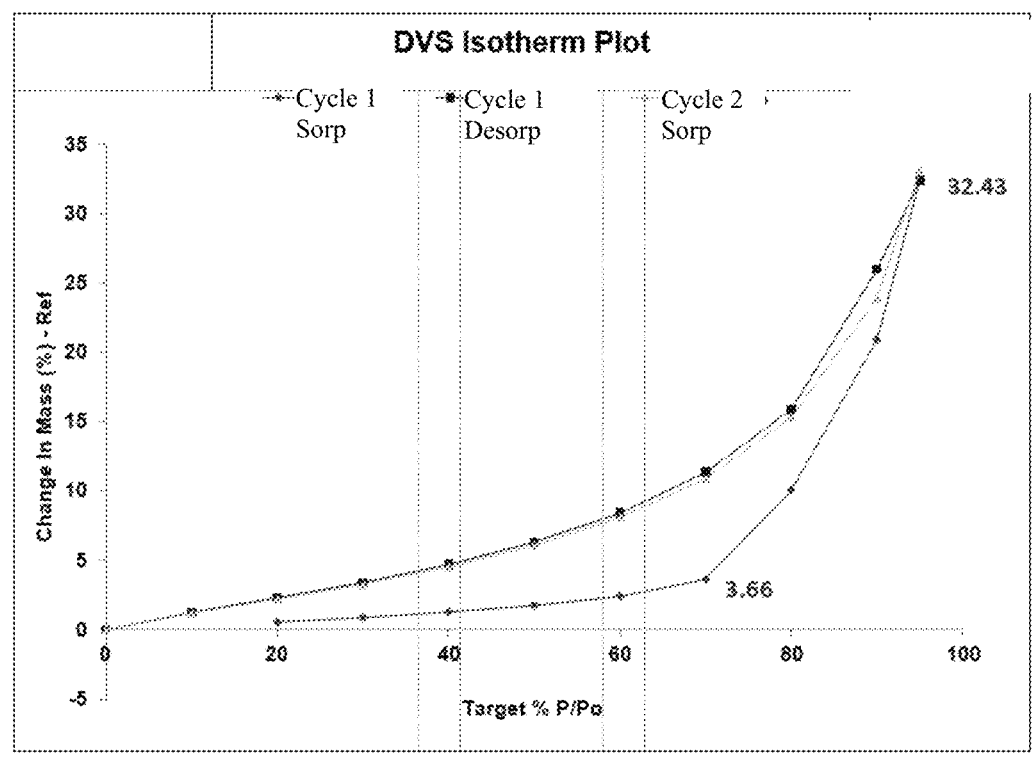
FIG. 22 is a DVS isotherm plot for a choline salt of compound I-18.

To investigate the solid form stability as a function of humidity, DVS isotherm plot of the K salt, Arginine salt, Choline salt and Tris salt were collected at 25° C. between 0 and 95% RH. The DVS plot of the K salt is shown in FIG. 20. The water uptake at 70% RH was 0.42%, and increased dramatically to 16.5% at 95% RH. The DVS plot of Arginine salt is shown in FIG. 21. A water uptake of 1.43% was observed at 80% RH, indicating Arginine salt was slight hygroscopic. The DVS plot of Choline salt is shown in FIG. 22. The water uptake at 70% RH was 3.66%, and increased

TABLE 5

Characterization results of initial salts

| Salt Hits | Weight loss (%, temp.) | DSC endotherm (peak, ° C.) | Molar ratio (base/free acid) | Speculated form |
|---|---|---|---|---|
| K Salt | 3.1 (to 150° C.) | 170.3, 248.1 | 0.7:1 | Anhydrate/Hydrate |
| K Salt | 5.3 (to 140° C.) 6.7 (140° C.~240° C.) | 94.6*, 174.0* | 1.1:1 | Hydrate |
| K Salt | 4.0 (to 130° C.) 4.7 (130° C.~230° C.) | 101.7*, 168.5* | 1.0:1 | Hydrate |
| K Salt | 5.9 (to 125° C.) | 100.6, 149.0 | 1.4:1 | Anhydrate |
| Arginine Salt | 2.1 (to 190° C.) | 130.7, 216.1 | 1.2:1 | Anhydrate |
| Choline Salt | 5.1 (to 160° C.) | 67.7, 158.7, 195.0 | 0.8:1 | Anhydrate |
| Choline Salt | 3.3 (to 160° C.) | 67.2, 159.4, 195.7 | NA | Anhydrate/Hydrate |
| Tris Salt | 1.2 (to 150° C.) | 61.3, 174.3 | 1.1:1 | Channel hydrate |
| Tris Salt | 2.4 (to 140° C.) | 63.0, 135.2, 175.6 | 0.9:1 | Channel hydrate |
| Na Salt) | 5.5 (to 240° C.) 6.0 (110° C.~240° C.) | 97.6, 176.4, 195.0 | 1.5:1 | Anhydrate/Hydrate |
| Na Salt | 13.5 (to 250° C.) | 109.9, 183.1, 226.0 | 1.6:1 | Anhydrate/Hydrate |
| Na Salt | 6.1 (to 150° C.) | 66.6, 110.7, 200.7 | 1.6:1 | Anhydrate/Hydrate |
| Ammonium Salt | 3.0 (to 115° C.) 2.6 (115° C.~200° C.) | 97.9, 160.2, 192.9, 238.8 | 0.6:1# | Anhydrate/Hydrate |
| Arginine Salt) | 4.0 (to 160° C.) | 80.8, 119.4, 145.1, 177.1 | 1.0:1 | Anhydrate/Hydrate |
| Lysine Salt | 5.0 (to 140° C.) | 69.3, 175.4, 227.3 | 0.7:1 | Anhydrate/Hydrate |
| Mg Salt | 11.7 (to 230° C.) | 69.4, 116.4, 183.2 | 1.0:1# | Anhydrate/Hydrate |
| Ca Salt | 6.9 (to 180° C.) | 114.0*, 190.5* | 0.8:1# | Anhydrate/Hydrate |

*Onset temperature.
Solid could not be dissolved completely before HPLC and IC test, so the stoichiometric ratio was for reference only.

Based on the above, a potassium salt, arginine salt, choline salt and tris salt were selected for further evaluation.

TABLE 6

Characterization of evaluation salts

Figure 23:
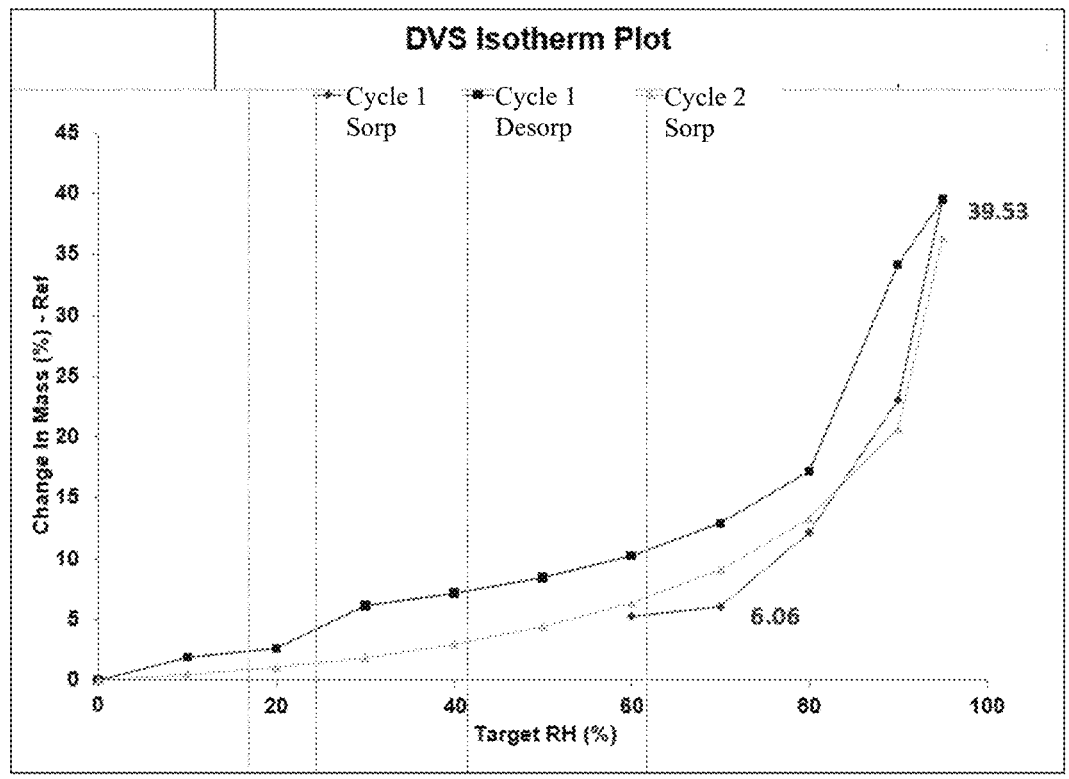
FIG. 23 is a DVS isotherm plot for a Tris salt of compound I-18.

| Salt form | TGA weight loss (%, temp.) | DSC endotherm (° C., peak) | Molar ratio (base/API) |
|---|---|---|---|
| K salt | 6.6 (to 220° C.) | 199.8 | 1:1 |
| Arginine salt | 3.3 (to 190° C.) | 131.6, 217.1 | 1:1 |
| Choline salt | 2.3 (to 160° C.) | 64.3, 186.7 | 0.9:1 |
| Tris salt | 5.8 (to 150° C.) | 156.5, 176.2 | 1.1:1 | dramatically to 32.4% at 95% RH. The DVS plot of Tris salt is shown in FIG. 23. The water uptake at 70% RH was 6.06%, and increased dramatically to 39.5% at 95% RH.

Physical and Chemical Stability

The physical and chemical stability of the K salt, Arginine salt, Choline salt and Tris salt were evaluated under conditions of 25° C./60% RH and 40° C./75% RH for 1 week. Each sample was added into 3 mL glass vials, sealed by parafilm with several holes, and kept under tested condition. After one week, samples was taken for XRPD and HPLC purity test. All the characterization data are summarized in Table 7.

TABLE 7

Summary of physiochemical stability evaluation

| Salt | Initial purity (area %) | 25° C./60% RH/ 1 week Purity/ Initial purity (%) | 25° C./60% RH/ 1 week Form change | 40° C./75% RH/ 1 week Purity/ Initial purity (%) | 40° C./75% RH/ 1 week Form change |
|---|---|---|---|---|---|
| K salt | 97.27 | 99.0 | No | 99.1 | Yes |
| Arginine salt | 95.91 | 99.4 | No | 99.6 | No |
| Choline salt | 98.70 | 100.0 | No | 99.1 | No |
| Tris salt | 96.06 | 100.6 | No | 98.9 | No |

The XRPD patterns showed that no form change was observed after storage under the two conditions for the Arginine salt, Choline salt and Tris salt. For the K salt, no form change was observed under 25° C./60% RH while a form change was observed under 40° C./75% RH. For both the K salt and Arginine salt, a slight purity decrease was observed under both conditions after 1 week. For Choline salt and Tris salt, no HPLC purity decrease was observed under 25° C./60% RH while a purity decrease was observed under 40° C./75% RH. Impurities summary for all salt hits are shown in Tables 8-11. The peak at RRT=1.17 corresponds to I-1, the parent compound of I-18 that is formed by hydrolysis. Decrease in purity of I-18 salt is typically correlated with a corresponding increase in I-1 parent impurity level.

TABLE 8

Impurity summary of the potassium salt

| # Peak | RRT | Area (%) Initial | Area (%) 25° C./60% RH | Area (%) 40° C./75% RH |
|---|---|---|---|---|
| 1 | 1.00 | 97.27 | 96.26 | 96.40 |
| 2 | 1.14 | <0.04 | <0.04 | 0.05 |
| 3 | 1.17 | 1.33 | 2.14 | 1.80 |
| 4 | 1.40 | 0.23 | 0.25 | 0.39 |
| 5 | 1.44 | 0.21 | 0.30 | 0.24 |
| 6 | 1.70 | 0.18 | 0.27 | 0.24 |
| 7 | 1.72 | 0.77 | 0.78 | 0.83 |
| 8 | 1.81 | <0.04 | <0.04 | 0.04 |

TABLE 9

Impurity summary of the arginine salt

| # Peak | RRT | Area (%) Initial | Area (%) 25° C./60% RH | Area (%) 40° C./75% RH |
|---|---|---|---|---|
| 1 | 0.77 | <0.03 | 0.03 | 0.04 |
| 2 | 1.00 | 95.91 | 95.31 | 95.50 |
| 3 | 1.13 | <0.03 | 0.06 | 0.06 |
| 4 | 1.17 | 2.39 | 2.68 | 2.48 |
| 5 | 1.35 | <0.03 | 0.06 | 0.11 |
| 6 | 1.45 | 0.44 | 0.50 | 0.47 |
| 7 | 1.71 | 0.73 | 0.74 | 0.73 |
| 8 | 1.73 | <0.53 | 0.61 | 0.60 |

TABLE 10

Impurity summary of the choline salt

| # Peak | RRT | Area (%) Initial | Area (%) 25° C./60% RH | Area (%) 40° C./75% RH |
|---|---|---|---|---|
| 1 | 0.77 | 0.03 | 0.04 | 0.04 |
| 2 | 1.00 | 98.70 | 98.66 | 97.81 |
| 3 | 1.13 | 0.06 | 0.06 | 0.06 |
| 4 | 1.17 | 0.75 | 0.58 | 1.31 |
| 5 | 1.35 | <0.03 | 0.10 | 0.14 |
| 6 | 1.45 | 0.06 | 0.07 | 0.11 |
| 7 | 1.71 | 0.06 | 0.05 | 0.08 |
| 8 | 1.73 | 0.33 | 0.46 | 0.46 |

TABLE 11

Impurity summary of the tris salt

| # Peak | RRT | Area (%) Initial | Area (%) 25° C./60% RH | Area (%) 40° C./75% RH |
|---|---|---|---|---|
| 1 | 0.77 | <0.03 | <0.03 | 0.03 |
| 2 | 1.00 | 96.06 | 96.61 | 95.03 |
| 3 | 1.13 | 0.07 | 0.06 | 0.06 |
| 4 | 1.17 | 1.87 | 1.63 | 2.69 |
| 5 | 1.45 | 0.37 | 0.35 | 0.47 |
| 6 | 1.71 | 0.86 | 0.80 | 0.88 |
| 7 | 1.73 | 0.76 | 0.55 | 0.84 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, having a formula

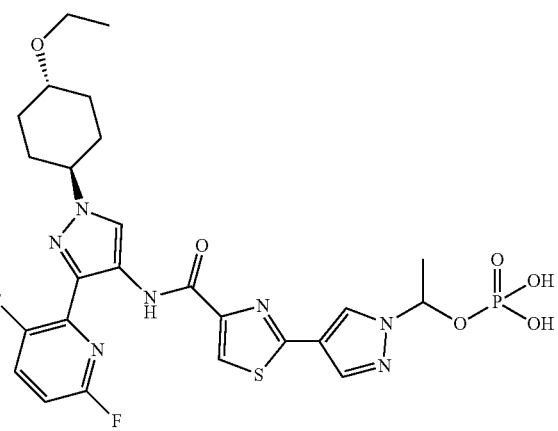

or a pharmaceutically acceptable salt thereof.

2. The compound of claim 1, wherein the compound is an alkali metal salt, an alkaline earth metal salt, an ammonium salt, an amino acid salt, an amino sugar salt, or a tris salt.

3. The compound of claim 1, wherein the compound is a mono-salt, or a di-salt.

4. The compound of claim 1, wherein the alkyl phosphate is a mono- or di-sodium salt, mono- or di-potassium salt, calcium salt, magnesium salt, arginine salt, lysine salt, mono- or di-tris salt, ammonium salt, choline salt, or meglumine salt.

5. The compound of claim 1, selected from:

I-18: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate;

I-20: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl phosphate disodium salt;

I-49: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate tris salt;

I-107: sodium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl hydrogen phosphate;

I-108: potassium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl hydrogen phosphate;

I-109: potassium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl phosphate;

I-110: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate arginine salt;

I-111: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate choline salt;

I-112: ammonium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl hydrogen phosphate;

I-113: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate lysine salt;

I-114: 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl dihydrogen phosphate meglumine salt;

I-115: magnesium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl phosphate; or I-116: Calcium 1-(4-(4-((3-(3,6-difluoropyridin-2-yl)-1-((1r,4r)-4-ethoxycyclohexyl)-1H-pyrazol-4-yl)carbamoyl)thiazol-2-yl)-1H-pyrazol-1-yl)ethyl phosphate.

6. A composition, comprising a compound according to claim 1, and a pharmaceutically acceptable excipient.

7. A compound, wherein the compound is an organic base salt of a compound having a formula

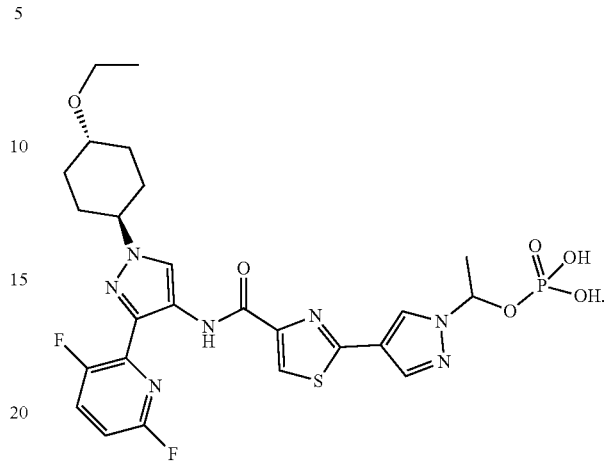

8. The compound of claim 7, wherein the organic base salt is a mono-salt, or a di-salt.

9. The compound of claim 7, wherein the organic base salt is a tris salt.

10. The compound of claim 7, wherein the organic base salt is an amino acid salt.

11. The compound of claim 7, wherein the organic base salt is an arginine salt, lysine salt, mono-tris salt, di-tris salt, choline salt, or meglumine salt.

12. A compound, wherein the compound is an inorganic base salt of a compound having a formula

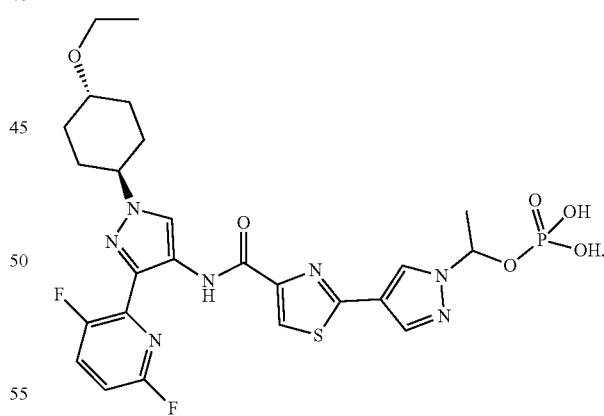

13. The compound of claim 12, wherein the inorganic base salt is an alkali metal salt, an alkaline earth metal salt, or an ammonium salt.

14. The compound of claim 12, wherein the inorganic base salt is a mono-salt, or a di-salt.

15. The compound of claim 12, wherein the inorganic base salt is a mono-sodium salt, di-sodium salt, mono-potassium salt, di-potassium salt, calcium salt, magnesium salt, or mono-ammonium salt.

16. A spray-dried composition, comprising a polymer carrier and a compound having a formula

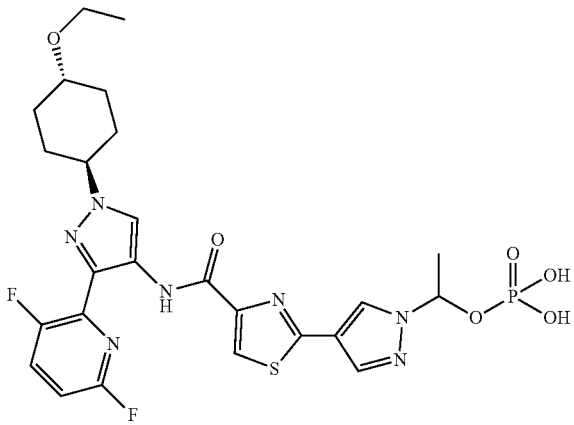 [SMILES: CCO[C@H]1CC[C@H](n2cc(NC(=O)c3csc(-c4cnn(C(C)OP(=O)(O)O)c4)n3)c(-c3nc(F)ccc3F)n2)CC1]

or a pharmaceutically acceptable salt thereof.

17. The spray-dried composition of claim 16, wherein the spray-dried composition comprises from 1% to 50% w/w of the compound with respect to the carrier.

18. The spray-dried composition of claim 16, wherein the polymer is a cellulose derivative, vinyl polymer, lactide polymer, sugar, or a combination thereof.

19. The spray-dried composition of claim 16, wherein the composition is amorphous and/or has a glass transition temperature of from 100° C. to 120° C.

20. A method of making a spray-dried composition, comprising:

forming a mixture comprising a carrier, a solvent and a compound having a formula

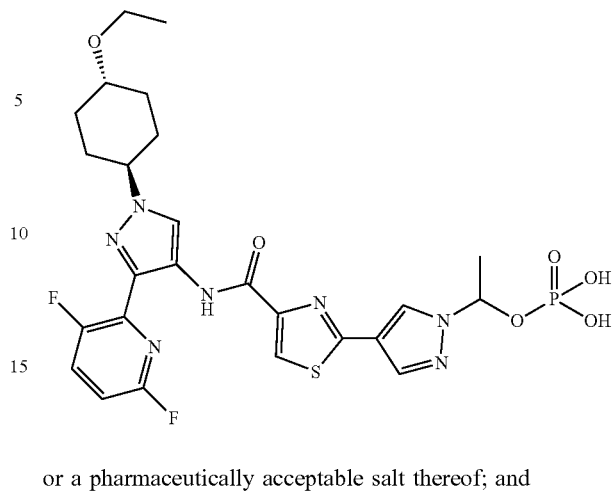

or a pharmaceutically acceptable salt thereof; and spray drying the mixture to form a spray-dried formulation comprising the compound and the carrier.

21. A method for treating a disease or condition for which an IRAK inhibitor is indicated, comprising administering to a subject in need thereof an effective amount of a compound according to claim 1 or a composition thereof, wherein the subject has a disease or condition selected from an autoimmune disease, inflammatory disorder, cardiovascular disease, neurodegenerative disorder, allergic disorder, multiorgan failure, kidney disease, platelet aggregation, cancer, transplantation, sperm motility, erythrocyte deficiency, graft rejection, lung injury, respiratory disease, ischemic condition, bacterial infection, viral infection, immune regulatory disorder or a combination thereof.

22. The method of claim 21, further comprising administering a second therapeutic agent.

23. The method of claim 22, wherein the second therapeutic agent is an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof.

* * * * *